US010920254B2

(12) United States Patent
Conradie et al.

(10) Patent No.: US 10,920,254 B2
(45) Date of Patent: Feb. 16, 2021

(54) METHODS AND MATERIALS FOR PRODUCING 5 AND 7-CARBON MONOMERS

(71) Applicant: INVISTA North America S.á.r.l., Wilmington, DE (US)

(72) Inventors: Alex Van Eck Conradie, Eaglescliffe (GB); Adriana Leonora Botes, Rosedale East (GB)

(73) Assignee: INV Nylon Chemicals Americas, LLC, Wilmington, DE (US)

(*) Notice: Subject to any disclaimer, the term of this patent is extended or adjusted under 35 U.S.C. 154(b) by 0 days.

(21) Appl. No.: 16/683,570

(22) Filed: Nov. 14, 2019

(65) Prior Publication Data

US 2020/0283809 A1 Sep. 10, 2020

Related U.S. Application Data

(63) Continuation of application No. 16/373,493, filed on Apr. 2, 2019, now abandoned, which is a continuation of application No. 15/348,370, filed on Nov. 10, 2016, now abandoned.

(60) Provisional application No. 62/255,303, filed on Nov. 13, 2015.

(51) Int. Cl.

| | |
|---|---|
| ***C12N 15/52*** | (2006.01) |
| ***C12P 13/00*** | (2006.01) |
| ***C12P 7/42*** | (2006.01) |
| ***C12P 7/44*** | (2006.01) |
| ***C12P 11/00*** | (2006.01) |
| ***C12P 19/32*** | (2006.01) |
| ***C12P 7/26*** | (2006.01) |
| ***C12P 7/18*** | (2006.01) |
| ***C08G 69/28*** | (2006.01) |
| ***C12N 9/10*** | (2006.01) |
| ***C12P 7/04*** | (2006.01) |

(52) U.S. Cl.

CPC ............ *C12P 13/001* (2013.01); *C08G 69/28* (2013.01); *C12N 9/1029* (2013.01); *C12N 9/1096* (2013.01); *C12N 15/52* (2013.01); *C12P 7/04* (2013.01); *C12P 7/18* (2013.01); *C12P 7/26* (2013.01); *C12P 7/42* (2013.01); *C12P 7/44* (2013.01); *C12P 11/00* (2013.01); *C12P 13/00* (2013.01); *C12P 13/005* (2013.01); *C12P 19/32* (2013.01); *C12Y 203/01016* (2013.01); *C12Y 203/01174* (2013.01); *C12Y 206/01002* (2013.01)

(58) Field of Classification Search

CPC .. C12N 15/52; C12P 7/42; C12P 13/00; C12P 11/00

See application file for complete search history.

(56) References Cited

U.S. PATENT DOCUMENTS

2014/0193863 A1 7/2014 Botes et al.
2014/0248673 A1 9/2014 Botes et al.

FOREIGN PATENT DOCUMENTS

KR 10-2015-0104450 A 9/2015
WO WO 2016/077745 A1 5/2016
WO WO 2017/083493 A1 5/2017

OTHER PUBLICATIONS

Barker, et al., "Enzymatic Reactions in the Degradation of 5-Aminovalerate by Clostridium Aminovalericum," *The Journal of Biological Chemistry*, vol. 262, No. 19, 1987, pp. 8994-9003.

Bartsch, et al., "Molecular Analysis of Two Genes of the *Escherichia Colil* Gab Cluster: Nucleotide Sequence of the Glutamate: Succinic Semialdehyde Transaminase Gene (gabT) and Charcterization of the Succinic Semialdehyde Dehydrogenase Gene (gabD)," *Journal of Bacteriology*, vol. 172, No. 12, 1990, pp. 7035-7042.

Becker, et al., "Metabolic Flux Engineering of L-Lysine Production in Corynebacterium Glutamicum—Over Expression and Modification of G6P Dehydrogenase," *Journal of Biotechnology*, vol. 132, 2007, pp. 99-109.

Bellmann, et al., "Expression Control and Specificity of the Basic Amino Acid Exporter LysE of Corynebacterium Glutamicum," *Microbiology*, vol. 147, 2001, pp. 1765-1774.

Berndt, H., et al., "Kinetics and Properties of β-Ketothiolase from *Clostridium pasteurianum*," *Arch. Microbiol.*, 103, 21-30 (1975); © by Springer-Verlag 1975, 10 pages.

Bond-Watts, et al., "Biochemical and Structural Characterization of the Trans-Enoyl-CoA Reductase from Treponema Denticola," Biochemistry, vol. 51, 2012, pp. 6827-6837.

Brigham, et al., "Engineering Ralstonia Eutropha for Production of Isobutanol from CO2, H2, and O2," *Advanced Biofuels and Bioproducts*, Springer New York, Chapter 39, 2013, pp. 1065-1090.

Budde, et al., "Roles of Multiple Acetoacetyl Coenzyme A Reductases in Polyhydroxybutyrate Biosynthesis in Ralstonia Eutropha H16," *Journal of Bacteriology*, vol. 192, No. 20, 2010, pp. 5319-5328.

Bugg, et al., "The Emerging Role for Bacteria in Lignin Degradation and Bio-Product Formation," *Current Opinion in Biotechnology*, vol. 22, 2011, pp. 394-400.

(Continued)

*Primary Examiner* — Tekchand Saidha

(57) ABSTRACT

This document describes biochemical pathways for biosynthesizing a 3-oxo-7-hydroxyheptanoyl-CoA intermediate using a β-ketothiolase, and enzymatically converting 3-oxo-7-hydroxyheptanoyl-CoA to 7-hydroxyheptanoic acid. —7-hydroxyheptanoic acid can be further enzymatically converted to pimelic acid, 7-aminoheptanoic acid, heptamethylenediamine or 1,7-heptanediol. This document also describes recombinant hosts producing 7-hydroxyheptanoic acid as well as pimelic acid, 7-aminoheptanoic acid, heptamethylenediamine and 1,7-heptanediol.

27 Claims, 42 Drawing Sheets

Specification includes a Sequence Listing.

(56) References Cited

OTHER PUBLICATIONS

Cantu, et al., "Thioesterases: A New Perspective Based on their Primary and Tertiary Structures," *Protein Science*, vol. 19, 2010, pp. 1281-1295.
Elkins, et al., "Substrate Specificity of the RND-Type Multidrug Efflux Pumps AcrB and AcrD of *Escherichia coli* is Determined Predominately by Two Large Periplasmic Loops," *Journal of Bacteriology*, vol. 184, No. 23, 2002, pp. 6490-6498.
Fukui, et al., "Expression and Characterization of (R)-Specific Enoyl Coenzyme A Hydratase Involved in Polyhydroxyalkanoate Biosynthesis by Aeromnas Caviae," *Journal of Bacteriology*, vol. 180, No. 3, 1998, pp. 667-673.
Gloerich, et al., "Peroxisomal Trans—2—Enoyl—CoA Reductase is Involved in Phytol Degradation," *FEBS Letters*, vol. 580, 2006, pp. 2092-2096.
Guerrillot, et al., "Purification and Characterization of Two Aldehyde Dehydrogenases from Pseudomonas Aeruginosa," *European Journal of Biochemistry*, vol. 81, 1977, pp. 185-192.
Haywood, et al., "Characterization of Two 3-Ketothiolases Possessing Differing Substrate Specificities in the Polyhydroxyalkanoate Synthesizing Organism Alcaligenes Eutrophus," *FEMS Microbiology Letters*, vol. 52, 1998, pp. 91-96.
Hermann, Thomas, "Industrial Production of Amino Acids by Coryneform Bacteria," *Journal of Biotechnology*, vol. 104, 2003, pp. 155-172.
Huhn, et al., "Identification of the Membrane Protein SucE and its Role in Succinate Transport in Corynebacterium Glutamicum," *Applied Microbiology and Biotechnology*, vol. 89, 2011, pp. 327-335.
International Patent Application No. PCT/US2016/061287, filed Nov. 10, 2016, by Invista North America S.a.r.l.: International Search Report and Written Opinion, dated Mar. 2, 2017, (15 pages).
Inui, et al., "Fatty Acids Synthesis in Mitochrondria of Euglena Gracilis," *European Journal of Biochemistry*, vol. 142, 1984, pp. 121-126.
Iwaki, et al., "Cloning and Characterization of a Gene Cluster Involved in Cyclopentanol Metabolism in *comamonas* sp. Strain NCIMB 9872 and Biotransformations Effected by *Escherichia coli*—Expressed Cyclopentanone 1, 2-Monooxygenase," *Applied and Environmental Microbiology*, vol. 68, No. 11, 2002, pp. 5671-5684.
Iwaki, et al., "Identification of a Transcriptional Activator (ChnR) and a 6-Oxohexanoate Dehydrogenase (ChnE) in the Cyclohexanol Catabolic Pathway in *acinetobacter* sp. Strain NCIMB 9871 and Localization of the Genes That Encode Them," *Applied and Environmental Microbiology*, vol. 65, No. 11, 1999, pp. 5158-5162.
Jarboe, Laura R., "YghD: A Broad-Substrate Range Aldehyde Reductase with Various Applications in Production of Biorenewable Fuels and Chemicals," *Applied Microbiology and Biotechnology*, vol. 89, No. 2, 2011, pp. 249-257.
Kaulmann, et al., "Substrate Spectrum of ω-Transaminase from Chromobacterium Violaceum DSM30191 and its Potential for Biocatalysis," *Enzyme and Microbial Technology*, vol. 41, 2007, pp. 628-637.
Kim, Ki-Han, "Purification and Properties of a Mine α-Ketoglutarate Transaminase from *Escherichia coli*," *Journal of Biological Chemistry*, vol. 239, No. 3, 1964, pp. 783-786.
Köpke, et al., "2, 3-Butanediol Production by Acetogenic Bacteria, An Alternative Route to Chemical Synthesis, Using Industrial Waste Gas," *Applied and Environmental Microbiology*, vol. 77, No. 15, 2011, pp. 5467-5475.
Larroy, et al., "Characterization of the *Saccharomyces cerevisiae* YMR318C (ADH6) Gene Product As a Broad Specificity NADPH-Dependent Alcohol Dehydrogenase: Relevance in Aldehyde Reduction," *Biochemical Journal*, vol. 361, No. 1, 2002, 163-172.
Lee, et al., "Synthesis of Pure Meso-2, 3-Butanediol from Crude Glycerol Using an Engineered Metabolic Pathway in *Escherichia Coli*," *Applied Biochemistry and Biotechnology*, vol. 166, No. 7, 2012, pp. 1801-1813.
Lee, et al.,"Metabolic Engineering of Pentose Phosphate Pathway in Ralstonia Eutropha for Enhanced Biosynthesis of Poly—β—Hydroxybutyrate," *Biotechnology Process*, vol. 19, No. 5, 2003, pp. 1444-1449.
Li, et al., "Cupriavidus Necator JMP134 Rapidly Reduces Furfural With a Zn-Dependent Alcohol Dehydrogenase," *Biodegradation*, vol. 22, No. 6, 2011, pp. 1215-1225.
Lim, et al., "Amplification of the NADPH-Related Genes zwf and gnd for the Oddball Biosynthesis of PHB in an *E. coli* Transformant Harboring a Cloned phbCAB Operon," *Journal of Bioscience and Bioengineering*, vol. 93, No. 6, 2002, pp. 543-549.
Liu, et al., "Production and Characterization of Medium-Chain-Length Polyhydroxyalkanoate with High 3-Hydroxytetradecanoate Monomer Content by fadB and fadA Knockout Mutant of Pseudomonas Putida KT2442," *Applied Microbiology and Biotechnology*, vol. 76, No. 5, 2007, pp. 1153-1159.
Liu, et al.,"Two Novel Metal-Independent Long-Chain Alkyl Alcohol Dehydrogenases from Geobacillus Thermodenitrificans NG80-2," *Microbiology*, vol. 155, No. 6, 2009, pp. 2078-2085.
Lopez-Sánchez, et al., "Tetralin-Induced and ThnR-Regulated Aldehyde Dehydrogenase and β-Oxidation Genes in Sphingomonas Macrogolitabida Strain TFA," *Applied and Environmental Microbiology*, vol. 76, No. 1, 2010, pp. 110-118.
Lütke-Eversloh, et al., "Biochemical and Molecular Characterization of a Succinate Semialdehyde Dehydrogenase Involved in the Catabolism of 4-Hydroxybutyric Acid in Ralstonia Eutropha," *FEMS Microbiology Letters*, No. 181, No. 1, 1999, pp. 63-71.
Martin, et al., "High-Titer Production of Monomeric Hydroxyvalerates from Levulinic Acid in Pseudomanas Putida," *Journal of Biotechnology*, vol. 139, No. 1, 2009, pp. 61-67.
Meijnen, et al., "Improved p-Hydroxybenzoate Production by Engineered Pseudomonas Putida S12 by Using a Mixed-Substrate Feeding Strategy," *Applied Microbiology and Biotechnology*, vol. 90, No. 3, 2011, pp. 885-893.
Naggert, et al., "Cloning, Sequencing, and Characterization of *Escherichia coli* Thioesterase II," *The Journal of Biological Chemistry*, vol. 266, No. 17, 1991, pp. 11044-11050.
Neyfakh, Alexander A., et al., "The Multidrug Efflux Transporter of Bacillus Subtillis is a Structural and Functional Homolog of the *Staphylococcus* NorA Protein," *Antimcrobial Agents and Chemotherapy*, vol. 36, No. 2, 1992, pp. 484-485.
Ng, et al., "Quinolone Resistance Mediated by NorA: Physiologic Characterization and Relationship to flqB, A Quinolone Resistance Locus on the *Staphyloccus aureus* Chromosome," *Antimicrobial Agents and Chemotherapy*, vol. 38, No. 6, 1994, pp. 1345-1355.
Nishimaki, et al., "Studies on the Metabolism of Unsaturated Fatty Acids XIV, Purification and Properties of NADPH-Dependent Trans-2-Enoyl-CoA Reductase of *Escherichia coli* K-12," *The Journal of Biochemistry*, vol. 95, No. 5, 1984, pp. 1315-1321.
Nogales, et al., "Characterization of the Last Step of the Aerobic Phenylacetic Acid Degradation Pathway," *Microbiology*, vol. 153, 2007, pp. 357-365.
Nomura, et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," *Applied Environmental Microbiology*, vol. 71, No. 8, 2005, pp. 4297-4306.
Ohashi, et al., "Continuous Production of Lactic Acid from Molasses by Perfusion Culture of Lactococcus Lactis Using a Stirred Ceramic Membrane Reactor," *Journal of Bioscience and Bioengineering*, vol. 87, No. 5, 1999, pp. 647-654.
Papanikolaou, et al., "Citric Acid Production by Yarrowia Lipolytica Cultivated on Olive-Mill Wastewater-Based Media," *Bioresource Technology*, vol. 99, 2008, pp. 2419-2428.
PCT International Preliminary Report on Patentability issued in PCT/US2016/061287, dated May 15, 2018, 11 pages.
Perez-Pantoja, et al., "Metabolic Reconstruction of Aromatic Compounds Degradation from the Genome of the Amazing Pollutant-Degrading Bacterium Cupriavidus Necator JMP134," *FEMS Microbiology Reviews*, vol. 32, 2008, pp. 736-794.
Przbylski, et al., "Third-Generation Feed Stocks for the Clean and Sustainable Biotechnological Production of Bulk Chemicals: Syn-

(56) References Cited

OTHER PUBLICATIONS thesis of 2-Hydroxyisobutric Acid," *Energy, Sustainability and Society*, vol. 2, No. 11, 2012, pp. 1-9.
Ramsay, et al., "Use of a Nylon Manufacturing Waste As an Industrial Fermentation Substrate," *Applied and Environmental Microbiology*, vol. 52, No. 1, 1986, pp. 152-156.
Saito, et al., "Metabolite Profiling Reveals YihU as a Novel Hydroxybutyrate Dehydrogenase for Alternative Succinic Semialdehyde Metabolism in *Escherichia coli*," *The Journal of Biological Chemistry*, vol. 284, No. 24, 2009, pp. 16442-16451.
Samsonova, et al., "Molecular Cloning and Characterization of *Escherichia coli* K12 ygjG Gene," *BMC Microbiology*, vol. 3, No. 2, 2003, pp. 1-10.
Sanders, et al., "Characterization of the Human ω-Oxidation Pathway for ω-Hydroxy-Very-Long-Chain Fatty Acids," *The FASEB Journal*, vol. 22, No. 6, 2008, pp. 2064-2071.
Sanders, et al., "Evidence for Two Enzymatic Pathways for ω-Oxidation of Docosanoic Acid in Rat Liver Microsomes," Journal of Lipid Research, vol. 46, 2005, pp. 1001-1008.
Satoh, et al., "Enzyme-Catalyzed Poly (3-Hydroxybutyrate) Synthesis from Acetate with CoA Recycling and NADPH Regeneration in Vitro," *Journal of Bioscience and Bioengineering*, vol. 95, No. 4, 2003, pp. 335-341.
Scheller, et al., "Generation of the Soluble and Functional Cytosolic Domain of Microsomal Cytochrome P450 52A3," *Journal of Biological Chemistry*, vol. 269, No. 17, 1994, pp. 12779-12783.
Seedorf, et al., "The Genome of Clostridium Kluyveri, a Strict Anaerobe with Unique Metabolic Features," Proceedings of the National Academy of Sciences, vol. 105, No. 6, 2008, pp. 2128-2133.
Shen, et al., "Driving Forces Enable High-Titer Anaerobic 1-Butanol Synthesis in *Escherichia Coli*," Applied and Environmental Microbiology, vol. 77, No. 9, 2011, pp. 2905-2915.
Slater, et al., "Multiple β-Ketothiolases Mediate Poly(β-Hydroxyalkanoate) Copolymer Synthesis in Ralstonia eutropha," *Journal of Bacteriology*, vol. 180, No. 8, 1998, pp. 1979-1987.
Suzuki, et al., "GriC and GriD Constitute a Carboxylic Acid Reductase Involved in Grixazone Biosynthesis in Streptomyces Griseus," *Journal of Antibiotics*, vol. 60, No. 6, 2007, pp. 380-387.
Venkitasubramanian, et al., "Aldehyde Oxidoreductase As a Biocatalyst: Reduction of Vanillic Acid," *Enzyme and Microbial Technology*, vol. 42, No. 2, 2008, pp. 130-137.
Wee, et al., "Biotechnological Production of Lactic Acid and its Recent Applications," *Food Technology and Biotechnology*, vol. 44, No. 2, 2006, pp. 163-172.
Woolridge, et al., "Efflux of the Natural Polyamine Spermidine Facilitated by the Bacillus Subtillis Multidrug Transporter Blt," *Journal of Biological Chemistry*, vol. 272, No. 14, 1997, pp. 8864-8866.
Yang, et al., "Value-Added Uses for Crude Glycerol—A Byproduct of Biodiesel Production," *Biotechnology for Biofuels*, vol. 5, No. 13, 2012, pp. 1-10.
Yonaha, et al., "4-Aminobutyrate: 2-Oxoglutarate Aminotransferase of Streptomyces Griseus," *European Journal of Biochemistry*, vol. 146, 1985, pp. 101-106.
Zhuang, et al., "Divergence of Function in the Hot Dog Fold Enzyme Superfamily: the Bacterial Thioesterase YciA," *Biochemistry*, vol. 47, No. 9, 2008, pp. 2789-2796.

7-hydroxyheptanoate pimelate semialdehyde 7-aminoheptanoate

FIG. 6A

| SEQ ID NO | Organism | GENBANK reference | Amino acid sequence |
|---|---|---|---|
| 1 | *Cupriavidus necator* | AAC38322.1 | MTREVVVVSGVRTAIGTFGGSLKDVAPAELGALVVREALARAQVSGDDVGHVVFGNVIQT<br>EPRDMYLGRVAAVNGGVTINAPALTVNRLCGSGLQAIVSAAQTILLGDTDVAIGGGAESM<br>SRAPYLAPAARWGARMGDAGLVDMMLGALHDPFHRIHMGVTAENVAKEYDISRAQQDEAA<br>LESHRRASAAIKAGYFKDQIVPVVSKGRKGDVTFDTDEHVRHDATIDDMTKLRPVFVKEN<br>GTVTAGNASGLNDAAAAVVMMERAEAERRGLKPLARLVSYGHAGVDPKAMGIGPVPATKI<br>ALERAGLQVSDLDVIEANEAFAAQACAVTKALGLDPAKVNPNGSGISLGHPIGATGALIT<br>VKALHELNRVQGRYALVTMCIGGGQGIAAIFERI |
| 2 | *Mycobacterium marinum* | ACC40567.1 | MSPITREERLERRIQDLYANDPQFAAAKPATAITAAIERPGLPLPQIIETVMTGYADRPA<br>LAQRSVEFVTDAGTGHTTLRLLPHFETISYGELWDRISALADVLSTEQTVKPGDRVCLLG<br>FNSVDYATIDMTLARLGAVAVPLQTSAAITQLQPIVAETQPTMIAASVDALADATELALS<br>GQTATRVLVFDHHRQVDAHRAAVESARERLAGSAVVETLAEAIARGDVPRGASAGSAPGT<br>DVSDDSLALLIYTSGSTGAPKGAMYPRRNVATFWRKRTWFEGGYEPSITLNFMPMSHVMG<br>RQILYGTLCNGGTAYFVAKSDLSTLFEDLALVRPTELTFVPRVWDMVFDEFQSEVDRRLV<br>DGADRVALEAQVKAEIRNDVLGGRYTSALTGSAPISDEMKAWVEELLDMHLVEGYGSTEA<br>GMILIDGAIRRPAVLDYKLVDVPDLGYFLTDRPHPRGELLVKTDSLFPGYYQRAEVTADV<br>FDADGFYRTGDIMAEVGPEQFVYLDRRNNVLKLSQGEFVTVSKLEAVFGDSPLVRQIYIY<br>GNSARAYLLAVIVPTQEALDAVPVEELKARLGDSLQEVAKAAGLQSYEIPRDFIIETTPW<br>TLENGLLTGIRKLARPQLKKHYGELLEQIYTDLAHGQADELRSLRQSGADAPVLVTVCRA<br>AAALLGGSASDVQPDAHFTDLGGDSLSALSFTNLLHEIFDIEVPVGVIVSPANDLQALAD<br>YVEAARKPGSSRPTFASVHGASNGQVTEVHAGDLSLDKFIDAATLAEAPRLPAANTQVRT<br>VLLTGATGFLGRYLALEWLERMDLVDGKLICLVRAKSDTEARARLDKTFDSGDPELLAHY<br>RALAGDHLEVLAGDKGEADLGLDRQTWQRLADTVDLIVDPAALVNHVLPYSQLFGPNALG<br>TAELLRLALTSKIKPYSYTSTIGVADQIPPSAFTEDADIRVISATRAVDDSYANGYSNSK<br>WAGEVLLREAHDLCGLPVAVFRCDMILADTTWAGQLNVPDMFTRMILSLAATGIAPGSFY<br>ELAADGARQRAHYDGLPVEFIAEAISTLGAQSQDGFHTYHVMNPYDDGIGLDEFVDWLNE<br>SGCPIQRIADYGDWLQRFETALRALPDRQRHSSLLPLLHNYRQPERPVRGSIAPTDRFRA<br>AVQEAKIGPDKDIPHVGAPIIVKYVSDLRLLGLL |

FIG. 6B

| SEQ ID NO | Organism | GENBANK reference | Amino acid sequence |
|---|---|---|---|
| 3 | *Mycobacterium smegmatis* | ABK71854.1 | MTSDVHDATDGVTETALDDEQSTRRIAELYATDPEFAAAAPLPAVVDAAHKPGLRLAEIL<br>QTLFTGYGDRPALGYRARELATDEGGRTVTRLLPRFDTLTYAQVWSRVQAVAAALRHNFA<br>QPIYPGDAVATIGFASPDYLTLDLVCAYLGLVSVPLQHNAPVSRLAPILAEVEPRILTVS<br>AEYLDLAVESVRDVNSVSQLVVFDHHPEVDDHRDALARAREQLAGKGIAVTTLDAIADEG<br>AGLPAEPIYTADHDQRLAMILYTSGSTGAPKGAMYTEAMVARLWTMSFITGDPTPVINVN<br>FMPLNHLGGRIPISTAVQNGGTSYFVPESDMSTLFEDLALVRPTELGLVPRVADMLYQHH<br>LATVDRLVTQGADELTAEKQAGAELREQVLGGRVITGFVSTAPLAAEMRAFLDITLGAHI<br>VDGYGLTETGAVTRDGVIVRPPVIDYKLIDVPELGYFSTDKPYPRGELLVRSQTLTPGYY<br>KRPEVTASVFDRDGYYHTGDVMAETAPDHLVYVDRRNNVLKLAQGEFVAVANLEAVFSGA<br>ALVRQIFVYGNSERSFLLAVVVPTPEALEQYDPAALKAALADSLQRTARDAELQSYEVPA<br>DFIVETEPFSAANGLLSGVGKLLRPNLKDRYGQRLEQMYADIAATQANQLRELRRAAATQ<br>PVIDTLTQAAATILGTGSEVASDAHFTDLGGDSLSALTLSNLLSDFFGFEVPVGTIVNPA<br>TNLAQLAQHIEAQRTAGDRRPSFTTVHGADATEIRASELTLDKFIDAETLRAAPGLPKVT<br>TEPRTVLLSGANGWLGRFLTLQWLERLAPVGGTLITIVRGRDDAAARARLTQAYDTDPEL<br>SRRFAELADRHLRVVAGDIGDPNLGLTPEIWHRLAAEVDLVVHPAALVNHVLPYRQLFGP<br>NVVGTAEVIKLALTERIKPVTYLSTVSVAMGIPDFEEDGDIRTVSPVRPLDGGYANGYGN<br>SKWAGEVLLREAHDLCGLPVATFRSDMILAHPRYRGQVNVPDMFTRLLLSLLITGVAPRS<br>FYIGDGERPRAHYPGLTVDFVAEAVTTLGAQQREGYVSYDVMNPHDDGISLDVFVDWLIR<br>AGHPIDRVDDYDDWVRRFETALTALPEKRRAQTVLPLLHAFRAPQAPLRGAPEPTEVFHA<br>AVRTAKVGPGDIPHLDEALIDKYIRDLREFGLI |

FIG. 6C

| SEQ ID NO | Organism | GENBANK reference | Amino acid sequence |
|---|---|---|---|
| 4 | *Segniliparus rugosus* | EFV11917.1 | MGDGEERAKRFFQRIGELSATDPQFAAAAPDPAVVEAVSDPSLSFTRYLDTLMRGYAERP<br>ALAHRVGAGYETISYGELWARVGAIAAAWQADGLAPGDFVATVGFTSPDYVAVDLAAARS<br>GLVSVPLQAGASLAQLVGILEETEPKVLAASASSLEGAVACALAAPSVQRLVVFDLRGPD<br>ASESAADERRGALADAEEQLARAGRAVVVETLADLAARGEALPEAPLFEPAEGEDPLALL<br>IYTSGSTGAPKGAMYSQRLVSQLWGRTPVVPGMPNISLHYMPLSHSYGRAVLAGALSAGG<br>TAHFTANSDLSTLFEDIALARPTFLALVPRVCEMLFQESQRGQDVAELRERVLGGRLLVA<br>VCGSAPLSPEMRAFMEEVLGFPLLDGYGSTEALGVMRNGIIQRPPVIDYKLVDVPELGYR<br>TTDKPYPRGELCIRSTSLISGYYKRPEITAEVFDAQGYYKTGDVMAEIAPDHLVYVDRSK<br>NVLKLSQGEFVAVAKLEAAYGTSPYVKQIFVYGNSERSFLLAVVVPNAEVLGARDQEEAK<br>PLIAASLQKIAKEAGLQSYEVPRDFLIETEPFTTQNGLLSEVGKLLRPKLKARYGEALEA<br>RYDEIAHGQADELRALRDGAGQRPVVETVVRAAVAISGSEGAEVGPEANFADLGGDSLSA<br>LSLANLLHDVFEVEVPVRIIIGPTASLAGIAKHIEAERAGASAPTAASVHGAGATRIRAS<br>ELTLEKFLPEDLLAAAKGLPAADQVRTVLLTGANGWLGRFLALEQLERLARSGQDGGKLI<br>CLVRGKDAAAARRRIEETLGTDPALAARFAELAEGRLEVVPGDVGEPKFGLDDAAWDRLA<br>EEVDVIVHPAALVNHVLPYHQLFGPNVVGTAEIIRLAITAKRKPVTYLSTVAVAAGVEPS<br>SFEEDGDIRAVVPERPLGDGYANGYGNSKWAGEVLLREAHELVGLPVAVFRSDMILAHTR<br>YTGQLNVPDQFTRLVLSLLATGIAPKSFYQQGAAGERQRAHYDGIPVDFTAEAITTLGAE<br>PSWFDGGAGFRSFDVFNPHHDGVGLDEFVDWLIEAGHPISRIDDHKEWFARFETAVRGLP<br>EAQRQHSLLPLLRAYSFPHPPVDGSVYPTGKFQGAVKAAQVGSDHDVPHLGKALIVKYAD<br>DLKALGLL |

FIG. 6D

| SEQ ID NO | Organism | GENBANK reference | Amino acid sequence |
|---|---|---|---|
| 5 | *Mycobacterium abscessus subsp. bolletii* | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTTYGELWSRTTSVAAAWHHDATHPVKAGDLVA TLGFTSIDYTVLDLAIMILGGVAVPLQTSAPASQWTTILAEAEPNTLAVSIELIGAAMES VRATPSIKQVVVFDYTPEVDDQREAFEAASTQLAGTGIALETLDAVIARGAALPAAPLYA PSAGDDPLALLIYTSGSTGAPKGAMHSENIVRRWWIREDVMAGTENLPMIGLNFMPMSHI MGRGTLTSTLSTGGTGYFAASSDMSTLFEDMELIRPTALALVPRVCDMVFQRFQTEVDRR LASGDTASAEAVAAEVKADIRDNLFGGRVSAVMVGSAPLSEELGEFIESCFELNLTDGYG STEAGMVFRDGIVQRPPVIDYKLVDVPELGYFSTDKPHPRGELLLKTDGMFLGYYKRPEV TASVFDADGFYMTGDIVAELAHDNIEIIDRRNNVLKLSQGEFVAVATLEAEYANSPVVHQ IYVYGSSERSYLLAVVVPTPEAVAAAKGDAAALKTTIADSLQDIAKEIQLQSYEVPRDFI IEPQPFTQGNGLLTGIAKLARPNLKAHYGPRLEQMYAEIAEQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLIVIVRGKNAEAAYGRLEEAFDTGDTELL AHFRSLADKHLEVLAGDIGDPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITTLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIG. 6E

| SEQ ID NO | Organism | GENBANK reference | Amino acid sequence |
|---|---|---|---|
| *6* | *Segniliparus rotundus* | ADG98140.1 | MTQSHTQGPQASAAHSRLARRAAELLATDPQAAATLPDPEVVRQATRPGLRLAERVDAIL<br>SGYADRPALGQRSFQTVKDPITGRSSVELLPTFDTITYRELRERATAIASDLAHHPQAPA<br>KPGDFLASIGFISVDYVAIDIAGVFAGLTAVPLQTGATLATLTAITAETAPTLFAASIEH<br>LPTAVDAVLATPSVRRLLVFDYRAGSDEDREAVEAAKRKIADAGSSVLVDVLDEVIARGK<br>SAPKAPLPPATDAGDDSLSLLIYTSGSTGTPKGAMYPERNVAHFWGGVWAAAFDEDAAPP<br>VPAINITFLPLSHVASRLSLMPTLARGGLMHFVAKSDLSTLFEDLKLARPTNLFLVPRVV<br>EMLYQHYQSELDRRGVQDGTREAEAVKDDLRTGLLGGRILTAGFGSAPLSAELAGFIESL<br>LQIHLVDGYGSTEAGPVWRDGYLVKPPVTDYKLIDVPELGYFSTDSPHPRGELAIKTQTI<br>LPGYYKRPETTAEVFDEDGFYLTGDVVAQIGPEQFAYVDRRKNVLKLSQGEFVTLAKLEA<br>AYSSSPLVRQLFVYGSSERSYLLAVIVPTPDALKKFGVGEAAKAALGESLQKIARDEGLQ<br>SYEVPRDFIIETDPFTVENGLLSDARKSLRPKLKEHYGERLEAMYKELADGQANELRDIR<br>RGVQQRPTLETVRRAAAAMLGASAAEIKPDAHFTDLGGDSLSALTFSNFLHDLFEVDVPV<br>GVIVSAANTLGSVAEHIDAQLAGGRARPTFATVHGKGSTTIKASDLTLDKFIDEQTLEAA<br>KHLPKPADPPRTVLLTGANGWLGRFLALEWLERLAPAGGKLITIVRGKDAAQAKARLDAA<br>YESGDPKLAGHYQDLAATTLEVLAGDFSEPRLGLDEATWNRLADEVDFISHPGALVNHVL<br>PYNQLFGPNVAGVAEIIKLAITTRIKPVTYLSTVAVAAGVEPSALDEDGDIRTVSAERSV<br>DEGYANGYGNSKWGGEVLLREAHDRTGLPVRVFRSDMILAHQKYTGQVNATDQFTRLVQS<br>LLATGLAPKSFYELDAQGNRQRAHYDGIPVDFTAESITTLGGDGLEGYRSYNVFNPHRDG<br>VGLDEFVDWLIEAGHPITRIDDYDQWLSRFETSLRGLPESKRQASVLPLLHAFARPGPAV<br>DGSPFRNTVFRTDVQKAKIGAEHDIPHLGKALVLKYADDIKQLGLL |
| *7* | *Chromobacterium violaceum* | AAQ59697.1 | MQKQRTTSQWRELDAAHHLHPFTDTASLNQAGARVMTRGEGVYLWDSEGNKIIDGMAGLW<br>CVNVGYGRKDFAEAARRQMEELPFYNTFFKTTHPAVVELSSLLAEVTPAGFDRVFYTNSG<br>SESVDTMIRMVRRYWDVQGKPEKKTLIGRWNGYHGSTIGGASLGGMKYMHEQGDLPIPGM<br>AHIEQPWWYKHGKDMTPDEFGVVAARWLEEKILEIGADKVAAFVGEPIQGAGGVIVPPAT<br>YWPEIERICRKYDVLLVADEVICGFGRTGEWFGHQHFGFQPDLFTAAKGLSSGYLPIGAV<br>FVGKRVAEGLIAGGDFNHGFTYSGHPVCAAVAHANVAALRDEGIVQRVKDDIGPYMQKRW<br>RETFSRFEHVDDVRGVGMVQAFTLVKNKAKRELFPDFGEIGTLCRDIFFRNNLIMRACGD<br>HIVSAPPLVMTRAEVDEMLAVAERCLEEFEQTLKARGLA |
| *8* | *Pseudomonas aeruginosa* | AAG08191.1 | MNARLHATSPLGDADLVRADQAHYMHGYHVFDDHRVNGSLNIAAGDGAYIYDTAGNRYLD<br>AVGGMWCTNIGLGREEMARTVAEQTRLLAYSNPFCDMANPRAIELCRKLAELAPGDLDHV<br>FLTTGGSTAVDTAIRLMHYYQNCRGKRAKKHVITRINAYHGSTFLGMSLGGKSADRPAEF<br>DFLDERIHHLACPYYYRAPEGLGEAEFLDGLVDEFERKILELGADRVGAFISEPVFGSGG<br>VIVPPAGYHRRMWELCQRYDVLYISDEVVTSFGRLGHFFASQAVFGVQPDIILTAKGLTS<br>GYQPLGACIFSRRIWEVIAEPDKGRCFSHGFTYSGHPVACAAALKNIEIIEREGLLAHAD<br>EVGRYFEERLQSLRDLPIVGDVRGMRFMACVEFVADKASKALFPESLNIGEWVHLRAQKR<br>GLLVRPIVHLNVMSPPLILTREQVDTVVRVLRESIEETVEDLVRAGHR |

FIG. 6F

| SEQ ID NO | Organism | GENBANK reference | Amino acid sequence |
|---|---|---|---|
| *9* | *Pseudomonas syringae* | AAY39893.1 | MSANNPQTLEWQALSSEHHLAPFSDYKQLKEKGPRIITRAEGVYLWDSEGNKILDGMSGL<br>WCVAIGYGREELADAASKQMRELPYYNLFFQTAHPPVLELAKAISDIAPEGMNHVFFTGS<br>GSEGNDTMLRMVRHYWALKGQPNKKTIISRVNGYHGSTVAGASLGGMTYMHEQGDLPIPG<br>VVHIPQPYWFGEGGDMTPDEFGIWAAEQLEKKILELGVENVGAFIAEPIQGAGGVIVPPD<br>SYWPKIKEILSRYDILFAADEVICGFGRTSEWFGSDFYGLRPDMMTIAKGLTSGYVPMGG<br>LIVRDEIVAVLNEGGDFNHGFTYSGHPVAAAVALENIRILREEKIVERVRSETAPYLQKR<br>LRELSDHPLVGEVRGVGLLGAIELVKDKTTRERYTDKGAGMICRTFCFDNGLIMRAVGDT<br>MIIAPPLVISFAQIDELVEKARTCLDLTLAVLQG |
| *10* | *Rhodobacter sphaeroides* | ABA81135.1 | MTRNDATNAAGAVGAAMRDHILLPAQEMAKLGKSAQPVLTHAEGIYVHTEDGRRLIDGPA<br>GMWCAQVGYGRREIVDAMAHQAMVLPYASPWYMATSPAARLAEKIATLTPGDLNRIFFTT<br>GGSTAVDSALRFSEFYNNVLGRPQKKRIIVRYDGYHGSTALTAACTGRTGNWPNFDIAQD<br>RISFLSSPNPRHAGNRSQEAFLDDLVQEFEDRIESLGPDTIAAFLAEPILASGGVIIPPA<br>GYHARFKAICEKHDILYISDEVVTGFGRCGEWFASEKVFGVVPDIITFAKGVTSGYVPLG<br>GLAISEAVLARISGENAKGSWFTNGYTYSNQPVACAAALANIELMEREGIVDQAREMADY<br>FAAALASLRDLPGVAETRSVGLVGCVQCLLDPTRADGTAEDKAFTLKIDERCFELGLIVR<br>PLGDLCVISPPLIISRAQIDEMVAIMRQAITEVSAAHGLTAKEPAAV |
| *11* | *Escherichia coli* | AAA57874.1 | MNRLPSSASALACSAHALNLIEKRTLDHEEMKALNREVIEYFKEHVNPGFLEYRKSVTAG<br>GDYGAVEWQAGSLNTLVDTQGQEFIDCLGGFGIFNVGHRNPVVVSAVQNQLAKQPLHSQE<br>LLDPLRAMLAKTLAALTPGKLKYSFFCNSGTESVEAALKLAKAYQSPRGKFTFIATSGAF<br>HGKSLGALSATAKSTFRKPFMPLLPGFRHVPFGNIEAMRTALNECKKTGDDVAAVILEPI<br>QGEGGVILPPPGYLTAVRKLCDEFGALMILDEVQTGMGRTGKMFACEHENVQPDILCLAK<br>ALGGGVMPIGATIATEEVFSVLFDNPFLHTTTFGGNPLACAAALATINVLLEQNLPAQAE<br>QKGDMLLDGFRQLAREYPDLVQEARGKGMLMAIEFVDNEIGYNFASEMFRQRVLVAGTLN<br>NAKTIRIEPPLTLTIEQCELVIKAARKALAAMRVSVEEA |
| *12* | *Vibrio fluvialis* | AEA39183.1 | MNKPQSWEARAETYSLYGFTDMPSLHQRGTVVVTHGEGPYIVDVNGRRYLDANSGLWNMV<br>AGFDHKGLIDAAKAQYERFPGYHAFFGRMSDQTVMLSEKLVEVSPFDSGRVFYTNSGSEA<br>NDTMVKMLWFLHAAEGKPQKRKILTRWNAYHGVTAVSASMTGKPYNSVFGLPLPGFVHLT<br>CPHYWRYGEEGETEEQFVARLARELEETIQREGADTIAGFFAEPVMGAGGVIPPAKGYFQ<br>AILPILRKYDIPVISDEVICGFGRTGNTWGCVTYDFTPDAIISSKNLTAGFFPMGAVILG<br>PELSKRLETAIEAIEEFPHGFTASGHPVGCAIALKAIDVVMNEGLAENVRRLAPRFEERL<br>KHIAERPNIGEYRGIGFMWALEAVKDKASKTPFDGNLSVSERIANTCTDLGLICRPLGQS<br>VVLCPPFILTEAQMDEMFDKLEKALDKVFAEVA |

FIG. 6G

| SEQ ID NO | Organism | GENBANK reference | Amino acid sequence |
|---|---|---|---|
| 13 | *Escherichia coli* | AAC74479.1 | MREAFICDGIRTPIGRYGGALSSVRADDLAAIPLRELLVRNPRLDAECIDDVILGCANQA<br>GEDNRNVARMATLLAGLPQSVSGTTINRLCGSGLDALGFAARAIKAGDGDLLIAGGVESM<br>SRAPFVMGKAASAFSRQAEMFDTTIGWRFVNPLMAQQFGTDSMPETAENVAELLKISRED<br>QDSFALRSQQRTAKAQSSGILAEEIVPVVLKNKKGVVTEIQHDEHLRPETTLEQLRGLKA<br>PFRANGVITAGNASGVNDGAAALIIASEQMAAAQGLTPRARIVAMATAGVEPRLMGLGPV<br>PATRRVLERAGLSIHDMDVIELNEAFAAQALGVLRELGLPDDAPHVNPNGGAIALGHPLG<br>MSGARLALAASHELHRRNGRYALCTMCIGVGQGIAMILERV |
| 14 | *Mycobacterium smegmatis* | ABK75684.1 | MTIETREDRFNRRIDHLFETDPQFAAARPDEAISAAAADPELRLPAAVKQILAGYADRPALGKRA<br>VEFVTDEEGRTTAKLLPRFDTITYRQLAGRIQAVTNAWHNHPVNAGDRVAILGFTSVDYTTIDIA<br>LLELGAVSVPLQTSAPVAQLQPIVAETEPKVIASSVDFLADAVALVESGPAPSRLVVFDYSHEVD<br>DQREAFEAAKGKLAGTGVVVETITDALDRGRSLADAPLYVPDEADPLTLLIYTSGSTGTPKGAM<br>YPESKTATMWQAGSKARWDETLGVMPSITLNFMPMSHVMGRGILCSTLASGGTAYFAARSDLS<br>TFLEDLALVRPTQLNFVPRIWDMLFQEYQSRLDNRRAEGSEDRAEAAVLEEVRTQLLGGRFVSA<br>LTGSAPISAEMKSWVEDLLDMHLLEGYGSTEAGAVFIDGQIQRPPVIDYKLVDVPDLGYFATDRP<br>YPRGELLVKSEQMFPGYYKRPEITAEMFDEDGYYRTGDIVAELGPDHLEYLDRRNNVLKLSQGE<br>FVTVSKLEAVFGDSPLVRQIYVYGNSARSYLLAVVVPTEEALSRWDGDELKSRISDSLQDAARA<br>AGLQSYEIPRDFLVETTPFTLENGLLTGIRKLARPKLKAHYGERLEQLYTDLAEGQANELRELRR<br>NGADRPVVETVSRAAVALLGASVTDLRSDAHFTDLGGDSLSALSFSNLLHEIFDVDVPVGVIVSP<br>ATDLAGVAAYIEGELRGSKRPTYASVHGRDATEVRARDLALGKFIDAKTLSAAPGLPRSGTEIRT<br>VLLTGATGFLGRYLALEWLERMDLVDGKVICLVRARSDDEARARLDATFDTGDATLLEHYRAL<br>AADHLEVIAGDKGEADLGLDHDTWQRLADTVDLIVDPAALVNHVLPYSQMFGPNALGTAELIRI<br>ALTTTIKPYVYVSTIGVGQGISPEAFVEDADIREISATRRVDDSYANGYGNSKWAGEVLLREAHD<br>WCGLPVSVFRCDMILADTTYSGQLNLPDMFTRLMLSLVATGIAPGSFYELDADGNRQRAHYDGL<br>PVEFIAEAISTIGSQVTDGFETFHVMNPYDDGIGLDEYVDWLIEAGYPVHRVDDYATWLSRFETA<br>LRALPERQRQASLLPLLHNYQQPSPPVCGAMAPTDRFRAAVQDAKIGPDKDIPHVTADVIVKYIS<br>NLQMLGLL |
| 15 | *Pseudomonas putida* | AAN70209.2 | MNDVVIVAATRTAIGSFQGALATVPAVDLGAAVIKQLLKQTGLDPAQVDEVILGQVLTAG<br>AGQNPARQAAIKAGLPFSVPALTLNKVCGSGLKALHLAAQAIRCGDAEVVIAGGQENMSL<br>APYVMPSARTGQRMGHGQLIDSMITDGLWDAFNDYHMGITAENLVDKYGLSREQQDAFAA<br>ESQRKAVAAIEAGRFDAEITPIVLPQKKGEPKVFARDEQPRPDTTAESLAKLRPAFKKDG<br>SVTAGNASSLNDGAAAVLLMSAAKAEALGLPVLAKIAAYASAGVDPAIMGIGPVSATQRC<br>LDKAGWQLAELDLIEANEAFAAQALAVGNALAWDAARVNVNGGAIALGHPIGASGCRVLV<br>TLLHEMIKRDVKKGLATLCIGGGQGVALAIER |

FIG. 6H

| SEQ ID NO | Organism | GENBANK reference | Amino acid sequence |
|---|---|---|---|
| *16* | *Sphingomonas wittichii* | ABQ69245.1 | MEDIYIVGAARTAIADFGGALKDVPPADLGVIVARAALERAGLEPGDVQNVVMGQVMPTE PRDAYLARMVGVTAGVPIETPALTLNRLCGSGVEAIVTGAKAMVLGESDIVLAGGAEVMS RVPHVVKGARWGTKMGNVEMTDGLIEALSDPFDKVHMGITAENVAERYQITREAQDALAL QGHQRAARAIAEGRFKAQIVPVEVKTRKGVVAFDTDEHVRGDVSAEELAKLRPVFKKDGT VTAANASGINDGAAMVVLATKKAVDAKGLKPLARILSWGHAGVEPLYMGIGPVKAVPIAL ERAGLTLADIDVIEANEAFAAQACAVAQELGFDPDKVNPNGSGVALGHPVGATGAILTVK TVYELERIGGRYGLITMCIGGGQGIAMVVERCA |
| *17* | *Pseudomonas reinekei* | ACZ63623.1 | MKNALIVSPLRTPIGKFGGALAPLTAEHLASFMISQVMARTGVPGHSLDEVIVAQSYASS EAPCIGRYAALSAGLPVEVPGYTLDRRCGSGLQAVIDASMMVKTGNAEAVLVVGVESMSN IEYYSTDMRWGARAGSVRFHDRLERGRERSQPSERFGHISGMPETADNLALDYGISREEA DSFSVRSHQNAAAAWREGRFADEVVAVDVPGKRGAVTRVTIDEGIREDASLESMKALRLI RPEGVCTAGNSSQQNDAAAGCLVVSPEYAARHGLTPMARLVDWAAAGCEPSRMGIGPVPA TQKLLMRTGLSLAELDLIELNEAFAAQALAVLKTWGLDDLSRVNVNGSGISLGHPIGATG VRIMTTLLHEMRRREARYGLETMCIGGGQGLAALFERV |
| *18* | *Pseudomonas putida* | AAA85138.1 | MRDVFICDAIRTPIGRFGGALAGVRADDLAAVPLKALIEPNPAVQWDQVDEVFFGCANQA GEDNRNVARMALLLAGLPESIPGVTLNRLCASGMDAIGTAFRAIASGEMELAIAGGVESM SRAPFVMGKAESGYSRNMKLEDTTIGWRFINPLMKSQYGVDSMPETADNVADDYQVSRAD QDAFALRSQQKAAAAQAAGFFAEEIVPVRIAHKKGETIVERDEHLRPETTLEALTKLKPV NGPDKTVTAGNASGVNDGAAALILASAEAVKKHGLTPRARVLGMASGGVAPRVMGIGPVP AVRKLTERLGVAVSDFDVIELNEAFASQGLAVLRELGVADDAPQVNPNGGAIALGHPLGM SGARLVLTALHQLEKSGGRKGLATMCVGVGQGLALAIERV |
| *19* | *Burkholderia xenovorans* | ABE28745.1 | MSETHMSGTKADPIVIVGVARTPMAAFQGDFATLSAPQLGSVAIQAAVQRAGLKPEQIDE VVMGCVLPAGLGQAPARQAALGAGLPLATGSTTVNKMCGSGMRAAMFAHDMLAAGSVDVI VAGGMESMTNAPYLLPKARAGMRMGHGQVIDHMFYDGLEDAYEKGRLMGSFAEECAASFD FTREAQDAFAVESLARAKRANEDGSFAWEIAPVKVESRKGEVTIDRDEQPFKANIEKIPT LKPAFSKTGTVTAANSSSISDGAAALVMMRESTAKRLGVQPIARVVGHSTLAQEPAKFTT APVGAIRKLFEKNGWRADEVDLFEVNEAFAVVTMAAMKEHHLPHEKVNVNGGACALGHPI GASGARILVTLIGALKKRGGKRGVATLCIGGGEATAMGIELV |
| *20* | *Burkholderia xenovorans* | ABE33819.1 | MTEAFLCDAIRTPIGRYAGALSSVRADDLGAVPLKALMERNKEVDWNAIDDVIYGCANQA GEDNRNVARMSLLLAGLPQGVPGTTVNRLCGSGMDAVGIAARAIKSGEAALMVAGGVESM SRAPFVTGKATSAFSRQAEIYDTTIGWRFVNPLMKKLYGVDSMPETGENVATDYNISRAD QDAFALRSQQKAARAQRDGTLAQEIVGVTIAQKKGDPVTVSQDEHPRETSLDALAKLKGV VRPDGTVTAGNASGVNDGAAALLLANEETARRFGLTPRARVLGIATAGVAPRVMGIGPAP ATQKLLARLNMSLDQFDVIELNEAFASQGIAVLRALGVADDDTRVNPNGGAIALGHPLGM SGARLVTTAMYQLHRTQGRFALCTMCIGVGQGIAIAIERV |

FIG. 6I

| SEQ ID NO | Organism | GENBANK reference | Amino acid sequence |
|---|---|---|---|
| 21 | *Rhodococcus jostii* | ABG94668.1 | MAEVFLVDGARTPQGRYGGALAGVRPDDLAGLVVAEAARRAGIPGDAVDEVILGAANQAG<br>EDNRDVARMAVLLAGLPDSVPGYTVNRLCASGLTAVASAAHTIRSGEADIVIAGGVESMT<br>RAPWVMAKPGTPWARPGEVADTSLGWRFTNPRFTAADRDVPAGAGPDVRKVTLSMGETAE<br>EVAALEGVTRAESDAFALRSQERAIAAVDAGRFEREIVPVPVRDGELAADETPRRGTTLE<br>KLGSLKPVFRTGGIVTAGSSSSLSDGAAALVVASEAAVEKYGLTVRGRIVTSASAGIAPN<br>VMGLGPVPATRKALARANWSISDLGAAELNEAFAAQSLGVIRQLKLDESIVNADGGAIAL<br>GHPLGCSGARILLTLLGRMEREGARRGLATLCVGVGQGVAMLIEAP |
| 22 | *Bdellovibrio bacteriovorus* | CAE79693.1 | MKSPRDVVLVEGVRTPFAKAGTKLKKVHPAELGKVALKQVIAQTNLDVNLVDEVIIGNTG<br>NPPDSVNISRVVALNAGIPLKTSAYTVHRNCASALESISNGYEKIKSGTMDVILAGGTEN<br>MSQMPTLPPKKFQEIYEKLFAAKGPKQALPLLWSLFKADVKQIKALLSGNMRDEYFPVIS<br>VMMGLTDPFVGINMGQTAEILAKEWGLSRETQDKFALRSHQLASKAMKEGRMREEIAPVY<br>LAPEYKEVISEDIGPRDTQTMEALAKLKPFFDKATGSITAGNSCPITDGAAMVLMMSREK<br>AEALGYKPLATIRSYGFAGLEPERMGLGPVYSTPVALKRAGLSMKDIGLVELNEAFAAQV<br>LSCQKAFDSDKFGQEKLGLSSKIGEIRDDILNVNGGAIALGHPVGATGTRIVLTLAKEMK<br>RRNTQFGLATLCIGGGQGGSMILENEG |
| 23 | *Cronobacter turicensis* | CBA32535.1 | MFSLLQGNVMSQALPLVTRQGDRIAIVSGLRTPFARQATAYHGVPAVDLGKMVVGELLAR<br>SEIPPDVIEQLVFGQVVQMPEAPNIAREIVLGTGMSVHTDAYSVSRACATSFQAVANVAE<br>SLMAGTIRAGIAGGADSSSVLPIGVSKKLARTLVDANKARTAGQRLKLFSRLRLRDLLPV<br>PPAVAEYSTGLRMGDTAEQMAKTHGITREQQDALAHRSHQLAAQAWAEGKLREEVMTAYT<br>PPYREPLSEDNNIRKNSSLADYTKLRPAFDRKHGTVTAANSTPLTDGAAAVILMTESRAR<br>ELGLTPLGYLRSYAFTAVDVWQDMLLGPAWSTPLALERAGLTMADLTLIDMHEAFASQTL<br>ANLKLLASDRFAREVLGRSQATGEVDESKFNVLGGSIAYGHPFAATGARMITQTLNELRR<br>RGGGFGLVTACAAGGLGAAMVLEAE |
| 24 | *Arthrobacter sp.* | ABK03524.1 | MSFNGQSATGPDESAAAPAATPGAGLLRKAVVVGGNRIPFARTGGAYTKSSNQDMLTAAL<br>DGLIARFGLADERIGEVAAGAVLKHSRDFNLTREAVLGSALSAETPAYDLQQACATGLET<br>VLGLANKIKLGQIDSAIAGGVDSASDAPIAVSEGLREVLLDLNRAKTLPQRLKVLGRLRP<br>KDLAPDAPNTGEPRTGLSMGEHQALTTAQWKITREAQDELAYNSHRNLAAAYDAGFFDDL<br>LTPYRGLNRDSNLRADTTREKLSTLKPVFGKNLGAEATMTAGNSTPLTDGASTVLLASEE<br>WADAHELPKLATVVDGEAAAVDFVHGKDGLLMAPAFAVPRLLARNGLTLDDIDFFEIHEA<br>FAGTVLSTLAAWEDEEFGRTRLGLDGPLGSIDRAKLNVNGSSLAAGHPFAATGGRIVATL<br>AKMLHDKGQVDGRPARGLISICAAGGQGVVAILEAS |

FIG. 6J

| SEQ ID NO | Organism | GENBANK reference | Amino acid sequence |
|---|---|---|---|
| 25 | *Caulobacter segnis* | ADG08907.1 | MATASSSAASSSGVWLAAGVRSPFAKVDGALAGHDAIGLSVPVVKAMLARAKPDFAVWGT<br>VIPNLTWSNLAREVLLDAGGDPTIPAFSTVMACSTSMIGAIEAAGMVDGRGRDLALVGGV<br>ESMSRVQLGLSVALSDWIRKFQNAKTGQQRLAALGALNLKDVRLFIPKVVNRVTGLSMGE<br>HTEITAKEWNLSRADQDAIALASHQGAVKGWESGFFDDLVIPVGEVKRDGIPRKDTSLEK<br>LAKLGPAFDKTSGKGTLTAGNSSPLTDGAAAVWVGSAAGMARLPGETPKVRLVDYEVTSI<br>DLRHEGLLMAPAYGVPRMLARNGLTYADVGLWEIHEAFAAQVLSHIAAWESAKFLSEKAG<br>VTTPMGAFPRERMNPNGGSLALGHPFGATGARIISQTVKELAARPKGERAIVSICADGGQ<br>GTMMLLESA |
| 26 | *Dinoroseobacter shibae* | ABV92581.1 | MTEAYIYDAIRSPRGKGRKDGSLHEVTAVSLSAQTLNAIKDRNGLTGHAVEDVIWGNVTQ<br>VMEQGGCLARTAVLASDLDESIPGLAINRFCASGLEAVNLAANQVRGGGGQAYIAGGVEM<br>MGRVPMGSDGAAIAADPSVAMKTYFVPQGISADIIATEYGISRDDADALAVASQRRAKAA<br>WDENRFNGSVFTVRDQNGLNILDHDEYMRPETDMQSLGALKPAFKDMGEQMPGFDKIALM<br>KYPHLEKIEHIHHAGNSSGIVDGSAALLIGNKAFGEAHGLKPRAVIKATAKIGTDPTIML<br>TGPVPATEKILADSGMSISDIDLFEVNEAFSSVVLRFMQAFDVDHDKVNVNGGAIAMGHP<br>LGATGAMILGTLLDELERTGKGTGLATLCVASGMGAATIIERV |
| 27 | *Burkholderia xenovorans* | ABE36495.1 | MTRDTRDVVIVDAVRTPIGKFRGALAGVRADHLGALVIDELIRRAGVKPQAVNDVVFGCV<br>TQIGEQSANIARTSVLGAGWPETIPGLTIDRKCGSGEEAVHIAAGLIAFGAADVIVAGGA<br>ESMSRVPMGSNRDLHGEAFGWMASERFELTSQGEAAERLCDCWALTRAQLDAYSVESHRR<br>AAAAAAEGWFAREIVPVPVGQVREKSLEGEAALFAADETIRPGTNADKLATLKSSFRSDG<br>RLTAGNSSQISDGAAALLLMSSDKARELGVKARARVRAVTTVGSDPTLMLTGPILATCQV<br>LEKAGLGLSDIDLFEINEAFAPVPLVWMKEFGVPHAKLNVNGGAIALGHPLGASGARIMT<br>SMLHELERRGARYGLQAICCAGGMGTATLIERLD |
| 28 | *Geobacillus kaustophilus* | BAD75605.1 | MREAVIVEAVRTPVGKRNGVFRDVHPVHLAAVVLDEVVRRAGMDKGAVEDIVMGCVTPVA<br>EQGYNIGRLAALEAGFPIEVPAVQINRMCGSGQQAIHFAAQEIRSGDMDVTIAAGVESMT<br>KVPILSDGNERTIPPSLHEKYEFIHQGVSAERIAKKYGLTREELDAYAYESHQRALAALR<br>EGKFRAEIVPVKGLDRDGREILVTDDEGPRADTSPEALAALKPVFQEDGLITAGNASQMS<br>DGAAAVLLMEREAARRFGLKPKARIVAQTVVGSDPTYMLDGVIPATRQVLKKAGLSIDDI<br>DLIEINEAFAPVVLAWQKEIGAPLEKVNVNGGAIALGHPLGATGAKLMTSLVHELERRGG<br>RYGLLTICIGHGMATATIIERE |
| 29 | *Beijerinckia indica* | ACB95386.1 | MTKVVIAGYIRSPFTLAKKGELATVRPDDLAAQVVKGLIKKTGIPAEDIEDLLLGCAFPE<br>GEQGFNVARLVSFLAGLPLSVGASTVNRFCGSSMTTVHMAAGAIQMNAGNAFIAAGVESM<br>SRVPMMGFNPLPNPELAATMPGAYMGMGDTAENVAAKWTISRKEQEEFALRSHQRATAAQ<br>KEGRLTGEIIPITGRKGTITTDGCIRPDTTLEGLAELKPAFSANGVVTAGTSSPLTDGAA<br>AVLVCSEDYAKHHHLDVLASVKAIAVSGCSPEIMGIGPVAASRKALARAGLEAGQIDIVE<br>LNEAFASQSIACMRELNLSPDRVNIDGGAIALGHPLGATGARIVGKAASLLKREKGKYAL<br>ATQCIGGGQGIATVLEAF |

FIG. 6K

| SEQ ID NO | Organism | GENBANK reference | Amino acid sequence |
|---|---|---|---|
| *30* | *Citrobacter freundii* | EKS55037.1 | MEQVVIVDAIRTPMGRSKGGAFRNVRAEDLSAHLMRSLLARNPALDPTALDDIYWGCVQQ<br>TLEQGFNIARNAALLAEIPHSVPAVTVNRLCGSSMQALHDAARMIMTGDAQACLIGGVEH<br>MGHVPMSHGVDFHPGMSRNVAKAAGMMGLTAEMLSRMHGISREMQDAFAARSHARAWAAT<br>QSGAFKNEIIPTGGHDADGVLKQFNYDEVIRPETTVEALSTLRPAFDPVSGTVTAGTSSA<br>LSDGAAAMLVMSESRARELGLTPRARIRSMAVVGCDPSIMGYGPVPASKLALKKAGLSTS<br>DIGLFEMNEAFAAQILPCIKDLGLMEQIDEKINLNGGAIALGHPLGCSGARISTTLLNLM<br>ERKDVQFGLATMCIGLGQGIATVFERV |
| *31* | *Cupriavidus necator* | AEI75849.1 | MKQLQDAYIVAATRSPIGKAPKGAFKNTRPDDLLATILKAAVAQVPNLDPKLIEDAIVGC<br>AIPEAQQGLNVARIGALLSGLPNTVGGITVNRFCASGVSAVAMAADRIRVGESDVMIAAG<br>VESMSMVPMMGNSPSMSPEIFTRDENVGIAYGMGLTAEKVAQQWQVSREDQDAFSLASHQ<br>KAIAAQQAGEFKDEITPIEIVERFPDLASGQVNVKTRTISLDEGPRPETSLEGLGKLRPV<br>FANKGSVTAGNSSQTSDGAGALILVSEKILKQFNLVPLARFVSFAVRGVPPEIMGIGPKE<br>AIPAALKAAGLTQDQLDWIELNEAFAAQSLAVMRDLQLDPAKVNRMGGAIALGHPLGATG<br>AIRSATVVHALRRHNLKYGMVTMCVGTGMGAAGIFERV |
| *32* | *Gordonia bronchialis* | ACY20886.1 | MAPCSVKAMPEAVIVAHARSPIGRAGKGSLKDVRPDELSRQMVAAALAKVPELAPSDIED<br>IHWGIGQPGGQGGYNIARVIAVELGYDHIPGVTVNRYCSSSLQTTRMALHAIKAGEADVL<br>ISGGVESVSSFGISGGADGAPDSKNPVFDDAQARTAKAAEGGAPAWTDPREQGLIPDVYI<br>AMGQTAENVASFTGISREDQDRWSVLSQNRAEEAINAGFFEREIDPVTLPDGSTVNTDDG<br>PRAGTTYEKVSQLKPVFRPDGTVTAGNACPLNDGAAALVIMSDSKAKQLGLTPLARVVAT<br>AATGLSPEIMGLGPIEAIRKVLRISGMSLSDIDLVEINEAFAVQVLGSANELGIDHDKLN<br>VSGGAIALGHPFGMTGARITTTLLNNLQTRDKTFGIESMCVGGGQGMAMVLERLS |
| *33* | *Burkholderia sp.* | ADG18081.1 | MREAVIVSTARTPLTKAHRGEFNITPGPTLASFAVRAAVERSGVDPDIIEDAILGCGYPE<br>GTTGRNVARQSVIRAGLPLSIAGTTVNRFCASGLQAIAMAAGRIVVDGAPAMIAGGVESI<br>SNIQTREDGVSGLDPWIVEHKPSLYTAMIDTADIVARRYGISREAQDQFSVESQRRTAEA<br>QQAGRYADEIIPVTTTMAITDKETRAVSYREVTVSADNCNRPGTTYEALAKLAPVKGPDQ<br>FITAGNASQNADGASACVLMEAKAAERANFAPLGAFRGLALAGCEPDEMGIGPVLAVPKL<br>LARHGLTVDDIGLWELNEAFASQAVYCQKRLEIPSERLNVNGGAISIGHPFGMTGSRLVG<br>HVLIEGRRRGVKYAVVTMCMAGGMGAAGLFEIY |
| *34* | *Glutamicibacter arilaitensis* | CBT74677.1 | MQQAYLYDAIRTPFGKIGGALSSHRPDDLAAHVVRELVARSPKLDVADIDESIFGNANGA<br>GEENRNVARMATLLAGLPTSLPGTTMNRLCGSSLDASIAASRQIATGDADLVLVGGVESM<br>SRAPWVLPKTERPFPMSNLELANTTLGWRLVNPAMPGEWTVSLGEATEQLREKHGISRED<br>QDEFSAASHQRAAAAWQAGKYDNLVVPVPPANKRGTEVTRDETIRADSTAQTLSKLRTVF<br>RTGENATVTAGNASPMSDGASAAFIGSERGGELLGAAPIARIASNGAAALDPQFFGFAPV<br>EAANKALAKAGLKWSDIAAVELNEAFAAQSLACIRAWDIDPAIVNAWGGAISIGHPLGAS<br>GLRILGTVARRLAESGERYGLAAICIGVGQGLAVVVENINATK |

FIG. 6L

| SEQ ID NO | Organism | GENBANK reference | Amino acid sequence |
|---|---|---|---|
| 35 | *Escherichia coli* | AAC74479.1 | MREAFICDGIRTPIGRYGGALSSVRADDLAAIPLRELLVRNPRLDAECIDDVILGCANQA<br>GEDNRNVARMATLLAGLPQSVSGTTINRLCGSGLDALGFAARAIKAGDGDLLIAGGVESM<br>SRAPFVMGKAASAFSRQAEMFDTTIGWRFVNPLMAQQFGTDSMPETAENVAELLKISRED<br>QDSFALRSQQRTAKAQSSGILAEEIVPVVLKNKKGVVTEIQHDEHLRPETTLEQLRGLKA<br>PFRANGVITAGNASGVNDGAAALIIASEQMAAAQGLTPRARIVAMATAGVEPRLMGLGPV<br>PATRRVLERAGLSIHDMDVIELNEAFAAQALGVLRELGLPDDAPHVNPNGGAIALGHPLG<br>MSGARLALAASHELHRRNGRYALCTMCIGVGQGIAMILERV |
| 36 | *Cupriavidus necator* | AAC38322.1 | MTREVVVVSGVRTAIGTFGGSLKDVAPAELGALVVREALARAQVSGDDVGHVVFGNVIQT<br>EPRDMYLGRVAAVNGGVTINAPALTVNRLCGSGLQAIVSAAQTILLGDTDVAIGGGAESM<br>SRAPYLAPAARWGARMGDAGLVDMMLGALHDPFHRIHMGVTAENVAKEYDISRAQQDEAA<br>LESHRRASAAIKAGYFKDQIVPVVSKGRKGDVTFDTDEHVRHDATIDDMTKLRPVFVKEN<br>GTVTAGNASGLNDAAAAVVMMERAEAERRGLKPLARLVSYGHAGVDPKAMGIGPVPATKI<br>ALERAGLQVSDLDVIEANEAFAAQACAVTKALGLDPAKVNPNGSGISLGHPIGATGALIT<br>VKALHELNRVQGRYALVTMCIGGGQGIAAIFERI |
| 37 | *Clostridium viride* | NCBI Reference Sequence: NZ_KK211198.1 | MAQFVTAQEAVKHIPNGSRVVLAHSTGEPRTLVKAMVENYEQYKDVEVCHMLGLGPYEYTNPE<br>MKGHLWHNSLFMGPGGRKAFNENRLDFTPGYFCDSIKFFREGYLPVDVLMMTVSPPDKHGYVT<br>CGITCDFTMPAFECAKMVIVQVNKNMPRTFGQTAIHLDDIDFAVEADDPLYGSVPGELTDIDRKI<br>GEHCASLINDGACLQLGIGGIPNAVLTYLTEKNDMGIHSEMLSDGILQLIKAGNINNSKKQIHVGK<br>SAVTFLNGSQELYDYVDDNPSVEFYPVDYINDPYVIGKNDNMVSVNSALSVDLMGQIVADNLSA<br>TRQISGAGGFVDFVRGATISKGGISIVAMPSTAAGGKASRIEMMFDAGRPITLTRFESFYVVTEYGI<br>AKMRGNSLRTRARQLIEIAHPDFRDEMKEFYE KRFGEKY |

FIG. 19A

| SEQ ID NO | Nucleic acid sequence |
|---|---|
| 38 | ATG AAC GAT GTG GTC ATT GTG GCT GCA ACG CGC ACT GCA ATT GGC AGC TTT CAG GGA GCG TTG GCT ACG<br>GTG CCA GCC GTA GAT CTG GGA GCT GCC GTC ATC AAA CAG CTC CTG AAA CAG ACC GGC TTA GAC CCA GCA<br>CAG GTA GAT GAG GTA ATC CTG GGG CAA GTG CTC ACT GCT GGT GCC GGC CAG AAT CCG GCA CGC CAA GCG<br>GCA ATC AAA GCT GGA CTG CCG TTT TCG GTT CCG GCA TTA ACC CTG AAC AAA GTG TGT GGC TCT GGT CTG<br>AAA GCA CTG CAT CTG GCA GCA CAA GCG ATT CGC TGT GGT GAT GCG GAG GTA GTT ATC GCA GGT GGC CAG<br>GAG AAC ATG TCC TTG GCC CCT TAT GTG ATG CCT AGC GCG CGT ACC GGG CAA CGC ATG GGC CAT GGC CAG<br>CTC ATT GAT AGC ATG ATT ACC GAC GGT TTA TGG GAT GCG TTC AAT GAC TAC CAC ATG GGC ATT ACG GCC<br>GAG AAC CTG GTG GAC AAG TAC GGC CTG TCT CGC GAA CAG CAG GAT GCT TTT GCG GCT GAA TCG CAG CGC<br>AAA GCG GTC GCG GCT ATC GAA GCA GGC CGG TTT GAC GCG GAG ATC ACG CCC ATT GTG TTG CCG CAG AAG<br>AAA GGG GAA CCG AAA GTG TTC GCA CGT GAT GAA CAA CCG CGT CCG GAT ACC ACA GCC GAA TCG CTT GCC<br>AAA TTA CGT CCT GCG TTC AAG AAA GAT GGC AGT GTA ACA GCC GGG AAC GCG TCA AGC CTG AAT GAT GGC<br>GCT GCC GCC GTT CTG CTG ATG AGC GCC GCT AAA GCG GAA GCG CTG GGG TTA CCC GTT TTG GCG AAA ATC<br>GCC GCT TAT GCG TCA GCC GGT GTC GAT CCG GCG ATT ATG GGT ATC GGT CCA GTG TCC GCC ACT CAG CGT<br>TGC TTG GAC AAA GCC GGT TGG CAG CTG GCG GAA CTT GAC CTG ATT GAA GCG AAC GAA GCC TTT GCG GCG<br>CAA GCA CTG GCC GTT GGC AAT GCA CTT GCG TGG GAT GCG GCA CGC GTG AAC GTT AAT GGC GGT GCG ATT<br>GCC CTT GGA CAT CCG ATT GGG GCT AGT GGT TGC CGT GTC CTG GTT ACC CTC CTG CAC GAA ATG ATC AAA<br>CGG GAC GTC AAG AAA GGC CTG GCG ACC CTG TGC ATT GGT GGT GGT CAA GGC GTT GCG CTG GCC ATT GAA<br>CGC taa |
| 39 | ATG GAG GAC ATT TAC ATT GTT GGC GCT GCC CGT ACG GCA ATT GCG GAC TTT GGA GGC GCC TTA AAG GAC<br>GTT CCA CCA GCT GAT CTT GGC GTC ATT GTG GCA CGT GCT GCT CTG GAA CGC GCT GGG CTC GAA CCG GGT<br>GAT GTT CAG AAC GTA GTA ATG GGC CAG GTG ATG CCT ACC GAA CCG CGT GAT GCC TAC TTA GCT CGC ATG<br>GTG GGT GTG ACT GCT GGT GTC CCG ATC GAA ACC CCA GCC CTC ACA CTG AAT CGC CTG TGT GGA AGC GGA<br>GTT GAG GCA ATC GTT ACC GGC GCA AAA GCC ATG GTT CTG GGA GAA TCG GAT ATT GTC CTT GCG GGT GGC<br>GCG GAA GTC ATG AGC CGT GTT CCT CAC GTG GTA AAA GGT GCG CGT TGG GGT ACC AAA ATG GGG AAT GTC<br>GAG ATG ACC GAT GGT CTG ATC GAG GCG TTG TCC GAT CCG TTC GAC AAA GTG CAC ATG GGC ATT ACC GCG<br>GAA AAC GTC GCC GAA CGG TAC CAG ATC ACT CGC GAA GCA CAG GAT GCT CTT GCT CTG CAG GGT CAT CAA<br>CGT GCG GCA CGC GCG ATC GCC GAG GGT CGC TTC AAA GCC CAG ATT GTC CCT GTG GAA GTG AAA ACG CGC<br>AAA GGC GTT GTG GCG TTC GAT ACC GAC GAG CAC GTT CGC GGG GAT GTG TCT GCG GAA GAA CTG GCG AAA<br>CTG CGT CCG GTC TTT AAG AAG GAT GGC ACC GTA ACA GCC GCC AAT GCG TCA GGC ATC AAC GAT GGC GCA<br>GCA ATG GTG GTC TTG GCA ACG AAG AAA GCC GTC GAC GCG AAA GGG TTG AAA CCC TTA GCC CGC ATC TTG<br>TCG TGG GGT CAT GCA GGG GTA GAA CCG CTG TAT ATG GGC ATT GGC CCC GTA AAA GCT GTT CCG ATT GCG<br>CTG GAA CGC GCA GGC TTA ACT CTG GCG GAT ATC GAC GTG ATT GAG GCC AAT GAA GCC TTT GCC GCG CAA<br>GCA TGC GCA GTT GCG CAG GAA CTC GGG TTT GAC CCG GAT AAA GTG AAC CCG AAC GGC AGT GGC GTT GCG<br>CTG GGC CAT CCG GTA GGT GCG ACA GGT GCG ATC CTG ACC GTG AAA ACG GTG TAT GAG CTG GAA CGG ATT<br>GGA GGT CGC TAT GGT CTG ATC ACG ATG TGC ATT GGC GGC GGT CAA GGG ATT GCC ATG GTG GTG GAA CGT<br>TGT GCG taa |

FIG. 19B

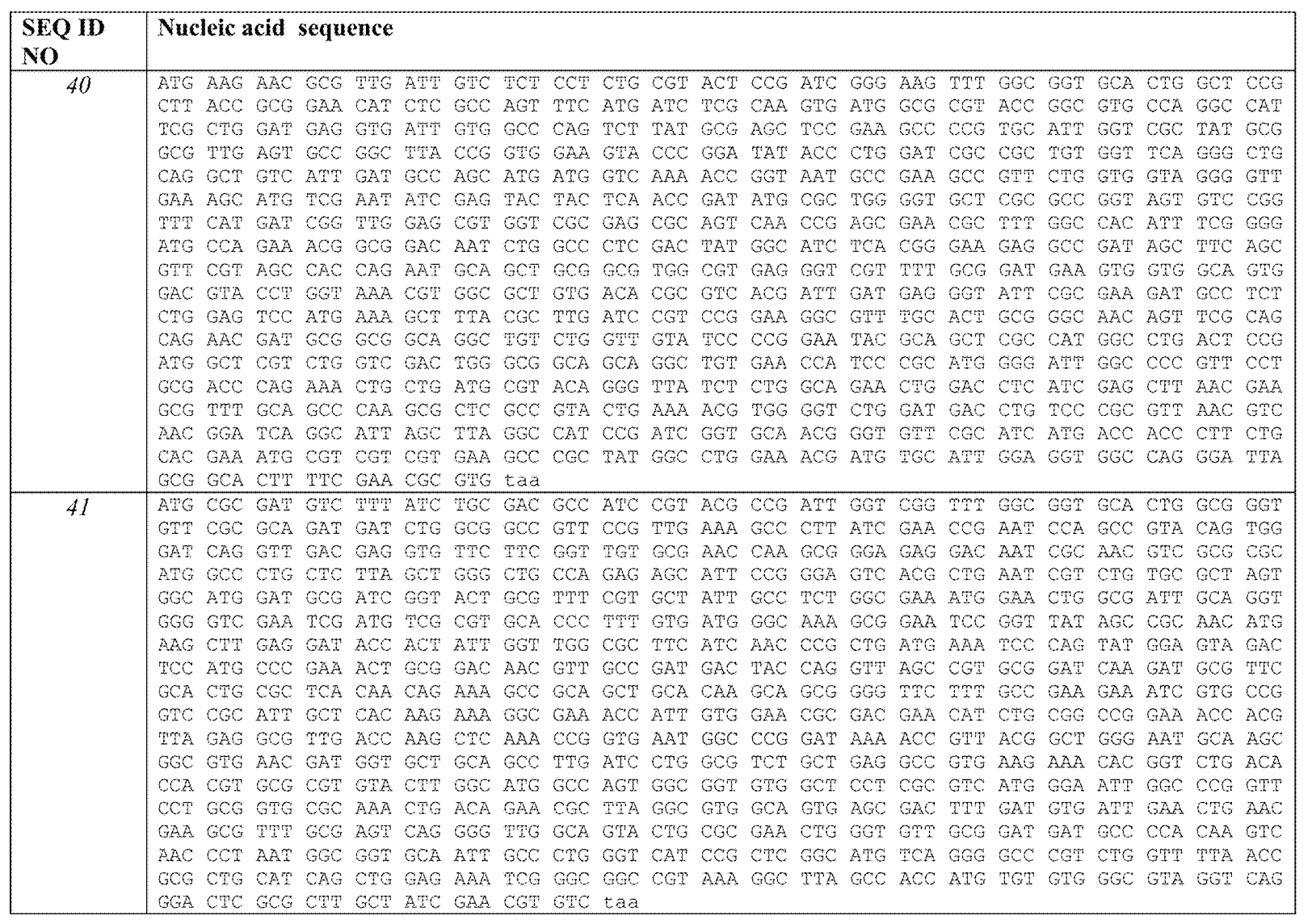

| SEQ ID NO | Nucleic acid sequence |
|---|---|
| 40 | ATG AAG AAC GCG TTG ATT GTC TCT CCT CTG CGT ACT CCG ATC GGG AAG TTT GGC GGT GCA CTG GCT CCG<br>CTT ACC GCG GAA CAT CTC GCC AGT TTC ATG ATC TCG CAA GTG ATG GCG CGT ACC GGC GTG CCA GGC CAT<br>TCG CTG GAT GAG GTG ATT GTG GCC CAG TCT TAT GCG AGC TCC GAA GCC CCG TGC ATT GGT CGC TAT GCG<br>GCG TTG AGT GCC GGC TTA CCG GTG GAA GTA CCC GGA TAT ACC CTG GAT CGC CGC TGT GGT TCA GGG CTG<br>CAG GCT GTC ATT GAT GCC AGC ATG ATG GTC AAA ACC GGT AAT GCC GAA GCC GTT CTG GTG GTA GGG GTT<br>GAA AGC ATG TCG AAT ATC GAG TAC TAC TCA ACC GAT ATG CGC TGG GGT GCT CGC GCC GGT AGT GTC CGG<br>TTT CAT GAT CGG TTG GAG CGT GGT CGC GAG CGC AGT CAA CCG AGC GAA CGC TTT GGC CAC ATT TCG GGG<br>ATG CCA GAA ACG GCG GAC AAT CTG GCC CTC GAC TAT GGC ATC TCA CGG GAA GAG GCC GAT AGC TTC AGC<br>GTT CGT AGC CAC CAG AAT GCA GCT GCG GCG TGG CGT GAG GGT CGT TTT GCG GAT GAA GTG GTG GCA GTG<br>GAC GTA CCT GGT AAA CGT GGC GCT GTG ACA CGC GTC ACG ATT GAT GAG GGT ATT CGC GAA GAT GCC TCT<br>CTG GAG TCC ATG AAA GCT TTA CGC TTG ATC CGT CCG GAA GGC GTT TGC ACT GCG GGC AAC AGT TCG CAG<br>CAG AAC GAT GCG GCG GCA GGC TGT CTG GTT GTA TCC CCG GAA TAC GCA GCT CGC CAT GGC CTG ACT CCG<br>ATG GCT CGT CTG GTC GAC TGG GCG GCA GCA GGC TGT GAA CCA TCC CGC ATG GGG ATT GGC CCC GTT CCT<br>GCG ACC CAG AAA CTG CTG ATG CGT ACA GGG TTA TCT CTG GCA GAA CTG GAC CTC ATC GAG CTT AAC GAA<br>GCG TTT GCA GCC CAA GCG CTC GCC GTA CTG AAA ACG TGG GGT CTG GAT GAC CTG TCC CGC GTT AAC GTC<br>AAC GGA TCA GGC ATT AGC TTA GGC CAT CCG ATC GGT GCA ACG GGT GTT CGC ATC ATG ACC ACC CTT CTG<br>CAC GAA ATG CGT CGT CGT GAA GCC CGC TAT GGC CTG GAA ACG ATG TGC ATT GGA GGT GGC CAG GGA TTA<br>GCG GCA CTT TTC GAA CGC GTG taa |
| 41 | ATG CGC GAT GTC TTT ATC TGC GAC GCC ATC CGT ACG CCG ATT GGT CGG TTT GGC GGT GCA CTG GCG GGT<br>GTT CGC GCA GAT GAT CTG GCG GCC GTT CCG TTG AAA GCC CTT ATC GAA CCG AAT CCA GCC GTA CAG TGG<br>GAT CAG GTT GAC GAG GTG TTC TTC GGT TGT GCG AAC CAA GCG GGA GAG GAC AAT CGC AAC GTC GCG CGC<br>ATG GCC CTG CTC TTA GCT GGG CTG CCA GAG AGC ATT CCG GGA GTC ACG CTG AAT CGT CTG TGC GCT AGT<br>GGC ATG GAT GCG ATC GGT ACT GCG TTT CGT GCT ATT GCC TCT GGC GAA ATG GAA CTG GCG ATT GCA GGT<br>GGG GTC GAA TCG ATG TCG CGT GCA CCC TTT GTG ATG GGC AAA GCG GAA TCC GGT TAT AGC CGC AAC ATG<br>AAG CTT GAG GAT ACC ACT ATT GGT TGG CGC TTC ATC AAC CCG CTG ATG AAA TCC CAG TAT GGA GTA GAC<br>TCC ATG CCC GAA ACT GCG GAC AAC GTT GCC GAT GAC TAC CAG GTT AGC CGT GCG GAT CAA GAT GCG TTC<br>GCA CTG CGC TCA CAA CAG AAA GCC GCA GCT GCA CAA GCA GCG GGG TTC TTT GCC GAA GAA ATC GTG CCG<br>GTC CGC ATT GCT CAC AAG AAA GGC GAA ACC ATT GTG GAA CGC GAC GAA CAT CTG CGG CCG GAA ACC ACG<br>TTA GAG GCG TTG ACC AAG CTC AAA CCG GTG AAT GGC CCG GAT AAA ACC GTT ACG GCT GGG AAT GCA AGC<br>GGC GTG AAC GAT GGT GCT GCA GCC TTG ATC CTG GCG TCT GCT GAG GCC GTG AAG AAA CAC GGT CTG ACA<br>CCA CGT GCG CGT GTA CTT GGC ATG GCC AGT GGC GGT GTG GCT CCT CGC GTC ATG GGA ATT GGC CCG GTT<br>CCT GCG GTG CGC AAA CTG ACA GAA CGC TTA GGC GTG GCA GTG AGC GAC TTT GAT GTG ATT GAA CTG AAC<br>GAA GCG TTT GCG AGT CAG GGG TTG GCA GTA CTG CGC GAA CTG GGT GTT GCG GAT GAT GCC CCA CAA GTC<br>AAC CCT AAT GGC GGT GCA ATT GCC CTG GGT CAT CCG CTC GGC ATG TCA GGG GCC CGT CTG GTT TTA ACC<br>GCG CTG CAT CAG CTG GAG AAA TCG GGC GGC CGT AAA GGC TTA GCC ACC ATG TGT GTG GGC GTA GGT CAG<br>GGA CTC GCG CTT GCT ATC GAA CGT GTC taa |

FIG. 19C

| SEQ ID NO | Nucleic acid sequence |
|---|---|
| *42* | ATG AGC GAA ACG CAC ATG AGC GGC ACC AAA GCC GAT CCC ATC GTG ATT GTC GGA GTG GCT CGC ACC CCT<br>ATG GCA GCC TTT CAG GGC GAC TTT GCG ACC TTG TCG GCA CCG CAG TTA GGG TCA GTG GCC ATT CAA GCC<br>GCT GTT CAG CGT GCC GGA CTG AAA CCG GAA CAG ATC GAT GAA GTC GTA ATG GGG TGT GTA CTG CCA GCT<br>GGT CTG GGT CAG GCT CCT GCA CGG CAA GCT GCG CTT GGC GCG GGA TTA CCG CTG GCC ACT GGC TCA ACG<br>ACG GTC AAC AAA ATG TGC GGC TCT GGC ATG CGT GCA GCG ATG TTT GCC CAC GAC ATG CTC GCT GCC GGC<br>TCA GTT GAC GTA ATT GTA GCG GGC GGT ATG GAA TCC ATG ACA AAT GCG CCG TAT CTG CTT CCC AAG GCG<br>CGT GCG GGA ATG CGC ATG GGG CAT GGG CAG GTG ATT GAC CAC ATG TTC TAT GAT GGT CTG GAA GAT GCA<br>TAC GAG AAA GGT CGC CTT ATG GGC AGC TTT GCC GAG GAA TGT GCA GCG AGT TTC GAC TTC ACC CGT GAA<br>GCG CAA GAT GCT TTT GCG GTG GAA TCG CTG GCC CGT GCG AAA CGT GCA AAT GAA GAT GGC TCG TTT GCC<br>TGG GAA ATT GCC CCA GTT AAA GTC GAA TCT CGC AAA GGT GAA GTG ACG ATC GAT CGG GAT GAG CAG CCG<br>TTT AAA GCG AAC ATC GAG AAA ATC CCG ACC TTA AAG CCG GCG TTC AGC AAA ACG GGG ACT GTT ACG GCG<br>GCC AAC AGC AGT TCC ATT TCC GAT GGT GCA GCT GCG CTG GTT ATG ATG CGC GAA AGC ACT GCC AAA CGC<br>CTC GGC GTT CAG CCG ATT GCG CGC GTT GTC GGC CAT TCT ACC CTG GCA CAA GAA CCG GCG AAA TTT ACC<br>ACC GCC CCA GTT GGT GCT ATC CGC AAG CTG TTC GAG AAG AAT GGC TGG CGT GCG GAT GAA GTC GAC CTG<br>TTC GAA GTG AAC GAA GCG TTT GCG GTG GTG ACA ATG GCG GCA ATG AAA GAA CAC CAT CTG CCT CAT GAG<br>AAA GTG AAC GTC AAT GGT GGT GCC TGC GCA TTA GGC CAT CCG ATT GGC GCA AGT GGA GCA CGC ATC TTG<br>GTA ACC TTG ATT GGT GCC CTG AAG AAA CGC GGT GGT AAA CGT GGT GTG GCT ACT CTG TGC ATT GGC GGT<br>GGC GAG GCA ACA GCG ATG GGG ATC GAG CTC GTG taa |
| *43* | ATG ACG GAA GCG TTC CTG TGT GAT GCG ATC CGC ACG CCG ATT GGC CGG TAT GCG GGC GCG CTT AGC TCC<br>GTA CGC GCA GAT GAT CTG GGT GCG GTA CCG TTG AAA GCC CTT ATG GAG CGT AAC AAA GAG GTT GAC TGG<br>AAT GCC ATC GAC GAC GTT ATC TAC GGG TGC GCA AAC CAA GCT GGA GAG GAT AAC CGC AAC GTT GCC CGG<br>ATG TCG CTC CTC TTA GCT GGC CTG CCG CAA GGT GTT CCT GGA ACG ACA GTG AAT CGC TTG TGT GGC AGT<br>GGC ATG GAC GCG GTT GGC ATT GCA GCA CGT GCC ATC AAG TCA GGG GAA GCA GCT CTG ATG GTT GCA GGC<br>GGG GTG GAA AGC ATG TCA CGT GCG CCG TTT GTG ACG GGA AAA GCC ACC AGC GCC TTT TCC CGG CAG GCA<br>GAA ATC TAC GAT ACC ACC ATT GGT TGG CGC TTT GTC AAC CCG CTG ATG AAG AAA CTC TAT GGC GTC GAT<br>AGC ATG CCG GAA ACC GGT GAG AAT GTT GCC ACC GAC TAC AAC ATT AGC CGC GCA GAT CAA GAC GCT TTC<br>GCC TTA CGC TCT CAG CAG AAA GCG GCA CGT GCG CAG CGT GAT GGC ACT CTG GCA CAG GAA ATC GTG GGT<br>GTT ACC ATT GCC CAG AAG AAA GGC GAT CCA GTC ACC GTG TCG CAG GAC GAA CAT CCG CGC GAA ACC AGT<br>CTT GAC GCC CTG GCT AAA CTG AAA GGT GTG GTG CGT CCC GAT GGG ACC GTA ACT GCT GGC AAC GCT AGT<br>GGG GTC AAC GAT GGG GCA GCG GCG TTG CTG CTG GCG AAT GAG GAA ACA GCC CGT CGT TTC GGT TTG ACT<br>CCC CGT GCA CGC GTG CTT GGT ATT GCC ACC GCA GGT GTA GCT CCT CGC GTG ATG GGC ATT GGA CCA GCC<br>CCT GCG ACG CAG AAA CTG TTA GCG CGT CTG AAT ATG TCC CTG GAT CAG TTC GAT GTC ATC GAA CTG AAC<br>GAA GCG TTT GCG TCG CAA GGC ATT GCG GTC CTG CGC GCG TTA GGA GTC GCT GAT GAC GAT ACC CGT GTG<br>AAT CCG AAT GGC GGT GCC ATT GCC CTC GGT CAT CCA CTG GGT ATG TCT GGT GCG CGC CTG GTG ACT ACG<br>GCG ATG TAT CAA CTG CAC CGC ACA CAA GGC CGC TTT GCT CTG TGC ACG ATG TGC ATC GGC GTG GGT CAG<br>GGC ATT GCG ATT GCC ATT GAA CGC GTA taa |

FIG. 19D

| SEQ ID NO | Nucleic acid sequence |
|---|---|
| 44 | ATG GCC GAA GTG TTC CTC GTG GAT GGT GCG CGT ACC CCA CAA GGT CGC TAT GGA GGT GCC CTG GCG GGT<br>GTT CGC CCT GAC GAT CTG GCA GGC TTG GTG GTT GCG GAA GCC GCG CGT CGC GCA GGA ATT CCG GGA GAT<br>GCG GTG GAC GAA GTG ATC CTT GGG GCA GCG AAT CAA GCA GGC GAG GAT AAC CGC GAT GTG GCT CGT ATG<br>GCT GTA CTC CTG GCG GGC CTG CCC GAT AGC GTC CCA GGC TAT ACC GTC AAT CGC CTG TGT GCG TCG GGC<br>CTT ACT GCT GTG GCG AGT GCC GCG CAC ACC ATT CGC AGC GGC GAA GCT GAC ATC GTC ATT GCG GGA GGG<br>GTG GAA TCA ATG ACG CGT GCT CCT TGG GTA ATG GCC AAA CCG GGT ACC CCA TGG GCA CGT CCG GGT GAA<br>GTT GCG GAC ACG AGC TTG GGC TGG CGT TTC ACG AAT CCC CGC TTT ACC GCC GCT GAT CGC GAT GTA CCG<br>GCC GGT GCT GGG CCT GAT GTC CGC AAA GTA ACC CTG TCG ATG GGC GAA ACT GCG GAG GAA GTT GCC GCC<br>CTG GAA GGC GTA ACC CGT GCG GAA TCC GAC GCA TTT GCT CTC CGT TCT CAG GAA CGT GCG ATC GCA GCG<br>GTT GAT GCC GGT CGG TTT GAA CGG GAG ATT GTT CCG GTG CCG GTT CGC GAT GGC GAA CTG GCA GCG GAC<br>GAG ACA CCG CGT CGT GGT ACG ACA CTG GAG AAA TTA GGG AGT CTG AAA CCC GTG TTT CGT ACG GGC GGT<br>ATT GTC ACT GCA GGG TCC AGC AGT TCT CTG TCT GAT GGC GCG GCA GCC TTA GTT GTC GCC AGC GAA GCA<br>GCG GTG GAA AAG TAC GGC CTG ACC GTC CGC GGC CGC ATT GTC ACG TCG GCC TCA GCG GGC ATT GCA CCG<br>AAC GTG ATG GGT CTT GGT CCG GTG CCA GCG ACT CGC AAA GCG CTG GCA CGG GCG AAC TGG TCC ATC AGC<br>GAT CTG GGT GCT GCG GAG TTG AAC GAA GCG TTC GCA GCA CAG AGT CTG GGC GTT ATC CGC CAG TTA AAG<br>CTG GAC GAG TCG ATC GTA AAT GCT GAC GGT GGG GCC ATT GCT CTC GGA CAT CCG TTG GGC TGC TCA GGT<br>GCC CGC ATC TTA CTG ACC CTG TTA GGG CGC ATG GAA CGC GAA GGC GCC CGT CGC GGT CTT GCC ACA CTG<br>TGC GTG GGT GTT GGC CAG GGC GTG GCC ATG CTG ATT GAG GCC CCG taa |
| 45 | ATG AAG TCA CCA CGC GAC GTT GTG CTC GTC GAA GGT GTT CGG ACA CCG TTC GCA AAA GCG GGT ACC AAA<br>CTG AAA AAA GTC CAC CCA GCT GAA CTG GGC AAA GTG GCG CTT AAA CAG GTC ATT GCG CAA ACG AAC CTG<br>GAT GTC AAC CTT GTG GAT GAA GTG ATC ATC GGG AAT ACT GGA AAC CCA CCA GAT TCG GTG AAC ATC TCT<br>CGT GTT GTT GCC CTG AAT GCC GGT ATT CCG CTC AAA ACC TCA GCG TAC ACG GTA CAC CGC AAT TGC GCA<br>TCT GCC CTT GAA AGC ATT AGT AAC GGC TAT GAG AAA ATC AAA TCC GGC ACG ATG GAT GTT ATT CTG GCG<br>GGT GGT ACC GAG AAT ATG TCA CAA ATG CCG ACT TTA CCG CCG AAG AAA TTC CAG GAA ATC TAT GAG AAA<br>CTG TTT GCT GCA AAA GGC CCG AAA CAA GCT CTG CCC CTG CTG TGG AGT CTG TTC AAA GCG GAT GTG AAG<br>CAG ATC AAA GCC CTG TTA AGT GGG AAT ATG CGT GAC GAG TAC TTC CCG GTG ATT TCG GTG ATG ATG GGC<br>TTA ACC GAT CCC TTT GTG GGC ATT AAC ATG GGC CAG ACT GCC GAA ATC TTG GCG AAA GAA TGG GGC CTG<br>TCT CGC GAA ACC CAG GAT AAG TTC GCC CTG CGT TCC CAT CAG CTG GCG AGC AAA GCC ATG AAA GAG GGT<br>CGT ATG CGG GAA GAA ATT GCA CCG GTG TAT CTC GCC CCG GAA TAC AAG GAA GTT ATT AGC GAG GAT ATC<br>GGT CCT CGT GAT ACC CAG ACG ATG GAA GCG CTG GCC AAA CTG AAA CCG TTC TTT GAC AAA GCG ACA GGC<br>TCT ATT ACC GCA GGC AAC AGC TGT CCC ATT ACC GAT GGA GCG GCC ATG GTT CTG ATG ATG TCG CGC GAG<br>AAA GCA GAA GCG CTG GGC TAT AAG CCT TTG GCA ACC ATT CGC TCC TAT GGG TTT GCG GGC TTG GAA CCG<br>GAA CGC ATG GGT TTA GGT CCT GTA TAC TCC ACA CCT GTA GCT CTC AAA CGC GCA GGA TTA AGC ATG AAA<br>GAC ATT GGG TTG GTC GAA TTG AAT GAA GCG TTT GCT GCT CAA GTC TTA TCG TGC CAG AAA GCG TTT GAT<br>AGC GAC AAG TTT GGC CAG GAA AAG CTT GGT CTG AGT AGC AAA ATC GGC GAA ATC CGC GAC GAC ATT CTG<br>AAC GTG AAT GGC GGT GCT ATT GCA CTG GGT CAT CCG GTA GGT GCC ACC GGT ACG CGC ATC GTT CTG ACG<br>CTG GCG AAA GAG ATG AAA CGT CGT AAC ACC CAG TTT GGG TTG GCC ACT CTG TGT ATT GGC GGA GGC CAA<br>GGA GGT AGC ATG ATT CTC GAA AAT GAG GGG taa |

FIG. 19E

| SEQ ID NO | Nucleic acid sequence |
|---|---|
| 46 | ATG TTT TCG CTT CTG CAG GGG AAC GTC ATG TCT CAA GCT CTG CCG CTT GTC ACG CGT CAG GGC GAT CGC<br>ATT GCG ATC GTT TCC GGC TTG CGC ACC CCA TTT GCC CGC CAA GCT ACC GCG TAT CAC GGG GTT CCT GCC<br>GTG GAT CTG GGC AAA ATG GTA GTT GGG GAG CTG CTG GCC CGT TCG GAA ATT CCA CCG GAT GTC ATT GAG<br>CAG CTG GTA TTC GGT CAG GTA GTA CAG ATG CCA GAA GCG CCG AAC ATT GCA CGG GAG ATT GTG CTG GGT<br>ACG GGT ATG TCC GTT CAC ACA GAT GCG TAT AGC GTC AGC CGC GCC TGT GCG ACT AGC TTC CAG GCA GTG<br>GCC AAT GTG GCG GAA AGT CTG ATG GCT GGC ACG ATT CGT GCA GGA ATC GCA GGC GGA GCC GAT AGC TCA<br>AGT GTG CTG CCG ATT GGT GTC AGC AAG AAA CTG GCT CGT ACC CTG GTG GAC GCG AAT AAA GCC CGT ACA<br>GCC GGC CAG CGC CTG AAA CTG TTC TCT CGC TTA CGC CTG CGT GAT CTG TTG CCG GTT CCT CCG GCG GTT<br>GCT GAG TAC TCA ACG GGT TTA CGC ATG GGA GAT ACG GCC GAA CAG ATG GCG AAA ACG CAT GGG ATC ACG<br>CGT GAA CAG CAA GAT GCA CTT GCG CAT CGT TCT CAC CAA CTC GCA GCC CAA GCG TGG GCA GAG GGC AAA<br>CTC CGC GAA GAA GTT ATG ACC GCT TAC ACC CCA CCG TAT CGT GAA CCG CTG AGT GAG GAC AAT AAC ATC<br>CGG AAG AAT TCG AGC TTG GCG GAC TAC ACC AAA CTG CGT CCG GCA TTT GAC CGG AAA CAT GGC ACT GTG<br>ACA GCT GCA AAC TCC ACC CCT CTT ACG GAT GGC GCC GCG GCA GTG ATC CTG ATG ACA GAA TCA CGC GCC<br>CGC GAA CTG GGG TTG ACC CCG TTG GGT TAT CTG CGC TCG TAC GCT TTC ACC GCT GTC GAT GTC TGG CAG<br>GAC ATG TTG TTA GGT CCC GCC TGG AGT ACT CCC CTC GCG CTG GAA CGC GCG GGT TTA ACC ATG GCC GAT<br>CTG ACG CTG ATC GAC ATG CAT GAA GCG TTT GCC TCT CAG ACC CTT GCG AAC CTC AAA CTG CTC GCG TCA<br>GAT CGC TTT GCA CGC GAA GTG TTA GGT CGT TCC CAA GCT ACC GGC GAA GTA GAC GAG AGC AAG TTC AAT<br>GTG TTG GGT GGC AGC ATT GCG TAT GGC CAT CCG TTT GCG GCG ACT GGT GCG CGC ATG ATT ACC CAG ACT<br>CTG AAC GAA CTG CGT CGT CGC GGT GGA GGC TTT GGC TTA GTT ACC GCA TGC GCA GCG GGC GGT TTA GGG<br>GCA GCC ATG GTG CTG GAA GCC GAA taa |

FIG. 19F

| SEQ ID NO | Nucleic acid sequence |
|---|---|
| 47 | ATG TCC TTT AAC GGG CAA TCC GCA ACC GGT CCG GAT GAA AGT GCA GCG GCG CCT GCT GCC ACA CCT GGT<br>GCG GGT CTG TTG CGC AAA GCG GTA GTT GTG GGC GGA AAC CGC ATC CCA TTT GCC CGT ACG GGT GGT GCT<br>TAT ACG AAG AGC AGC AAT CAG GAC ATG CTG ACA GCG GCG CTG GAC GGC CTG ATT GCT CGC TTT GGC CTG<br>GCG GAT GAA CGC ATT GGG GAA GTG GCG GCT GGT GCG GTT CTG AAG CAT TCA CGC GAC TTC AAC TTA ACG<br>CGG GAA GCC GTG TTA GGC AGT GCC CTC TCT GCC GAA ACC CCG GCA TAC GAT CTG CAG CAG GCA TGT GCG<br>ACA GGA CTG GAA ACG GTA CTC GGT CTG GCC AAC AAA ATC AAA TTA GGC CAG ATT GAT TCC GCC ATT GCC<br>GGT GGA GTT GAT TCT GCG TCT GAC GCC CCG ATT GCG GTT AGC GAG GGT CTG CGC GAA GTC CTG CTG GAC<br>CTG AAT CGC GCG AAA ACC CTG CCG CAA CGC CTC AAA GTG CTG GGG CGC TTA CGT CCC AAA GAT CTG GCC<br>CCA GAT GCG CCG AAT ACG GGA GAA CCC CGT ACC GGA CTG TCC ATG GGC GAA CAT CAG GCC CTG ACA ACT<br>GCA CAG TGG AAG ATT ACC CGC GAA GCA CAG GAC GAG TTG GCA TAC AAC AGC CAT CGC AAC CTC GCG GCT<br>GCG TAT GAC GCA GGC TTC TTT GAC GAC CTC TTG ACG CCG TAT CGT GGT CTT AAC CGT GAC TCG AAC TTA<br>CGC GCG GAT ACC ACG CGT GAG AAA TTG TCA ACG CTG AAA CCG GTC TTT GGC AAG AAT CTG GGC GCT GAA<br>GCG ACT ATG ACC GCC GGC AAC TCG ACC CCG CTT ACC GAT GGC GCC AGT ACC GTG CTT CTG GCG AGC GAG<br>GAA TGG GCT GAT GCG CAC GAA TTA CCG AAA CTG GCC ACT GTG GTG GAT GGC GAA GCA GCA GCG GTC GAT<br>TTT GTC CAT GGC AAA GAC GGT CTG TTA ATG GCG CCA GCG TTC GCG GTA CCT CGG CTG TTG GCA CGC AAT<br>GGC CTT ACT CTC GAC GAT ATC GAT TTC TTC GAG ATT CAT GAG GCC TTT GCT GGC ACC GTG TTG AGT ACC<br>CTT GCA GCT TGG GAA GAT GAA GAG TTC GGT CGT ACC CGT CTG GGC CTT GAT GGT CCA CTG GGG TCG ATT<br>GAT CGT GCA AAA CTG AAT GTG AAT GGG TCG TCA TTG GCA GCT GGG CAC CCG TTT GCG GCG ACT GGC GGC<br>CGT ATC GTA GCC ACC CTG GCC AAA ATG CTG CAC GAT AAA GGG CAA GTT GAT GGT CGG CCG GCT CGC GGT<br>CTG ATC AGC ATC TGC GCA GCC GGC GGT CAA GGC GTC GTT GCC ATT CTG GAA GCT AGC taa |

FIG. 19G

| SEQ ID NO | Nucleic acid sequence |
|---|---|
| 48 | ATG GCC ACA GCG AGT TCC TCG GCG GCA TCC TCT TCC GGT GTC TGG TTA GCT GCG GGT GTT CGC AGC CCA<br>TTT GCC AAA GTA GAT GGT GCG TTA GCC GGT CAT GAC GCC ATT GGG TTA TCG GTG CCC GTG GTC AAA GCG<br>ATG TTA GCA CGT GCC AAA CCG GAC TTT GCG GTT TGG GGT ACT GTG ATC CCG AAC CTC ACG TGG AGT AAC<br>CTG GCC CGT GAG GTC CTG TTG GAT GCC GGT GGT GAT CCG ACG ATT CCG GCG TTT TCC ACG GTT ATG GCT<br>TGC AGC ACC AGC ATG ATT GGC GCG ATT GAA GCA GCC GGC ATG GTG GAT GGC CGT GGT CGC GAT CTG GCG<br>CTG GTA GGC GGC GTG GAA AGC ATG TCA CGT GTG CAG TTG GGC CTG AGT GTT GCA CTG AGC GAT TGG ATT<br>CGC AAG TTC CAG AAC GCG AAA ACC GGC CAA CAG CGG CTC GCG GCT CTG GGA GCC CTT AAC CTG AAA GAT<br>GTA CGC TTA TTC ATC CCG AAG GTC GTT AAC CGT GTT ACG GGA CTG TCA ATG GGA GAA CAT ACC GAG ATT<br>ACC GCG AAA GAG TGG AAT TTG TCT CGT GCA GAC CAA GAT GCC ATT GCT CTG GCT TCG CAT CAG GGT GCC<br>GTG AAA GGC TGG GAA AGC GGA TTC TTT GAC GAC CTG GTC ATT CCA GTG GGC GAA GTG AAA CGC GAT GGA<br>ATC CCG CGC AAA GAC ACA TCT CTG GAG AAG CTC GCA AAA CTG GGC CCA GCC TTT GAC AAA ACC AGT GGC<br>AAA GGC ACC CTG ACC GCG GGG AAT TCC TCA CCC CTT ACC GAT GGT GCG GCT GCG GTT TGG GTA GGT TCT<br>GCA GCT GGC ATG GCG CGT TTA CCG GGT GAG ACA CCG AAG GTT CGT CTG GTC GAC TAC GAA GTC ACC AGC<br>ATC GAT CTG CGT CAT GAA GGC CTG TTG ATG GCG CCG GCT TAT GGG GTA CCG CGC ATG CTC GCC CGC AAT<br>GGG CTG ACT TAT GCC GAT GTT GGG CTG TGG GAA ATC CAC GAA GCT TTC GCA GCA CAG GTG TTG AGC CAC<br>ATT GCG GCA TGG GAA TCG GCC AAG TTC CTG AGC GAG AAA GCC GGC GTG ACT ACG CCT ATG GGT GCA TTT<br>CCT CGC GAA CGC ATG AAC CCG AAT GGC GGC TCT CTG GCT CTT GGT CAC CCA TTT GGT GCA ACT GGC GCG<br>CGC ATC ATT TCG CAG ACC GTG AAA GAA CTG GCA GCG CGC CCT AAA GGG GAA CGG GCG ATC GTG AGT ATC<br>TGT GCG GAT GGT GGG CAA GGC ACG ATG ATG CTT CTG GAA TCA GCC taa |
| 49 | ATG ACG GAA GCC TAC ATC TAT GAC GCG ATT CGC TCA CCA CGT GGT AAA GGG CGC AAA GAT GGC TCC CTG<br>CAT GAA GTC ACT GCG GTC AGC CTG AGT GCC CAA ACC CTG AAT GCG ATT AAA GAC CGC AAT GGC CTG ACC<br>GGG CAT GCG GTT GAA GAT GTG ATT TGG GGT AAC GTC ACC CAG GTA ATG GAA CAG GGT GGA TGT CTG GCA<br>CGT ACG GCG GTA CTT GCG TCT GAT CTG GAT GAG AGC ATT CCT GGC TTA GCG ATC AAC CGC TTT TGC GCC<br>AGC GGT TTA GAA GCC GTC AAT TTG GCG GCC AAT CAA GTG CGT GGA GGC GGT GGA CAG GCA TAC ATT GCT<br>GGC GGC GTT GAG ATG ATG GGT CGC GTT CCC ATG GGT AGC GAT GGC GCC GCA ATC GCA GCC GAC CCG TCT<br>GTG GCG ATG AAA ACC TAC TTT GTG CCG CAA GGT ATT TCC GCC GAT ATC ATC GCA ACG GAA TAT GGC ATT<br>AGC CGC GAT GAT GCG GAT GCC CTG GCT GTA GCG TCG CAA CGT CGG GCT AAA GCT GCG TGG GAT GAG AAC<br>CGC TTC AAT GGG TCC GTG TTT ACC GTT CGC GAT CAG AAC GGT CTG AAC ATT CTG GAC CAC GAC GAG TAT<br>ATG CGT CCT GAA ACT GAC ATG CAG AGC CTG GGT GCA CTG AAA CCG GCT TTC AAA GAT ATG GGT GAA CAG<br>ATG CCC GGT TTC GAC AAG ATT GCG CTC ATG AAG TAT CCG CAT TTA GAG AAA ATC GAA CAC ATT CAT CAC<br>GCC GGT AAC TCG TCA GGC ATT GTT GAT GGG AGT GCA GCG CTC CTT ATC GGC AAT AAA GCC TTC GGC GAA<br>GCT CAT GGC CTT AAA CCA CGT GCA GTG ATC AAA GCC ACA GCC AAG ATC GGA ACC GAT CCG ACG ATT ATG<br>CTG ACT GGC CCG GTT CCA GCG ACC GAA AAG ATT TTG GCA GAT TCT GGC ATG AGT ATC TCA GAC ATT GAT<br>CTG TTC GAA GTG AAC GAG GCC TTT TCG TCG GTC GTG TTG CGG TTT ATG CAG GCG TTT GAT GTC GAC CAC<br>GAC AAA GTG AAC GTG AAT GGC GGT GCG ATT GCA ATG GGG CAT CCG TTG GGT GCA ACA GGC GCG ATG ATT<br>CTG GGC ACC CTG CTC GAT GAG CTG GAA CGT ACG GGC AAA GGG ACC GGG TTA GCT ACA CTG TGC GTT GCT<br>AGT GGA ATG GGC GCG GCT ACG ATC ATC GAA CGC GTA taa |

FIG. 19H

| SEQ ID NO | Nucleic acid sequence |
|---|---|
| 50 | ATG ACT CGC GAT ACG CGC GAC GTG GTG ATC GTA GAT GCG GTT CGC ACA CCA ATT GGC AAA TTC CGT GGT<br>GCC TTG GCT GGT GTA CGT GCC GAT CAT CTG GGT GCA CTC GTC ATT GAC GAA CTG ATC CGC CGT GCC GGT<br>GTC AAA CCG CAG GCG GTG AAC GAT GTG GTC TTT GGG TGC GTT ACC CAG ATC GGT GAG CAG TCA GCG AAC<br>ATT GCC CGC ACC TCT GTG TTA GGG GCG GGA TGG CCG GAA ACC ATC CCA GGC CTG ACC ATT GAC CGC AAG<br>TGT GGT AGT GGG GAA GAA GCA GTG CAC ATT GCC GCC GGC CTG ATC GCG TTT GGC GCA GCG GAT GTG ATC<br>GTT GCC GGT GGC GCT GAA TCT ATG TCG CGT GTC CCG ATG GGT AGC AAT CGG GAT CTG CAT GGC GAA GCA<br>TTC GGG TGG ATG GCT TCA GAG CGC TTC GAG CTG ACC TCG CAA GGC GAG GCC GCC GAA CGT CTG TGC GAT<br>TGT TGG GCG CTG ACA CGT GCG CAA CTT GAC GCG TAC TCG GTA GAG TCT CAT CGC CGC GCT GCA GCG GCT<br>GCG GCT GAA GGC TGG TTT GCG CGC GAG ATT GTG CCC GTT CCA GTT GGT CAG GTG CGC GAA AAG TCC CTC<br>GAA GGC GAA GCC GCG TTA TTT GCC GCT GAT GAA ACG ATT CGC CCT GGC ACC AAT GCG GAC AAA CTG GCG<br>ACC TTG AAA TCC TCG TTT CGC AGT GAT GGT CGC CTG ACA GCC GGG AAT AGC TCA CAG ATT AGC GAT GGT<br>GCG GCA GCA CTT CTG CTG ATG AGC AGT GAC AAA GCA CGT GAA CTC GGA GTC AAA GCT CGT GCC CGG GTT<br>CGT GCG GTT ACC ACG GTG GGT AGT GAT CCG ACC CTC ATG CTT ACG GGA CCG ATT CTT GCG ACT TGT CAG<br>GTA CTG GAG AAA GCG GGC TTA GGT TTG AGC GAT ATC GAC CTG TTC GAG ATC AAC GAA GCG TTT GCG CCT<br>GTA CCG CTG GTC TGG ATG AAG GAA TTC GGT GTT CCC CAC GCA AAA CTG AAC GTG AAT GGC GGG GCC ATT<br>GCA CTG GGC CAT CCG TTA GGC GCA TCC GGC GCA CGT ATC ATG ACG AGC ATG TTG CAC GAA CTG GAA CGC<br>CGG GGA GCA CGT TAT GGC CTG CAA GCC ATT TGC TGC GCT GGA GGT ATG GGC ACT GCC ACG CTG ATT GAA<br>CGC TTA GAT taa |
| 51 | ATG CGT GAA GCT GTG ATT GTA GAA GCC GTA CGC ACA CCT GTC GGG AAA CGG AAT GGC GTA TTC CGC GAT<br>GTG CAT CCC GTA CAT CTG GCA GCG GTC GTG TTG GAT GAA GTC GTC CGT CGC GCA GGG ATG GAT AAA GGT<br>GCG GTT GAG GAC ATC GTG ATG GGG TGT GTG ACC CCT GTG GCA GAG CAA GGT TAC AAC ATT GGC CGT TTA<br>GCA GCT CTG GAG GCC GGC TTC CCG ATT GAG GTG CCA GCG GTT CAG ATT AAC CGC ATG TGC GGC AGT GGA<br>CAG CAG GCC ATC CAT TTT GCC GCC CAA GAA ATC CGC AGT GGC GAT ATG GAT GTC ACG ATT GCG GCC GGT<br>GTG GAA TCG ATG ACC AAA GTC CCC ATT CTC AGC GAT GGG AAT GAG CGC ACC ATT CCG CCA AGC CTC CAC<br>GAA AAG TAC GAG TTC ATC CAC CAA GGT GTA TCT GCG GAA CGC ATT GCG AAG AAA TAC GGA CTG ACA CGC<br>GAA GAG TTG GAC GCG TAT GCG TAT GAA AGC CAC CAG CGT GCC CTT GCT GCA CTG CGT GAA GGC AAA TTT<br>CGG GCG GAA ATC GTT CCG GTA AAA GGC CTT GAT CGT GAT GGC CGC GAA ATC CTG GTG ACC GAC GAT GAA<br>GGT CCG CGT GCT GAT ACT AGC CCG GAA GCC TTA GCA GCG CTG AAA CCG GTG TTT CAG GAA GAT GGC CTG<br>ATT ACC GCG GGT AAT GCT TCC CAG ATG TCT GAT GGC GCA GCC GCC GTT CTC CTT ATG GAA CGT GAA GCG<br>GCA CGT CGC TTT GGC CTG AAA CCT AAA GCT CGC ATT GTC GCG CAA ACC GTT GTG GGA TCA GAC CCG ACC<br>TAT ATG CTG GAT GGT GTT ATT CCG GCA ACT CGT CAG GTC CTG AAG AAG GCC GGG CTG TCG ATC GAC GAC<br>ATT GAC CTG ATC GAA ATC AAC GAG GCG TTT GCG CCG GTT GTT CTG GCT TGG CAG AAA GAA ATT GGC GCC<br>CCG CTG GAG AAA GTG AAC GTG AAT GGT GGT GCG ATT GCC TTA GGC CAT CCA CTG GGT GCA ACT GGC GCG<br>AAA CTG ATG ACG TCC TTG GTT CAC GAG TTA GAA CGG CGC GGT GGA CGC TAT GGC CTG TTG ACG ATC TGC<br>ATT GGG CAT GGT ATG GCG ACG GCT ACG ATC ATT GAA CGC GAA taa |

FIG. 19I

| SEQ ID NO | Nucleic acid sequence |
|---|---|
| 52 | ATG ACC AAA GTG GTC ATT GCA GGC TAC ATT CGC TCA CCG TTT ACC CTG GCG AAG AAA GGG GAA CTG GCC<br>ACG GTG CGT CCT GAC GAT TTG GCA GCT CAA GTC GTG AAA GGC CTG ATC AAG AAA ACC GGC ATT CCG GCC<br>GAG GAC ATC GAA GAT CTG CTT CTG GGG TGT GCG TTC CCA GAA GGT GAA CAG GGC TTC AAC GTA GCT CGC<br>CTG GTT TCG TTT CTG GCG GGT CTG CCG CTG TCG GTG GGC GCA AGC ACC GTG AAT CGC TTT TGT GGC TCT<br>TCG ATG ACT ACC GTT CAC ATG GCA GCA GGA GCC ATT CAG ATG AAC GCA GGA AAC GCC TTT ATC GCG GCT<br>GGT GTC GAA AGC ATG AGC CGC GTA CCG ATG ATG GGC TTC AAT CCT CTG CCG AAT CCC GAA TTG GCC GCG<br>ACA ATG CCT GGC GCC TAT ATG GGC ATG GGT GAT ACG GCT GAG AAT GTG GCT GCC AAA TGG ACC ATT TCC<br>CGG AAA GAA CAG GAA GAA TTC GCC CTG CGT AGC CAT CAA CGT GCG ACT GCC GCG CAG AAG GAA GGA CGT<br>TTG ACC GGT GAA ATT ATC CCG ATT ACC GGC CGG AAA GGG ACG ATC ACG ACG GAT GGC TGC ATT CGT CCC<br>GAT ACC ACA CTT GAG GGT CTG GCA GAA CTC AAA CCG GCG TTC TCA GCT AAT GGA GTC GTA ACC GCG GGT<br>ACT TCC TCT CCG CTG ACG GAT GGC GCC GCT GCC GTT CTC GTG TGC AGT GAG GAC TAT GCG AAA CAT CAC<br>CAC TTA GAC GTT TTA GCG AGC GTG AAA GCT ATC GCG GTA AGC GGT TGC TCT CCG GAG ATT ATG GGG ATT<br>GGT CCA GTT GCG GCC TCA CGC AAG GCC TTA GCG CGT GCA GGC CTG GAA GCG GGT CAG ATC GAT ATT GTC<br>GAA TTG AAC GAA GCT TTT GCC AGT CAG TCC ATT GCG TGT ATG CGC GAA CTG AAC CTG AGT CCG GAC CGC<br>GTT AAC ATC GAT GGT GGC GCG ATT GCA CTG GGC CAT CCA CTC GGG GCG ACA GGG GCG CGC ATC GTG GGA<br>AAA GCA GCA TCG CTG CTC AAA CGC GAG AAA GGC AAA TAC GCC TTA GCG ACT CAG TGC ATT GGT GGT GGC<br>CAA GGT ATC GCC ACC GTT CTT GAG GCA TTT taa |
| 53 | ATG GAA CAG GTC GTG ATC GTC GAT GCC ATT CGC ACG CCA ATG GGC CGT TCA AAA GGT GGA GCC TTT CGC<br>AAT GTG CGC GCC GAA GAT CTG TCT GCA CAT CTG ATG CGC TCT CTG CTG GCC CGT AAC CCC GCA TTA GAT<br>CCG ACA GCG CTG GAC GAC ATC TAT TGG GGC TGT GTG CAG CAG ACA CTG GAA CAA GGG TTC AAC ATT GCG<br>CGT AAT GCT GCT CTG CTG GCG GAA ATC CCT CAC AGT GTG CCA GCA GTA ACG GTT AAT CGC TTG TGT GGC<br>TCC AGC ATG CAA GCT CTC CAT GAT GCT GCA CGC ATG ATC ATG ACC GGC GAT GCG CAA GCG TGC CTC ATT<br>GGT GGT GTA GAA CAC ATG GGC CAT GTC CCC ATG TCA CAC GGG GTA GAC TTT CAC CCG GGT ATG AGC CGC<br>AAT GTG GCC AAA GCA GCC GGT ATG ATG GGC TTA ACT GCG GAG ATG CTG TCC CGC ATG CAC GGC ATT AGT<br>CGT GAA ATG CAG GAT GCC TTT GCA GCG CGC AGT CAT GCG CGT GCT TGG GCG GCC ACT CAA TCT GGG GCC<br>TTC AAG AAC GAG ATT ATT CCG ACT GGC GGC CAT GAT GCG GAT GGG GTA CTC AAA CAG TTC AAC TAC GAT<br>GAG GTG ATT CGG CCG GAA ACC ACC GTT GAA GCC TTG TCG ACC TTA CGC CCG GCC TTT GAT CCT GTT TCT<br>GGT ACC GTT ACC GCG GGC ACG TCG TCC GCG TTG AGC GAC GGT GCG GCA GCC ATG CTT GTG ATG TCA GAA<br>AGC CGT GCT CGT GAA CTT GGC TTA ACA CCG CGT GCG CGC ATT CGT AGC ATG GCA GTG GTT GGA TGT GAT<br>CCG AGC ATT ATG GGG TAT GGA CCA GTC CCG GCT TCG AAA CTC GCC TTG AAG AAA GCG GGC CTG AGC ACG<br>TCC GAC ATT GGG CTG TTT GAA ATG AAC GAA GCT TTT GCA GCG CAG ATT CTG CCG TGC ATC AAA GAC CTG<br>GGT CTG ATG GAG CAG ATC GAC GAG AAA ATC AAC CTG AAT GGC GGT GCA ATC GCC CTT GGC CAT CCT CTG<br>GGT TGC AGT GGT GCG CGC ATT TCG ACC ACG CTG TTA AAC CTG ATG GAA CGC AAA GAT GTC CAG TTC GGT<br>CTT GCG ACC ATG TGC ATT GGA CTG GGT CAA GGC ATC GCA ACC GTG TTC GAG CGG GTT taa |

FIG. 19J

| SEQ ID NO | Nucleic acid sequence |
|---|---|
| 54 | ATG AAA CAG TTA CAG GAT GCG TAC ATT GTT GCG GCC ACT CGC AGT CCG ATT GGA AAA GCA CCC AAG GGA<br>GCC TTC AAG AAT ACG CGC CCG GAC GAT CTG TTA GCG ACG ATC CTT AAA GCC GCT GTG GCC CAG GTG CCG<br>AAT CTC GAT CCG AAA CTG ATC GAA GAT GCG ATC GTC GGT TGC GCA ATC CCT GAG GCT CAG CAA GGC CTG<br>AAT GTA GCC CGC ATT GGT GCG CTG CTG AGT GGA CTG CCA AAC ACG GTT GGC GGC ATT ACC GTT AAT CGG<br>TTT TGC GCA TCT GGG GTC AGC GCT GTT GCG ATG GCA GCC GAT CGC ATT CGC GTC GGT GAA TCC GAC GTC<br>ATG ATT GCT GCC GGT GTG GAG TCA ATG AGC ATG GTG CCC ATG ATG GGT AAC TCT CCG AGC ATG AGT CCG<br>GAA ATC TTT ACC CGT GAC GAA AAC GTT GGC ATT GCC TAT GGG ATG GGT CTG ACA GCC GAG AAA GTG GCT<br>CAG CAG TGG CAA GTA AGC CGC GAA GAT CAG GAT GCG TTT TCG CTG GCA TCC CAC CAG AAA GCA ATT GCC<br>GCG CAA CAG GCA GGC GAA TTC AAG GAT GAG ATC ACC CCG ATT GAG ATT GTG GAG CGT TTC CCT GAC CTG<br>GCA AGT GGG CAA GTG AAC GTA AAG ACC CGC ACG ATT AGC CTG GAT GAA GGC CCA CGT CCG GAA ACC TCT<br>CTT GAA GGC TTG GGT AAA CTC CGT CCG GTC TTT GCC AAC AAA GGC TCA GTA ACC GCA GGC AAT AGC TCG<br>CAG ACT TCG GAC GGT GCA GGC GCG CTG ATT TTG GTG TCG GAG AAA ATC CTG AAA CAG TTC AAC CTG GTA<br>CCG TTG GCG CGG TTT GTG TCA TTT GCC GTC CGT GGT GTT CCG CCG GAA ATC ATG GGT ATT GGT CCC AAA<br>GAA GCG ATC CCT GCA GCT CTG AAA GCC GCG GGC CTG ACC CAA GAC CAA CTG GAT TGG ATC GAA CTC AAC<br>GAA GCC TTT GCG GCG CAA TCC CTC GCT GTG ATG CGT GAC CTT CAG TTA GAT CCA GCA AAA GTG AAT CGC<br>ATG GGT GGC GCG ATT GCG CTG GGC CAT CCA TTG GGA GCT ACC GGC GCG ATC CGT AGC GCG ACA GTC GTT<br>CAT GCC TTA CGT CGC CAC AAC CTG AAA TAT GGG ATG GTT ACG ATG TGT GTG GGG ACT GGG ATG GGT GCT<br>GCG GGC ATT TTC GAA CGC GTT taa |
| 55 | ATG GCC CCT TGC TCA GTG AAA GCG ATG CCA GAA GCA GTG ATC GTA GCT CAT GCA CGT AGT CCC ATT GGT<br>CGT GCT GGT AAA GGC TCG TTA AAG GAT GTC CGT CCT GAC GAA CTG AGC CGC CAG ATG GTA GCC GCT GCT<br>CTC GCG AAA GTG CCG GAA CTG GCA CCC TCG GAC ATC GAG GAT ATT CAC TGG GGT ATT GGC CAG CCA GGC<br>GGC CAA GGT GGG TAC AAT ATT GCG CGT GTC ATT GCC GTG GAA TTG GGC TAT GAT CAC ATC CCG GGT GTG<br>ACC GTG AAT CGT TAT TGC TCG TCG AGC CTG CAG ACC ACA CGC ATG GCA CTG CAT GCG ATT AAA GCA GGA<br>GAA GCG GAT GTT CTC ATT AGT GGA GGG GTT GAG AGT GTT AGC AGC TTT GGC ATT TCC GGT GGG GCA GAT<br>GGC GCC CCG GAT AGT AAG AAC CCA GTA TTC GAT GAC GCG CAA GCA CGG ACC GCG AAA GCT GCC GAA GGT<br>GGA GCA CCG GCT TGG ACT GAT CCA CGT GAG CAA GGC TTG ATT CCG GAT GTT TAC ATC GCA ATG GGC CAA<br>ACG GCC GAA AAC GTA GCC TCT TTT ACC GGC ATC TCT CGC GAA GAT CAG GAT CGG TGG TCT GTC CTG AGC<br>CAG AAT CGC GCC GAA GAG GCC ATT AAC GCG GGC TTC TTC GAA CGC GAG ATC GAC CCG GTT ACG CTT CCG<br>GAT GGT AGC ACG GTT AAC ACC GAT GAT GGC CCT CGT GCG GGC ACT ACC TAT GAG AAA GTC TCA CAG CTG<br>AAA CCG GTG TTT CGC CCT GAT GGC ACC GTG ACT GCG GGC AAT GCG TGT CCG CTC AAT GAC GGT GCT GCC<br>GCA CTG GTG ATT ATG TCC GAC AGC AAA GCG AAG CAA CTG GGT TTA ACG CCC TTA GCG CGT GTG GTG GCG<br>ACA GCG GCC ACT GGA CTG TCA CCG GAA ATC ATG GGT CTG GGT CCG ATT GAA GCC ATC CGC AAA GTT CTG<br>CGC ATC TCT GGG ATG TCC CTG AGC GAC ATT GAC CTG GTC GAA ATC AAC GAA GCC TTT GCA GTC CAG GTA<br>CTG GGG AGT GCG AAC GAG TTG GGG ATT GAC CAC GAC AAA CTG AAC GTG TCA GGT GGC GCT ATT GCG TTG<br>GGT CAT CCG TTT GGC ATG ACC GGG GCC CGC ATT ACC ACG ACG CTT CTG AAC AAT CTG CAG ACA CGC GAT<br>AAA ACC TTC GGA ATC GAA TCC ATG TGT GTT GGC GGT GGC CAG GGT ATG GCG ATG GTC CTT GAA CGC TTA<br>TCG taa |

FIG. 19K

| SEQ ID NO | Nucleic acid sequence |
|---|---|
| 56 | ATG CGT GAG GCT GTG ATT GTC TCC ACC GCA CGT ACG CCC TTG ACC AAA GCG CAT CGT GGC GAG TTC AAC<br>ATC ACA CCA GGC CCA ACC CTC GCC TCG TTT GCT GTT CGC GCA GCA GTA GAA CGG AGT GGT GTC GAC CCT<br>GAT ATC ATT GAG GAT GCG ATC CTG GGT TGC GGC TAT CCG GAA GGC ACC ACT GGC CGC AAT GTT GCA CGC<br>CAA AGC GTT ATT CGT GCC GGT CTG CCA CTG TCC ATT GCA GGC ACA ACG GTC AAT CGG TTT TGT GCC TCA<br>GGC CTT CAG GCA ATT GCG ATG GCA GCT GGG CGC ATT GTG GTC GAT GGA GCG CCG GCA ATG ATT GCG GGC<br>GGT GTT GAG AGC ATT TCG AAC ATC CAG ACC CGC GAA GAT GGA GTG TCT GGC CTG GAC CCG TGG ATT GTC<br>GAG CAC AAA CCC TCA CTG TAC ACT GCG ATG ATC GAT ACA GCG GAT ATT GTT GCT CGC CGT TAT GGG ATT<br>AGT CGC GAA GCT CAG GAT CAG TTT AGC GTG GAG AGC CAA CGT CGC ACT GCC GAG GCG CAA CAA GCG GGA<br>CGT TAT GCA GAC GAG ATT ATC CCG GTT ACC ACG ACC ATG GCC ATT ACG GAC AAG GAA ACC CGT GCG GTA<br>AGC TAT CGC GAA GTG ACG GTG TCT GCC GAC AAT TGC AAC CGT CCG GGG ACG ACC TAC GAA GCA TTA GCG<br>AAA CTT GCG CCG GTA AAA GGT CCT GAT CAG TTC ATT ACC GCA GGG AAT GCG TCC CAG AAC GCG GAT GGT<br>GCC TCG GCG TGC GTA CTG ATG GAA GCG AAA GCC GCC GAA CGG GCC AAC TTT GCG CCA CTG GGC GCG TTT<br>CGC GGC TTA GCT TTG GCT GGG TGT GAA CCG GAT GAA ATG GGG ATT GGT CCG GTT CTT GCT GTC CCG AAA<br>CTC CTG GCA CGC CAT GGC TTA ACG GTG GAC GAT ATC GGT TTG TGG GAA CTC AAC GAA GCC TTT GCC AGT<br>CAG GCC GTA TAC TGC CAG AAA CGC CTG GAA ATC CCT TCT GAA CGC CTG AAC GTG AAT GGT GGT GCC ATT<br>TCA ATC GGT CAT CCG TTC GGC ATG ACT GGC AGC CGT CTG GTG GGC CAC GTT CTG ATC GAA GGA CGC CGC<br>CGT GGC GTC AAG TAC GCG GTG GTG ACC ATG TGT ATG GCC GGT GGC ATG GGT GCG GCT GGT CTG TTC GAA<br>ATC TAT taa |
| 57 | ATG CAG CAG GCA TAC CTG TAT GAC GCG ATT CGC ACC CCG TTC GGT AAG ATC GGT GGT GCC CTG AGC AGT<br>CAC CGT CCC GAT GAT CTG GCC GCA CAT GTC GTA CGC GAA CTG GTT GCA CGC AGC CCC AAA CTG GAC GTA<br>GCC GAT ATC GAC GAA AGC ATC TTT GGC AAT GCC AAC GGT GCT GGC GAA GAA AAC CGC AAT GTA GCG CGT<br>ATG GCT ACG TTA CTC GCG GGA TTG CCG ACT TCG CTC CCG GGA ACG ACC ATG AAC CGC CTT TGC GGT TCT<br>AGC TTG GAT GCG AGT ATT GCC GCC TCA CGC CAG ATT GCC ACA GGC GAT GCG GAC CTT GTT CTG GTG GGT<br>GGC GTG GAA AGC ATG TCC CGT GCG CCA TGG GTC CTG CCT AAA ACC GAA CGT CCA TTT CCG ATG TCG AAC<br>CTG GAA TTA GCG AAT ACG ACG CTT GGA TGG CGT CTG GTG AAT CCG GCA ATG CCA GGG GAA TGG ACT GTG<br>TCG TTA GGC GAA GCG ACC GAA CAA CTG CGC GAA AAG CAC GGT ATC TCG CGC GAG GAT CAG GAC GAG TTC<br>AGT GCT GCG TCA CAT CAG CGT GCA GCA GCA GCC TGG CAA GCG GGC AAA TAC GAC AAC CTC GTG GTT CCT<br>GTC CCG CCG GCA AAC AAA CGC GGC ACG GAA GTG ACA CGC GAT GAA ACG ATT CGC GCC GAT AGC ACT GCG<br>CAA ACC CTG TCC AAA TTA CGT ACC GTC TTT CGC ACC GGC GAA AAC GCG ACT GTC ACC GCT GGG AAT GCC<br>TCT CCA ATG AGT GAT GGT GCG AGC GCT GCT TTC ATT GGG TCA GAA CGT GGC GGT GAA CTG TTA GGC GCC<br>GCG CCT ATT GCT CGC ATC GCG TCT AAT GGC GCC GCT GCG CTT GAT CCG CAG TTC TTT GGG TTT GCC CCG<br>GTT GAG GCA GCG AAC AAA GCA CTG GCG AAA GCA GGA CTG AAG TGG TCC GAC ATT GCT GCG GTG GAG CTG<br>AAC GAG GCC TTT GCA GCC CAG TCT CTC GCG TGT ATC CGG GCG TGG GAT ATT GAT CCG GCG ATT GTG AAT<br>GCA TGG GGC GGT GCA ATC TCC ATT GGC CAT CCG TTG GGT GCT AGC GGG CTG CGT ATT CTG GGC ACA GTT<br>GCG CGT CGC CTG GCG GAA TCA GGG GAG CGG TAT GGT CTG GCC GCC ATC TGC ATT GGC GTT GGT CAA GGC<br>TTG GCT GTT GTA GTG GAG AAC ATC AAT GCC ACC AAA taa |

FIG. 19L

| SEQ ID NO | Nucleic acid sequence |
|---|---|
| *58* | ATGCGTGAAGCCTTTATTTGTGACGGAATTCGTACGCCAATTGGTCGCTACGGCGGGGCATTATCAAGTG<br>TTCGGGCTGATGATCTGGCTGCTATCCCTTTGCGGGAACTGCTGGTGCGAAACCCGCGTCTCGATGCGGA<br>GTGTATCGATGATGTGATCCTCGGCTGTGCTAATCAGGCGGGAGAAGATAACCGTAACGTAGCCCGGATG<br>GCGACTTTACTGGCGGGGCTGCCGCAGAGTGTTTCCGGCACAACCATTAACCGCTTGTGTGGTTCCGGGC<br>TGGACGCACTGGGGTTTGCCGCACGGGCGATTAAAGCGGGCGATGGCGATTTGCTGATCGCCGGTGGCGT<br>GGAGTCAATGTCACGGGCACCGTTTGTTATGGGCAAGGCAGCCAGTGCATTTTCTCGTCAGGCTGAGATG<br>TTCGATACCACTATTGGCTGGCGATTTGTGAACCCGCTCATGGCTCAGCAATTTGGAACTGACAGCATGC<br>CGGAAACGGCAGAGAATGTAGCTGAACTGTTAAAAATCTCACGAGAAGATCAAGATAGTTTTGCGCTACG<br>CAGTCAGCAACGTACGGCAAAAGCGCAATCCTCAGGCATTCTGGCTGAGGAGATTGTTCCGGTTGTGTTG<br>AAAAACAAGAAAGGTGTTGTAACAGAAATACAACATGATGAGCATCTGCGCCCGGAAACGACGCTGGAAC<br>AGTTACGTGGGTTAAAAGCACCATTTCGTGCCAATGGGGTGATTACCGCAGGCAATGCTTCCGGGGTGAA<br>TGACGGAGCCGCTGCGTTGATTATTGCCAGTGAACAGATGGCAGCAGCGCAAGGACTGACACCGCGGGCG<br>CGTATCGTAGCCATGGCAACCGCCGGGGTGGAACCGCGCCTGATGGGGCTTGGTCCGGTGCCTGCAACTC<br>GCCGGGTGCTGGAACGCGCAGGGCTGAGTATTCACGATATGGACGTGATTGAACTGAACGAAGCGTTCGC<br>GGCCCAGGCGTTGGGTGTACTACGCGAATTGGGGCTGCCTGATGATGCCCCACATGTTAACCCCAACGGA<br>GGCGCTATCGCCTTAGGCCATCCGTTGGGAATGAGTGGTGCCCGCCTGGCACTGGCTGCCAGCCATGAGC<br>TGCATCGGCGTAACGGTCGTTACGCATTGTGCACCATGTGCATCGGTGTCGGTCAGGGCATCGCCATGAT<br>TCTGGAGCGTGTTTGA |
| *59* | ATGACGCGTGAAGTGGTAGTGGTAAGCGGTGTCCGTACCGCGATCGGGACCTTTGGCGGC<br>AGCCTGAAGGATGTGGCACCGGCGGAGCTGGGCGCACTGGTGGTGCGCGAGGCGCTGGCG<br>CGCGCGCAGGTGTCGGGCGACGATGTCGGCCACGTGGTATTCGGCAACGTGATCCAGACC<br>GAGCCGCGCGACATGTATCTGGGCCGCGTCGCGGCCGTCAACGGCGGGGTGACGATCAAC<br>GCCCCCGCGCTGACCGTGAACCGCCTGTGCGGCTCGGGCCTGCAGGCCATTGTCAGCGCC<br>GCGCAGACCATCCTGCTGGGCGATACCGACGTCGCCATCGGCGGCGGCGCGGAAAGCATG<br>AGCCGCGCACCGTACCTGGCGCCGGCAGCGCGCTGGGGCGCACGCATGGGCGACGCCGGC<br>CTGGTCGACATGATGCTGGGTGCGCTGCACGATCCCTTCCATCGCATCCACATGGGCGTG<br>ACCGCCGAGAATGTCGCCAAGGAATACGACATCTCGCGCGCGCAGCAGGACGAGGCCGCG<br>CTGGAATCGCACCGCCGCGCTTCGGCAGCGATCAAGGCCGGCTACTTCAAGGACCAGATC<br>GTCCCGGTGGTGAGCAAGGGCCGCAAGGGCGACGTGACCTTCGACACCGACGAGCACGTG<br>CGCCATGACGCCACCATCGACGACATGACCAAGCTCAGGCCGGTCTTCGTCAAGGAAAAC<br>GGCACGGTCACGGCCGGCAATGCCTCGGGCCTGAACGACGCCGCCGCCGCGGTGGTGATG<br>ATGGAGCGCGCCGAAGCCGAGCGCCGCGGCCTGAAGCCGCTGGCCCGCCTGGTGTCGTAC<br>GGCCATGCCGGCGTGGACCCGAAGGCCATGGGCATCGGCCCGGTGCCGGCGACGAAGATC<br>GCGCTGGAGCGCGCCGGCCTGCAGGTGTCGGACCTGGACGTGATCGAAGCCAACGAAGCC<br>TTTGCCGCACAGGCGTGCGCCGTGACCAAGGCGCTCGGTCTGGACCCGGCCAAGGTTAAC<br>CCGAACGGCTCGGGCATCTCGCTGGGCCACCCGATCGGCGCCACCGGTGCCCTGATCACG<br>GTGAAGGCGCTGCATGAGCTGAACCGCGTGCAGGGCCGCTACGCGCTGGTGACGATGTGC<br>ATCGGCGGCGGGCAGGGCATTGCCGCCATCTTCGAGCGTATCTGA |

FIG. 19M

| SEQ ID NO | Nucleic acid sequence |
|---|---|
| 60 | ATG GCG CAG TTT GTC ACT GCT CAG GAA GCC GTT AAA CAC ATC CCG AAT GGC AGC CGT GTG GTG CTT GCG<br>CAT TCT ACA GGA GAA CCG CGT ACT CTG GTG AAG GCA ATG GTT GAA AAC TAC GAG CAG TAT AAA GAC GTC<br>GAG GTT TGC CAC ATG CTG GGC CTG GGA CCT TAC GAA TAC ACC AAT CCG GAG ATG AAA GGG CAT CTG TGG<br>CAC AAC TCG CTC TTT ATG GGC CCA GGT GGA CGG AAA GCC TTT AAC GAA AAT CGC CTT GAC TTT ACG CCA<br>GGG TAC TTC TGC GAT AGC ATC AAA TTC TTT CGT GAG GGC TAT CTG CCC GTT GAT GTG CTG ATG ATG ACC<br>GTA TCG CCT CCA GAT AAA CAT GGG TAT GTG ACG TGT GGG ATT ACG TGC GAT TTC ACT ATG CCA GCA TTT<br>GAA TGC GCC AAA ATG GTC ATC GTC CAG GTG AAC AAG AAT ATG CCG CGC ACG TTC GGT CAA ACC GCA ATC<br>CAC CTG GAC GAC ATC GAT TTC GCG GTA GAA GCA GAT GAT CCG CTG TAT GGC AGT GTA CCG GGT GAA TTG<br>ACA GAC ATT GAT CGC AAA ATT GGT GAA CAT TGT GCC TCG TTA ATC AAC GAT GGC GCT TGT CTG CAA TTA<br>GGG ATT GGC GGC ATT CCG AAT GCC GTC TTG ACC TAT CTC ACC GAA AAA AAC GAT ATG GGC ATT CAT TCC<br>GAG ATG CTC TCT GAT GGC ATT CTG CAG CTG ATT AAA GCC GGC AAC ATC AAC AAT AGC AAG AAA CAG ATT<br>CAC GTG GGT AAA TCA GCG GTT ACC TTC TTG AAC GGT AGT CAG GAA CTG TAC GAT TAT GTG GAC GAT AAT<br>CCG AGC GTA GAA TTT TAT CCG GTG GAT TAC ATC AAC GAC CCC TAC GTT ATT GGC AAG AAC GAC AAT ATG<br>GTG TCC GTT AAT TCA GCG TTA TCG GTG GAT CTG ATG GGG CAA ATT GTT GCA GAT AAC CTG AGT GCG ACG<br>CGC CAG ATC TCT GGT GCT GGT GGT TTC GTA GAC TTT GTC CGT GGA GCC ACC ATC TCA AAA GGC GGC ATC<br>AGC ATT GTG GCT ATG CCT AGC ACT GCG GCT GGT GGT AAA GCG AGT CGG ATT GAA ATG ATG TTT GAT GCC<br>GGT CGC CCG ATT ACC CTG ACA CGC TTT GAG AGC TTC TAT GTT GTC ACG GAA TAC GGC ATT GCG AAA ATG<br>CGC GGT AAT TCC TTA CGT ACC CGT GCA CGC CAA CTT ATC GAA ATT GCG CAT CCG GAT TTT CGT GAC GAA<br>ATG AAA GAG TTC TAT GAA AAG CGC TTT GGC GAG AAA TAT taa |

METHODS AND MATERIALS FOR PRODUCING 5 AND 7-CARBON MONOMERS

CROSS-REFERENCE

This application is a continuation of U.S. application Ser. No. 16/373,493, filed Apr. 2, 2019, which is a continuation of U.S. application Ser. No. 15/348,370, filed Nov. 10, 2016, which claims the benefit of U.S. Provisional Application No. 62/255,303, filed Nov. 13, 2015, all of which are incorporated herein by reference.

SEQUENCE LISTING

The instant application contains a Sequence Listing which has been filed electronically in ASCII format and is hereby incorporated by reference in its entirety. Said ASCII copy, created on Dec. 22, 2016, is named 12444_0617-00000_SL.txt and is 212,419 bytes in size.

TECHNICAL FIELD

This invention provides materials and methods for biosynthesizing 5 carbon and 7 carbon monomers. For example, the invention provides 3-oxo-7-hydroxyheptanoyl-CoA using a β-ketothiolase, and enzymatically converting 3-oxo-7-hydroxyheptanoyl-CoA to 7-hydroxyheptanoic acid using one or more of an isolated 3-hydroxyacyl-CoA dehydrogenase, a 3-oxoacyl-CoA reductase, an enoyl-CoA hydratase, a trans-2-enoyl-CoA reductase, and a thioesterase, or using host having at least one exogenous nucleic acid capable of making one or more of such enzymes. This invention also provides methods for converting 7-hydroxyheptanoic acid to one or more of pimelic acid, 7-aminoheptanoic acid, heptamethylenediamine, and 1,7-heptanediol using one or more isolated enzymes such as dehydrogenases, reductases, hydratases, thioesterases, monooxygenases, and transaminases or using host cells expressing one or more such enzymes.

BACKGROUND

Nylons are polyamides which are generally synthesized by the condensation polymerization of a diamine with a dicarboxylic acid. Similarly, Nylons also may be produced by the condensation polymerization of lactams. Nylon 7 is produced by polymerisation of 7-aminoheptanoic acid, whereas Nylon 7,7 is produced by condensation polymerisation of pimelic acid and heptamethylenediamine. No economically viable petrochemical routes exist for producing the monomers for Nylon 7 and Nylon 7,7.

Given that there are no economically viable petrochemical monomer feedstocks, biotechnology offers an alternative approach via biocatalysis. Biocatalysis is the use of biological catalysts, such as enzymes, to perform biochemical transformations of chemical compounds.

Both bioderived feedstocks and petrochemical feedstocks can be viable starting materials for the biocatalysis processes.

SUMMARY

Accordingly, against this background, it is clear that there is a need for sustainable methods for producing one or more of pimelic acid, 7-hydroxyheptanoic acid, 7-aminoheptanoic acid, heptamethylenediamine, and 1,7-heptanediol or derivatives thereof, wherein the methods are biocatalyst based. This document is based at least in part on the discovery that it is possible to construct biochemical pathways for using, inter alia, a β-ketothiolase to produce, for example, 7-hydroxyheptanoate, which can be converted in one or more enzymatic steps to pimelic acid, 7-aminoheptanoic acid, heptamethylenediamine, or 1,7-heptanediol. "Pimelic acid" and "pimelate," "7-hydroxyheptanoic acid" and "7-hydroxyheptanoate," and "7-aminoheptanoic acid" and "7-aminoheptanoate" are used interchangeably herein to refer to the compound in any of its neutral or ionized forms, including any salt forms thereof. It is understood by those skilled in the art that the specific form will depend on inter alia pH.

For compounds containing carboxylic acid groups such as organic monoacids, hydroxyacids, aminoacids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as but not limited to organic amines, aminoacids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid Acceptable inorganic bases include aluminum hydroxide, calcium hydroxide, potassium hydroxide, sodium carbonate, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

In the face of the optimality principle, it surprisingly has been discovered that appropriate non-natural metabolic pathways, feedstocks, cells (hosts or microorganisms), attenuation(s) to a cell's biochemical network, and/or cultivation strategies may be combined to efficiently produce 7-hydroxyheptanoate as a C7 (7-carbon) building block, or convert 7-hydroxyheptanoate to other C7 building blocks such as pimelic acid, 7-aminoheptanoic acid, heptamethylenediamine, or 1,7-heptanediol.

In some embodiments, a terminal carboxyl group can be enzymatically formed using a thioesterase, an aldehyde dehydrogenase, a 6-oxohexanoate dehydrogenase, a 7-oxoheptanoate dehydrogenase, or a monooxgenase (e.g., in combination with an oxidoreductase and ferredoxin). See FIG. 1 and FIG. 2.

In some embodiments, a terminal amine group can be enzymatically formed using a ω-transaminase or a deacylase. See FIG. 4. The ω-transaminase can have at least 70% sequence identity to any one of the amino acid sequences set forth in SEQ ID NOs.: 7-12.

In some embodiments, a terminal hydroxyl group can be enzymatically formed using an alcohol dehydrogenase. See FIG. 1 and FIG. 5.

In one aspect, this document features a method of producing 3-oxo-7-hydroxyheptanoyl-CoA. The method includes enzymatically converting 5-hydroxypentanoyl-CoA to 3-oxo-7-hydroxyheptanoyl-CoA using a β-ketothiolase classified under EC. 2.3.1.- (e.g., EC 2.3.1.16 or EC 2.3.1.174). The β-ketothiolase can have at least 70% sequence identity to the amino acid sequence set forth in SEQ ID NO: 1 or SEQ ID NO: 13.

In one aspect, this document features a method of producing 3-oxo-7-hydroxyheptanoyl-CoA. The method includes enzymatically converting 5-hydroxypentanoyl-CoA to 3-oxo-7-hydroxyheptanoyl-CoA using a thiolase. The thiolase can have at least 70% sequence identity to the amino acid sequence set forth in any one of SEQ ID NOs: 15-36.

In one aspect, this document features a method of producing 5-hydroxypentanoyl-CoA. The method includes enzymatically converting 5-hydroxypentanoate to 5-hydroxypentanoyl-CoA using a 5-hydroxyvalerate CoA transferase. The 5-hydroxyvalerate CoA transferase can have at least 70% sequence identity to the amino acid sequence set forth in SEQ ID NO: 37.

In one aspect, this document features a method of producing 3-oxo-7-hydroxyheptanoyl-CoA from 5-hydroxypentanoate in a two-step enzymatic reaction catalyzed by a 5-hydroxyvalerate CoA transferase and a thiolase. The 5-hydroxyvalerate CoA transferase can have at least 70% sequence identity to the amino acid sequence set forth in SEQ ID NO: 37. The thiolase can have at least 70% sequence identity to the amino acid sequence set forth in any one of SEQ ID NOs: 15-36.

In one aspect, this document features a method for enzymatically converting 3-oxo-7-hydroxyheptanoyl-CoA to 7-hydroxyheptanoate using a 3-hydroxyacyl-CoA dehydrogenase or a 3-oxoacyl-CoA reductase, an enoyl-CoA hydratase, a trans-2-enoyl-CoA reductase, and a thioesterase or a CoA transferase. The 3-hydroxyacyl-CoA dehydrogenase or 3-oxoacyl-CoA reductase can be classified under EC 1.1.1.35, EC 1.1.1.36, EC 1.1.1.100, or EC 1.1.1.157. The enoyl-CoA hydratase can be classified under EC 4.2.1.17 or EC 4.2.1.119. The trans-2-enoyl-CoA reductase can be classified under EC 1.3.1.38, EC 1.3.1.44, or EC 1.3.1.8.

In one aspect, this document features a method for biosynthesizing 7-hydroxyheptanoate. The method includes enzymatically synthesizing 3-oxo-7-hydroxyheptanoyl-CoA from 5-hydroxypentanoyl-CoA using a β-ketothiolase classified under EC. 2.3.1.- (e.g., EC 2.3.1.16 or EC 2.3.1.174) and enzymatically converting 3-oxo-7-hydroxyheptanoyl-CoA to 7-hydroxyheptanoate. The β-ketothiolase can have at least 70% sequence identity to the amino acid sequence set forth in SEQ ID NO: 1 or SEQ ID NO: 13. 3-oxo-7-hydroxyheptanoyl-CoA can be converted to 3-hydroxy-7-hydroxyheptanoyl-CoA using a 3-hydroxyacyl-CoA dehydrogenase or a 3-oxoacyl-CoA reductase, 3-hydroxy-7-hydroxyheptanoyl-CoA can be converted to 2,3-dehydro-7-hydroxyheptanoyl-CoA using an enoyl-CoA hydratase, 2,3-dehydro-7-hydroxyheptanoyl-CoA can be converted to 7-hydroxyheptanoyl-CoA using a trans-2-enoyl-CoA reductase, and 7-hydroxyheptanoyl-CoA can be converted to 7-hydroxyheptanoate using a thioesterase or a CoA transferase.

Any of the methods further can include enzymatically converting 7-hydroxyheptanoate to pimelic acid, 7-aminoheptanoate, heptamethylenediamine, or 1,7-heptanediol in one or more steps.

For example, 7-hydroxyheptanoate can be enzymatically converted to pimelic acid using one or more of a monooxygenase, an alcohol dehydrogenase, a 4-hydroxybutyrate dehydrogenase, a 5-hydroxyvalerate dehydrogenase, a 6-hydroxyhexanoate dehydrogenase, a 7-oxoheptanoate dehydrogenase, a 6-oxohexanoate dehydrogenase, a 5-oxovalerate dehydrogenase, or an aldehyde dehydrogenase.

For example, 7-hydroxyheptanoate can be converted to 7-aminoheptanoate using one or more of an alcohol dehydrogenase, a 6-hydroxyhexanoate dehydrogenase, a 5-hydroxypentanoate dehydrogenase, a 4-hydroxybutyrate dehydrogenase, and a ω-transaminase. The ω-transaminase can have at least 70% sequence identity to any one of the amino acid sequences set forth in SEQ ID NOs.: 7-12.

For example, 7-hydroxyheptanoate can be converted to heptamethylenediamine using one or more of a carboxylate reductase, a ω-transaminase, an alcohol dehydrogenase, an N-acetyltransferase, and an acetylputrescine deacylase. The ω-transaminase can have at least 70% sequence identity to any one of the amino acid sequences set forth in SEQ ID NOs.: 7-12.

For example, 7-hydroxyheptanoate can be converted to 1,7-heptanediol using a carboxylate reductase and an alcohol dehydrogenase. The carboxylate reductase can have at least 70% sequence identity to any one of the amino acid sequences set forth in SEQ ID NOs.: 2-6.

In any of the methods, 5-hydroxypentanoyl-CoA can be enzymatically produced from 2-oxoadipate. For example, 5-hydroxypentanoyl-CoA can be enzymatically produced from 2-oxoadipate using one or more of a α-aminotransaminase; a 2-oxoadipate decarboxylase; a branch chain decarboxylase; a glutamate decarboxylase; a ω-transaminase; a CoA transferase, a CoA ligase, and an alcohol dehydrogenase.

In any of the methods, 5-hydroxypentanoyl-CoA can be enzymatically produced from malonyl-CoA. For example, 5-hydroxypentanoyl-CoA can be enzymatically produced from malonyl-CoA using one or more of a malonyl-CoA reductase; a 3-hydroxypropionate dehydrogenase; a 3-hydroxypropionyl-CoA synthase; a CoA-transferase; a β-ketothiolase; a 3-hydroxyacyl-CoA dehydrogenase; a 3-oxoacyl-CoA reductase, an enoyl-CoA hydratase, and a trans-2-enoyl-CoA reductase.

In any of the methods described herein, pimelic acid can be produced by forming the second terminal functional group in pimelate semialdehyde (also known as 7-oxoheptanoate) using (i) an aldehyde dehydrogenase classified under EC 1.2.1.3, (ii) a 7-oxohexanoate dehydrogenase classified under EC 1.2.1.63 such as that encoded by ChnE or a 7-oxoheptanoate dehydrogenase classified under EC 1.2.1.- (e.g., the gene product of ThnG), or iii) a monooxygenase in the cytochrome P450 family.

In any of the methods described herein, 7-aminoheptanoic acid can be produced by forming the second terminal functional group in pimelate semialdehyde using a ω-transaminase classified under EC 2.6.1.18, EC 2.6.1.19, EC 2.6.1.29, EC 2.6.1.48, or EC 2.6.1.82.

In any of the methods described herein, heptamethylenediamine can be produced by forming a second terminal functional group in (i) 7-aminoheptanal using a ω-transaminase classified under EC 2.6.1.18, EC 2.6.1.19, EC 2.6.1.29, EC 2.6.1.48 or EC 2.6.1.82, or in (ii) N7-acetyl-1,7-diaminoheptane using a deacylase classified, for example, under EC 3.5.1.17.

In any of the methods described herein, 1,7-heptanediol can be produced by forming the second terminal functional group in 7-hydroxyheptanal using an alcohol dehydrogenase classified under EC 1.1.1.- (e.g., EC 1.1.1.1, 1.1.1.2, 1.1.1.21, or 1.1.1.184) such as that encoded by YMR318C, YqhD, or CAA81612.1.

In some embodiments, the biological feedstock can be or can derive from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock can be or can derive from natural gas, syngas, $CO_2/H_2$, methanol, ethanol, benzoate, non-volatile residue (NVR) or a caustic wash waste stream from cycloheptane oxidation processes, or terephthalic acid/isophthalic acid mixture waste streams.

In some embodiments, the host microorganism's tolerance to high concentrations of one or more C7 building blocks is improved through continuous cultivation in a selective environment.

In some embodiments, the host microorganism's biochemical network is attenuated or augmented to (1) ensure the intracellular availability of acetyl-CoA and 5-hydroxypentanoyl-CoA, (2) create an NADH or NADPH imbalance that may only be balanced via the formation of one or more C7 building blocks, (3) prevent degradation of central metabolites, central precursors leading to and including C7 building blocks, and/or (4) ensure efficient efflux from the cell.

In some embodiments, a cultivation strategy is used to achieve anaerobic, micro-aerobic, or aerobic cultivation conditions.

In some embodiments, the cultivation strategy includes limiting nutrients, such as limiting nitrogen, phosphate or oxygen.

In some embodiments, one or more C7 building blocks are produced by a single type of microorganism, e.g., a recombinant host containing one or more exogenous nucleic acids, using, for example, a fermentation strategy.

In some embodiments, one or more C7 building blocks are produced by a single type of microorganism having one or more exogenous nucleic acids which encode a polypeptide having a β-ketothiolase activity, (ii) a thioesterase activity or a CoA transferase activity, and one or more of (iii) a 3-hydroxyacyl-CoA dehydrogenase activity or a 3-oxoacyl-CoA reductase activity, (iv) an enoyl-CoA hydratase activity, and (v) a trans-2-enoyl-CoA reductase activity, using, for example, a fermentation strategy.

In another aspect, this document features a recombinant host that includes at least one exogenous nucleic acid encoding (i) a β-ketothiolase, (ii) a thioesterase or a CoA transferase, and one or more of (iii) a 3-hydroxyacyl-CoA dehydrogenase or a 3-oxoacyl-CoA reductase, (iv) an enoyl-CoA hydratase, and (v) a trans-2-enoyl-CoA reductase, the host producing 7-hydroxyheptanoate.

A host producing 7-hydroxyheptanoate further can include one or more of the following exogenous enzymes: a monooxygenase, an alcohol dehydrogenase, a 4-hydroxybutyrate dehydrogenase, a 5-hydroxyvalerate dehydrogenase, a 6-hydroxyhexanoate dehydrogenase, a 7-oxoheptanoate dehydrogenase, a 6-oxohexanoate dehydrogenase, a 5-oxovalerate dehydrogenase, or an aldehyde dehydrogenase, the host further producing pimelic acid.

A host producing 7-hydroxyheptanoate further can include one or more of the following exogenous enzymes: a monooxygenase, a transaminase, a 6-hydroxyhexanoate dehydrogenase, a 4-hydroxybutyrate dehydrogenase, a 5-hydroxypentanoate dehydrogenase, and an alcohol dehydrogenase, the host further producing 7-aminoheptanoate.

A host producing 7-hydroxyheptanoate further can include one or more of the following exogenous enzymes: a carboxylate reductase, a ω-transaminase, a deacylase, a N-acetyl transferase, or an alcohol dehydrogenase, said host further producing heptamethylenediamine.

A host producing 7-hydroxyheptanoate further can include an exogenous carboxylate reductase and an exogenous alcohol dehydrogenase, the host further producing 1,7-heptanediol.

Any of the recombinant hosts described herein further can include one or more of the following exogenous enzymes: an alpha-aminotransaminase; a 2-oxoadipate decarboxylase; a branch-chain decarboxylase; a glutamate decarboxylase; a ω-transaminase; a CoA-ligase; a CoA-transferase; and an alcohol dehydrogenase.

Any of the recombinant hosts described herein further can include one or more of the following exogenous enzymes: a malonyl-CoA reductase; a 3-hydroxypropionate dehydrogenase; a 3-hydroxypropionyl-CoA synthase; a CoA-transferase; a β-ketothiolase; a 3-hydroxyacyl-CoA dehydrogenase; a 3-oxoacyl-CoA reductase; an enoyl-CoA hydratase; and a trans-2-enoyl-CoA reductase.

Any of the recombinant hosts can be a prokaryote such as a prokaryote from a genus selected from the group consisting of *Escherichia; Clostridia; Corynebacteria; Cupriavidus; Pseudomonas; Delftia; Bacilluss; Lactobacillus; Lactococcus*; and *Rhodococcus*. For example, the prokaryote can be selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans. Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*. Such prokaryotes also can be sources of genes for constructing recombinant host cells described herein that are capable of producing C7 building blocks.

Any of the recombinant hosts can be a eukaryote such as a eukaryote from a genus selected from the group consisting of *Aspergillus, Saccharomyces, Pichia, Yarrowia, Issatchenkia, Debaryomyces, Arxula*, and *Kluyveromyces*. For example, the eukaryote can be selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*. Such eukaryotes also can be sources of genes for constructing recombinant host cells described herein that are capable of producing C7 building blocks.

Any of the recombinant hosts described herein further can include attenuation of one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase, an acyl-CoA dehydrogenase accepting C7 building blocks and central precursors as substrates, a butyryl-CoA dehydrogenase, or an adipyl-CoA synthetase.

Any of the recombinant hosts described herein further can overexpress one or more genes encoding: an acetyl-CoA synthetase; a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

This document also features a biobased polymer comprising the bioderived pimelic acid, 7-aminoheptanoic acid, heptamethylenediamine, or 1,7-heptanediol.

This document also features a biobased resin comprising the bioderived pimelic acid, 7-aminoheptanoic acid, heptamethylenediamine, or 1,7-heptanediol, as well as a molded product obtained by molding a biobased resin.

In another aspect, this document features a process for producing a biobased polymer that includes chemically reacting the bioderived pimelic acid, 7-aminoheptanoic acid, heptamethylenediamine, or 1,7-heptanediol, with itself or another compound in a polymer producing reaction.

In another aspect, this document features a process for producing a biobased resin that includes chemically reacting the bioderived pimelic acid, 7-aminoheptanoic acid, heptamethylenediamine, or 1,7-heptanediol, with itself or another compound in a resin producing reaction.

Also, described herein is a biochemical network comprising a polypeptide having β-ketothiolase activity, wherein the polypeptide having β-ketothiolase activity enzymatically converts 5-hydroxypentanoyl-CoA to 3-oxo-7-hydroxyheptanoyl-CoA.

The biochemical network can further include a polypeptide having 3-hydroxyacyl-CoA dehydrogenase or a polypeptide having 3-oxoacyl-CoA reductase activity, a polypeptide having enoyl-CoA hydratase activity, a polypeptide having thioesterase activity, a polypeptide having CoA transferase, and a polypeptide having trans-2-enoyl-CoA reductase activity. In one aspect, the biochemical network is a non-naturally occurring biochemical network comprising at least one substrate of FIG. 1, at least one exogenous nucleic acid encoding a polypeptide having the activity of at least one enzyme of FIG. 1 and at least one product of FIG. 1. In another aspect of the invention, the biochemical network is a non-naturally occurring biochemical network comprising a 3-hydroxypropionyl-CoA, an exogenous nucleic acid encoding a polypeptide having the activity of a β-ketothiolase classified under EC. 2.3.1 and a 3-hydroxypropionyl-CoA.

In one aspect, this document features a method for producing a bioderived five and seven carbon compounds. The method for producing a bioderived five and seven carbon compounds can include culturing or growing a recombinant host as described herein under conditions and for a sufficient period of time to produce the bioderived five and seven carbon compounds, wherein, optionally, the bioderived carbon compound is pimelic acid, 7-aminoheptanoic acid, heptamethylenediamine, or 1,7-heptanediol.

In one aspect, this document features composition comprising a bioderived five and seven carbon compounds as described herein and a compound other than the bioderived five and seven carbon compound, wherein the bioderived carbon compound is pimelic acid, 7-aminoheptanoic acid, heptamethylenediamine, and 1,7-heptanediol. For example, the bioderived four carbon compound is a cellular portion of a host cell or an organism.

In one aspect, this document features nucleic acid constructs or expression vectors comprising a polynucleotide encoding a polypeptide having β-ketothiolase activity, wherein the polynucleotide is operably linked to one or more heterologous control sequences that direct production of the polypeptide and wherein the polypeptide having β-ketothiolase activity is selected from the group consisting of: (a) a polypeptide having at least 70% sequence identity to the polypeptide of SEQ ID NOs: 1 or 13; a polynucleotide encoding a polypeptide having ω-transaminase activity, wherein the polynucleotide is operably linked to one or more heterologous control sequences that direct production of the polypeptide and wherein the polypeptide having ω-transaminase activity is selected from the group consisting of: (a) a polypeptide having at least 70% sequence identity to the polypeptide of SEQ ID NOs: 7-12. Further, this document features compositions comprising the nucleic acid construct or expression vector as described above.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the application, including the written description and drawings and the claims. The word "comprising" in the claims may be replaced by "consisting essentially of" or with "consisting of," according to standard practice in patent law.

DESCRIPTION OF DRAWINGS

FIG. 6A contains the amino acid sequences of a *Cupriavidus necator* β-ketothiolase (see GenBank Accession No. AAC38322.1, SEQ ID NO: 1) and a *Mycobacterium marinum* carboxylate reductase (see Genbank Accession No. ACC40567.1, SEQ ID NO: 2). FIG. 6B contains the amino acid sequence of a *Mycobacterium smegmatis* carboxylate reductase (see Genbank Accession No. ABK71854.1, SEQ ID NO: 3). FIG. 6C contains the amino acid sequence of a *Segniliparus rugosus* carboxylate reductase (see Genbank Accession No. EFV11917.1, SEQ ID NO: 4). FIG. 6D contains the amino acid sequence of a *Mycobacterium massiliense* carboxylate reductase (see Genbank Accession No. EIV11143.1, SEQ ID NO: 5). FIG. 6E contains the amino acid sequences of a *Segniliparus rotundus* carboxylate reductase (see Genbank Accession No. ADG98140.1, SEQ ID NO: 6), a *Chromobacterium violaceum* ω-transaminase (see Genbank Accession No. AAQ59697.1, SEQ ID NO: 7), and a *Pseudomonas aeruginosa* ω-transaminase (see Genbank Accession No. AAG08191.1, SEQ ID NO: 8). FIG. 6F contains the amino acid sequences of a *Pseudomonas syringae* ω-transaminase (see Genbank Accession No. AAY39893.1, SEQ ID NO: 9), a *Rhodobacter sphaeroides* ω-transaminase (see Genbank Accession No. ABA81135.1, SEQ ID NO: 10), an *Escherichia coli* ω-transaminase (see Genbank Accession No. AAA57874.1, SEQ ID NO: 11), and a *Vibrio fluvialis* ω-transaminase (see Genbank Accession No. AEA39183.1, SEQ ID NO: 12). FIG. 6G contains the amino acid sequences of an *Escherichia coli* β-ketothiolase (see GenBank Accession No. AAC74479.1, SEQ ID NO: 13), a *Mycobacterium smegmatis* carboxylate reductase (see Genbank Accession No. ABK75684.1, SEQ ID NO: 14), and a *Pseudomonas putida* thiolase (see Genbank Accession No. AAN70209.2, SEQ ID NO: 15). FIG. 6H contains the amino acid sequences of a *Sphingomonas wittichii* thiolase (see Genbank Accession No. ABQ69245.1, SEQ ID NO: 16), a *Pseudomonas reinekei* thiolase (see Genbank Accession No. ACZ63623.1, SEQ ID NO: 17), a *Pseudomonas putida* thiolase (see Genbank Accession No. AAA85138.1, SEQ ID NO: 18), a *Burkholderia xenovorans* thiolase (see Genbank Accession No. ABE28745.1, SEQ ID NO: 19), and a *Burkholderia xenovorans* thiolase (see Genbank Accession No. ABE33819.1, SEQ ID NO: 20). FIG. 6I contains the amino acid sequences of a *Rhodococcus jostii* thiolase (see Genbank Accession No. ABG94668.1, SEQ ID NO: 21), a *Bdellovibrio bacteriovorus* thiolase (see Genbank Accession No. CAE79693.1, SEQ ID NO: 22), a *Cronobacter turicensis* thiolase (see Genbank Accession No. CBA32535.1, SEQ ID NO: 23), and an *Arthrobacter* sp. thiolase (see Genbank Accession No. ABK03524.1, SEQ ID NO: 24). FIG. 6J contains the amino acid sequences of a *Caulobacter segnis* thiolase (see Genbank Accession No. ADG08907.1, SEQ ID NO: 25), a *Dinoroseobacter shibae* thiolase (see Genbank Accession No. ABV92581.1, SEQ ID NO: 26), a *Burkholderia xenovorans* thiolase (see Genbank Accession No. ABE36495.1, SEQ ID NO: 27), a *Geobacillus kaustophilus* thiolase (see Genbank Accession No. BAD75605.1, SEQ ID NO: 28), and a *Beijerinckia indica* thiolase (see Genbank Accession No. ACB95386.1, SEQ ID NO: 29). FIG. 6K contains the amino acid sequences of a *Citrobacter freundii* thiolase (see Genbank Accession No. EKS55037.1, SEQ ID NO: 30), a *Cupriavidus necator* thiolase (see Genbank Accession No. AEI75849.1, SEQ ID NO: 31), a *Gordonia bronchialis* thiolase (see Genbank Accession No. ACY20886.1, SEQ ID NO: 32), a *Burkholderia* sp. thiolase (see Genbank Accession No. ADG18081.1, SEQ ID NO: 33), and a *Glutamicibacter arilaitensis* thiolase (see Genbank Accession No. CBT74677.1, SEQ ID NO: 34). FIG. 6L contains the amino acid sequences of an *Escherichia coli* thiolase (see Genbank Accession No. AAC74479.1, SEQ ID NO: 35), a *Cupriavidus necator* thiolase (see Genbank Accession No. AAC38322.1, SEQ ID NO: 36), and a *Clostridium viride* 5-hydroxyvalerate CoA transferase (see NCBI Reference Sequence: NZ_KK211198.1, SEQ ID NO: 37).

FIG. 19A contains a nucleic acid sequence (SEQ ID NO: 38) encoding a *Pseudomonas putida* thiolase and a nucleic acid sequence (SEQ ID NO: 39) encoding a *Sphingomonas wittichii* thiolase. FIG. 19B contains a nucleic acid sequence (SEQ ID NO: 40) encoding a *Pseudomonas reinekei* thiolase and a nucleic acid sequence (SEQ ID NO: 41) encoding a *Pseudomonas putida* thiolase. FIG. 19C contains a nucleic acid sequence (SEQ ID NO: 42) encoding a *Burkholderia xenovorans* thiolase and a nucleic acid sequence (SEQ ID NO: 43) encoding a *Burkholderia xenovorans* thiolase. FIG. 19D contains a nucleic acid sequence (SEQ ID NO: 44) encoding a *Rhodococcus jostii* thiolase and a nucleic acid sequence (SEQ ID NO: 45) encoding a *Bdellovibrio bacteriovorus* thiolase. FIG. 19E contains a nucleic acid sequence (SEQ ID NO: 46) encoding a *Cronobacter turicensis* thiolase. FIG. 19F contains a nucleic acid sequence (SEQ ID NO: 47) encoding an *Arthrobacter* sp. thiolase. FIG. 19G contains a nucleic acid sequence (SEQ ID NO: 48) encoding a *Caulobacter segnis* thiolase and a nucleic acid sequence (SEQ ID NO: 49) encoding a *Dinoroseobacter shibae* thiolase. FIG. 19H contains a nucleic acid sequence (SEQ ID NO: 50) encoding a *Burkholderia xenovorans* thiolase and a nucleic acid sequence (SEQ ID NO: 51) encoding a *Geobacillus kaustophilus* thiolase. FIG. 19I contains a nucleic acid sequence (SEQ ID NO: 52) encoding a *Beijerinckia indica* thiolase and a nucleic acid sequence (SEQ ID NO: 53) encoding a *Citrobacter freundii* thiolase. FIG. 19J contains a nucleic acid sequence (SEQ ID NO: 54) encoding a *Cupriavidus necator* thiolase and a nucleic acid sequence (SEQ ID NO: 55) encoding a *Gordonia bronchialis* thiolase. FIG. 19K contains a nucleic acid sequence (SEQ ID NO: 56) encoding a *Burkholderia* sp. thiolase and a nucleic acid sequence (SEQ ID NO: 57) encoding a *Glutamicibacter arilaitensis* thiolase. FIG. 19L contains a nucleic acid sequence (SEQ ID NO: 58) encoding an *Escherichia coli* thiolase and a nucleic acid sequence (SEQ ID NO: 59) encoding a *Cupriavidus necator* thiolase. FIG. 19M contains a nucleic acid sequence (SEQ ID NO: 60) encoding a *Clostridium viride* 5-hydroxyvalerate CoA transferase.

DETAILED DESCRIPTION

Figure 1:
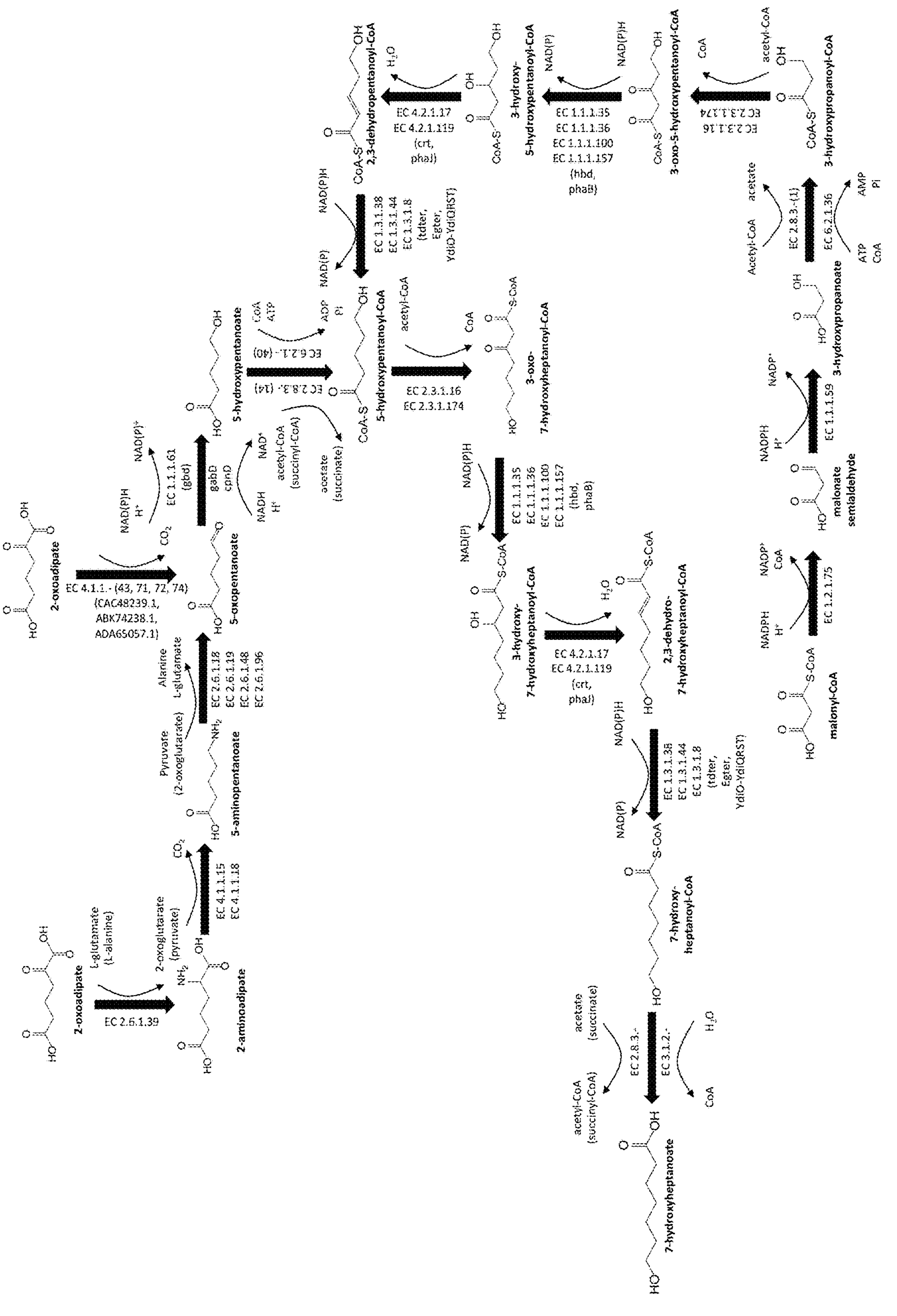
FIG. 1 is a schematic of exemplary biochemical pathways leading to 7-hydroxyheptanoate using 2-oxo-adipate and malonyl-CoA as central metabolites.

In general, this document provides enzymes, non-natural pathways, cultivation strategies, feedstocks, host microorganisms and attenuations to the host's biochemical network, for producing 7-hydroxyheptanoate or one or more of pimelic acid, 7-aminoheptanoic acid, heptamethylenediamine, or 1,7-heptanediol, all of which are referred to as C7 building blocks herein. As used herein, the term "central precursor" is used to denote any metabolite in any metabolic pathway shown herein leading to the synthesis of a C7 building block. The term "central metabolite" is used herein to denote a metabolite that is produced in all microorganisms to support growth.

Host microorganisms described herein can include endogenous pathways that can be manipulated such that 7-hydroxyheptanoate or one or more other C7 building blocks can be produced. In an endogenous pathway, the host microorganism naturally expresses all of the enzymes catalyzing the reactions within the pathway. In one aspect of the invention, a host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature, provided the nucleic acid as a whole does not exist in nature. For example, a nucleic acid molecule containing a genomic DNA sequence within an expression vector is a non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. Genomic DNA fragments produced by PCR or restriction endonuclease treatment as well as cDNAs are considered to be non-naturally-occurring nucleic acid since they exist as separate molecules not found in nature. Any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host in addition to a β-ketothiolase: a 3-hydroxyacyl-CoA dehydrogenase, a 3-oxoacyl-CoA reductase, an enoyl-CoA hydratase, a trans-2-enoyl-CoA reductase, a thioesterase, a CoA transferase, an aldehyde dehydrogenase, a monooxygenase, an alcohol dehydrogenase, a 7-oxoheptanoate dehydrogenase, a 7-oxoheptanoate dehydrogenase, a ω transaminase, a 6-hydroxyhexanoate dehydrogenase, a 4-hydroxybutyrate dehydrogenase, a 5-hydroxypentanoate dehydrogenase, a carboxylate reductase, a deacylase, an N-acetyl transferase, a ω-transaminase, or an amidohydrolase. In recombinant hosts expressing a carboxylate reductase, a phosphopantetheinyl transferase also can be expressed as it enhances activity of the carboxylate reductase. In recombinant hosts expressing a monooxygenase, an electron transfer chain protein such as an oxidoreductase or ferredoxin polypeptide also can be expressed.

For example, a recombinant host can include an exogenous β-ketothiolase and produce 3-oxo-7-hydroxyheptanoyl-CoA, which can be converted to 7-hydroxyheptanoate.

For example, a recombinant host can include an exogenous enzyme from the thiolase family and produce 3-oxo-7-hydroxyheptanoyl-CoA, which can be converted to 7-hydroxyheptanoate.

For example, a recombinant host can include an exogenous β-ketothiolase and an exogenous thioesterase or CoA-transferase, and one or more of the following exogenous enzymes: 3-hydroxyacyl-CoA dehydrogenase or a 3-oxoacyl-CoA reductase, an enoyl-CoA hydratase, and a trans-2-enoyl-CoA reductase, and produce 7-hydroxyheptanoate. For example, a recombinant host can include an exogenous β-ketothiolase, an exogenous thioesterase or CoA-transferase, an enoyl-CoA hydratase, an exogenous trans-2-enoyl-CoA reductase, and an exogenous 3-hydroxyacyl-CoA dehydrogenase or an exogenous 3-oxoacyl-CoA reductase, and produce 7-hydroxyheptanoate.

For example, a recombinant host producing 7-hydroxyheptanoate can include one or more of the following exogenous enzymes: a monooxygenase, an alcohol dehydrogenase, a 4-hydroxybutyrate dehydrogenase, a 5-hydroxypentanoate dehydrogenase, a 6-hydroxyhexanoate dehydrogenase, a 7-oxoheptanoate dehydrogenase, a 5-oxovalerate dehydrogenase, a 6-oxohexanoate dehydrogenase, or an aldehyde dehydrogenase, and further produce pimelic acid. For example, a recombinant host producing 7-hydroxyheptanoate can include an exogenous monooxygenase and produce pimelic acid. For example, a recombinant host producing 7-hydroxyheptanoate can include an exogenous 6-hydroxyhexanoate dehydrogenase and an aldehyde dehydrogenase and produce pimelic acid. For example, a recombinant host producing 7-hydroxyheptanoate can include an exogenous alcohol dehydrogenase and one of the following exogenous enzymes: a 5-oxovalerate dehydrogenase, a 6-oxohexanoate dehydrogenase, or a 7-oxoheptanoate dehydrogenase, and produce pimelic acid.

For example, a recombinant host producing 7-hydroxyheptanoate can include one or more of the following exogenous enzymes: an alcohol dehydrogenase, a 6-hydroxyhexanoate dehydrogenase, or a transaminase, and further produce 7-aminoheptanoate. For example, a recombinant host producing 7-hydroxyheptanoate can include an exogenous alcohol dehydrogenase and an exogenous transaminase and produce 7-aminoheptanoate. For example, a recombinant host producing 7-hydroxyheptanoate can include an exogenous 6-hydroxyhexanoate dehydrogenase and an exogenous transaminase and produce 7-aminoheptanoate.

For example, a recombinant host producing 7-hydroxyheptanoate can include one or more of the following exogenous enzymes: a carboxylate reductase, a ω-transaminase, a deacylase, an N-acetyl transferase, or an alcohol dehydrogenase, and produce heptamethylenediamine. For example, a recombinant host producing 7-hydroxyheptanoate can include an exogenous carboxylate reductase, an exogenous alcohol dehydrogenase, and one or more exogenous transaminases (e.g., one transaminase or two different transaminases), and produce heptamethylenediamine. For example, a recombinant host producing 7-hydroxyheptanoate can include an exogenous carboxylate reductase and one or more exogenous transaminases (e.g., one transaminase or two different transaminases) and produce heptamethylenediamine. For example, a recombinant host producing 7-hydroxyheptanoate can include an exogenous alcohol dehydrogenase, an exogenous carboxylate reductase, and one or more exogenous transaminases (e.g., one transaminase, or two or three different transaminases) and produce heptamethylenediamine. For example, a recombinant host producing 7-hydroxyheptanoate can include an exogenous alcohol dehydrogenase, an exogenous N-acetyl transferase, a carboxylate reductase, a deacylase, and one or more exogenous transaminases (e.g., one transaminase or two different transaminases) and produce heptamethylenediamine.

For example, a recombinant host producing 7-hydroxyheptanoate can include one or more of the following exogenous enzymes: a carboxylate reductase and an exogenous alcohol dehydrogenase, and further produce 1,7-heptanediol.

In any of the recombinant hosts, the recombinant host also can include one or more (e.g., one, two, three, or four) of the following exogenous enzymes used to convert 2-oxoadipate- to 5-hydroxypentanoyl-CoA: an alpha-aminotransaminase; a 2-oxoadipate decarboxylase; a branch-chain decarboxylase; a glutamate decarboxylase; a CoA-ligase; a CoA-transferase; a ω-transaminase; and an alcohol dehydrogenase. For example, a recombinant host can include an exogenous alpha-aminotransaminase; a glutamate decarboxylase; a CoA-ligase or a CoA-transferase; a ω-transaminase; and an alcohol dehydrogenase. For example, a recombinant host can include an exogenous 2-oxoadipate decarboxylase or a branch-chain decarboxylase; a CoA-ligase; a CoA-transferase; and an alcohol dehydrogenase.

In any of the recombinant hosts, the recombinant host also can include one or more (e.g., one, two, three, or four) of the following exogenous enzymes used to convert manonyl-CoA to 5-hydroxypentanoyl-CoA: a malonyl-CoA reductase; a 3-hydroxypropionate dehydrogenase; a 3-hydroxypropionyl-CoA synthase; a CoA-transferase; a β-ketothiolase; a 3-hydroxyacyl-CoA dehydrogenase; a 3-oxoacyl-CoA reductase; an enoyl-CoA hydratase; and a trans-2-enoyl-CoA reductase. For example, a recombinant host can include an exogenous malonyl-CoA reductase; a 3-hydroxypropionate dehydrogenase; a 3-hydroxypropionyl-CoA synthase; a CoA-transferase; a β-ketothiolase; a 3-hydroxyacyl-CoA dehydrogenase; a 3-oxoacyl-CoA reductase; an enoyl-CoA hydratase; and a trans-2-enoyl-CoA reductase.

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C7 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a β-ketothiolase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Cupriavidus necator* (see GenBank Accession No. AAC38322.1, SEQ ID NO: 1) or an *Escherichia coli* (see GenBank Accession No. AAC74479.1, SEQ ID NO: 13) β-ketothiolase. See FIG. 6A and FIG. 6G.

For example, a carboxylate reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV11143.1, SEQ ID NO: 5), or a *Segniliparus rotundus* (see Genbank Accession No. ADG98140.1, SEQ ID NO: 6) carboxylate reductase. See, FIGS. 6A-6E.

For example, a ω-transaminase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12) ω-transaminase. Some of these ω-transaminases are diamine ω-transaminases. See, FIGS. 6E-6F.

For example, a thiolase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Pseudomonas putida* thiolase (see Genbank Accession No. AAN70209.2, SEQ ID NO: 15), a *Sphingomonas wittichii* thiolase (see Genbank Accession No. ABQ69245.1, SEQ ID NO: 16), a *Pseudomonas reinekei* thiolase (see Genbank Accession No. ACZ63623.1, SEQ ID NO: 17), a *Pseudomonas putida* thiolase (see Genbank Accession No. AAA85138.1, SEQ ID NO: 18), a *Burkholderia xenovorans* thiolase (see Genbank Accession No. ABE28745.1, SEQ ID NO: 19), a *Burkholderia xenovorans* thiolase (see Genbank Accession No. ABE33819.1, SEQ ID NO: 20), a *Rhodococcus jostii* thiolase (see Genbank Accession No. ABG94668.1, SEQ ID NO: 21), a *Bdellovibrio bacteriovorus* thiolase (see Genbank Accession No. CAE79693.1, SEQ ID NO: 22), a *Cronobacter turicensis* thiolase (see Genbank Accession No. CBA32535.1, SEQ ID NO: 23), an *Arthrobacter* sp. thiolase (see Genbank Accession No. ABK03524.1, SEQ ID NO: 24), a *Caulobacter segnis* thiolase (see Genbank Accession No. ADG08907.1, SEQ ID NO: 25), a *Dinoroseobacter shibae* thiolase (see Genbank Accession No. ABV92581.1, SEQ ID NO: 26), a *Burkholderia xenovorans* thiolase (see Genbank Accession No. ABE36495.1, SEQ ID NO: 27), a *Geobacillus kaustophilus* thiolase (see Genbank Accession No. BAD75605.1, SEQ ID NO: 28), a *Beijerinckia indica* thiolase (see Genbank Accession No. ACB95386.1, SEQ ID NO: 29), a *Citrobacter freundii* thiolase (see Genbank Accession No. EKS55037.1, SEQ ID NO: 30), a *Cupriavidus necator* thiolase (see Genbank Accession No. AEI75849.1, SEQ ID NO: 31), a *Gordonia bronchialis* thiolase (see Genbank Accession No. ACY20886.1, SEQ ID NO: 32), a *Burkholderia* sp. thiolase (see Genbank Accession No. ADG18081.1, SEQ ID NO: 33), a *Glutamicibacter arilaitensis* thiolase (see Genbank Accession No. CBT74677.1, SEQ ID NO: 34), an *Escherichia coli* thiolase (see Genbank Accession No. AAC74479.1, SEQ ID NO: 35), or a *Cupriavidus necator* thiolase (see Genbank Accession No. AAC38322.1, SEQ ID NO: 36). See FIGS. 6G-6L.

For example, a 5-hydroxyvalerate CoA transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Clostridium viride* 5-hydroxyvalerate CoA transferase (see NCBI Reference Sequence: NZ_KK211198.1, SEQ ID NO: 37). See, FIG. 6L.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. In one aspect of the invention, enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine, and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Any substitution of one member of the above-mentioned polar, basic, or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., heptahistidine (SEQ ID NO: 61)), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation or ER or Golgi apparatus retention signals. Heterologous sequences can be of varying length and in some cases can be longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a β-ketothiolase, a dehydrogenase, a synthase, a decarboxylase, a reductase, a hydratase, a thioesterase, a monooxygenase, a thioesterase, amidohydrolase, and transaminase as described herein.

In addition, the production of C7 building blocks can be performed in vitro using the isolated enzymes described herein, using a lysate (e.g., a cell lysate) from a host microorganism as a source of the enzymes, or using a plurality of lysates from different host microorganisms as the sources of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be isolated from of the above types of host cells and used in a purified or semi-purified form. Moreover, such isolates or extracts include lysates (e.g. cell lysates) that can be used as sources of relevant enzymes. In the methods provided by the document, all the steps can be performed in host cells, all the steps can be performed using isolated or extracted enzymes, or some of the steps can be performed in cells and others can be performed using isolated or extracted enzymes.

Enzymes Generating 7-Hydroxyheptanoate

As depicted in FIG. 1, 7-hydroxyheptanaote can be biosynthesized from 2-oxoadipate or malonyl-CoA through the intermediate 3-oxo-7-hydroxyheptanoyl-CoA, which can be produced from 5-hydroxypentanoyl-CoA using a β-ketothiolase. 3-oxo-7-hydroxyheptanoyl-CoA can be converted to 7-hydroxyheptanoate using a 3-hydroxyacyl-CoA dehydrogenase or 3-oxoacyl-CoA dehydrogenase, an enoyl-CoA hydratase, a trans-2-enoyl-CoA reductase, and a thioesterase or a CoA transferase.

In some embodiments, a β-ketothiolase may be classified under EC 2.3.1.16, such as the gene product of bktB, or may be classified under EC 2.3.1.174 such as the gene product of paaJ. The β-ketothiolase encoded by bktB from *Cupriavidus necator* accepts acetyl-CoA and butanoyl-CoA as substrates, forming a CoA-activated C7 aliphatic backbone (see, e.g., Haywood et al., *FEMS Microbiology Letters,* 1988, 52:91-96; Slater et al., *J. Bacteriol.,* 1998, 180(8): 1979-1987). The β-ketothiolase encoded by paaJ from *Escherichia coli* accepts succinyl-CoA and acetyl-CoA as substrates, forming a CoA-activated backbone (Nogales et al., *Microbiology,* 2007, 153, 357-365). See, for example, SEQ ID NO:1 and SEQ ID NO: 13 in FIG. 6A and FIG. 6G.

In some embodiments, a 3-hydroxyacyl-CoA dehydrogenase or 3-oxoacyl-CoA dehydrogenase can be classified under EC 1.1.1.-. For example, the 3-hydroxyacyl-CoA dehydrogenase can be classified under EC 1.1.1.35, such as the gene product of fadB; classified under EC 1.1.1.157, such as the gene product of hbd (also referred to as a 3-hydroxybutyryl-CoA dehydrogenase); or classified under EC 1.1.1.36, such as the acetoacetyl-CoA reductase gene product of phaB (Liu & Chen, *Appl. Microbiol. Biotechnol.,* 2007, 76(5): 1153-1159; Shen et al., *Appl. Environ. Microbiol.,* 2011, 77(9):2905-2915; Budde et al., *J. Bacteriol.,* 2010, 192(20):5319-5328).

In some embodiments, a 3-oxoacyl-CoA reductase can be classified under EC 1.1.1.100, such as the gene product of fabG (Budde et al., *J. Bacteriol.,* 2010, 192(20):5319-5328; Nomura et al., *Appl. Environ. Microbiol.,* 2005, 71(8):4297-4306).

In some embodiments, an enoyl-CoA hydratase can be classified under EC 4.2.1.17, such as the gene product of crt, or classified under EC 4.2.1.119, such as the gene product of phaJ (Shen et al., 2011, supra; Fukui et al., *J. Bacteriol.,* 1998, 180(3):667-673).

In some embodiments, a trans-2-enoyl-CoA reductase can be classified under EC 1.3.1.38 or EC 1.3.1.44, such as the gene product of ter (Nishimaki et al., *J. Biochem.,* 1984, 95:1315-1321; Shen et al., 2011, supra) or tdter (Bond-Watts et al., *Biochemistry,* 2012, 51:6827-6837), or EC 1.3.1.8 (Inui et al., *Eur. J. Biochem.,* 1984, 142, 121-126).

In some embodiments, the terminal carboxyl group leading to the synthesis of 7-hydroxyheptanoate is enzymatically formed in 7-hydroxyheptanoyl-CoA by a thioesterase classified under EC 3.1.2.-, resulting in the production of 7-hydroxyheptanoate. The thioesterase can be the gene product of YciA or Acot13 (Cantu et al., *Protein Science,* 2010, 19, 1281-1295; Zhuang et al., *Biochemistry,* 2008, 47(9):2789-2796; Naggert et al., *J. Biol. Chem.,* 1991, 266(17):11044-11050).

In some embodiments, the terminal carboxyl group leading to the synthesis of 7-hydroxyheptanoate is enzymatically formed in 7-hydroxyheptanoyl-CoA by a CoA-transferase classified under, for example, EC 2.8.3- such as the gene product of cat2 from *Clostridium kluyveri*, abfT from *Clostridium aminobutyricum*, or the 4-hydroxybutyrate CoA-transferase from *Clostridium viride.*

Figure 2:
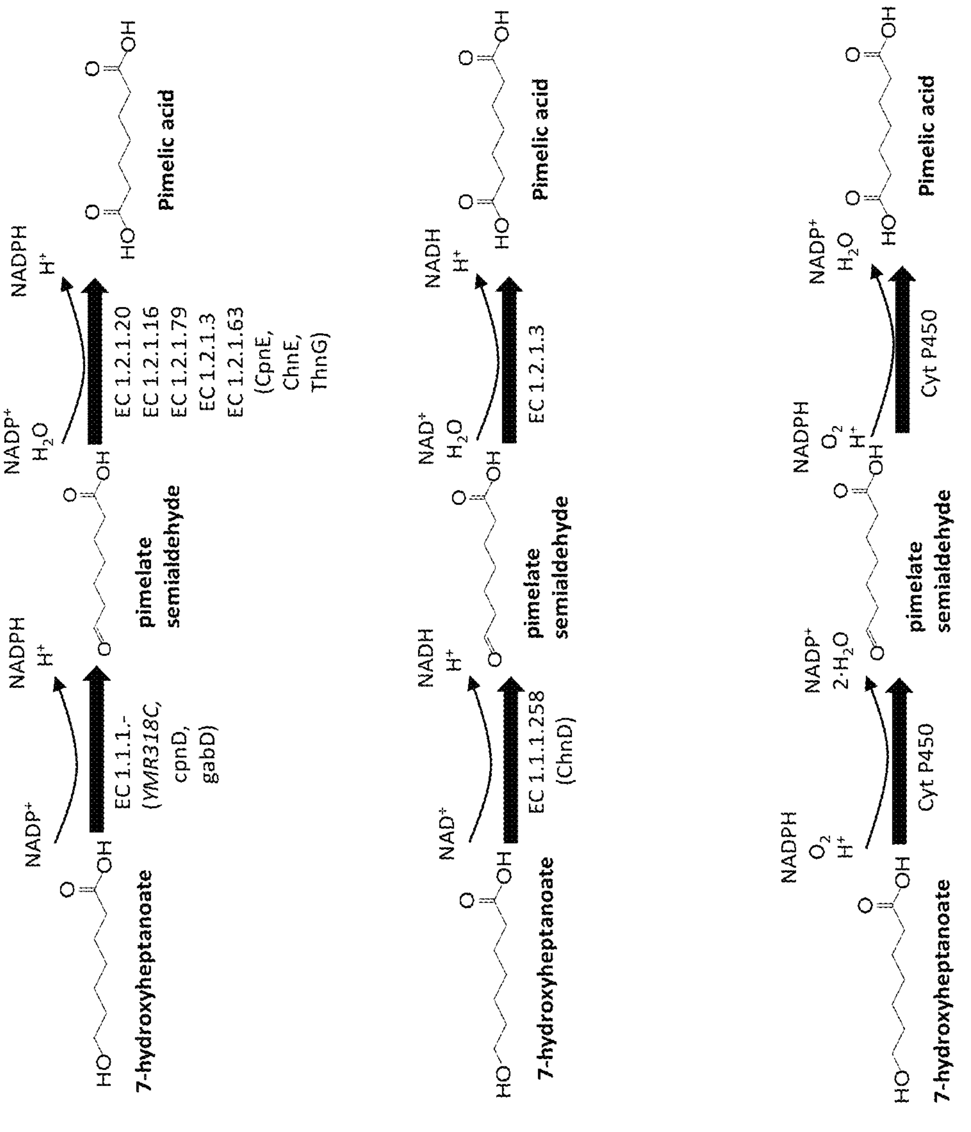
FIG. 2 is a schematic of exemplary biochemical pathways leading to pimelic acid using 7-hydroxyheptanoate as a central precursor.

Enzymes Generating the Terminal Carboxyl Groups in the Biosynthesis of Pimelic Acid As depicted in FIG. 2, the terminal carboxyl group leading to the production of pimelic acid can be enzymatically formed using an aldehyde dehydrogenase, a 5-oxovalerate dehydrogenase, a 6-oxohexanoate dehydrogenase, a 7-oxoheptanoate dehydrogenase, or a monooxygenase.

In some embodiments, the second terminal carboxyl group leading to the synthesis of pimelic acid can be enzymatically formed in pimelate semialdehyde by an aldehyde dehydrogenase classified under EC 1.2.1.3 (Guerrillot & Vandecasteele, *Eur. J. Biochem.,* 1977, 81, 185-192). See, FIG. 2.

In some embodiments, the second terminal carboxyl group leading to the synthesis of pimelic acid is enzymatically formed in pimelate semialdehyde by EC 1.2.1.- such as a 5-oxovalerate dehydrogenase classified, for example, under EC 1.2.1.20, such as the gene product of CpnE; a 6-oxohexanoate dehydrogenase classified, for example, EC 1.2.1.63 such as the gene product of ChnE from *Acinetobacter* sp.; or a 7-oxoheptanoate dehydrogenase such as the gene product of ThnG from *Sphingomonas macrogolitabida* (Iwaki et al., *Appl. Environ. Microbiol.,* 1999, 65(11), 5158-5162; López-Sánchez et al., *Appl. Environ. Microbiol.,* 2010, 76(1), 110-118)). See, FIG. 2.

In some embodiments, the second terminal carboxyl group leading to the synthesis of pimelic acid is enzymatically formed in pimelate semialdehyde by a monooxygenase in the cytochrome P450 family such as CYP4F3B (see, e.g., Sanders et al., *J. Lipid Research,* 2005, 46(5):1001-1008; Sanders et al., *The FASEB Journal,* 2008, 22(6):2064-2071). See, FIG. 2.

Figure 3:
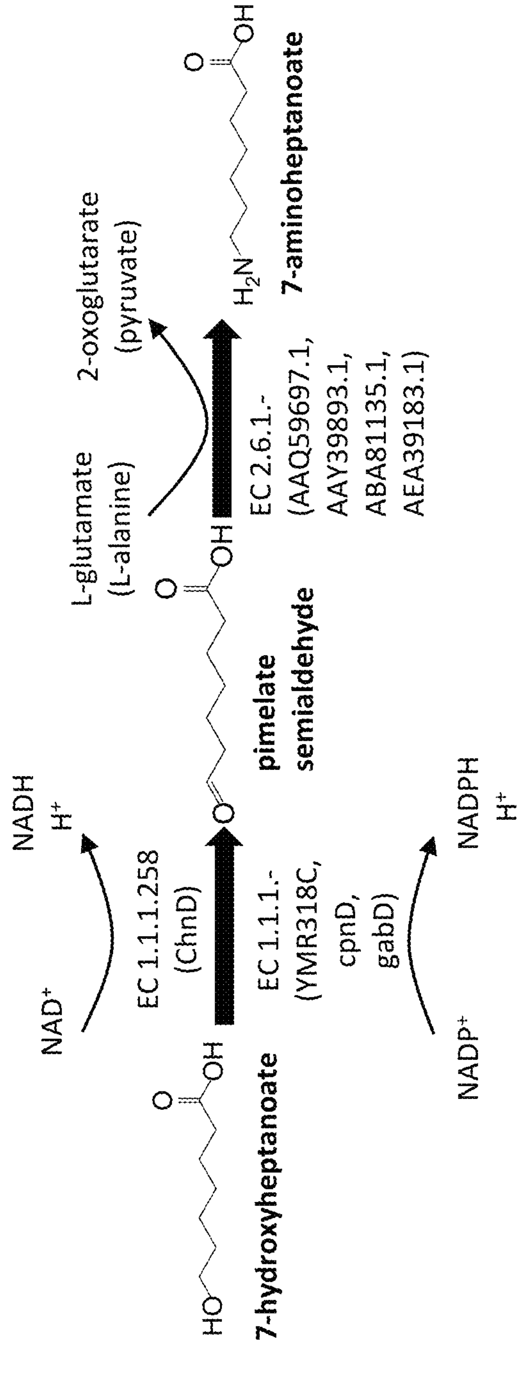
FIG. 3 is a schematic of an exemplary biochemical pathway leading to 7-aminoheptanoate using 7-hydroxyheptanoate as a central precursor.
Figure 4:
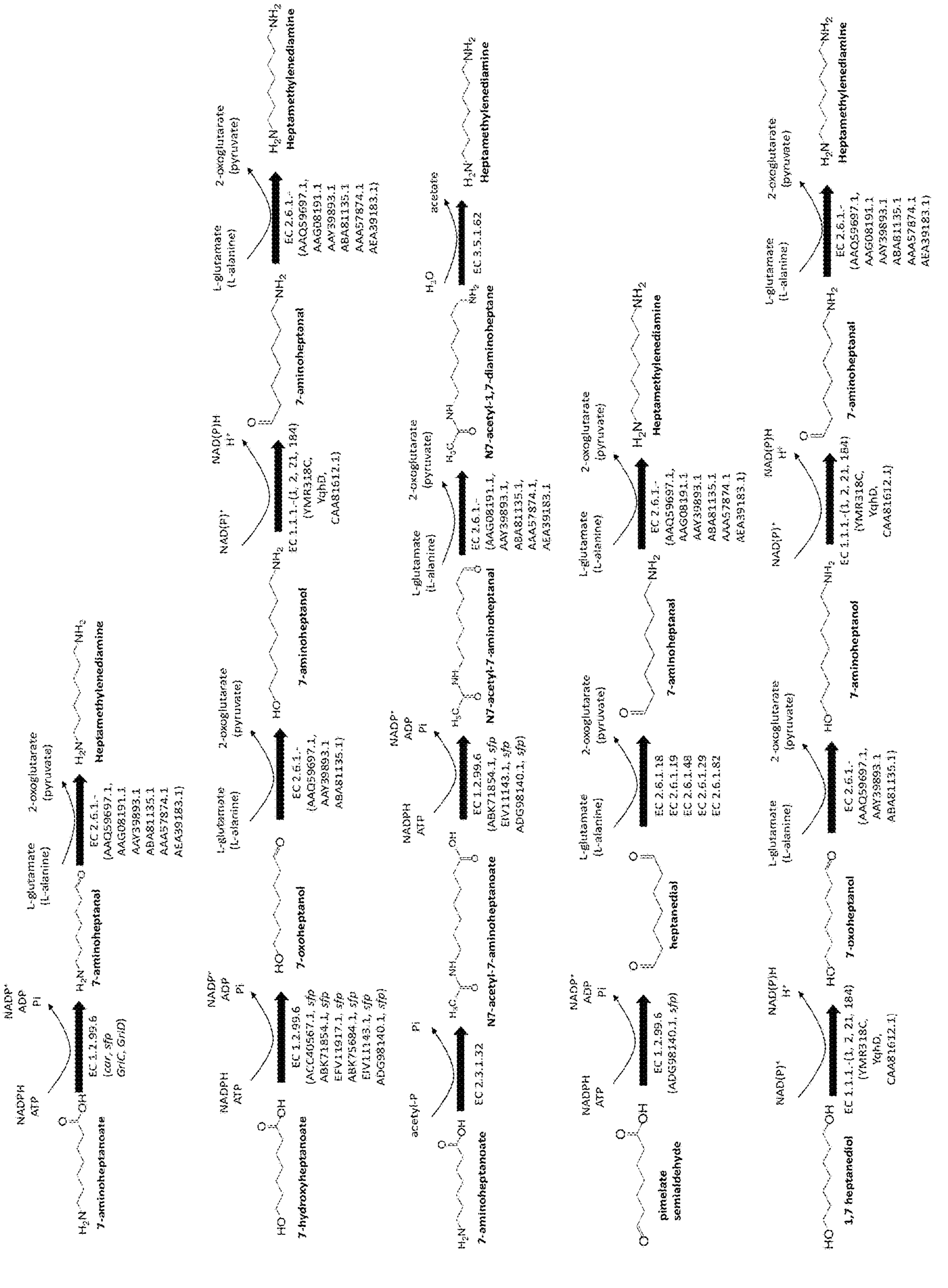
FIG. 4 is a schematic of exemplary biochemical pathways leading to heptamethylenediamine using 7-aminoheptanoate, 7-hydroxyheptanoate, pimelate semialdehyde, or 1,7-heptanediol as a central precursor.

Enzymes Generating the Terminal Amine Groups in the Biosynthesis of Heptamethylenediamine or 7-Aminoheptanoate As depicted in FIG. 3 and FIG. 4, terminal amine groups can be enzymatically formed using a ω-transaminase or a deacylase.

In some embodiments, a terminal amine group leading to the synthesis of 7-aminoheptanoic acid is enzymatically formed in pimelate semialdehyde by a ω-transaminase classified, for example, under EC 2.6.1.- (e.g., EC 2.6.1.18, EC 2.6.1.19, EC 2.6.1.29, EC 2.6.1.48, or EC 2.6.1.82) such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio fluvialis* (Genbank Accession No. AEA39183.1, SEQ ID NO: 12), *Streptomyces griseus*, or *Clostridium viride*. See, FIG. 3.

An additional ω-transaminase that can be used in the methods and hosts described herein is from *Escherichia coli* (Genbank Accession No. AAA57874.1, SEQ ID NO: 11). Some of the ω-transaminases classified, for example, under EC 2.6.1.29 or EC 2.6.1.82 are diamine ω-transaminases (e.g., SEQ ID NO: 11).

The reversible ω-transaminase from *Chromobacterium violaceum* (Genbank Accession No. AAQ59697.1, SEQ ID NO: 7) has demonstrated analogous activity accepting 7-aminoheptanoic acid as an amino donor, thus forming the first terminal amine group in pimelate semialdehyde (Kaulmann et al., *Enzyme and Microbial Technology,* 2007, 41, 628-637).

The reversible 4-aminobubyrate:2-oxoadipate transaminase from *Streptomyces griseus* has demonstrated activity for the conversion of 7-aminoheptanoate to pimelate semialdehyde (Yonaha et al., *Eur. J. Biochem.,* 1985, 146, 101-106).

The reversible 5-aminovalerate transaminase from *Clostridium viride* has demonstrated activity for the conversion of 7-aminoheptanoate to pimelate semialdehyde (Barker et al., *J. Biol. Chem.,* 1987, 262(19), 8994-9003).

In some embodiments, the second terminal amine group leading to the synthesis of heptamethylenediamine is enzymatically formed in 7-aminoheptanal by a diamine transaminase classified, for example, under EC 2.6.1.29; or classified, for example, under EC 2.6.1.82, such as the gene product of YgjG from *E. coli* (Genbank Accession No. AAA57874.1, SEQ ID NO: 12). The transaminases set forth in SEQ ID NOs:7-10 and 11 also can be used to produce heptamethylenediamine. See, FIG. 4.

The gene product of ygjG accepts a broad range of diamine carbon chain length substrates, such as putrescine, cadaverine, and spermidine (Samsonova et al., *BMC Microbiology,* 2003, 3:2).

The diamine transaminase from *E. coli* strain B has demonstrated activity for 1,7 diaminoheptane (Kim, *The Journal of Chemistry,* 1964, 239(3), 783-786).

In some embodiments, the second terminal amine group leading to the synthesis of heptamethylenediamine is enzymatically formed in N7-acetyl-1,7-diaminoheptane by a deacylase classified, for example, under EC 3.5.1.17 such as an acyl lysine deacylase.

Figure 5:
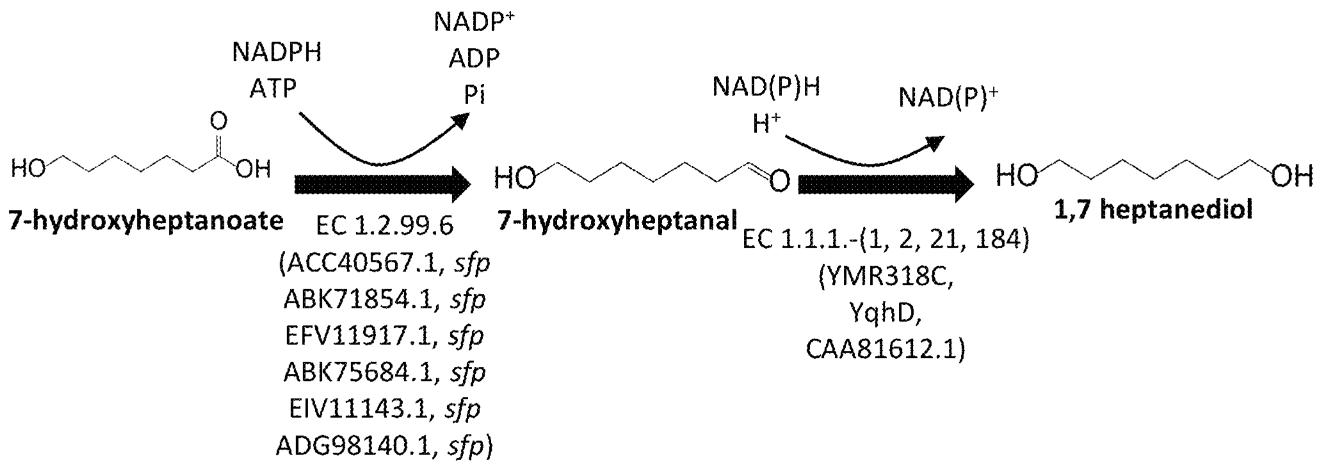
FIG. 5 is a schematic of an exemplary biochemical pathway leading to 1,7-heptanediol using 7-hydroxyheptanoate as a central precursor.

Enzymes Generating the Terminal Hydroxyl Groups in the Biosynthesis of 1,7 Heptanediol As depicted in FIG. 5, the terminal hydroxyl group can be enzymatically formed using an alcohol dehydrogenase. For example, the second terminal hydroxyl group leading to the synthesis of 1,7 heptanediol can be enzymatically formed in 7-hydroxyheptanal by an alcohol dehydrogenase classified under EC 1.1.1.- (e.g., EC 1.1.1.1, 1.1.1.2, 1.1.1.21, or 1.1.1.184) such as the gene product of YMR318C or YqhD (Liu et al., *Microbiology,* 2009, 155, 2078-2085; Larroy et al., 2002, *Biochem J.,* 361(Pt 1), 163-172; Jarboe, 2011, *Appl. Microbiol. Biotechnol.,* 89(2), 249-257) or the protein having GenBank Accession No. CAA81612.1.

Biochemical Pathways

Pathways to 7-Hydroxyheptanoate

In some embodiments, 5-hydroxypentanoyl-CoA is synthesized from the central metabolite, 2-oxoadipate, by conversion of 2-oxoadipate to 2-aminoadipate by a α-aminotransaminase classified, for example, under EC 2.6.1.39; followed by conversion of 2-aminoadipate to 5-aminopentanoate by a glutamate decarboxylase classified, for example, under EC 4.1.1.15; followed by conversion of 5-aminopentanoate to 5-oxopentanoate—by a ω-transaminase classified, for example, under EC 2.6.1.18, EC 2.6.1.19, EC 2.6.1.48, or EC 2.6.1.96 such as the gene product of gabT from *Escherichia coli* (Bartsch et al., *J. Bacteriol.,* 1990, 172(12), 7035); followed by conversion of 5-oxopentanoate to 5-hydroxypentanoate by an alcohol dehydrogenase classified, for example, under EC 1.1.1.61 such as the gene product of gbd (e.g., from *Sorangium cellulosum*), gabD (Bartsch et al., *J. Bacteriol.,* 1990, 172(12), 7035), or YihU (Saito et al., *J. Biol. Chem.,* 2009, 284(24), 16442-16452), or a 5-hydroxyvalerate dehydrogenase such as the gene product of cpnD (see, for example, Iwaki et al., 2002, *Appl. Environ. Microbiol.,* 68(11):5671-5684); followed by conversion of 5-hydroxypentanoate to 5-hydroxypentanoyl-CoA using a CoA-ligase classified under, for example, EC 6.2.1- (e.g., EC 6.2.1.40), or a CoA-transferase classified under, for example, EC 2.8.3.- such as the gene product of cat2 from *Clostridium kluyveri*, abfT from *Clostridium aminobutyricum*, or the 4-hydroxybutyrate CoA-transferase from *Clostridium viride*. See FIG. 1.

In some embodiments, 2-oxoadipate is converted to 5-oxopentanoate—using a 2-oxoadipate decarboxylase classified, for example, under EC 4.1.1.71 or a branch-chain decarboxylase classified, for example, under EC 4.1.1.72 such as the gene product of kdcA or kivD. 5-oxopentanoate—produced in this fashion can be converted to 5-hydroxypentanoyl-CoA as described above. See, FIG. 1.

In some embodiments, 5-hydroxypentanoyl-CoA is synthesized from the central metabolite, malonyl-CoA, by conversion of malonyl-CoA to malonate semialdehyde by a malonyl-CoA reductase classified, for example, under EC 1.2.1.75; followed by conversion of malonate semialdehyde to 3-hydroxypropanoate by a 3-hydroxypropionate dehydrogenase classified, for example, under EC 1.1.1.59; followed by conversion of 3-hydroxypropanoate to 3-hydroxypropanoyl-CoA by a 3-hydroxypropionyl-CoA synthase classified, for example, under EC 6.2.1.36, or a CoA-transferase classified, for example, under EC 2.8.3.1; followed by conversion of 3-hydropropanoyl-CoA to 3-oxo-5-hydroxypentanoyl-CoA using a β-ketothiolase classified, for example, under EC 2.3.1.16 or EC 2.3.1.174 such as the gene product of bktB or paaJ (e.g., SEQ ID NO: 1 or 13); followed by conversion to 3-hydroxy-5-hydroxypentanoyl-CoA using a 3-hydroxyacyl-CoA dehydrogenase classified, for example, under EC 1.1.1.- such as EC 1.1.1.35 (e.g., the gene product of fadB), EC 1.1.1.36 (e.g., the gene product of phaB), or EC 1.1.1.157 (e.g., the gene product of hbd), or a 3-oxoacyl-CoA reductase classified, for example, under EC 1.1.1.100, such as the gene product of fabG; followed by conversion of 3-hydroxy-5-hydroxypentanoyl-CoA to 2,3-dehydro-5-hydroxypentanoyl-CoA using an enoyl-CoA hydratase classified, for example, under EC 4.2.1.17 such as the gene product of crt or classified under EC 4.2.1.119 such as the gene product of phaJ; followed by conversion of 2,3-dehydro-5-hydroxypentanoyl-CoA to 5-hydroxypentanoyl-CoA by a trans-2-enoyl-CoA reductase classified, for example, under EC 1.3.1.38, EC 1.3.1.44, or EC 1.3.1.8 such as the gene product of ter or tdter. See FIG. 1.

In some embodiments, 7-hydroxyheptanoate is synthesized from the central precursor, 5-hydroxypentanoyl-CoA, by conversion of 5-hydroxypentanoyl-CoA to 3-oxo-7-hydroxyheptanoyl-CoA using a β-ketothiolase classified, for example, under EC 2.3.1.16 or EC 2.3.1.174 such as the gene product of bktB or paaJ (e.g., SEQ ID NO: 1 or 13); followed by conversion to 3-hydroxy-7-hydroxyheptanoyl-CoA using a 3-hydroxyacyl-CoA dehydrogenase classified, for example, under EC 1.1.1.- such as EC 1.1.1.35 (e.g., the gene product of fadB), EC 1.1.1.36 (e.g., the gene product of phaB), or EC 1.1.1.157 (e.g., the gene product of hbd), or a 3-oxoacyl-CoA reductase classified, for example, under EC 1.1.1.100 such as the gene product of fabG; followed by conversion of 3-hydroxy-7-hydroxyheptanoyl-CoA to 2,3-dehydro-7-hydroxyheptanoyl-CoA using an enoyl-CoA hydratase classified, for example, under EC 4.2.1.17 such as the gene product of crt, or classified under EC 4.2.1.119 such as the gene product of phaJ; followed by conversion of 2,3-dehydro-7-hydroxyheptanoyl-CoA to 7-hydroxyheptanoyl-CoA by a trans-2-enoyl-CoA reductase classified, for example, under EC 1.3.1.38, EC 1.3.1.44, or EC 1.3.1.8 such as the gene product of ter or tdter; followed by conversion of 7-hydroxyheptanoyl-CoA to 7-hydroxyheptanoate by a thioesterase classified, for example, under EC 3.1.2.- such as the gene product of YciA or Acot13, or a CoA-transferase classified, for example, under EC 2.8.3.-. See FIG. 1.

Pathways Using 7-Hydroxyheptanoate as Central Precursor to Pimelic Acid

In some embodiments, pimelic acid is synthesized from 7-hydroxyheptanoate, by conversion of 7-hydroxyheptanoate to pimelate semialdehyde by an alcohol dehydrogenase classified under EC 1.1.1.- such as the gene product of YMR318C (classified, for example, under EC 1.1.1.2, see Genbank Accession No. CAA90836.1) (Larroy et al., 2002, *Biochem J.,* 361(Pt 1), 163-172), cpnD (Iwaki et al., 2002, *Appl. Environ. Microbiol.,* 68(11):5671-5684), or gabD (Lüitke-Eversloh & Steinbüchel, 1999, *FEMS Microbiology Letters,* 181(1):63-71), or a 6-hydroxyheptanoate dehydrogenase classified, for example, under EC 1.1.1.258 such as the gene product of ChnD (Iwaki et al., *Appl. Environ. Microbiol.,* 1999, 65(11):5158-5162); followed by conversion of pimelate semialdehyde to pimelic acid by a dehydrogenase classified, for example, under EC 1.2.1.- such as a 7-oxoheptanoate dehydrogenase (e.g., the gene product of ThnG), a 7-oxoheptanoate dehydrogenase (e.g., the gene product of ChnE), a glutarate semialdehyde dehydrogenase classified, for example, under EC 1.2.1.20, a 5-oxovalerate dehydrogenase such as the gene product of CpnE, or an aldehyde dehydrogenase classified under EC 1.2.1.3. See FIG. 2. The alcohol dehydrogenase encoded by YMR318C has broad substrate specificity, including the oxidation of C7 alcohols.

In some embodiments, pimelic acid is synthesized from the central precursor, 7-hydroxyheptanoate, by conversion of 7-hydroxyheptanoate to pimelate semialdehyde by a cytochrome P450 (Sanders et al., *J. Lipid Research,* 2005, 46(5), 1001-1008; Sanders et al., *The FASEB Journal,* 2008, 22(6), 2064-2071); followed by conversion of pimelate semialdehyde to pimelic acid by a monooxygenase in the cytochrome P450 family such as CYP4F3B. See FIG. 2.

Pathway Using 7-Hydroxyheptanoate as Central Precursor to 7-Aminoheptanoate—

In some embodiments, 7-aminoheptanoate is synthesized from the central precursor, 7-hydroxyheptanoate, by conversion of 7-hydroxyheptanoate to pimelate semialdehyde by an alcohol dehydrogenase classified, for example, under EC 1.1.1.2 such as the gene product of YMR318C, a 6-hydroxyhexanoate dehydrogenase classified, for example, under EC 1.1.1.258, a 5-hydroxypentanoate dehydrogenase classified, for example, under EC 1.1.1.- such as the gene product of cpnD, or a 4-hydroxybutyrate dehydrogenase classified, for example, under EC 1.1.1.- such as the gene product of gabD; followed by conversion of pimelate semialdehyde to 7-aminoheptanoate by a ω-transaminase (EC 2.6.1.18, EC 2.6.1.19, EC 2.6.1.29, EC 2.6.1.48, or EC 2.6.1.82 such as one of SEQ ID NOs:7-10 or 12, see above). See FIG. 3.

Pathway Using 7-Aminoheptanoate, 7-Hydroxyheptanoate, Pimelate Semialdehyde, or 1,7-Heptanediol as a Central Precursor to Heptamethylenediamine In some embodiments, heptamethylenediamine is synthesized from the central precursor, 7-aminoheptanoate, by conversion of 7-aminoheptanoate to 7-aminoheptanal by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*), or the gene products of GriC and GriD from *Streptomyces griseus* (Suzuki et al., *J. Antibiot.,* 2007, 60(6), 380-387); followed by conversion of 7-aminoheptanal to heptamethylenediamine by a ω-transaminase such as a ω-transaminase in EC 2.6.1.-, (e.g., EC 2.6.1.18, EC 2.6.1.19, EC 2.6.1.48, EC 2.6.1.82 such as SEQ ID NOs:7-12). The carboxylate reductase can be obtained, for example, from *Mycobacterium marinum* (Genbank Accession No. ACC40567.1, SEQ ID NO: 2), *Mycobacterium smegmatis* (Genbank Accession No. ABK71854.1, SEQ ID NO: 3), *Segniliparus rugosus* (Genbank Accession No. EFV11917.1, SEQ ID NO: 4), *Mycobacterium massiliense* (Genbank Accession No. EIV11143.1, SEQ ID NO: 5), or *Segniliparus rotundus* (Genbank Accession No. ADG98140.1, SEQ ID NO: 6). See FIG. 4.

The carboxylate reductase encoded by the gene product of car and enhancer npt or sfp has broad substrate specificity, including terminal difunctional C4 and C5 carboxylic acids (Venkitasubramanian et al., *Enzyme and Microbial Technology,* 2008, 42, 130-137).

In some embodiments, heptamethylenediamine is synthesized from the central precursor, 7-hydroxyheptanoate (which can be produced as described in FIG. 1), by conversion of 7-hydroxyheptanoate to 7-hydroxyheptanal by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*), or the gene product of GriC & GriD (Suzuki et al., 2007, supra); followed by conversion of 7-hydroxyheptanal to 7-aminoheptanol by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to 7-aminoheptanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD (Liu et al., *Microbiology,* 2009, 155, 2078-2085; Larroy et al., 2002, *Biochem J,* 361 (Pt 1), 163-172; Jarboe, 2011, *Appl. Microbiol. Biotechnol.,* 89(2), 249-257) or the protein having GenBank Accession No. CAA81612.1; followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above. See FIG. 4.

In some embodiments, heptamethylenediamine is synthesized from the central precursor, 7-aminoheptanoate, by conversion of 7-aminoheptanoate to N7-acetyl-7-aminoheptanoate by an N-acetyltransferase such as a lysine N-acetyltransferase classified, for example, under EC 2.3.1.32; followed by conversion to N7-acetyl-7-aminoheptanal by a carboxylate reductase classified, for example, under EC 1.2.99.6 such as the gene product of car (see above, e.g., SEQ ID NO: 4, 5, or 6) in combination with a phosphopantetheine transferase enhancer (e.g., encoded by a sfp gene from *Bacillus subtilis* or npt gene from *Nocardia*), or the gene product of GriC & GriD; followed by conversion to N7-acetyl-1,7-diaminoheptane by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to heptamethylenediamine by an acyl lysine deacylase classified, for example, under EC 3.5.1.17. See, FIG. 4.

In some embodiments, heptamethylenediamine is synthesized from the central precursor, pimelate semialdehyde, by conversion of pimelate semialdehyde to heptanedial by a carboxylate reductase classified, for example, under EC 1.2.99.6 such as the gene product of car (see above, e.g., SEQ ID NO:6) in combination with a phosphopantetheine transferase enhancer (e.g., encoded by a sfp gene from *Bacillus subtilis* or npt gene from *Nocardia*) or the gene product of GriC & GriD; followed by conversion to 7-aminoheptanal by a ω-transaminase classified, for example, under EC 2.6.1.18, EC 2.6.1.19, EC 2.6.1.29, EC 2.6.1.48, or EC 2.6.1.82; followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 4.

In some embodiments, heptamethylenediamine is synthesized from 1,7-heptanediol by conversion of 1,7-heptanedion to 7-hydroxyheptanal using an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD or the protein having GenBank Accession No. CAA81612.1; followed by conversion to 7-aminoheptanol by a ω-transaminase classified, for example, under EC 2.6.1.18, EC 2.6.1.19, EC 2.6.1.29, EC 2.6.1.48, or EC 2.6.1.82 such as SEQ ID NOs:7-12, followed by conversion to 7-aminoheptanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD or the protein having GenBank Accession No. CAA81612.1, followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 4.

Pathways Using 7-Hydroxyheptanoate as Central Precursor to 1,7-Heptanediol

In some embodiments, 1,7 heptanediol is synthesized from the central precursor, 7-hydroxyheptanoate, by conversion of 7-hydroxyheptanoate to 7-hydroxyheptanal by a carboxylate reductase classified, for example, under EC 1.2.99.6 such as the gene product of car (see above, e.g., SEQ ID NO: 2, 3, 4, 5, or 6) in combination with a phosphopantetheine transferase enhancer (e.g., encoded by a sfp gene from *Bacillus subtilis* or npt gene from *Nocardia*) or the gene products of GriC and GriD from *Streptomyces griseus* (Suzuki et al., *J. Antibiot.*, 2007, 60(6), 380-387); followed by conversion of 7-hydroxyheptanal to 1,7 heptanediol by an alcohol dehydrogenase (classified, for example, under EC 1.1.1.- such as EC 1.1.1.1, EC 1.1.1.2, EC 1.1.1.21, or EC 1.1.1.184) such as the gene product of YMR318C or YqhD (from *E. coli*, GenBank Accession No. AAA69178.1) (see, e.g., Liu et al., *Microbiology,* 2009, 155, 2078-2085; Larroy et al., 2002, *Biochem J.,* 361(Pt 1), 163-172; or Jarboe, 2011, *Appl. Microbiol. Biotechnol.,* 89(2), 249-257), or the protein having GenBank Accession No. CAA81612.1 (from *Geobacillus stearothermophilus*). See, FIG. 5.

Cultivation Strategy

In some embodiments, one or more C7 building blocks are biosynthesized in a recombinant host using anaerobic, aerobic, or micro-aerobic cultivation conditions. In some embodiments, the cultivation strategy entails nutrient limitation such as nitrogen, phosphate, or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C7 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida*, and *Yarrowia lipolytica* (Lee et al., *Appl. Biochem. Biotechnol.,* 2012, 166:1801-1813; Yang et al., *Biotechnology for Biofuels,* 2012, 5:13; Meijnen et al., *Appl. Microbiol. Biotechnol.,* 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.,* 2009, 139:61-67).

The efficient catabolism of lignin-derived aromatic compounds such as benzoate analogues has been demonstrated in several microorganisms such as *Pseudomonas putida* and *Cupriavidus necator* (Bugg et al., *Current Opinion in Biotechnology,* 2011, 22, 394-400; Perez-Pantoja et al., *FEMS Microbiol. Rev.,* 2008, 32, 736-794).

The efficient utilization of agricultural waste, such as olive mill waste water has been demonstrated in several microorganisms, including *Yarrowia lipolytica* (Papanikolaou et al., *Bioresour. Technol.,* 2008, 99(7):2419-2428).

The efficient utilization of fermentable sugars such as monosaccharides and disaccharides derived from cellulosic, hemicellulosic, cane and beet molasses, cassava, corn, and other agricultural sources has been demonstrated for several microorganisms such as *Escherichia coli, Corynebacterium glutamicum, Lactobacillus delbrueckii*, and *Lactococcus lactis* (see, e.g., Hermann et al, *J. Biotechnol.,* 2003, 104: 155-172; Wee et al., *Food Technol. Biotechnol.,* 2006, 44(2): 163-172; Ohashi et al., *J. Bioscience and Bioengineering,* 1999, 87(5):647-654).

The efficient utilization of furfural, derived from a variety of agricultural lignocellulosic sources, has been demonstrated for *Cupriavidus necator* (Li et al., *Biodegradation,* 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cycloheptane oxidation processes, or terephthalic acid/isophthalic acid mixture waste streams.

The efficient catabolism of methanol has been demonstrated for the methylotrophic yeast *Pichia pastoris.*

The efficient catabolism of ethanol has been demonstrated for *Clostridium kluyveri* (Seedorf et al., *Proc. Natl. Acad. Sci. USA,* 2008, 105(6) 2128-2133).

The efficient catabolism of $CO_2$ and $H_2$, which may be derived from natural gas and other chemical and petrochemical sources, has been demonstrated for *Cupriavidus* necator (Prybylski et al., *Energy, Sustainability and Society,* 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology,* 2011, 77(15): 5467-5475).

The efficient catabolism of the non-volatile residue waste stream from cycloheptane processes has been demonstrated for numerous microorganisms, such as Delftia *acidovorans* and *Cupriavidus necator* (Ramsay et al., *Applied and Environmental Microbiology,* 1986, 52(1):152-156).

In some embodiments, the host microorganism is a prokaryote. For example, the prokaryote can be a bacterium from the genus *Escherichia* such as *Escherichia coli*; from the genus Clostridia such as *Clostridium ljungdahlii, Clostridium autoethanogenum* or *Clostridium kluyveri*; from the genus Corynebacteria such as *Corynebacterium glutamicum*; from the genus *Cupriavidus* such as *Cupriavidus necator*, or *Cupriavidus metallidurans*; from the genus *Pseudomonas* such as *Pseudomonas fluorescens, Pseudomonas putida*, or *Pseudomonas oleavorans*; from the genus *Delftia* such as *Delftia acidovorans*; from the genus *Bacillus* such as *Bacillus* subtillis; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C7 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C7 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C7 building block.

Attenuation strategies include, but are not limited to the use of transposons, homologous recombination (double cross-over approach), mutagenesis, enzyme inhibitors, and RNAi interference.

In some embodiments, fluxomic, metabolomic, and transcriptomal data can be utilized to inform or support genome-scale system biology techniques, thereby devising genome scale attenuation or knockout strategies in directing carbon flux to a C7 building block.

In some embodiments, the host microorganism's tolerance to high concentrations of a C7 building block can be improved through continuous cultivation in a selective environment.

In some embodiments, the host microorganism's endogenous biochemical network can be attenuated or augmented to (1) ensure the intracellular availability of acetyl-CoA and 5-hydroxypentanoyl-CoA, (2) create an NADH or NADPH imbalance that may only be balanced via the formation of one or more C7 building blocks, (3) prevent degradation of central metabolites/central precursors leading to and including one or more C7 building blocks, and/or (4) ensure efficient efflux from the cell.

In some embodiments requiring intracellular availability of acetyl-CoA for C7 building block synthesis, endogenous enzymes catalyzing the hydrolysis of acetyl-CoA such as short-chain length thioesterases can be attenuated in the host organism.

In some embodiments requiring the intracellular availability of acetyl-CoA for C7 building block synthesis, an endogenous phosphotransacetylase generating acetate such as pta can be attenuated (Shen et al., *Appl. Environ. Microbiol.,* 2011, 77(9):2905-2915).

In some embodiments requiring the intracellular availability of acetyl-CoA for C7 building block synthesis, an endogenous gene in an acetate synthesis pathway encoding an acetate kinase, such as ack, can be attenuated.

In some embodiments requiring the intracellular availability of acetyl-CoA and NADH for C7 building block synthesis, an endogenous gene encoding an enzyme that catalyzes the degradation of pyruvate to lactate such as lactate dehydrogenase encoded by IdhA can be attenuated (Shen et al., 2011, supra).

In some embodiments, enzymes that catalyze anapleurotic reactions such as PEP carboxylase and/or pyruvate carboxylase can be overexpressed in the host organism.

In some embodiments requiring the intracellular availability of acetyl-CoA and NADH for C7 building block synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for C7 building block synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for C7 building block synthesis, a recombinant formate dehydrogenase gene can be overexpressed in the host organism (Shen et al., 2011, supra).

In some embodiments, where pathways require excess NADH co-factor for C7 building block synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments requiring the intracellular availability of acetyl-CoA for C7 building block synthesis, a recombinant acetyl-CoA synthetase such as the gene product of acs can be overexpressed in the microorganism (Satoh et al., *J. Bioscience and Bioengineering,* 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression of a 6-phosphogluconate dehydrogenase and/or a transketolase (Lee et al., 2003, *Biotechnology Progress,* 19(5), 1444-1449).

In some embodiments, where pathways require excess NADPH co-factor in the synthesis of a C7 building block, a gene such as UdhA encoding a puridine nucleotide transhydrogenase can be overexpressed in the host organisms (Brigham et al., *Advanced Biofuels and Bioproducts,* 2012, Chapter 39, 1065-1090).

In some embodiments, where pathways require excess NADPH co-factor in the synthesis of a C7 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C7 building block, a recombinant malic enzyme gene such as maeA or maeB can be overexpressed in the host organisms (Brigham et al., 2012, supra).

In some embodiments, where pathways require excess NADPH co-factor in the synthesis of a C7 building block, a recombinant glucose-6-phosphate dehydrogenase gene such as zwf can be overexpressed in the host organisms (Lim et al., *J. Bioscience and Bioengineering,* 2002, 93(6), 543-549).

In some embodiments, where pathways require excess NADPH co-factor in the synthesis of a C7 building block, a recombinant fructose 1,6 diphosphatase gene such as fbp can be overexpressed in the host organisms (Becker et al., *J. Biotechnol.,* 2007, 132:99-109).

In some embodiments, where pathways require excess NADPH co-factor in the synthesis of a C7 building block, endogenous triose phosphate isomerase (EC 5.3.1.1) can be attenuated.

In some embodiments, where pathways require excess NADPH co-factor in the synthesis of a C7 building block, a recombinant glucose dehydrogenase such as the gene product of gdh can be overexpressed in the host organism (Satoh et al., *J. Bioscience and Bioengineering,* 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments, a membrane-bound cytochrome P450 such as CYP4F3B can be solubilized by only expressing the cytosolic domain and not the N-terminal region that anchors the P450 to the endoplasmic reticulum (Scheller et al., *J. Biol. Chem.,* 1994, 269(17):12779-12783).

In some embodiments, an enoyl-CoA reductase can be solubilized via expression as a fusion protein with a small soluble protein, for example, the maltose binding protein (Gloerich et al., *FEBS Letters,* 2006, 580, 2092-2096).

In some embodiments using hosts that naturally accumulate polyhydroxyalkanoates, the endogenous polymer synthase enzymes can be attenuated in the host strain.

In some embodiments, a L-alanine dehydrogenase can be overexpressed in the host to regenerate L-alanine from pyruvate as an amino donor for ω-transaminase reactions.

In some embodiments, a L-glutamate dehydrogenase, a L-glutamine synthetase, or a alpha-aminotransaminase can be overexpressed in the host to regenerate L-glutamate from 2-oxoadipate as an amino donor for ω-transaminase reactions.

In some embodiments, enzymes such as a pimeloyl-CoA dehydrogenase classified under, EC 1.3.1.62; an acyl-CoA dehydrogenase classified, for example, under EC 1.3.8.7, EC 1.3.8.1, or EC 1.3.99.-; and/or a butyryl-CoA dehydrogenase classified, for example, under EC 1.3.8.6 that degrade central metabolites and central precursors leading to and including C7 building blocks can be attenuated.

In some embodiments, endogenous enzymes activating C7 building blocks via Coenzyme A esterification such as CoA-ligases (e.g., an adipyl-CoA synthetase) classified under, for example, EC 6.2.1.- can be attenuated.

In some embodiments, the efflux of a C7 building block across the cell membrane to the extracellular media can be enhanced or amplified by genetically engineering structural modifications to the cell membrane or increasing any associated transporter activity for a C7 building block.

The efflux of heptamethylenediamine can be enhanced or amplified by overexpressing broad substrate range multidrug transporters such as Blt from *Bacillus subtilis* (Woolridge et al., 1997, *J. Biol. Chem.,* 272(14):8864-8866), AcrB and AcrD from *Escherichia coli* (Elkins & Nikaido, 2002, *J. Bacteriol.,* 184(23), 6490-6499), NorA from *Staphylococcus aereus* (Ng et al., 1994, *Antimicrob Agents Chemother,* 38(6), 1345-1355), or Bmr from *Bacillus subtilis* (Neyfakh, 1992, *Antimicrob Agents Chemother,* 36(2), 484-485).

The efflux of 7-aminoheptanoate and heptamethylenediamine can be enhanced or amplified by overexpressing the solute transporters such as the lysE transporter from *Corynebacterium glutamicum* (Bellmann et al., 2001, *Microbiology,* 147, 1765-1774).

The efflux of pimelic acid can be enhanced or amplified by overexpressing a dicarboxylate transporter such as the SucE transporter from *Corynebacterium glutamicum* (Huhn et al., *Appl. Microbiol. & Biotech.,* 89(2), 327-335).

Producing C7 Building Blocks Using a Recombinant Host

Typically, one or more C7 building blocks can be produced by providing a host microorganism and culturing the provided microorganism with a culture medium containing a suitable carbon source as described above. In general, the culture media and/or culture conditions can be such that the microorganisms grow to an adequate density and produce a C7 building block efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C7 building block. Once produced, any method can be used to isolate C7 building blocks. For example, C7 building blocks can be recovered selectively from the fermentation broth via adsorption processes. In the case of pimelic acid and 7-aminoheptanoic acid, the resulting eluate can be further concentrated via evaporation, crystallized via evaporative and/or cooling crystallization, and the crystals recovered via centrifugation. In the case of heptamethylenediamine and 1,7-heptanediol, distillation may be employed to achieve the desired product purity.

The invention will be further described in the following examples, which do not limit the scope of the invention described in the claims.

EXAMPLES

Example 1

Enzyme Activity of ω-Transaminase Using Pimelate Semialdehyde as Substrate and Forming 7-Aminoheptanoate A nucleotide sequence encoding an N-terminal His-tag was added to the nucleic acid sequences from *Chromobacterium violaceum, Pseudomonas syringae, Rhodobacter sphaeroides*, and *Vibrio fluvialis* encoding the ω-transaminases of SEQ ID NOs: 7, 9, 10, and 12, respectively (see FIGS. 6E-6F) such that N-terminal HIS tagged ω-transaminases could be produced. Each of the resulting modified genes was cloned into a pET21a expression vector under control of the T7 promoter and each expression vector was transformed into a BL21[DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanoate to pimelate semialdehyde) were performed in a buffer composed of a final concentration of 50 mM HEPES buffer (pH=7.5), 10 mM 7-aminoheptanoate, 10 mM pyruvate, and 100 μM pyridoxyl 5' phosphate. Each enzyme activity assay reaction was initiated by adding cell free extract of the ω-transaminase gene product or the empty vector control to the assay buffer containing the 7-aminoheptanoate and incubated at 25° C. for 4 h, with shaking at 250 rpm. The formation of L-alanine from pyruvate was quantified via RP-HPLC.

Figure 12:
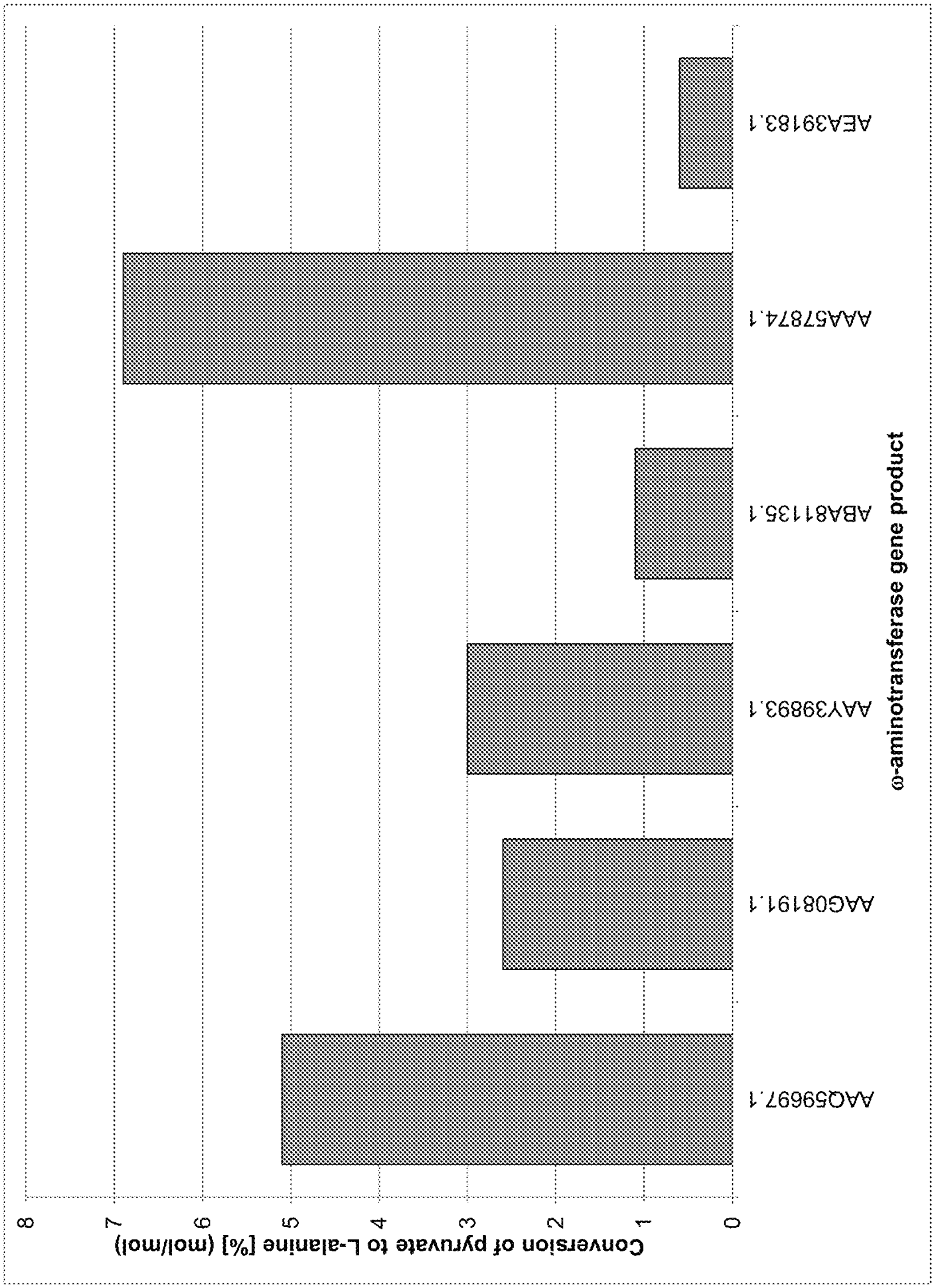
FIG. 12 is a bar graph summarizing the percent conversion of pyruvate to L-alanine (mol/mol) as a measure of the ω-transaminase activity of the enzyme only controls (no substrate).
Figure 13:
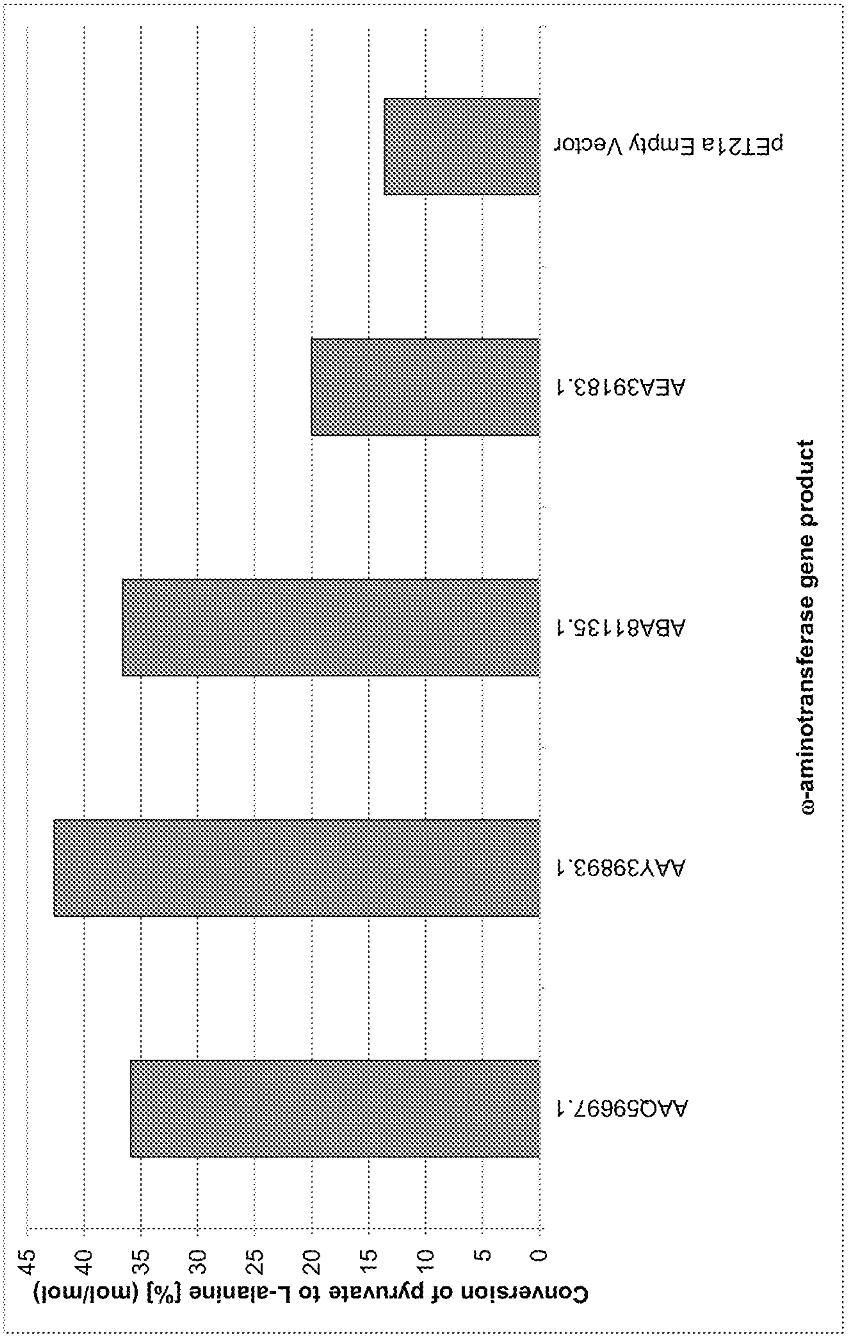
FIG. 13 is a bar graph of the percent conversion after 4 hours of pyruvate to L-alanine (mol/mol) as a measure of the ω-transaminase activity of four ω-transaminase preparations for converting 7-aminoheptanoate to pimelate semialdehyde relative to the empty vector control.

Each enzyme only control without 7-aminoheptanoate demonstrated low base line conversion of pyruvate to L-alanine. See FIG. 12. The gene products of SEQ ID NO: 7, SEQ ID NO: 9, SEQ ID NO: 10, and SEQ ID NO: 12 accepted 7-aminoheptanote as substrate as confirmed against the empty vector control. See FIG. 13.

Enzyme activity in the forward direction (i.e., pimelate semialdehyde to 7-aminoheptanoate) was confirmed for the transaminases of SEQ ID NO: 9, SEQ ID NO: 10, and SEQ ID NO: 12. Enzyme activity assays were performed in a buffer composed of a final concentration of 50 mM HEPES buffer (pH=7.5), 10 mM pimelate semialdehyde, 10 mM L-alanine, and 100 μM pyridoxyl 5' phosphate. Each enzyme activity assay reaction was initiated by adding a cell free extract of the ω-transaminase gene product or the empty vector control to the assay buffer containing the pimelate semialdehyde and incubated at 25° C. for 4 h, with shaking at 250 rpm. The formation of pyruvate was quantified via RP-HPLC.

Figure 14:
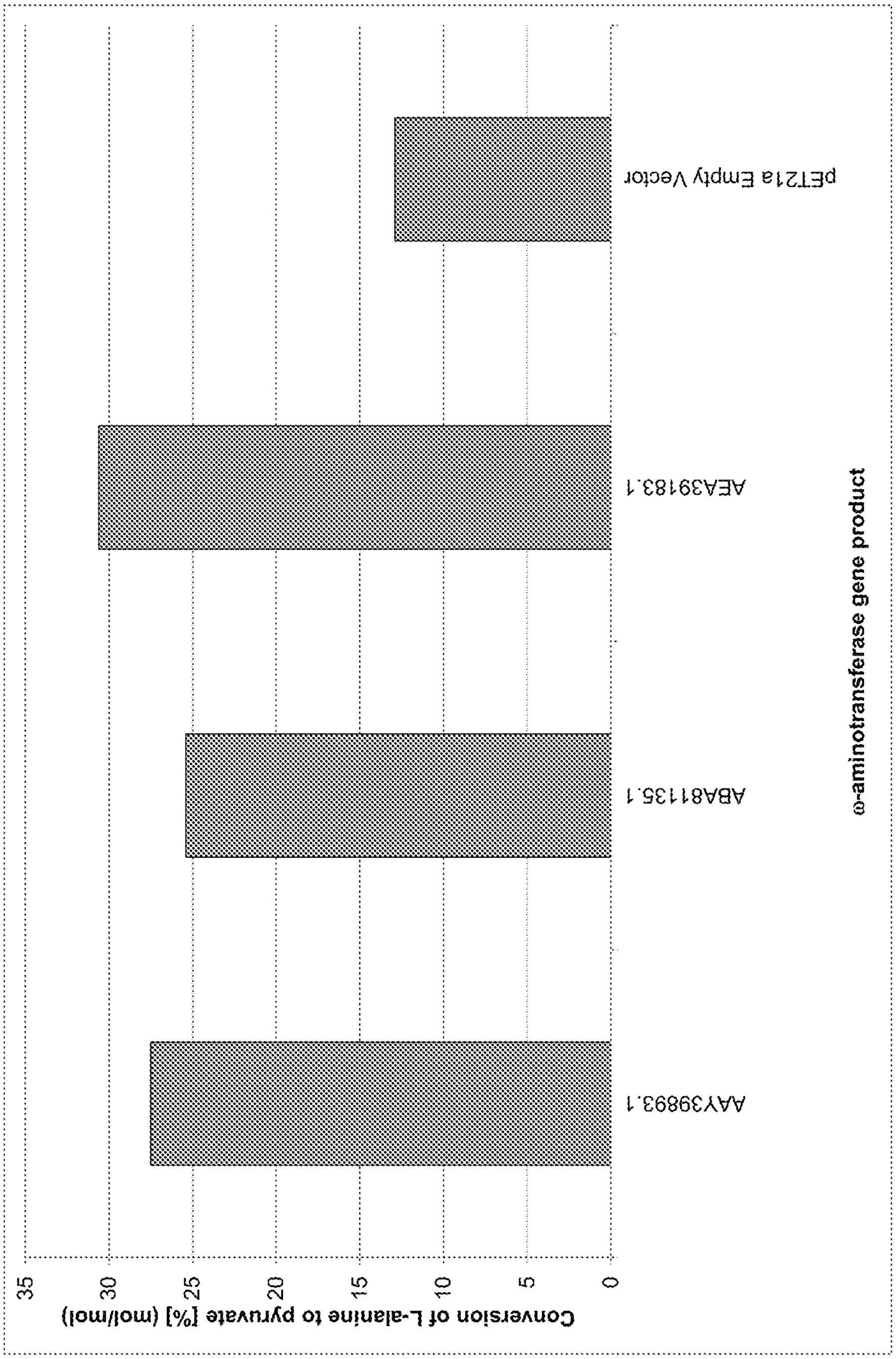
FIG. 14 is a bar graph of the percent conversion after 4 hours of L-alanine to pyruvate (mol/mol) as a measure of the ω-transaminase activity of three ω-transaminase preparations for converting pimelate semialdehyde to 7-aminoheptanoate relative to the empty vector control.

The gene products of SEQ ID NO: 9, SEQ ID NO: 10, and SEQ ID NO: 12 accepted pimelate semialdehyde as substrate as confirmed against the empty vector control. See FIG. 14. The reversibility of the ω-transaminase activity was confirmed, demonstrating that the ω-transaminases of SEQ ID NO: 7, SEQ ID NO: 9, SEQ ID NO: 10, and SEQ ID NO: 12 accepted pimelate semialdehyde as substrate and synthesized 7-aminoheptanoate as a reaction product.

Example 2

Enzyme Activity of Carboxylate Reductase Using Pimelate as Substrate and Forming Pimelate Semialdehyde A nucleotide sequence encoding a HIS-tag was added to the nucleic acid sequences from *Segniliparus rugosus* and *Segniliparus rotundus* that encode the carboxylate reductases of SEQ ID NOs: 4 (EFV11917.1) and 6 (ADG98140.1), respectively (see FIG. 6C and FIG. 6E), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21[DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Figure 7:
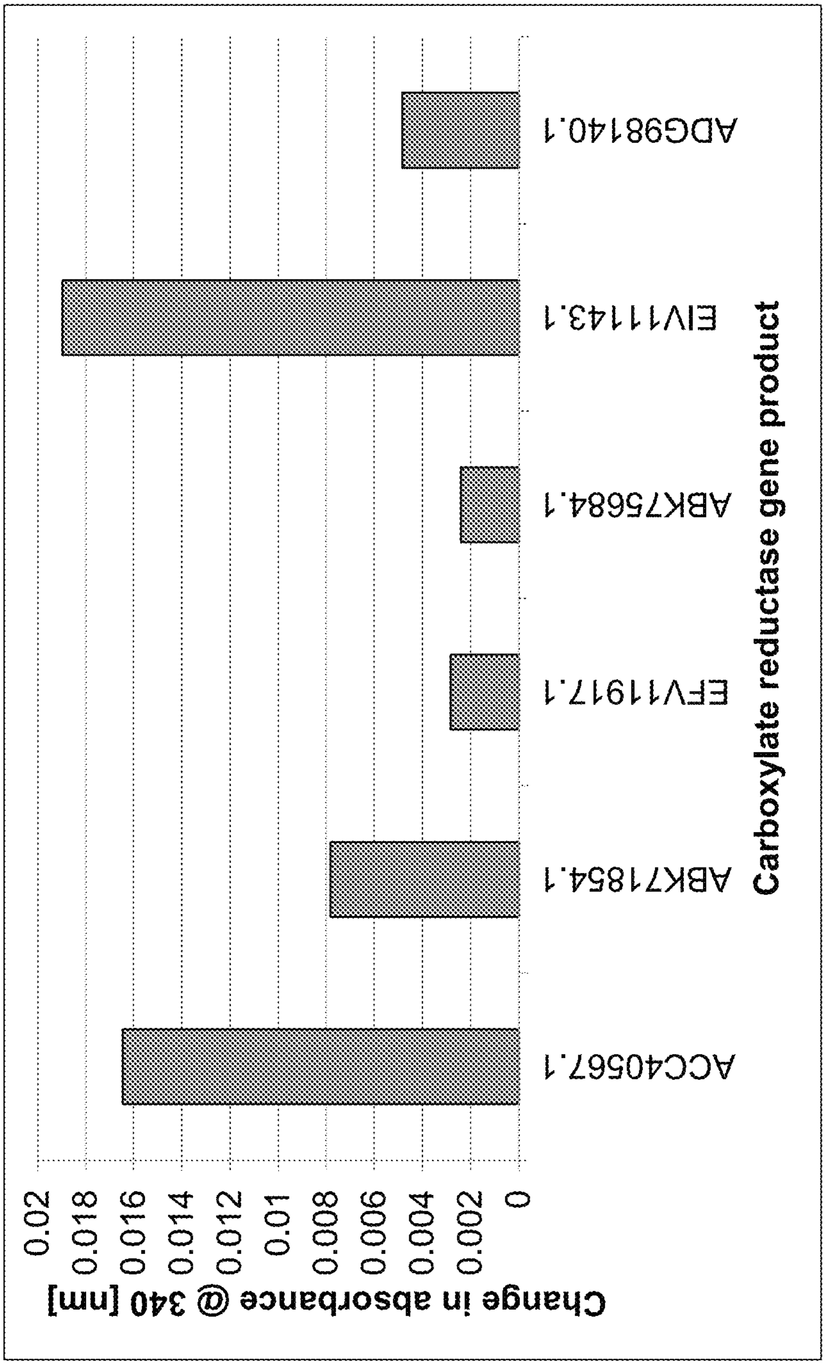
FIG. 7 is a bar graph summarizing the change in absorbance at 340 nm after 20 minutes, which is a measure of the consumption of NADPH and activity of six carboxylate reductase preparations in enzyme only controls (no substrate).

Enzyme activity assays (i.e., from pimelate to pimelate semialdehyde) were performed in triplicate in a buffer composed of a final concentration of 50 mM HEPES buffer (pH=7.5), 2 mM pimelate, 10 mM $MgCl_2$, 1 mM ATP, and 1 mM NADPH. Each enzyme activity assay reaction was initiated by adding purified carboxylate reductase and phosphopantetheine transferase gene products or the empty vector control to the assay buffer containing the pimelate and then incubated at room temperature for 20 min. The consumption of NADPH was monitored by absorbance at 340 nm. Each enzyme only control without pimelate demonstrated low base line consumption of NADPH. See bars for EFV11917.1 and ADG98140.1 in FIG. 7.

Figure 8:
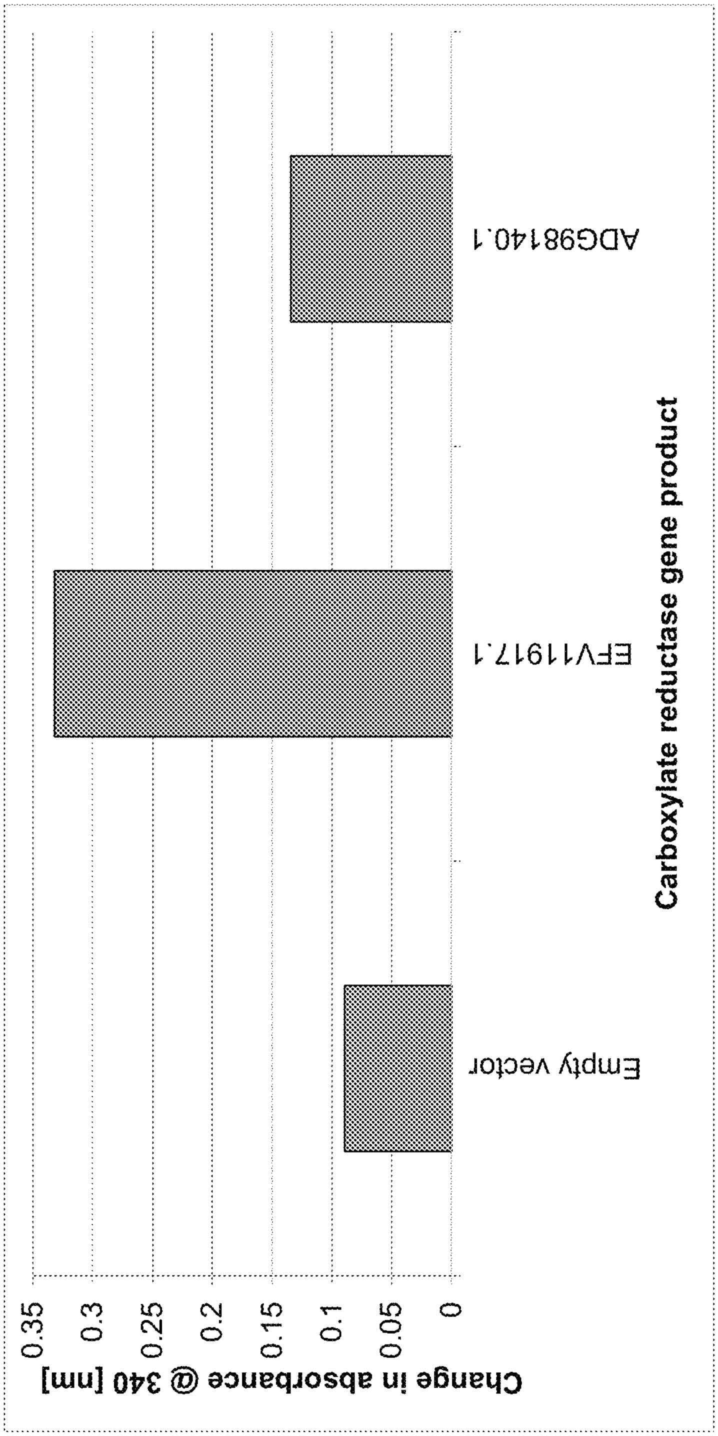
FIG. 8 is a bar graph of the change in absorbance at 340 nm after 20 minutes, which is a measure of the consumption of NADPH and the activity of two carboxylate reductase preparations for converting pimelate to pimelate semialdehyde relative to the empty vector control.

The gene products of SEQ ID NO: 4 (EFV11917.1) and SEQ ID NO: 6 (ADG98140.1), enhanced by the gene product of sfp, accepted pimelate as substrate, as confirmed against the empty vector control (see FIG. 8), and synthesized pimelate semialdehyde.

Example 3

Enzyme Activity of Carboxylate Reductase Using 7-Hydroxyheptanoate as Substrate and Forming 7-Hydroxyheptanal A nucleotide sequence encoding a His-tag was added to the nucleic acids from *Mycobacterium marinum, Mycobacterium smegmatis, Segniliparus rugosus, Mycobacterium abscessus* subsp. *bolletii, Segniliparus rotundus*, and *Mycobacterium smegmatis* that encode the carboxylate reductases of SEQ ID NOs: 2-6 and 14, respectively (GenBank Accession Nos. ACC40567.1, ABK71854.1, EFV11917.1, EIV11143.1, ADG98140.1, and ABK75684.1, respectively) (see FIGS. 6A-6E, and FIG. 6G) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* host along with the expression vectors from Example 3. Each resulting recombinant 20 *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5), and concentrated via ultrafiltration.

Enzyme activity (i.e., 7-hydroxyheptanoate to 7-hydroxyheptanal) assays were performed in triplicate in a buffer composed of a final concentration of 50 mM HEPES buffer (pH=7.5), 2 mM 7-hydroxyheptanal, 10 mM $MgCl_2$, 1 mM ATP, and 1 mM NADPH. Each enzyme activity assay reaction was initiated by adding purified carboxylate reductase and phosphopantetheine transferase or the empty vector control to the assay buffer containing the 7-hydroxyheptanoate and then incubated at room temperature for 20 min. The consumption of NADPH was monitored by absorbance at 340 nm. Each enzyme only control without 7-hydroxyheptanoate demonstrated low base line consumption of NADPH. See FIG. 7.

Figure 9:
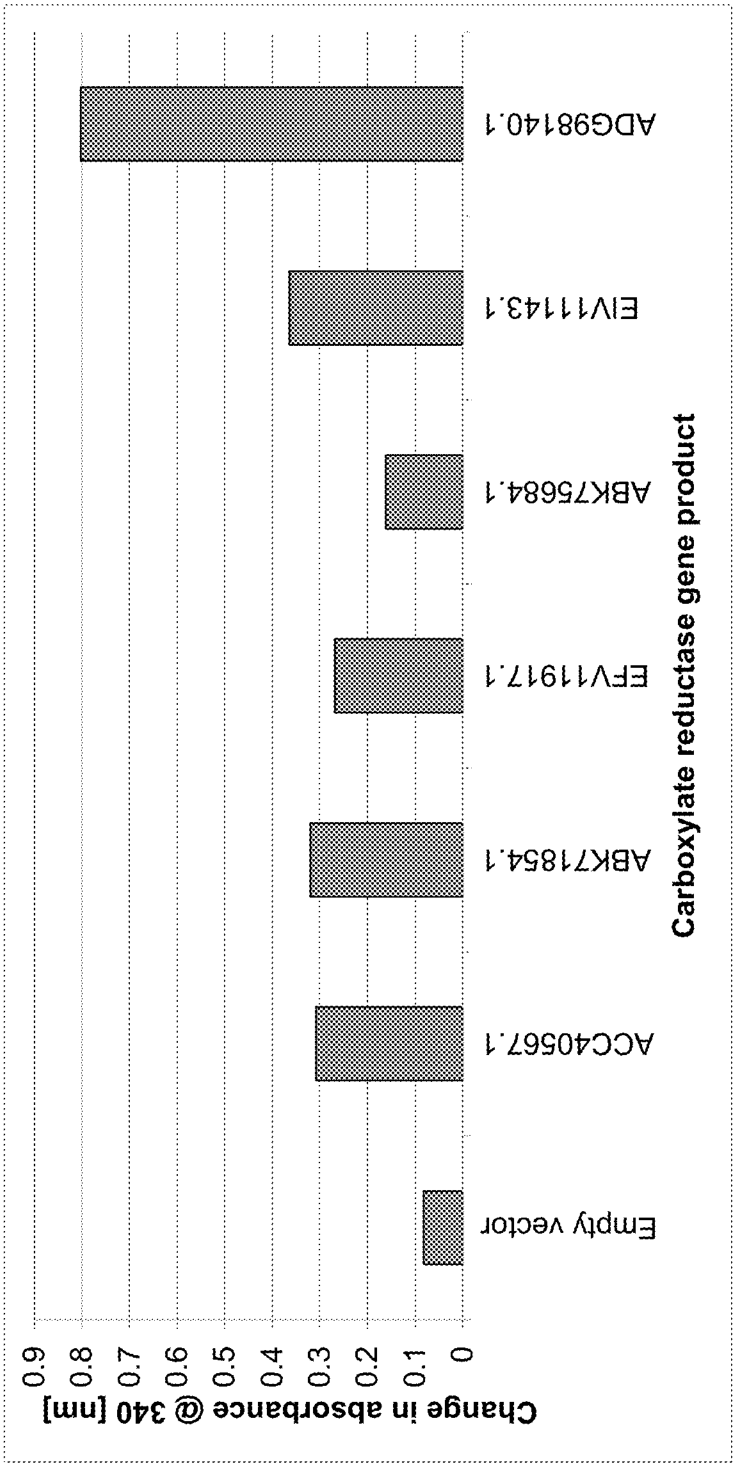
FIG. 9 is a bar graph of the change in absorbance at 340 nm after 20 minutes, which is a measure of the consumption of NADPH and the activity of six carboxylate reductase preparations for converting 7-hydroxyheptanoate to 7-hydroxyheptanal relative to the empty vector control.

The gene products of SEQ ID NOs: 2-6 and 14, enhanced by the gene product of sfp, accepted 7-hydroxyheptanoate as substrate as confirmed against the empty vector control (see FIG. 9), and synthesized 7-hydroxyheptanal.

Example 4

Enzyme Activity of ω-Transaminase for 7-Aminoheptanol, Forming 7-Oxoheptanol A nucleotide sequence encoding an N-terminal His-tag was added to the *Chromobacterium violaceum, Pseudomonas syringae*, and *Rhodobacter sphaeroides* nucleic acids encoding the ω-transaminases of SEQ ID NOs: 7, 9 and 10, respectively (see FIGS. 6E-6F), such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain was cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 7-aminoheptanol to 7-oxoheptanol) were performed in a buffer composed of a final concentration of 50 mM HEPES buffer (pH=7.5), 10 mM 7-aminoheptanol, 10 mM pyruvate, and 100 μM pyridoxyl 5' phosphate. Each enzyme activity assay reaction was initiated by adding cell free extract of the ω-transaminase gene product or the empty vector control to the assay buffer containing the 7-aminoheptanol and then incubated at 25° C. for 4 h, with shaking at 250 rpm. The formation of L-alanine was quantified via RP-HPLC.

Each enzyme only control without 7-aminoheptanol had low base line conversion of pyruvate to L-alanine. See FIG. 12.

Figure 17:
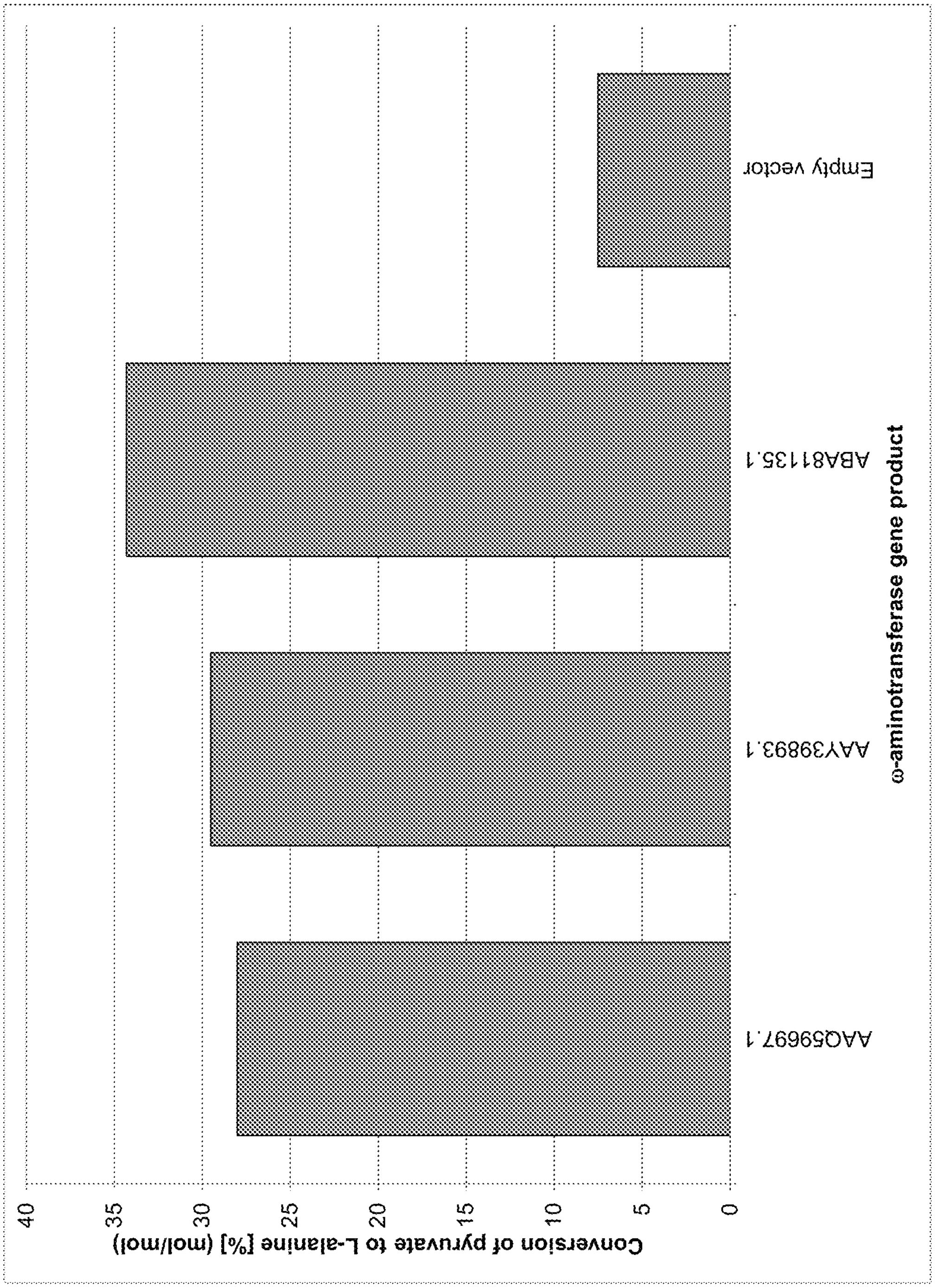
FIG. 17 is a bar graph of the percent conversion after 4 hours of pyruvate to L-alanine (mol/mol) as a measure of the ω-transaminase activity of three ω-transaminase preparations for converting 7-aminoheptanol to 7-oxoheptanol relative to the empty vector control.

The gene products of SEQ ID NOs: 7, 9 & 10 accepted 7-aminoheptanol as substrate as confirmed against the empty vector control (see FIG. 17) and synthesized 7-oxoheptanol as reaction product. Given the reversibility of the ω-transaminase activity (see Example 1), it can be concluded that the gene products of SEQ ID NOs: 7, 9 & 10 accept 7-oxoheptanol as substrate and form 7-aminoheptanol.

Example 5

Enzyme Activity of ω-Transaminase Using Heptamethylenediamine as Substrate and Forming 7-Aminoheptanal A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* nucleic acids encoding the ω-transaminases of SEQ ID NOs: 7-12, respectively (see FIGS. 6E-6F) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain was cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., heptamethylenediamine to 7-aminoheptanal) were performed in a buffer composed of a final concentration of 50 mM HEPES buffer (pH=7.5), 10 mM heptamethylenediamine, 10 mM pyruvate, and 100 μM pyridoxyl 5' phosphate. Each enzyme activity assay reaction was initiated by adding cell free extract of the ω-transaminase gene product or the empty vector control to the assay buffer containing the heptamethylenediamine and then incubated at 25° C. for 4 h, with shaking at 250 rpm. The formation of L-alanine was quantified via RP-HPLC.

Each enzyme only control without heptamethylenediamine had low base line conversion of pyruvate to L-alanine. See FIG. 12.

Figure 15:
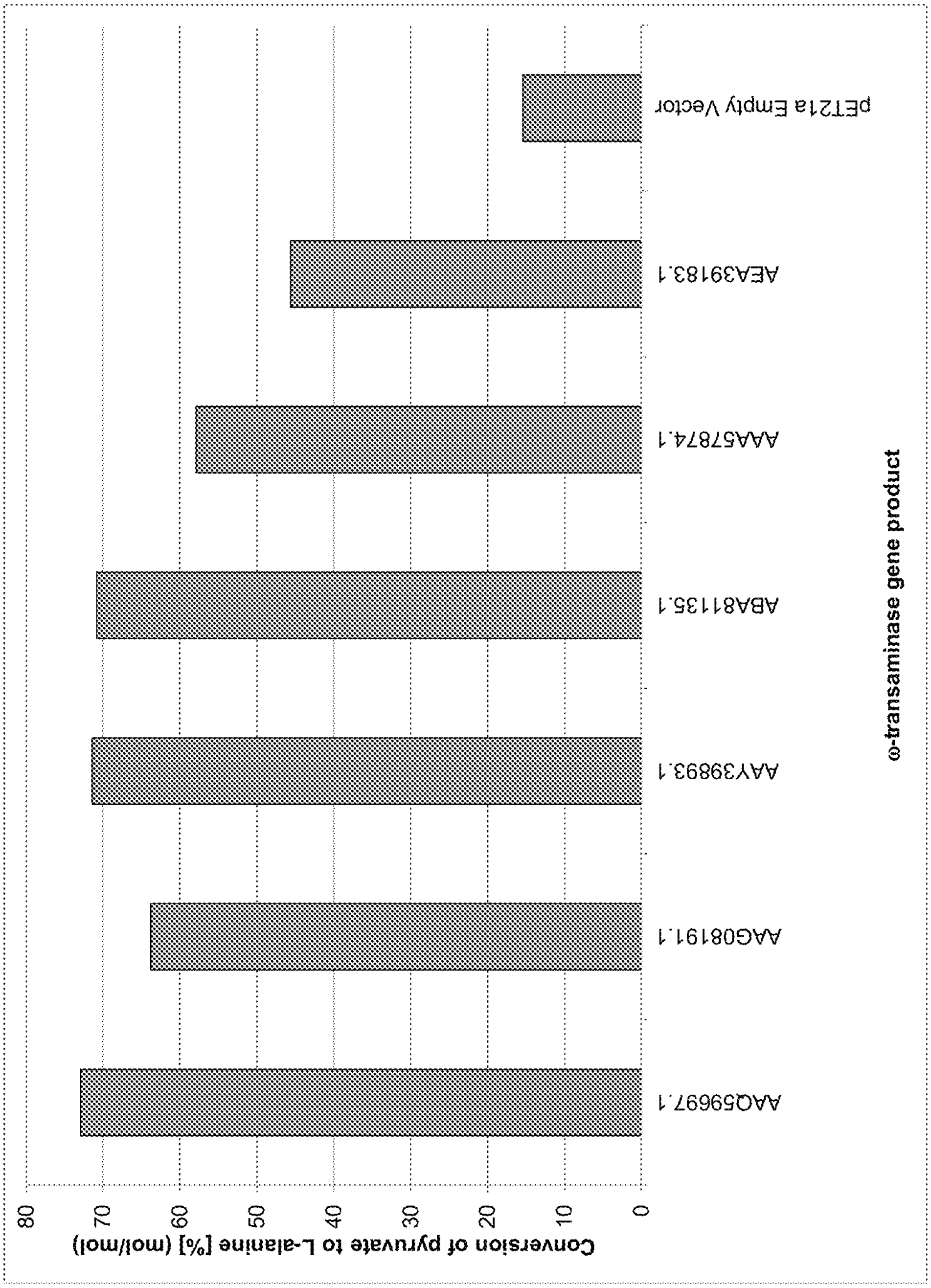
FIG. 15 is a bar graph of the percent conversion after 4 hours of pyruvate to L-alanine (mol/mol) as a measure of the ω-transaminase activity of six ω-transaminase preparations for converting heptamethylenediamine to 7-aminoheptanal relative to the empty vector control.

The gene products of SEQ ID NOs: 7-12 accepted heptamethylenediamine as substrate as confirmed against the empty vector control (see FIG. 15) and synthesized 7-aminoheptanal as reaction product. Given the reversibility of the ω-transaminase activity (see Example 1), it can be concluded that the gene products of SEQ ID NOs: 7-12 accept 7-aminoheptanal as substrate and form heptamethylenediamine.

Example 6

Enzyme Activity of Carboxylate Reductase for N7-Acetyl-7-Aminoheptanoate, Forming N7-Acetyl-7-Aminoheptanal The activity of each of the N-terminal His-tagged carboxylate reductases of SEQ ID NOs: 3, 5, and 6 (see Examples 2 and 3, and FIG. 6B, FIGS. 6D-6E) for converting N7-acetyl-7-aminoheptanoate to N7-acetyl-7-aminoheptanal was assayed in triplicate in a buffer composed of a final concentration of 50 mM HEPES buffer (pH=7.5), 2 mM N7-acetyl-7-aminoheptanoate, 10 mM $MgCl_2$, 1 mM ATP, and 1 mM NADPH. The assays were initiated by adding purified carboxylate reductase and phosphopantetheine transferase or the empty vector control to the assay buffer containing the N7-acetyl-7-aminoheptanoate then incubated at room temperature for 20 min. The consumption of NADPH was monitored by absorbance at 340 nm. Each enzyme only control without N7-acetyl-7-aminoheptanoate demonstrated low base line consumption of NADPH. See FIG. 7.

Figure 10:
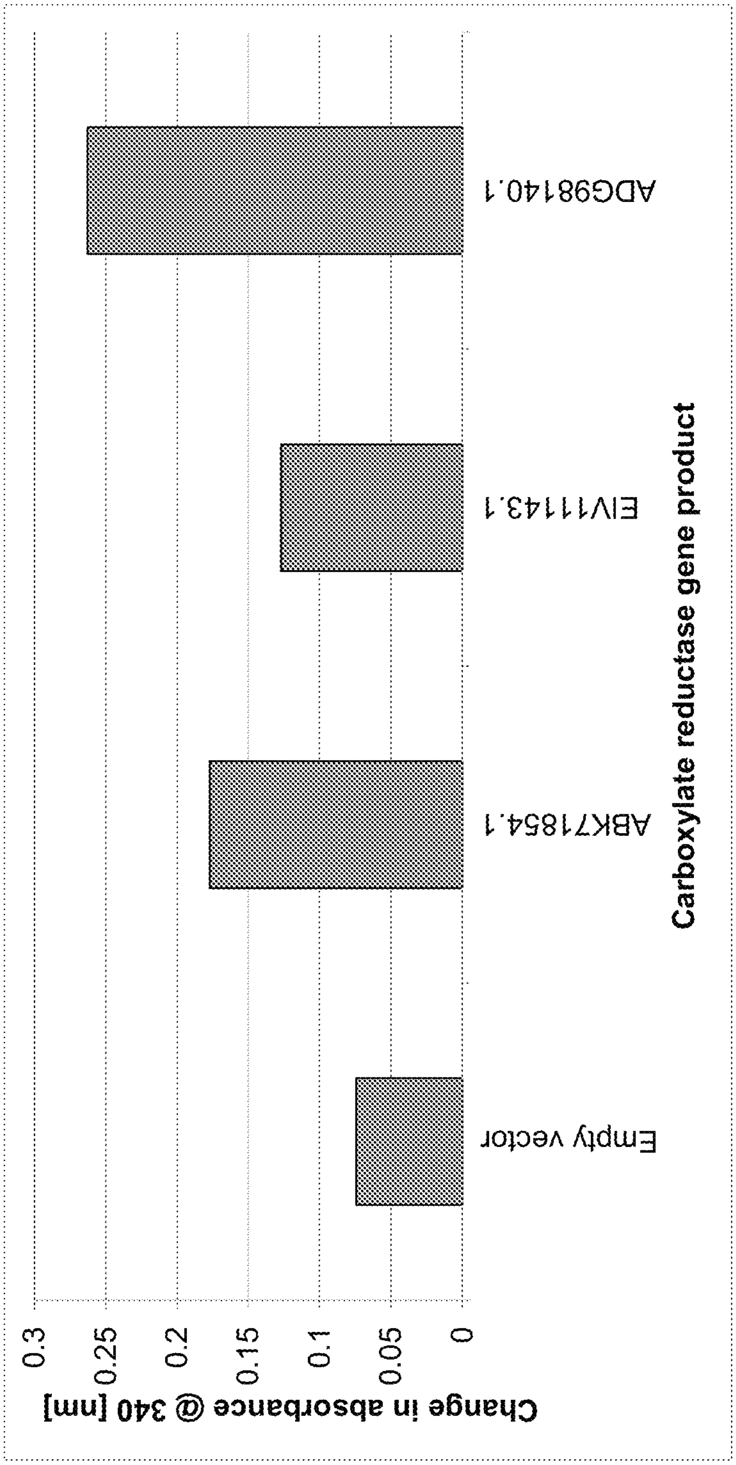
FIG. 10 is a bar graph of the change in absorbance at 340 nm after 20 minutes, which is a measure of the consumption of NADPH and the activity of three carboxylate reductase preparations for converting N7-acetyl-7-aminoheptanoate to N7-acetyl-7-aminoheptanal relative to the empty vector control.

The gene products of SEQ ID NOs: 3, 5, and 6, enhanced by the gene product of sfp, accepted N7-acetyl-7-aminoheptanoate as substrate as confirmed against the empty vector control (see FIG. 10), and synthesized N7-acetyl-7-aminoheptanal.

Example 7

Enzyme Activity of ω-Transaminase Using N7-Acetyl-1,7-Diaminoheptane, and Forming N7-Acetyl-7-Aminoheptanal The activity of the N-terminal His-tagged ω-transaminases of SEQ ID NOs: 7-12 (see Example 5, and FIGS. 6E-6F) for converting N7-acetyl-1,7-diaminoheptane to N7-acetyl-7-aminoheptanal was assayed using a buffer composed of a final concentration of 50 mM HEPES buffer (pH=7.5), 10 mM N7-acetyl-1,7-diaminoheptane, 10 mM pyruvate, and 100 μM pyridoxyl 5' phosphate. Each enzyme activity assay reaction was initiated by adding a cell free extract of the ω-transaminase or the empty vector control to the assay buffer containing the N7-acetyl-1,7-diaminoheptane then incubated at 25° C. for 4 h, with shaking at 250 rpm. The formation of L-alanine was quantified via RP-HPLC.

Each enzyme only control without N7-acetyl-1,7-diaminoheptane demonstrated low base line conversion of pyruvate to L-alanine. See FIG. 12.

Figure 16:
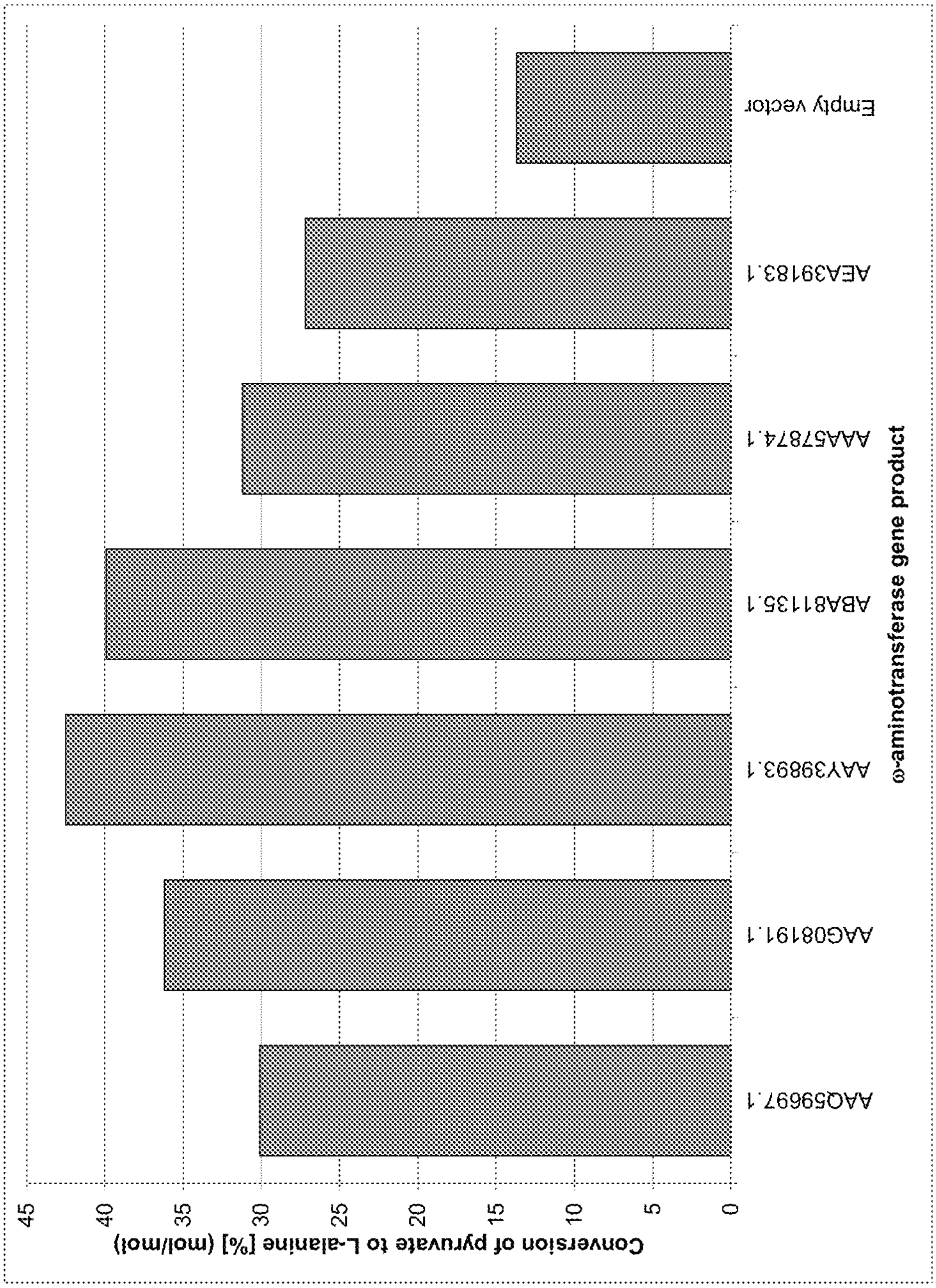
FIG. 16 is a bar graph of the percent conversion after 4 hours of pyruvate to L-alanine (mol/mol) as a measure of the ω-transaminase activity of six ω-transaminase preparations for converting N7-acetyl-1,7-diaminoheptane to N7-acetyl-7-aminoheptanal relative to the empty vector control.

The gene products of SEQ ID NOs: 7-12 accepted N7-acetyl-1,7-diaminoheptane as substrate as confirmed against the empty vector control (see FIG. 16) and synthesized N7-acetyl-7-aminoheptanal as reaction product.

Given the reversibility of the ω-transaminase activity (see Example 1), the gene products of SEQ ID NOs: 7-12 accept N7-acetyl-7-aminoheptanal as substrate forming N7-acetyl-1,7-diaminoheptane.

Example 8

Enzyme Activity of Carboxylate Reductase Using Pimelate Semialdehyde as Substrate and Forming Heptanedial The N-terminal His-tagged carboxylate reductase of SEQ ID NO: 6 (see Example 3 and FIG. 6E) was assayed using pimelate semialdehyde as substrate. The enzyme activity assay was performed in triplicate in a buffer composed of a final concentration of 50 mM HEPES buffer (pH=7.5), 2 mM pimelate semialdehyde, 10 mM $MgCl_2$, 1 mM ATP, and 1 mM NADPH. The enzyme activity assay reaction was initiated by adding purified carboxylate reductase and phosphopantetheine transferase or the empty vector control to the assay buffer containing the pimelate semialdehyde and then incubated at room temperature for 20 min. The consumption of NADPH was monitored by absorbance at 340 nm. The enzyme only control without pimelate semialdehyde demonstrated low base line consumption of NADPH. See FIG. 7.

Figure 11:
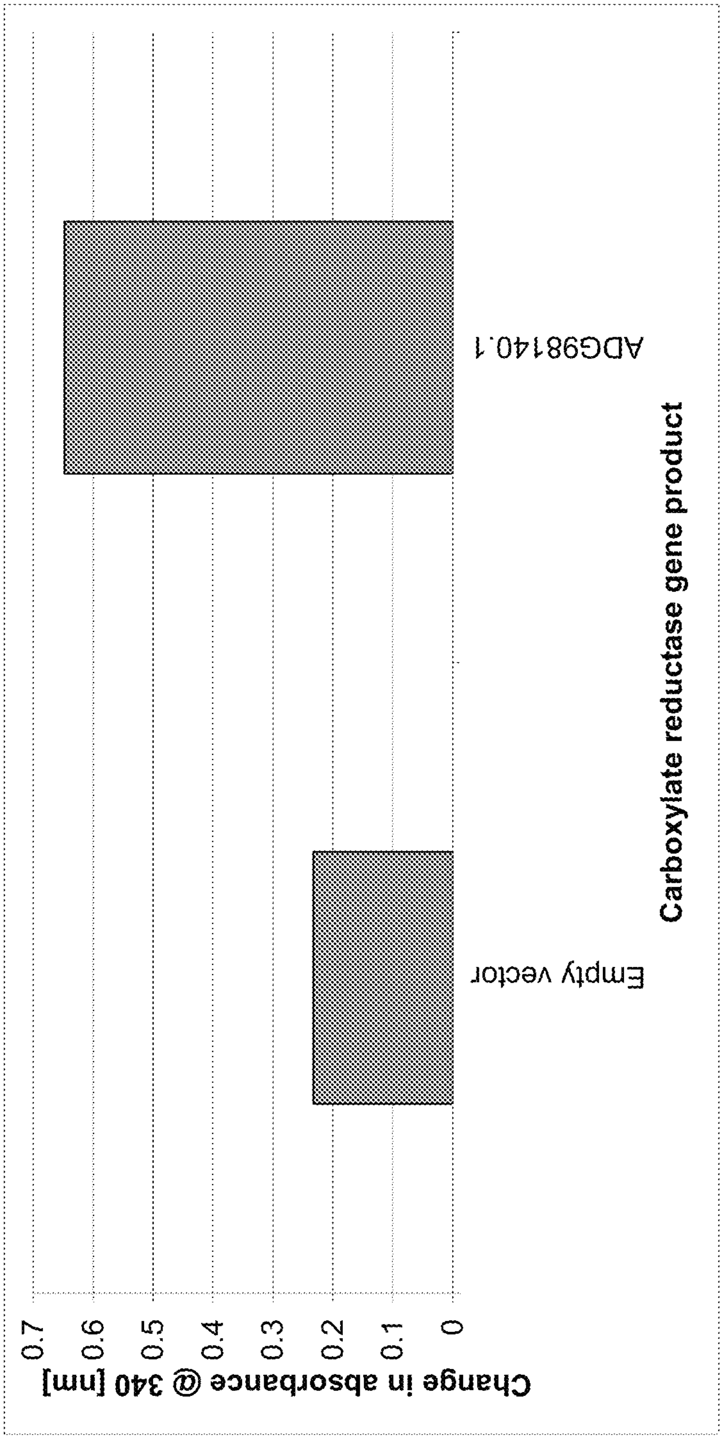
FIG. 11 is a bar graph of the change in absorbance at 340 nm after 20 minutes, which is a measure of the consumption of NADPH and activity of a carboxylate reductase preparation for converting pimelate semialdehyde to heptanedial relative to the empty vector control.

The gene product of SEQ ID NO: 6, enhanced by the gene product of sfp, accepted pimelate semialdehyde as substrate as confirmed against the empty vector control (see FIG. 11) and synthesized heptanedial.

Example 9

Biotransformation of 5-Hydroxypentanoate to 3-Oxo-7-Hydroxyheptanoyl-CoA in a Two-Step Enzymatic Reaction Catalyzed by a 5-Hydroxyvalerate CoA Transferase and an Enzyme from the Thiolase Family An enzyme with a 5-hydroxyvalerate CoA transferase activity was identified following the sequencing of *Clostridium viride* genome and subsequent analysis for putative CoA transferases. Five enzyme sequences were identified and two of these transferases acted upon 5-hydroxyvalerate. The CoA transferase selected for the reaction described in this Example is further called BDIGENE #246. The sequence is currently available publicly as NCBI Reference Sequence WP_027096059.1 (SEQ ID NO: 37). The gene (SEQ ID NO: 60) encoding the 5-hydroxyvalerate CoA transferase was codon-optimized for expression in *E. coli.*

Selected genes (SEQ ID NOs: 38-57) encoding various enzymes from thiolase family (see FIG. 18 for the list of the thiolases tested) were codon-optimized for expression in *E. coli*, synthesized and cloned into pET15b vector with the NdeI and BamHI restriction sites. Gene sequences were checked to ensure they did not contain the recognition sequences of these two restriction enzymes prior to cloning. The selection was supplemented by paaJ from *E. coli* which was cloned out of the respective genomic DNA. For P0C7L2 and Q0KBP1, the genes (SEQ ID NO: 58, and SEQ ID NO: 59, respectively) were cloned from naturally occurring sources. Specifically, the gene encoding P0C7L2 was from *Escherichia coli*, and the gene encoding Q0KBP1 was from *Cupriavidus necator*. The following chart shows the list of the genes expressed in this Example, as well as their corresponding thiolase designations as shown FIG. 18. See also FIGS. 19A-19M.

Figure 18:
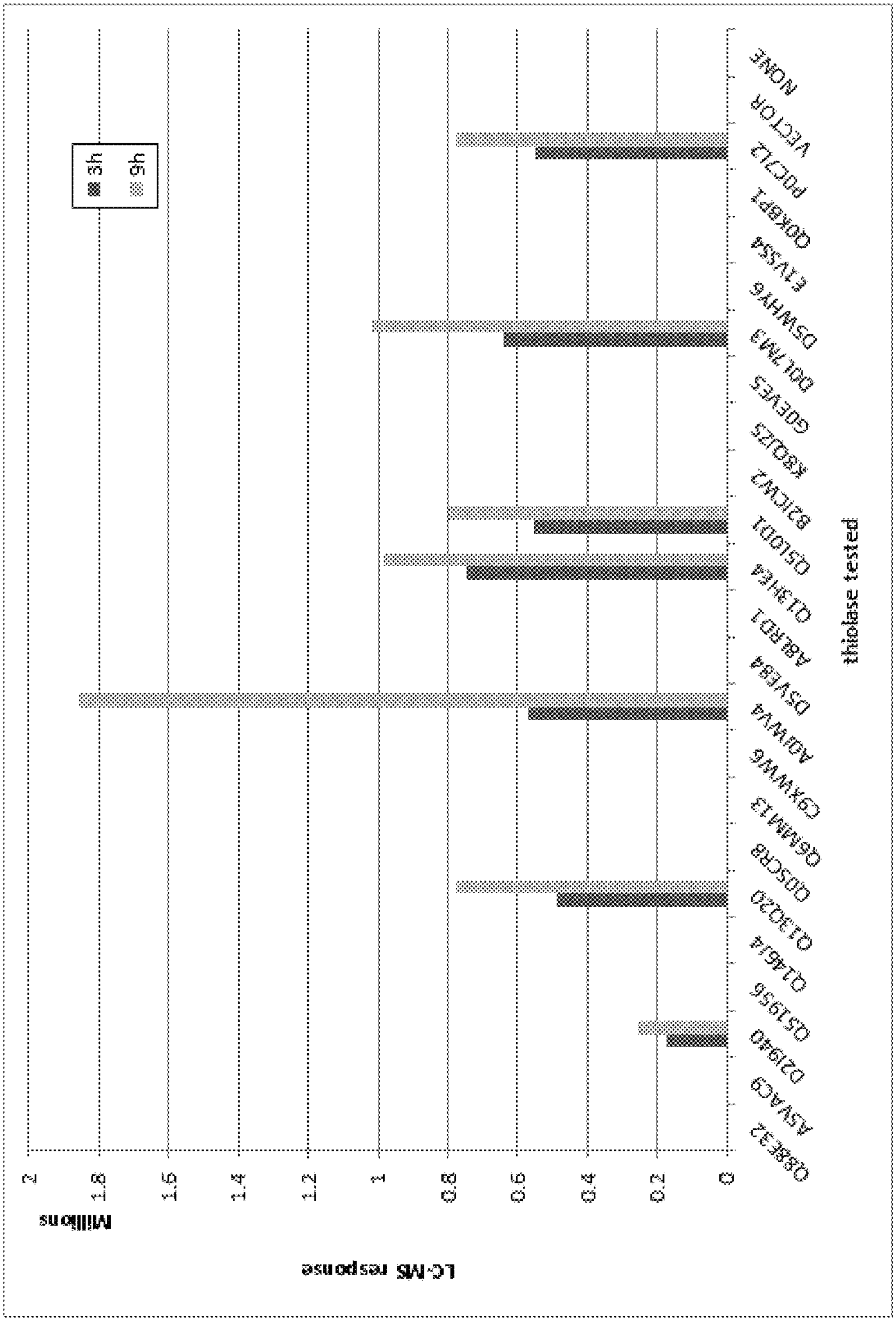
FIG. 18 is a bar graph of the production of 3-oxo-7-hydroxyheptanoyl-CoA after 3 hours and 9 hours in a two-step enzymatic reaction catalyzed by a 5-hydroxyvalerate CoA transferase and an enzyme from the thiolase family, relative to the empty vector control.

| SEQ ID NO | Designation in FIG. 18 |
|---|---|
| SEQ ID NO: 38 | Q88E32 from *Pseudomonas putida* |
| SEQ ID NO: 39 | A5VAC9 from *Sphingomonas wittichii* |
| SEQ ID NO: 40 | D2I940 from *Pseudomonas reinekei* |
| SEQ ID NO: 41 | Q51956 from *Pseudomonas putida* |
| SEQ ID NO: 42 | Q146J4 from *Burkholderia xenovorans* |
| SEQ ID NO: 43 | Q13Q20 from *Burkholderia xenovorans* |
| SEQ ID NO: 44 | Q0SCR8 from *Rhodococcus jostii* |
| SEQ ID NO: 45 | Q6MM13 from *Bdellovibrio bacteriovorus* |
| SEQ ID NO: 46 | C9XWW6 from *Cronobacter turicensis* |
| SEQ ID NO: 47 | A0JWV4 from *Arthrobacter* sp. |
| SEQ ID NO: 48 | D5VE84 from *Caulobacter segnis* |
| SEQ ID NO: 49 | A8LRD1 from *Dinoroseobacter shibae* |
| SEQ ID NO: 50 | Q13HE4 from *Burkholderia xenovorans* |
| SEQ ID NO: 51 | GK1320 from *Geobacillus kaustophilus* |
| SEQ ID NO: 52 | B2ICW2 from *Beijerinckia indica* |
| SEQ ID NO: 53 | K8QJZ5 from *Citrobacter freundii* |
| SEQ ID NO: 54 | G0EVE5 from *Cupriavidus necator* |
| SEQ ID NO: 55 | D0L7M3 from *Gordonia bronchialis* |
| SEQ ID NO: 56 | D5WHY6 from *Burkholderia* sp. |
| SEQ ID NO: 57 | E1VSS4 from *Arthrobacter arilaitensis* |
| SEQ ID NO: 58 | P0C7L2 from *Escherichia coli* |
| SEQ ID NO: 59 | Q0KBP1 from *Cupriavidus necator* |

For each culture, expression plasmids were freshly transformed into BL21(DE3) (Agilent). Colonies from fresh agar plates were used to inoculate 20 ml LB in 250 ml flask overnight pre-culture. For all constructs except 237, ampicillin was used, for 237 kanamycin was required. After incubation overnight at 37° C. and 200 rpm, pre-cultures were used to inoculate (1:100) larger cultures, 350 ml LB, with respective antibiotic in 11 flasks. After 2.5 h of shaking with 200 rpm at 37° C., cultures reached OD600 in the range 0.5-0.7 at which point they were induced with 1 mM IPTG and the temperature of the culture was changed to 25° C. Incubation continued overnight. Cells were harvested the next day and stored at −20° C. until protein purification was performed.

To purify an overexpressed protein, a bacterial pellet from a 350 ml culture was resuspended in up to total 20 ml of Binding Buffer (20 mM Sodium phosphate pH 7.4, 500 mM Sodium chloride, 20 mM imidazole, 5% glycerol) and sonicated for 2 min with a microtip (amplitude 50%, 1 s pulse ON, 2 s OFF). Cell suspension was centrifuged with 20,000 G for 30 min at 4° C. As all the tested proteins were His-tagged, the purification with Immobilized Metal Affinity Chromatography was sufficient to ensure both necessary purity and amount for the enzymatic assays. HisTrap (GE Healthcare) purification has been performed exactly according to manufacturer's protocol. Proteins were eluted with 2×60 μl of Elution Buffer (20 mM Sodium phosphate pH 7.4, 500 mM Sodium chloride, 500 mM imidazole, 5% glycerol) and stored frozen at −20° C.

Prior to tests with non-native substrates, enzymes were assayed for their native biological activity. Many of the selected enzymes are putative proteins, whose existence was inferred from homology to known thiolases and thus had not yet been biochemically investigated. In most cases there was no information available on what could be a possible native substrate. Therefore to assess their activity acetoacetyl-CoA was successfully used for all of them as a test substrate. The method from Slater (Slater et al., *J. Bacteriol.,* 1998, 180 (8):1979-1987) was used with minor modifications for assay of native enzyme activity. Assays were performed in disposable Corning UV-transparent 96-well plates without cover. Typically 200 μl reaction mix contained 150 mM Tris-HCl pH 8.0, 50 mM $MgCl_2$, 100 μM CoA, with or without 40 μM acetoacetyl-CoA (Sigma). Reaction was started by the addition of 10 μl enzyme prepared as described above. Absorbance at 304 nm, corresponding to the disappearing acetoacetyl-CoA, was followed every minute for 2 hours. Negative controls with/without main substrate or with/without enzyme, as well as with empty vector were always included. The method showed that there was a good correlation between the solubility of the enzyme as judged from the SDS-PAGE gels and the apparent thiolase activity tested with this assay.

The set of thiolases was tested to investigate whether they would be able to accept 5-hydroxyvaleryl-CoA as a substrate to produce 3-oxo-7-hydroxyheptanoyl-CoA. Selected thiolases were tested in a coupled assay with BDIGENE #246 CoA transferase using 5-hydroxyvalerate and acetyl-CoA as substrates.

LC-MS based assay performed in 96-well format with 300 μl total reaction volume in each well. Reaction mix contained 50 mM potassium phosphate pH 6.8, 1 mM acetyl-CoA (Applichem) and 1 mM of 5-hydroxyvalerate. Control samples without the substrate and/or without enzyme were always included. Samples with the empty vector control were included in each run as a reference. The reaction was initiated by the addition of 10 μl of enzyme aliquote to 300 μl reaction mix. The plate was covered with adhesive tape to minimize the evaporation and incubated at 30° C. with gentle shaking (600 rpm in the Eppendorf thermomixer) for 3 hours. After the incubation samples were transferred with multichannel pipette to the 96-format filter (AcroPrep Advanced Filter Plate 0.2 m Supor) and filtered by centrifugation at 1500 G for 4 min to a clean 96-well plate before the LC-MS analysis. There were no analytical standards available for the reaction products hence the analysis relied exclusively on the presence of ions with expected molecular weight.

Analysis of acyl-CoAs was performed using an Agilent Technologies 1290 Series Infinity HPLC system coupled to an Agilent 6530 Series Q-ToF mass spectrometer equipped with an ESI interface operating in positive polarity with centroid data storage. QToF parameters were as follows: source temperature 350° C., drying gas flow rate 13 l/min, nebulizer pressure 60 psig, sheath gas temperature 400° C., sheath gas flow rate 12 l/min, VCap 3500 V, nozzle voltage 1000 V, fragmentor voltage 100 V, skimmer voltage 60 V, Octopole 1 RF voltage 750 V; scan range 50-1100 m/z, scan rate 2 spectra/sec; reference masses of 121.0509 m/z and 922.0098 m/z were infused directly into the source of the MS to ensure accurate mass correction of the instrument. Mobile phase A was 10 mM ammonium acetate and mobile phase B was acetonitrile.

For acyl-CoA screening a C18 column measuring 2.1 mm×50 mm with a 1.8 m particle size, 95 Å pore size and 0.5 m frit was used (Agilent part no: 959757-902). Autosampler was kept at 4° C. and 5 μl of analyte was injected from each sample. Between injections the needle was washed with mobile phase in the flush port for 3 s to decrease the possibility of carryover contamination. Acyl-CoAs were eluted according to varying the percentage of mobile phase B as follows: 0-1 min, 3% B; 4-5.2 min, 100% B; 5.5-6.8 min, 3% B. Total run time was 6.8 minutes per sample. The intermediate product of the coupled reactions, 5-hydroxyvaleryl-CoA, was detected in all samples containing both substrates and BDIGENE #246. The final product, 3-oxo-7-hydroxyheptanoyl-CoA, was detected in several samples as illustrated in FIG. 18.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing 3-oxo-7-hydroxyheptanoyl-CoA or a salt thereof, said method comprising enzymatically converting 5-hydroxypentanoyl-CoA to 3-oxo-7-hydroxyheptanoyl-CoA using a polypeptide having the activity of a β-ketothiolase classified under EC 2.3.1.16 or EC 2.3.1.174.

2. The method of claim 1, wherein said β-ketothiolase (a) has at least 90% sequence identity to the amino acid sequence set forth in SEQ ID NO:1 or SEQ ID NO: 13 or (b) has at least 90% sequence identity to the amino acid sequence set forth in SEQ ID NO:1 or SEQ ID NO: 13 and is capable of converting 5-hydroxypentanoyl-CoA to 3-oxo-7-hydroxyheptanoyl-CoA.

3. The method of claim 1, further comprising enzymatically converting 3-oxo-7-hydroxyheptanoyl-CoA to 7-hydroxyheptanoate using a polypeptide having the activity of a 3-hydroxyacyl-CoA dehydrogenase or a 3-oxoacyl-CoA reductase, an enoyl-CoA hydratase, a trans-2-enoyl-CoA reductase, and a thioesterase or a CoA transferase.

4. The method of claim 3, wherein said 3-hydroxyacyl-CoA dehydrogenase or said 3-oxoacyl-CoA reductase is classified under EC 1.1.1.35, EC 1.1.1.36, EC 1.1.1.100, or EC 1.1.1.157.

5. The method of claim 3, wherein said enoyl-CoA hydratase is classified under EC 4.2.1.17 or EC 4.2.1.119.

6. The method of claim 5, wherein said trans-2-enoyl-CoA reductase is classified under EC 1.3.1.38, EC 1.3.1.44, or EC 1.3.1.8.

7. The method of claim 3, said method further comprising enzymatically converting 7-hydroxyheptanoate to pimelic acid, 7-aminoheptanoate, heptamethylenediamine, or 1,7-heptanediol in one or more steps.

8. The method of claim 7, wherein 7-hydroxyheptanoate is converted to pimelic acid using one or more of a monooxygenase, an alcohol dehydrogenase, a 4-hydroxybutyrate dehydrogenase, a 5-hydroxyvalerate dehydrogenase, a 6-hydroxyhexanoate dehydrogenase, a 7-oxoheptanoate dehydrogenase, a 6-oxohexanoate dehydrogenase, a 5-oxovalerate dehydrogenase, or an aldehyde dehydrogenase.

9. The method of claim 7, wherein 7-hydroxyheptanoate is converted to 7-aminoheptanoate using one or more of a polypeptide having the activity of an alcohol dehydrogenase, a 6-hydroxyhexanoate dehydrogenase, a 5-hydroxypentanoate dehydrogenase, a 4-hydroxybutyrate dehydrogenase, and a ω-transaminase.

10. The method of claim 7, wherein 7-hydroxyheptanoate is converted to heptamethylenediamine using one or more of a carboxylate reductase, a ω-transaminase, an alcohol dehydrogenase, an N-acetyltransferase, and an acetylputrescine deacylase.

11. The method of claim 9, wherein said ω-transaminase has at least 70% sequence identity to any one of the amino acid sequences set forth in SEQ ID NOs.: 7-12.

12. The method of claim 7, wherein 7-hydroxyheptanoate is converted to 1,7-heptanediol using a carboxylate reductase and an alcohol dehydrogenase.

13. The method of claim 12, wherein said carboxylate reductase has at least 70% sequence identity to any one of the amino acid sequences set forth in SEQ ID NOs.: 2-6.

14. The method of claim 1, wherein said 5-hydroxypentanoyl-CoA is enzymatically produced from 2-oxoadipate or malonyl-CoA.

15. The method of claim 14, wherein 5-hydroxypentanoyl-CoA is enzymatically produced from 2-oxoadipate—using one or more of an alpha-aminotransaminase; a 2-oxoadipate decarboxylase; a branch chain decarboxylase; a glutamate decarboxylase; a ω-transaminase; a CoA transferase, a CoA ligase, and an alcohol dehydrogenase.

16. The method of claim 14, wherein 5-hydroxypentanoyl-CoA is enzymatically produced from malonyl-CoA using one or more of a malonyl-CoA reductase; a 3-hydroxypropionate dehydrogenase; a 3-hydroxypropionyl-CoA synthase; a CoA-transferase; a β-ketothiolase; a 3-hydroxyacyl-CoA dehydrogenase; a 3-oxoacyl-CoA reductase, an enoyl-CoA hydratase, and a trans-2-enoyl-CoA reductase.

17. The method of claim 1, wherein said method is performed in a recombinant organism.

18. The method of claim 17, wherein said organism is subjected to a cultivation strategy under aerobic, anaerobic or, micro-aerobic cultivation conditions.

19. The method of claim 17, wherein said organism is cultured under conditions of nutrient limitation.

20. The method of claim 17, wherein the principal carbon source fed to the fermentation derives from a biological feedstock.

21. The method of claim 17, wherein the principal carbon source fed to the fermentation derives from a non-biological feedstock.

22. The method of claim 17, wherein the organism is a prokaryote.

23. The method of claim 17, wherein the organism is a eukaryote.

24. The method of claim 17, wherein the organism's tolerance to high concentrations of a C7 building block is improved through continuous cultivation in a selective environment.

25. The method of claim 17, wherein said host comprises an attenuation to one or more of the following enzymes: polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase, an acyl-CoA dehydrogenase accepting C7 building blocks and central precursors as substrates, a butaryl-CoA dehydrogenase, or an adipyl-CoA synthetase.

26. The method of claim 17, wherein said organism overexpresses one or more genes encoding: an acetyl-CoA synthetase; a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

27. The method of claim 10, wherein said ω-transaminase has at least 70% sequence identity to any one of the amino acid sequences set forth in SEQ ID NOs.: 7-12.

* * * * *

SEQUENCE LISTING

```
<160> NUMBER OF SEQ ID NOS: 61

<210> SEQ ID NO 1
<211> LENGTH: 394
<212> TYPE: PRT
<213> ORGANISM: Cupriavidus necator

<400> SEQUENCE: 1

Met Thr Arg Glu Val Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
    130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255
```

```
Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
    290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390


<210> SEQ ID NO 2
<211> LENGTH: 1174
<212> TYPE: PRT
<213> ORGANISM: Mycobacterium marinum

<400> SEQUENCE: 2

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
    210                 215                 220

Arg Gly Asp Val Pro Arg Gly Ala Ser Ala Gly Ser Ala Pro Gly Thr
```

-continued

```
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
        275                 280                 285

Thr Leu Asn Phe Met Pro Met Ser His Val Met Gly Arg Gln Ile Leu
    290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
        355                 360                 365

Glu Ala Gln Val Lys Ala Glu Ile Arg Asn Asp Val Leu Gly Gly Arg
    370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
        435                 440                 445

Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
    530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
        595                 600                 605

Gly Ile Arg Lys Leu Ala Arg Pro Gln Leu Lys Lys His Tyr Gly Glu
    610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655
```

-continued

```
Val Cys Arg Ala Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
        675                 680                 685

Leu Ser Phe Thr Asn Leu Leu His Glu Ile Phe Asp Ile Glu Val Pro
    690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
    770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
        835                 840                 845

Glu Val Leu Ala Gly Asp Lys Gly Glu Ala Asp Leu Gly Leu Asp Arg
    850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
    930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp  Met Phe Thr Arg Met  Ile Leu Ser
        995                 1000                1005

Leu Ala  Ala Thr Gly Ile Ala  Pro Gly Ser Phe Tyr  Glu Leu Ala
    1010                1015                1020

Ala Asp  Gly Ala Arg Gln Arg  Ala His Tyr Asp Gly  Leu Pro Val
    1025                1030                1035

Glu Phe  Ile Ala Glu Ala Ile  Ser Thr Leu Gly Ala  Gln Ser Gln
    1040                1045                1050

Asp Gly  Phe His Thr Tyr His  Val Met Asn Pro Tyr  Asp Asp Gly
    1055                1060                1065
```

```
Ile Gly  Leu Asp Glu Phe Val  Asp Trp Leu Asn Glu  Ser Gly Cys
    1070                 1075                 1080

Pro Ile  Gln Arg Ile Ala Asp  Tyr Gly Asp Trp Leu  Gln Arg Phe
    1085                 1090                 1095

Glu Thr  Ala Leu Arg Ala Leu  Pro Asp Arg Gln Arg  His Ser Ser
    1100                 1105                 1110

Leu Leu  Pro Leu Leu His Asn  Tyr Arg Gln Pro Glu  Arg Pro Val
    1115                 1120                 1125

Arg Gly  Ser Ile Ala Pro Thr  Asp Arg Phe Arg Ala  Ala Val Gln
    1130                 1135                 1140

Glu Ala  Lys Ile Gly Pro Asp  Lys Asp Ile Pro His  Val Gly Ala
    1145                 1150                 1155

Pro Ile  Ile Val Lys Tyr Val  Ser Asp Leu Arg Leu  Leu Gly Leu
    1160                 1165                 1170

Leu


<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255
```

-continued

```
Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
    610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
```

```
        675                 680                 685

Leu Gly Gly Asp Ser Leu Ser Ala Leu Thr Leu Ser Asn Leu Leu Ser
    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
        915                 920                 925

Ala Met Gly Ile Pro Asp Phe Glu Glu Asp Gly Asp Ile Arg Thr Val
    930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
            980                 985                 990

Arg Tyr Arg Gly Gln Val Asn Val  Pro Asp Met Phe Thr  Arg Leu Leu
        995                 1000                1005

Leu Ser  Leu Leu Ile Thr Gly  Val Ala Pro Arg Ser  Phe Tyr Ile
    1010                1015                1020

Gly Asp  Gly Glu Arg Pro Arg  Ala His Tyr Pro Gly  Leu Thr Val
    1025                1030                1035

Asp Phe  Val Ala Glu Ala Val  Thr Thr Leu Gly Ala  Gln Gln Arg
    1040                1045                1050

Glu Gly  Tyr Val Ser Tyr Asp  Val Met Asn Pro His  Asp Asp Gly
    1055                1060                1065

Ile Ser  Leu Asp Val Phe Val  Asp Trp Leu Ile Arg  Ala Gly His
    1070                1075                1080

Pro Ile  Asp Arg Val Asp Asp  Tyr Asp Asp Trp Val  Arg Arg Phe
    1085                1090                1095
```

```
Glu Thr  Ala Leu Thr Ala Leu  Pro Glu Lys Arg Arg  Ala Gln Thr
    1100                 1105                 1110

Val Leu  Pro Leu Leu His Ala  Phe Arg Ala Pro Gln  Ala Pro Leu
    1115                 1120                 1125

Arg Gly  Ala Pro Glu Pro Thr  Glu Val Phe His Ala  Ala Val Arg
    1130                 1135                 1140

Thr Ala  Lys Val Gly Pro Gly  Asp Ile Pro His Leu  Asp Glu Ala
    1145                 1150                 1155

Leu Ile  Asp Lys Tyr Ile Arg  Asp Leu Arg Glu Phe  Gly Leu Ile
    1160                 1165                 1170


<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Ala Trp Gln Ala Asp Gly Leu Ala Pro
                85                  90                  95

Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
        115                 120                 125

Ala Gly Ala Ser Leu Ala Gln Leu Val Gly Ile Leu Glu Glu Thr Glu
    130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
        195                 200                 205

Val Glu Thr Leu Ala Asp Leu Ala Ala Arg Gly Glu Ala Leu Pro Glu
    210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
            260                 265                 270

Met Pro Asn Ile Ser Leu His Tyr Met Pro Leu Ser His Ser Tyr Gly
        275                 280                 285

Arg Ala Val Leu Ala Gly Ala Leu Ser Ala Gly Gly Thr Ala His Phe
```

-continued

```
    290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
            340                 345                 350

Leu Gly Gly Arg Leu Leu Val Ala Val Cys Gly Ser Ala Pro Leu Ser
        355                 360                 365

Pro Glu Met Arg Ala Phe Met Glu Glu Val Leu Gly Phe Pro Leu Leu
    370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
            420                 425                 430

Ile Arg Ser Thr Ser Leu Ile Ser Gly Tyr Tyr Lys Arg Pro Glu Ile
        435                 440                 445

Thr Ala Glu Val Phe Asp Ala Gln Gly Tyr Tyr Lys Thr Gly Asp Val
    450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
            500                 505                 510

Gly Asn Ser Glu Arg Ser Phe Leu Leu Ala Val Val Val Pro Asn Ala
        515                 520                 525

Glu Val Leu Gly Ala Arg Asp Gln Glu Glu Ala Lys Pro Leu Ile Ala
    530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
            580                 585                 590

Arg Tyr Gly Glu Ala Leu Glu Ala Arg Tyr Asp Glu Ile Ala His Gly
        595                 600                 605

Gln Ala Asp Glu Leu Arg Ala Leu Arg Asp Gly Ala Gly Gln Arg Pro
    610                 615                 620

Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                645                 650                 655

Ser Leu Ser Ala Leu Ser Leu Ala Asn Leu Leu His Asp Val Phe Glu
            660                 665                 670

Val Glu Val Pro Val Arg Ile Ile Ile Gly Pro Thr Ala Ser Leu Ala
        675                 680                 685

Gly Ile Ala Lys His Ile Glu Ala Glu Arg Ala Gly Ala Ser Ala Pro
    690                 695                 700

Thr Ala Ala Ser Val His Gly Ala Gly Ala Thr Arg Ile Arg Ala Ser
705                 710                 715                 720
```

-continued

```
Glu Leu Thr Leu Glu Lys Phe Leu Pro Glu Asp Leu Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
        755                 760                 765

Leu Ala Arg Ser Gly Gln Asp Gly Gly Lys Leu Ile Cys Leu Val Arg
    770                 775                 780

Gly Lys Asp Ala Ala Ala Ala Arg Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Val Ile Val His
        835                 840                 845

Pro Ala Ala Leu Val Asn His Val Leu Pro Tyr His Gln Leu Phe Gly
    850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                885                 890                 895

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
        915                 920                 925

Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala  His Tyr Asp Gly Ile  Pro Val Asp
        995                 1000                 1005

Phe Thr  Ala Glu Ala Ile Thr  Thr Leu Gly Ala Glu  Pro Ser Trp
    1010                 1015                 1020

Phe Asp  Gly Gly Ala Gly Phe  Arg Ser Phe Asp Val  Phe Asn Pro
    1025                 1030                 1035

His His  Asp Gly Val Gly Leu  Asp Glu Phe Val Asp  Trp Leu Ile
    1040                 1045                 1050

Glu Ala  Gly His Pro Ile Ser  Arg Ile Asp Asp His  Lys Glu Trp
    1055                 1060                 1065

Phe Ala  Arg Phe Glu Thr Ala  Val Arg Gly Leu Pro  Glu Ala Gln
    1070                 1075                 1080

Arg Gln  His Ser Leu Leu Pro  Leu Leu Arg Ala Tyr  Ser Phe Pro
    1085                 1090                 1095

His Pro  Pro Val Asp Gly Ser  Val Tyr Pro Thr Gly  Lys Phe Gln
    1100                 1105                 1110

Gly Ala  Val Lys Ala Ala Gln  Val Gly Ser Asp His  Asp Val Pro
    1115                 1120                 1125
```

His Leu Gly Lys Ala Leu Ile Val Lys Tyr Ala Asp Asp Leu Lys
1130 1135 1140

Ala Leu Gly Leu Leu
1145

<210> SEQ ID NO 5
<211> LENGTH: 1185
<212> TYPE: PRT
<213> ORGANISM: Mycobacterium abscessus
<220> FEATURE:
<223> OTHER INFORMATION: Mycobacterium abscessus subsp. bolletii

<400> SEQUENCE: 5

Met Thr Asn Glu Thr Asn Pro Gln Gln Glu Gln Leu Ser Arg Arg Ile
1 5 10 15

Glu Ser Leu Arg Glu Ser Asp Pro Gln Phe Arg Ala Ala Gln Pro Asp
20 25 30

Pro Ala Val Ala Glu Gln Val Leu Arg Pro Gly Leu His Leu Ser Glu
35 40 45

Ala Ile Ala Ala Leu Met Thr Gly Tyr Ala Glu Arg Pro Ala Leu Gly
50 55 60

Glu Arg Ala Arg Glu Leu Val Ile Asp Gln Asp Gly Arg Thr Thr Leu
65 70 75 80

Arg Leu Leu Pro Arg Phe Asp Thr Thr Thr Tyr Gly Glu Leu Trp Ser
85 90 95

Arg Thr Thr Ser Val Ala Ala Ala Trp His His Asp Ala Thr His Pro
100 105 110

Val Lys Ala Gly Asp Leu Val Ala Thr Leu Gly Phe Thr Ser Ile Asp
115 120 125

Tyr Thr Val Leu Asp Leu Ala Ile Met Ile Leu Gly Gly Val Ala Val
130 135 140

Pro Leu Gln Thr Ser Ala Pro Ala Ser Gln Trp Thr Thr Ile Leu Ala
145 150 155 160

Glu Ala Glu Pro Asn Thr Leu Ala Val Ser Ile Glu Leu Ile Gly Ala
165 170 175

Ala Met Glu Ser Val Arg Ala Thr Pro Ser Ile Lys Gln Val Val Val
180 185 190

Phe Asp Tyr Thr Pro Glu Val Asp Asp Gln Arg Glu Ala Phe Glu Ala
195 200 205

Ala Ser Thr Gln Leu Ala Gly Thr Gly Ile Ala Leu Glu Thr Leu Asp
210 215 220

Ala Val Ile Ala Arg Gly Ala Ala Leu Pro Ala Ala Pro Leu Tyr Ala
225 230 235 240

Pro Ser Ala Gly Asp Asp Pro Leu Ala Leu Leu Ile Tyr Thr Ser Gly
245 250 255

Ser Thr Gly Ala Pro Lys Gly Ala Met His Ser Glu Asn Ile Val Arg
260 265 270

Arg Trp Trp Ile Arg Glu Asp Val Met Ala Gly Thr Glu Asn Leu Pro
275 280 285

Met Ile Gly Leu Asn Phe Met Pro Met Ser His Ile Met Gly Arg Gly
290 295 300

Thr Leu Thr Ser Thr Leu Ser Thr Gly Gly Thr Gly Tyr Phe Ala Ala
305 310 315 320

Ser Ser Asp Met Ser Thr Leu Phe Glu Asp Met Glu Leu Ile Arg Pro
325 330 335

-continued

```
Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
        355                 360                 365

Ala Glu Ala Val Ala Ala Glu Val Lys Ala Asp Ile Arg Asp Asn Leu
    370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
        515                 520                 525

Glu Ala Glu Tyr Ala Asn Ser Pro Val Val His Gln Ile Tyr Val Tyr
    530                 535                 540

Gly Ser Ser Glu Arg Ser Tyr Leu Leu Ala Val Val Val Pro Thr Pro
545                 550                 555                 560

Glu Ala Val Ala Ala Ala Lys Gly Asp Ala Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
        595                 600                 605

Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
        675                 680                 685

Gly Asp Ser Leu Ser Ala Leu Ser Phe Ser Asp Leu Leu Arg Asp Ile
    690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
```

```
        755                 760                 765

His Ala Ala Pro Ser Leu Pro Lys Ala Ala Gly Ile Pro His Thr Val
    770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
        835                 840                 845

Lys His Leu Glu Val Leu Ala Gly Asp Ile Gly Asp Pro Asn Leu Gly
    850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
        915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn  Val Pro Asp Gln Phe  Thr Arg Leu
        995                 1000                1005

Ile Leu  Ser Leu Ile Ala Thr  Gly Ile Ala Pro Gly  Ser Phe Tyr
    1010                1015                1020

Gln Ala  Gln Thr Thr Gly Glu  Arg Pro Leu Ala His  Tyr Asp Gly
    1025                1030                1035

Leu Pro  Gly Asp Phe Thr Ala  Glu Ala Ile Thr Thr  Leu Gly Thr
    1040                1045                1050

Gln Val  Pro Glu Gly Ser Glu  Gly Phe Val Thr Tyr  Asp Cys Val
    1055                1060                1065

Asn Pro  His Ala Asp Gly Ile  Ser Leu Asp Asn Phe  Val Asp Trp
    1070                1075                1080

Leu Ile  Glu Ala Gly Tyr Pro  Ile Ala Arg Ile Asp  Asn Tyr Thr
    1085                1090                1095

Glu Trp  Phe Thr Arg Phe Asp  Thr Ala Ile Arg Gly  Leu Ser Glu
    1100                1105                1110

Lys Gln  Lys Gln His Ser Leu  Leu Pro Leu Leu His  Ala Phe Glu
    1115                1120                1125

Gln Pro  Ser Ala Ala Glu Asn  His Gly Val Val Pro  Ala Lys Arg
    1130                1135                1140

Phe Gln  His Ala Val Gln Ala  Ala Gly Ile Gly Pro  Val Gly Gln
    1145                1150                1155

Asp Gly  Thr Thr Asp Ile Pro  His Leu Ser Arg Arg  Leu Ile Val
    1160                1165                1170
```

```
Lys Tyr  Ala Lys Asp Leu Glu  Gln Leu Gly Leu Leu
    1175                 1180                1185


<210> SEQ ID NO 6
<211> LENGTH: 1186
<212> TYPE: PRT
<213> ORGANISM: Segniliparus rotundus

<400> SEQUENCE: 6

Met Thr Gln Ser His Thr Gln Gly Pro Gln Ala Ser Ala Ala His Ser
1               5                   10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Pro Val Pro Ala Ile
    290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln
```

```
        355                 360                 365

Ser Glu Leu Asp Arg Arg Gly Val Gln Asp Gly Thr Arg Glu Ala Glu
    370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
        435                 440                 445

Thr Asp Tyr Lys Leu Ile Asp Val Pro Glu Leu Gly Tyr Phe Ser Thr
    450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
        515                 520                 525

Gln Gly Glu Phe Val Thr Leu Ala Lys Leu Glu Ala Ala Tyr Ser Ser
    530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

Ile Ile Glu Thr Asp Pro Phe Thr Val Glu Asn Gly Leu Leu Ser Asp
    610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Ala Met Leu Gly Ala Ser Ala Ala Glu Ile Lys
        675                 680                 685

Pro Asp Ala His Phe Thr Asp Leu Gly Gly Asp Ser Leu Ser Ala Leu
    690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780
```

-continued

```
Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
            820                 825                 830

Ala Lys Ala Arg Leu Asp Ala Ala Tyr Glu Ser Gly Asp Pro Lys Leu
        835                 840                 845

Ala Gly His Tyr Gln Asp Leu Ala Ala Thr Thr Leu Glu Val Leu Ala
    850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
            900                 905                 910

Val Ala Glu Ile Ile Lys Leu Ala Ile Thr Thr Arg Ile Lys Pro Val
        915                 920                 925

Thr Tyr Leu Ser Thr Val Ala Val Ala Ala Gly Val Glu Pro Ser Ala
    930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
            980                 985                 990

Phe Arg Ser Asp Met Ile Leu Ala  His Gln Lys Tyr Thr  Gly Gln Val
        995                 1000                1005

Asn Ala  Thr Asp Gln Phe Thr  Arg Leu Val Gln Ser  Leu Leu Ala
    1010                1015                1020

Thr Gly  Leu Ala Pro Lys Ser  Phe Tyr Glu Leu Asp  Ala Gln Gly
    1025                1030                1035

Asn Arg  Gln Arg Ala His Tyr  Asp Gly Ile Pro Val  Asp Phe Thr
    1040                1045                1050

Ala Glu  Ser Ile Thr Thr Leu  Gly Gly Asp Gly Leu  Glu Gly Tyr
    1055                1060                1065

Arg Ser  Tyr Asn Val Phe Asn  Pro His Arg Asp Gly  Val Gly Leu
    1070                1075                1080

Asp Glu  Phe Val Asp Trp Leu  Ile Glu Ala Gly His  Pro Ile Thr
    1085                1090                1095

Arg Ile  Asp Asp Tyr Asp Gln  Trp Leu Ser Arg Phe  Glu Thr Ser
    1100                1105                1110

Leu Arg  Gly Leu Pro Glu Ser  Lys Arg Gln Ala Ser  Val Leu Pro
    1115                1120                1125

Leu Leu  His Ala Phe Ala Arg  Pro Gly Pro Ala Val  Asp Gly Ser
    1130                1135                1140

Pro Phe  Arg Asn Thr Val Phe  Arg Thr Asp Val Gln  Lys Ala Lys
    1145                1150                1155

Ile Gly  Ala Glu His Asp Ile  Pro His Leu Gly Lys  Ala Leu Val
    1160                1165                1170

Leu Lys  Tyr Ala Asp Asp Ile  Lys Gln Leu Gly Leu  Leu
    1175                1180                1185
```

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

```
Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455


<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
```

```
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465


<210> SEQ ID NO 9
<211> LENGTH: 454
<212> TYPE: PRT
<213> ORGANISM: Pseudomonas syringae

<400> SEQUENCE: 9

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190
```

```
Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
        435                 440                 445

Leu Ala Val Leu Gln Gly
    450
```

<210> SEQ ID NO 10
<211> LENGTH: 467
<212> TYPE: PRT
<213> ORGANISM: Rhodobacter sphaeroides

<400> SEQUENCE: 10

```
Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110
```

```
Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Ala Leu Ala Ser Leu
        355                 360                 365

Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465


<210> SEQ ID NO 11
<211> LENGTH: 459
<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
```

-continued

```
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430
```

```
Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455


<210> SEQ ID NO 12
<211> LENGTH: 453
<212> TYPE: PRT
<213> ORGANISM: Vibrio fluvialis

<400> SEQUENCE: 12

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
```

340 345 350

Ala Pro Arg Phe Glu Glu Arg Leu Lys His Ile Ala Glu Arg Pro Asn
355 360 365

Ile Gly Glu Tyr Arg Gly Ile Gly Phe Met Trp Ala Leu Glu Ala Val
370 375 380

Lys Asp Lys Ala Ser Lys Thr Pro Phe Asp Gly Asn Leu Ser Val Ser
385 390 395 400

Glu Arg Ile Ala Asn Thr Cys Thr Asp Leu Gly Leu Ile Cys Arg Pro
405 410 415

Leu Gly Gln Ser Val Val Leu Cys Pro Pro Phe Ile Leu Thr Glu Ala
420 425 430

Gln Met Asp Glu Met Phe Asp Lys Leu Glu Lys Ala Leu Asp Lys Val
435 440 445

Phe Ala Glu Val Ala
450

<210> SEQ ID NO 13
<211> LENGTH: 401
<212> TYPE: PRT
<213> ORGANISM: Escherichia coli

<400> SEQUENCE: 13

Met Arg Glu Ala Phe Ile Cys Asp Gly Ile Arg Thr Pro Ile Gly Arg
1 5 10 15

Tyr Gly Gly Ala Leu Ser Ser Val Arg Ala Asp Asp Leu Ala Ala Ile
20 25 30

Pro Leu Arg Glu Leu Leu Val Arg Asn Pro Arg Leu Asp Ala Glu Cys
35 40 45

Ile Asp Asp Val Ile Leu Gly Cys Ala Asn Gln Ala Gly Glu Asp Asn
50 55 60

Arg Asn Val Ala Arg Met Ala Thr Leu Leu Ala Gly Leu Pro Gln Ser
65 70 75 80

Val Ser Gly Thr Thr Ile Asn Arg Leu Cys Gly Ser Gly Leu Asp Ala
85 90 95

Leu Gly Phe Ala Ala Arg Ala Ile Lys Ala Gly Asp Gly Asp Leu Leu
100 105 110

Ile Ala Gly Gly Val Glu Ser Met Ser Arg Ala Pro Phe Val Met Gly
115 120 125

Lys Ala Ala Ser Ala Phe Ser Arg Gln Ala Glu Met Phe Asp Thr Thr
130 135 140

Ile Gly Trp Arg Phe Val Asn Pro Leu Met Ala Gln Gln Phe Gly Thr
145 150 155 160

Asp Ser Met Pro Glu Thr Ala Glu Asn Val Ala Glu Leu Leu Lys Ile
165 170 175

Ser Arg Glu Asp Gln Asp Ser Phe Ala Leu Arg Ser Gln Gln Arg Thr
180 185 190

Ala Lys Ala Gln Ser Ser Gly Ile Leu Ala Glu Glu Ile Val Pro Val
195 200 205

Val Leu Lys Asn Lys Lys Gly Val Val Thr Glu Ile Gln His Asp Glu
210 215 220

His Leu Arg Pro Glu Thr Thr Leu Glu Gln Leu Arg Gly Leu Lys Ala
225 230 235 240

Pro Phe Arg Ala Asn Gly Val Ile Thr Ala Gly Asn Ala Ser Gly Val
245 250 255

-continued

```
Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
        275                 280                 285

Gly Val Glu Pro Arg Leu Met Gly Leu Gly Pro Val Pro Ala Thr Arg
    290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350

Ile Ala Leu Gly His Pro Leu Gly Met Ser Gly Ala Arg Leu Ala Leu
        355                 360                 365

Ala Ala Ser His Glu Leu His Arg Arg Asn Gly Arg Tyr Ala Leu Cys
    370                 375                 380

Thr Met Cys Ile Gly Val Gly Gln Gly Ile Ala Met Ile Leu Glu Arg
385                 390                 395                 400

Val
```

<210> SEQ ID NO 14
<211> LENGTH: 1168
<212> TYPE: PRT
<213> ORGANISM: Mycobacterium smegmatis

<400> SEQUENCE: 14

```
Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
            20                  25                  30

Ile Ser Ala Ala Ala Ala Asp Pro Glu Leu Arg Leu Pro Ala Ala Val
        35                  40                  45

Lys Gln Ile Leu Ala Gly Tyr Ala Asp Arg Pro Ala Leu Gly Lys Arg
    50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
    130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Val Glu Thr Ile Thr Asp Ala Leu Asp Arg
    210                 215                 220
```

-continued

```
Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

Leu Asn Phe Met Pro Met Ser His Val Met Gly Arg Gly Ile Leu Cys
    290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
        435                 440                 445

Asp Arg Pro Tyr Pro Arg Gly Glu Leu Leu Val Lys Ser Glu Gln Met
    450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
    530                 535                 540

Tyr Leu Leu Ala Val Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
        595                 600                 605

Arg Lys Leu Ala Arg Pro Lys Leu Lys Ala His Tyr Gly Glu Arg Leu
    610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
```

-continued

```
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
        675                 680                 685

Phe Ser Asn Leu Leu His Glu Ile Phe Asp Val Asp Val Pro Val Gly
    690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
                725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Ala Pro Gly Leu Pro Arg Ser
        755                 760                 765

Gly Thr Glu Ile Arg Thr Val Leu Leu Thr Gly Ala Thr Gly Phe Leu
    770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
        835                 840                 845

Lys Gly Glu Ala Asp Leu Gly Leu Asp His Asp Thr Trp Gln Arg Leu
    850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
        915                 920                 925

Glu Asp Ala Asp Ile Arg Glu Ile Ser Ala Thr Arg Arg Val Asp Asp
    930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met  Leu Ser Leu Val Ala  Thr Gly Ile
        995                 1000                1005

Ala Pro  Gly Ser Phe Tyr Glu  Leu Asp Ala Asp Gly  Asn Arg Gln
    1010                 1015                 1020

Arg Ala  His Tyr Asp Gly Leu  Pro Val Glu Phe Ile  Ala Glu Ala
    1025                 1030                 1035

Ile Ser  Thr Ile Gly Ser Gln  Val Thr Asp Gly Phe  Glu Thr Phe
    1040                 1045                 1050

His Val  Met Asn Pro Tyr Asp  Asp Gly Ile Gly Leu  Asp Glu Tyr
    1055                 1060                 1065
```

```
Val Asp  Trp Leu Ile Glu Ala  Gly Tyr Pro Val His  Arg Val Asp
    1070                 1075                 1080

Asp Tyr  Ala Thr Trp Leu Ser  Arg Phe Glu Thr Ala  Leu Arg Ala
    1085                 1090                 1095

Leu Pro  Glu Arg Gln Arg Gln  Ala Ser Leu Leu Pro  Leu Leu His
    1100                 1105                 1110

Asn Tyr  Gln Gln Pro Ser Pro  Pro Val Cys Gly Ala  Met Ala Pro
    1115                 1120                 1125

Thr Asp  Arg Phe Arg Ala Ala  Val Gln Asp Ala Lys  Ile Gly Pro
    1130                 1135                 1140

Asp Lys  Asp Ile Pro His Val  Thr Ala Asp Val Ile  Val Lys Tyr
    1145                 1150                 1155

Ile Ser  Asn Leu Gln Met Leu  Gly Leu Leu
    1160                 1165
```

<210> SEQ ID NO 15
<211> LENGTH: 392
<212> TYPE: PRT
<213> ORGANISM: Pseudomonas putida

<400> SEQUENCE: 15

```
Met Asn Asp Val Val Ile Val Ala Ala Thr Arg Thr Ala Ile Gly Ser
1               5                   10                  15

Phe Gln Gly Ala Leu Ala Thr Val Pro Ala Val Asp Leu Gly Ala Ala
            20                  25                  30

Val Ile Lys Gln Leu Leu Lys Gln Thr Gly Leu Asp Pro Ala Gln Val
        35                  40                  45

Asp Glu Val Ile Leu Gly Gln Val Leu Thr Ala Gly Ala Gly Gln Asn
    50                  55                  60

Pro Ala Arg Gln Ala Ala Ile Lys Ala Gly Leu Pro Phe Ser Val Pro
65                  70                  75                  80

Ala Leu Thr Leu Asn Lys Val Cys Gly Ser Gly Leu Lys Ala Leu His
                85                  90                  95

Leu Ala Ala Gln Ala Ile Arg Cys Gly Asp Ala Glu Val Val Ile Ala
            100                 105                 110

Gly Gly Gln Glu Asn Met Ser Leu Ala Pro Tyr Val Met Pro Ser Ala
        115                 120                 125

Arg Thr Gly Gln Arg Met Gly His Gly Gln Leu Ile Asp Ser Met Ile
    130                 135                 140

Thr Asp Gly Leu Trp Asp Ala Phe Asn Asp Tyr His Met Gly Ile Thr
145                 150                 155                 160

Ala Glu Asn Leu Val Asp Lys Tyr Gly Leu Ser Arg Glu Gln Gln Asp
                165                 170                 175

Ala Phe Ala Ala Glu Ser Gln Arg Lys Ala Val Ala Ala Ile Glu Ala
            180                 185                 190

Gly Arg Phe Asp Ala Glu Ile Thr Pro Ile Val Leu Pro Gln Lys Lys
        195                 200                 205

Gly Glu Pro Lys Val Phe Ala Arg Asp Glu Gln Pro Arg Pro Asp Thr
    210                 215                 220

Thr Ala Glu Ser Leu Ala Lys Leu Arg Pro Ala Phe Lys Lys Asp Gly
225                 230                 235                 240

Ser Val Thr Ala Gly Asn Ala Ser Ser Leu Asn Asp Gly Ala Ala Ala
                245                 250                 255

Val Leu Leu Met Ser Ala Ala Lys Ala Glu Ala Leu Gly Leu Pro Val
```

```
            260                 265                 270

Leu Ala Lys Ile Ala Ala Tyr Ala Ser Ala Gly Val Asp Pro Ala Ile
        275                 280                 285

Met Gly Ile Gly Pro Val Ser Ala Thr Gln Arg Cys Leu Asp Lys Ala
    290                 295                 300

Gly Trp Gln Leu Ala Glu Leu Asp Leu Ile Glu Ala Asn Glu Ala Phe
305                 310                 315                 320

Ala Ala Gln Ala Leu Ala Val Gly Asn Ala Leu Ala Trp Asp Ala Ala
                325                 330                 335

Arg Val Asn Val Asn Gly Gly Ala Ile Ala Leu Gly His Pro Ile Gly
            340                 345                 350

Ala Ser Gly Cys Arg Val Leu Val Thr Leu Leu His Glu Met Ile Lys
        355                 360                 365

Arg Asp Val Lys Lys Gly Leu Ala Thr Leu Cys Ile Gly Gly Gly Gln
    370                 375                 380

Gly Val Ala Leu Ala Ile Glu Arg
385                 390


<210> SEQ ID NO 16
<211> LENGTH: 393
<212> TYPE: PRT
<213> ORGANISM: Sphingomonas wittichii

<400> SEQUENCE: 16

Met Glu Asp Ile Tyr Ile Val Gly Ala Ala Arg Thr Ala Ile Ala Asp
1               5                   10                  15

Phe Gly Gly Ala Leu Lys Asp Val Pro Pro Ala Asp Leu Gly Val Ile
            20                  25                  30

Val Ala Arg Ala Ala Leu Glu Arg Ala Gly Leu Glu Pro Gly Asp Val
        35                  40                  45

Gln Asn Val Val Met Gly Gln Val Met Pro Thr Glu Pro Arg Asp Ala
    50                  55                  60

Tyr Leu Ala Arg Met Val Gly Val Thr Ala Gly Val Pro Ile Glu Thr
65                  70                  75                  80

Pro Ala Leu Thr Leu Asn Arg Leu Cys Gly Ser Gly Val Glu Ala Ile
                85                  90                  95

Val Thr Gly Ala Lys Ala Met Val Leu Gly Glu Ser Asp Ile Val Leu
            100                 105                 110

Ala Gly Gly Ala Glu Val Met Ser Arg Val Pro His Val Val Lys Gly
        115                 120                 125

Ala Arg Trp Gly Thr Lys Met Gly Asn Val Glu Met Thr Asp Gly Leu
    130                 135                 140

Ile Glu Ala Leu Ser Asp Pro Phe Asp Lys Val His Met Gly Ile Thr
145                 150                 155                 160

Ala Glu Asn Val Ala Glu Arg Tyr Gln Ile Thr Arg Glu Ala Gln Asp
                165                 170                 175

Ala Leu Ala Leu Gln Gly His Gln Arg Ala Ala Arg Ala Ile Ala Glu
            180                 185                 190

Gly Arg Phe Lys Ala Gln Ile Val Pro Val Glu Val Lys Thr Arg Lys
        195                 200                 205

Gly Val Val Ala Phe Asp Thr Asp Glu His Val Arg Gly Asp Val Ser
    210                 215                 220

Ala Glu Glu Leu Ala Lys Leu Arg Pro Val Phe Lys Lys Asp Gly Thr
225                 230                 235                 240
```

-continued

```
Val Thr Ala Ala Asn Ala Ser Gly Ile Asn Asp Gly Ala Ala Met Val
                245                 250                 255

Val Leu Ala Thr Lys Lys Ala Val Asp Ala Lys Gly Leu Lys Pro Leu
            260                 265                 270

Ala Arg Ile Leu Ser Trp Gly His Ala Gly Val Glu Pro Leu Tyr Met
        275                 280                 285

Gly Ile Gly Pro Val Lys Ala Val Pro Ile Ala Leu Glu Arg Ala Gly
    290                 295                 300

Leu Thr Leu Ala Asp Ile Asp Val Ile Glu Ala Asn Glu Ala Phe Ala
305                 310                 315                 320

Ala Gln Ala Cys Ala Val Ala Gln Glu Leu Gly Phe Asp Pro Asp Lys
                325                 330                 335

Val Asn Pro Asn Gly Ser Gly Val Ala Leu Gly His Pro Val Gly Ala
            340                 345                 350

Thr Gly Ala Ile Leu Thr Val Lys Thr Val Tyr Glu Leu Glu Arg Ile
        355                 360                 365

Gly Gly Arg Tyr Gly Leu Ile Thr Met Cys Ile Gly Gly Gly Gln Gly
    370                 375                 380

Ile Ala Met Val Val Glu Arg Cys Ala
385                 390


<210> SEQ ID NO 17
<211> LENGTH: 398
<212> TYPE: PRT
<213> ORGANISM: Pseudomonas reinekei

<400> SEQUENCE: 17

Met Lys Asn Ala Leu Ile Val Ser Pro Leu Arg Thr Pro Ile Gly Lys
1               5                   10                  15

Phe Gly Gly Ala Leu Ala Pro Leu Thr Ala Glu His Leu Ala Ser Phe
            20                  25                  30

Met Ile Ser Gln Val Met Ala Arg Thr Gly Val Pro Gly His Ser Leu
        35                  40                  45

Asp Glu Val Ile Val Ala Gln Ser Tyr Ala Ser Ser Glu Ala Pro Cys
    50                  55                  60

Ile Gly Arg Tyr Ala Ala Leu Ser Ala Gly Leu Pro Val Glu Val Pro
65                  70                  75                  80

Gly Tyr Thr Leu Asp Arg Arg Cys Gly Ser Gly Leu Gln Ala Val Ile
                85                  90                  95

Asp Ala Ser Met Met Val Lys Thr Gly Asn Ala Glu Ala Val Leu Val
            100                 105                 110

Val Gly Val Glu Ser Met Ser Asn Ile Glu Tyr Tyr Ser Thr Asp Met
        115                 120                 125

Arg Trp Gly Ala Arg Ala Gly Ser Val Arg Phe His Asp Arg Leu Glu
    130                 135                 140

Arg Gly Arg Glu Arg Ser Gln Pro Ser Glu Arg Phe Gly His Ile Ser
145                 150                 155                 160

Gly Met Pro Glu Thr Ala Asp Asn Leu Ala Leu Asp Tyr Gly Ile Ser
                165                 170                 175

Arg Glu Glu Ala Asp Ser Phe Ser Val Arg Ser His Gln Asn Ala Ala
            180                 185                 190

Ala Ala Trp Arg Glu Gly Arg Phe Ala Asp Glu Val Val Ala Val Asp
        195                 200                 205

Val Pro Gly Lys Arg Gly Ala Val Thr Arg Val Thr Ile Asp Glu Gly
    210                 215                 220
```

Ile Arg Glu Asp Ala Ser Leu Glu Ser Met Lys Ala Leu Arg Leu Ile
225 230 235 240

Arg Pro Glu Gly Val Cys Thr Ala Gly Asn Ser Ser Gln Gln Asn Asp
245 250 255

Ala Ala Ala Gly Cys Leu Val Val Ser Pro Glu Tyr Ala Ala Arg His
260 265 270

Gly Leu Thr Pro Met Ala Arg Leu Val Asp Trp Ala Ala Ala Gly Cys
275 280 285

Glu Pro Ser Arg Met Gly Ile Gly Pro Val Pro Ala Thr Gln Lys Leu
290 295 300

Leu Met Arg Thr Gly Leu Ser Leu Ala Glu Leu Asp Leu Ile Glu Leu
305 310 315 320

Asn Glu Ala Phe Ala Ala Gln Ala Leu Ala Val Leu Lys Thr Trp Gly
325 330 335

Leu Asp Asp Leu Ser Arg Val Asn Val Asn Gly Ser Gly Ile Ser Leu
340 345 350

Gly His Pro Ile Gly Ala Thr Gly Val Arg Ile Met Thr Thr Leu Leu
355 360 365

His Glu Met Arg Arg Arg Glu Ala Arg Tyr Gly Leu Glu Thr Met Cys
370 375 380

Ile Gly Gly Gly Gln Gly Leu Ala Ala Leu Phe Glu Arg Val
385 390 395

<210> SEQ ID NO 18
<211> LENGTH: 400
<212> TYPE: PRT
<213> ORGANISM: Pseudomonas putida

<400> SEQUENCE: 18

Met Arg Asp Val Phe Ile Cys Asp Ala Ile Arg Thr Pro Ile Gly Arg
1 5 10 15

Phe Gly Gly Ala Leu Ala Gly Val Arg Ala Asp Asp Leu Ala Ala Val
20 25 30

Pro Leu Lys Ala Leu Ile Glu Pro Asn Pro Ala Val Gln Trp Asp Gln
35 40 45

Val Asp Glu Val Phe Phe Gly Cys Ala Asn Gln Ala Gly Glu Asp Asn
50 55 60

Arg Asn Val Ala Arg Met Ala Leu Leu Leu Ala Gly Leu Pro Glu Ser
65 70 75 80

Ile Pro Gly Val Thr Leu Asn Arg Leu Cys Ala Ser Gly Met Asp Ala
85 90 95

Ile Gly Thr Ala Phe Arg Ala Ile Ala Ser Gly Glu Met Glu Leu Ala
100 105 110

Ile Ala Gly Gly Val Glu Ser Met Ser Arg Ala Pro Phe Val Met Gly
115 120 125

Lys Ala Glu Ser Gly Tyr Ser Arg Asn Met Lys Leu Glu Asp Thr Thr
130 135 140

Ile Gly Trp Arg Phe Ile Asn Pro Leu Met Lys Ser Gln Tyr Gly Val
145 150 155 160

Asp Ser Met Pro Glu Thr Ala Asp Asn Val Ala Asp Asp Tyr Gln Val
165 170 175

Ser Arg Ala Asp Gln Asp Ala Phe Ala Leu Arg Ser Gln Gln Lys Ala
180 185 190

Ala Ala Ala Gln Ala Ala Gly Phe Phe Ala Glu Glu Ile Val Pro Val

```
        195                 200                 205

Arg Ile Ala His Lys Lys Gly Glu Thr Ile Val Glu Arg Asp Glu His
    210                 215                 220

Leu Arg Pro Glu Thr Thr Leu Glu Ala Leu Thr Lys Leu Lys Pro Val
225                 230                 235                 240

Asn Gly Pro Asp Lys Thr Val Thr Ala Gly Asn Ala Ser Gly Val Asn
                245                 250                 255

Asp Gly Ala Ala Ala Leu Ile Leu Ala Ser Ala Glu Ala Val Lys Lys
            260                 265                 270

His Gly Leu Thr Pro Arg Ala Arg Val Leu Gly Met Ala Ser Gly Gly
        275                 280                 285

Val Ala Pro Arg Val Met Gly Ile Gly Pro Val Pro Ala Val Arg Lys
    290                 295                 300

Leu Thr Glu Arg Leu Gly Val Ala Val Ser Asp Phe Asp Val Ile Glu
305                 310                 315                 320

Leu Asn Glu Ala Phe Ala Ser Gln Gly Leu Ala Val Leu Arg Glu Leu
                325                 330                 335

Gly Val Ala Asp Asp Ala Pro Gln Val Asn Pro Asn Gly Gly Ala Ile
            340                 345                 350

Ala Leu Gly His Pro Leu Gly Met Ser Gly Ala Arg Leu Val Leu Thr
        355                 360                 365

Ala Leu His Gln Leu Glu Lys Ser Gly Gly Arg Lys Gly Leu Ala Thr
    370                 375                 380

Met Cys Val Gly Val Gly Gln Gly Leu Ala Leu Ala Ile Glu Arg Val
385                 390                 395                 400


<210> SEQ ID NO 19
<211> LENGTH: 402
<212> TYPE: PRT
<213> ORGANISM: Burkholderia xenovorans

<400> SEQUENCE: 19

Met Ser Glu Thr His Met Ser Gly Thr Lys Ala Asp Pro Ile Val Ile
1               5                   10                  15

Val Gly Val Ala Arg Thr Pro Met Ala Ala Phe Gln Gly Asp Phe Ala
            20                  25                  30

Thr Leu Ser Ala Pro Gln Leu Gly Ser Val Ala Ile Gln Ala Ala Val
        35                  40                  45

Gln Arg Ala Gly Leu Lys Pro Glu Gln Ile Asp Glu Val Val Met Gly
    50                  55                  60

Cys Val Leu Pro Ala Gly Leu Gly Gln Ala Pro Ala Arg Gln Ala Ala
65                  70                  75                  80

Leu Gly Ala Gly Leu Pro Leu Ala Thr Gly Ser Thr Thr Val Asn Lys
                85                  90                  95

Met Cys Gly Ser Gly Met Arg Ala Ala Met Phe Ala His Asp Met Leu
            100                 105                 110

Ala Ala Gly Ser Val Asp Val Ile Val Ala Gly Gly Met Glu Ser Met
        115                 120                 125

Thr Asn Ala Pro Tyr Leu Leu Pro Lys Ala Arg Ala Gly Met Arg Met
    130                 135                 140

Gly His Gly Gln Val Ile Asp His Met Phe Tyr Asp Gly Leu Glu Asp
145                 150                 155                 160

Ala Tyr Glu Lys Gly Arg Leu Met Gly Ser Phe Ala Glu Glu Cys Ala
                165                 170                 175
```

```
Ala Ser Phe Asp Phe Thr Arg Glu Ala Gln Asp Ala Phe Ala Val Glu
            180                185                190

Ser Leu Ala Arg Ala Lys Arg Ala Asn Glu Asp Gly Ser Phe Ala Trp
        195                200                205

Glu Ile Ala Pro Val Lys Val Glu Ser Arg Lys Gly Glu Val Thr Ile
    210                215                220

Asp Arg Asp Glu Gln Pro Phe Lys Ala Asn Ile Glu Lys Ile Pro Thr
225                230                235                240

Leu Lys Pro Ala Phe Ser Lys Thr Gly Thr Val Thr Ala Ala Asn Ser
                245                250                255

Ser Ser Ile Ser Asp Gly Ala Ala Ala Leu Val Met Met Arg Glu Ser
            260                265                270

Thr Ala Lys Arg Leu Gly Val Gln Pro Ile Ala Arg Val Val Gly His
        275                280                285

Ser Thr Leu Ala Gln Glu Pro Ala Lys Phe Thr Thr Ala Pro Val Gly
    290                295                300

Ala Ile Arg Lys Leu Phe Glu Lys Asn Gly Trp Arg Ala Asp Glu Val
305                310                315                320

Asp Leu Phe Glu Val Asn Glu Ala Phe Ala Val Val Thr Met Ala Ala
                325                330                335

Met Lys Glu His His Leu Pro His Glu Lys Val Asn Val Asn Gly Gly
            340                345                350

Ala Cys Ala Leu Gly His Pro Ile Gly Ala Ser Gly Ala Arg Ile Leu
        355                360                365

Val Thr Leu Ile Gly Ala Leu Lys Lys Arg Gly Gly Lys Arg Gly Val
    370                375                380

Ala Thr Leu Cys Ile Gly Gly Gly Glu Ala Thr Ala Met Gly Ile Glu
385                390                395                400

Leu Val


<210> SEQ ID NO 20
<211> LENGTH: 400
<212> TYPE: PRT
<213> ORGANISM: Burkholderia xenovorans

<400> SEQUENCE: 20

Met Thr Glu Ala Phe Leu Cys Asp Ala Ile Arg Thr Pro Ile Gly Arg
1               5                   10                  15

Tyr Ala Gly Ala Leu Ser Ser Val Arg Ala Asp Asp Leu Gly Ala Val
            20                  25                  30

Pro Leu Lys Ala Leu Met Glu Arg Asn Lys Glu Val Asp Trp Asn Ala
        35                  40                  45

Ile Asp Asp Val Ile Tyr Gly Cys Ala Asn Gln Ala Gly Glu Asp Asn
    50                  55                  60

Arg Asn Val Ala Arg Met Ser Leu Leu Leu Ala Gly Leu Pro Gln Gly
65                  70                  75                  80

Val Pro Gly Thr Thr Val Asn Arg Leu Cys Gly Ser Gly Met Asp Ala
                85                  90                  95

Val Gly Ile Ala Ala Arg Ala Ile Lys Ser Gly Glu Ala Ala Leu Met
            100                 105                 110

Val Ala Gly Gly Val Glu Ser Met Ser Arg Ala Pro Phe Val Thr Gly
        115                 120                 125

Lys Ala Thr Ser Ala Phe Ser Arg Gln Ala Glu Ile Tyr Asp Thr Thr
    130                 135                 140
```

-continued

Ile Gly Trp Arg Phe Val Asn Pro Leu Met Lys Lys Leu Tyr Gly Val
145 150 155 160

Asp Ser Met Pro Glu Thr Gly Glu Asn Val Ala Thr Asp Tyr Asn Ile
165 170 175

Ser Arg Ala Asp Gln Asp Ala Phe Ala Leu Arg Ser Gln Gln Lys Ala
180 185 190

Ala Arg Ala Gln Arg Asp Gly Thr Leu Ala Gln Glu Ile Val Gly Val
195 200 205

Thr Ile Ala Gln Lys Lys Gly Asp Pro Val Thr Val Ser Gln Asp Glu
210 215 220

His Pro Arg Glu Thr Ser Leu Asp Ala Leu Ala Lys Leu Lys Gly Val
225 230 235 240

Val Arg Pro Asp Gly Thr Val Thr Ala Gly Asn Ala Ser Gly Val Asn
245 250 255

Asp Gly Ala Ala Ala Leu Leu Leu Ala Asn Glu Glu Thr Ala Arg Arg
260 265 270

Phe Gly Leu Thr Pro Arg Ala Arg Val Leu Gly Ile Ala Thr Ala Gly
275 280 285

Val Ala Pro Arg Val Met Gly Ile Gly Pro Ala Pro Ala Thr Gln Lys
290 295 300

Leu Leu Ala Arg Leu Asn Met Ser Leu Asp Gln Phe Asp Val Ile Glu
305 310 315 320

Leu Asn Glu Ala Phe Ala Ser Gln Gly Ile Ala Val Leu Arg Ala Leu
325 330 335

Gly Val Ala Asp Asp Asp Thr Arg Val Asn Pro Asn Gly Gly Ala Ile
340 345 350

Ala Leu Gly His Pro Leu Gly Met Ser Gly Ala Arg Leu Val Thr Thr
355 360 365

Ala Met Tyr Gln Leu His Arg Thr Gln Gly Arg Phe Ala Leu Cys Thr
370 375 380

Met Cys Ile Gly Val Gly Gln Gly Ile Ala Ile Ala Ile Glu Arg Val
385 390 395 400

<210> SEQ ID NO 21
<211> LENGTH: 406
<212> TYPE: PRT
<213> ORGANISM: Rhodococcus jostii

<400> SEQUENCE: 21

Met Ala Glu Val Phe Leu Val Asp Gly Ala Arg Thr Pro Gln Gly Arg
1 5 10 15

Tyr Gly Gly Ala Leu Ala Gly Val Arg Pro Asp Asp Leu Ala Gly Leu
20 25 30

Val Val Ala Glu Ala Ala Arg Arg Ala Gly Ile Pro Gly Asp Ala Val
35 40 45

Asp Glu Val Ile Leu Gly Ala Ala Asn Gln Ala Gly Glu Asp Asn Arg
50 55 60

Asp Val Ala Arg Met Ala Val Leu Leu Ala Gly Leu Pro Asp Ser Val
65 70 75 80

Pro Gly Tyr Thr Val Asn Arg Leu Cys Ala Ser Gly Leu Thr Ala Val
85 90 95

Ala Ser Ala Ala His Thr Ile Arg Ser Gly Glu Ala Asp Ile Val Ile
100 105 110

Ala Gly Gly Val Glu Ser Met Thr Arg Ala Pro Trp Val Met Ala Lys
115 120 125

-continued

Pro Gly Thr Pro Trp Ala Arg Pro Gly Glu Val Ala Asp Thr Ser Leu
    130                 135                 140

Gly Trp Arg Phe Thr Asn Pro Arg Phe Thr Ala Ala Asp Arg Asp Val
145                 150                 155                 160

Pro Ala Gly Ala Gly Pro Asp Val Arg Lys Val Thr Leu Ser Met Gly
                165                 170                 175

Glu Thr Ala Glu Glu Val Ala Ala Leu Glu Gly Val Thr Arg Ala Glu
            180                 185                 190

Ser Asp Ala Phe Ala Leu Arg Ser Gln Glu Arg Ala Ile Ala Ala Val
        195                 200                 205

Asp Ala Gly Arg Phe Glu Arg Glu Ile Val Pro Val Pro Val Arg Asp
    210                 215                 220

Gly Glu Leu Ala Ala Asp Glu Thr Pro Arg Arg Gly Thr Thr Leu Glu
225                 230                 235                 240

Lys Leu Gly Ser Leu Lys Pro Val Phe Arg Thr Gly Gly Ile Val Thr
                245                 250                 255

Ala Gly Ser Ser Ser Ser Leu Ser Asp Gly Ala Ala Ala Leu Val Val
            260                 265                 270

Ala Ser Glu Ala Ala Val Glu Lys Tyr Gly Leu Thr Val Arg Gly Arg
        275                 280                 285

Ile Val Thr Ser Ala Ser Ala Gly Ile Ala Pro Asn Val Met Gly Leu
    290                 295                 300

Gly Pro Val Pro Ala Thr Arg Lys Ala Leu Ala Arg Ala Asn Trp Ser
305                 310                 315                 320

Ile Ser Asp Leu Gly Ala Ala Glu Leu Asn Glu Ala Phe Ala Ala Gln
                325                 330                 335

Ser Leu Gly Val Ile Arg Gln Leu Lys Leu Asp Glu Ser Ile Val Asn
            340                 345                 350

Ala Asp Gly Gly Ala Ile Ala Leu Gly His Pro Leu Gly Cys Ser Gly
        355                 360                 365

Ala Arg Ile Leu Leu Thr Leu Leu Gly Arg Met Glu Arg Glu Gly Ala
    370                 375                 380

Arg Arg Gly Leu Ala Thr Leu Cys Val Gly Val Gly Gln Gly Val Ala
385                 390                 395                 400

Met Leu Ile Glu Ala Pro
                405

<210> SEQ ID NO 22
<211> LENGTH: 447
<212> TYPE: PRT
<213> ORGANISM: Bdellovibrio bacteriovorus

<400> SEQUENCE: 22

Met Lys Ser Pro Arg Asp Val Val Leu Val Glu Gly Val Arg Thr Pro
1               5                   10                  15

Phe Ala Lys Ala Gly Thr Lys Leu Lys Lys Val His Pro Ala Glu Leu
            20                  25                  30

Gly Lys Val Ala Leu Lys Gln Val Ile Ala Gln Thr Asn Leu Asp Val
        35                  40                  45

Asn Leu Val Asp Glu Val Ile Ile Gly Asn Thr Gly Asn Pro Pro Asp
    50                  55                  60

Ser Val Asn Ile Ser Arg Val Val Ala Leu Asn Ala Gly Ile Pro Leu
65                  70                  75                  80

Lys Thr Ser Ala Tyr Thr Val His Arg Asn Cys Ala Ser Ala Leu Glu

```
                85                  90                  95

Ser Ile Ser Asn Gly Tyr Glu Lys Ile Lys Ser Gly Thr Met Asp Val
            100                 105                 110

Ile Leu Ala Gly Gly Thr Glu Asn Met Ser Gln Met Pro Thr Leu Pro
        115                 120                 125

Pro Lys Lys Phe Gln Glu Ile Tyr Glu Lys Leu Phe Ala Ala Lys Gly
    130                 135                 140

Pro Lys Gln Ala Leu Pro Leu Leu Trp Ser Leu Phe Lys Ala Asp Val
145                 150                 155                 160

Lys Gln Ile Lys Ala Leu Leu Ser Gly Asn Met Arg Asp Glu Tyr Phe
            165                 170                 175

Pro Val Ile Ser Val Met Met Gly Leu Thr Asp Pro Phe Val Gly Ile
            180                 185                 190

Asn Met Gly Gln Thr Ala Glu Ile Leu Ala Lys Glu Trp Gly Leu Ser
        195                 200                 205

Arg Glu Thr Gln Asp Lys Phe Ala Leu Arg Ser His Gln Leu Ala Ser
    210                 215                 220

Lys Ala Met Lys Glu Gly Arg Met Arg Glu Glu Ile Ala Pro Val Tyr
225                 230                 235                 240

Leu Ala Pro Glu Tyr Lys Glu Val Ile Ser Glu Asp Ile Gly Pro Arg
            245                 250                 255

Asp Thr Gln Thr Met Glu Ala Leu Ala Lys Leu Lys Pro Phe Phe Asp
            260                 265                 270

Lys Ala Thr Gly Ser Ile Thr Ala Gly Asn Ser Cys Pro Ile Thr Asp
        275                 280                 285

Gly Ala Ala Met Val Leu Met Met Ser Arg Glu Lys Ala Glu Ala Leu
    290                 295                 300

Gly Tyr Lys Pro Leu Ala Thr Ile Arg Ser Tyr Gly Phe Ala Gly Leu
305                 310                 315                 320

Glu Pro Glu Arg Met Gly Leu Gly Pro Val Tyr Ser Thr Pro Val Ala
            325                 330                 335

Leu Lys Arg Ala Gly Leu Ser Met Lys Asp Ile Gly Leu Val Glu Leu
            340                 345                 350

Asn Glu Ala Phe Ala Ala Gln Val Leu Ser Cys Gln Lys Ala Phe Asp
        355                 360                 365

Ser Asp Lys Phe Gly Gln Glu Lys Leu Gly Leu Ser Ser Lys Ile Gly
    370                 375                 380

Glu Ile Arg Asp Asp Ile Leu Asn Val Asn Gly Gly Ala Ile Ala Leu
385                 390                 395                 400

Gly His Pro Val Gly Ala Thr Gly Thr Arg Ile Val Leu Thr Leu Ala
            405                 410                 415

Lys Glu Met Lys Arg Arg Asn Thr Gln Phe Gly Leu Ala Thr Leu Cys
            420                 425                 430

Ile Gly Gly Gly Gln Gly Gly Ser Met Ile Leu Glu Asn Glu Gly
        435                 440                 445


<210> SEQ ID NO 23
<211> LENGTH: 445
<212> TYPE: PRT
<213> ORGANISM: Cronobacter turicensis

<400> SEQUENCE: 23

Met Phe Ser Leu Leu Gln Gly Asn Val Met Ser Gln Ala Leu Pro Leu
1               5                   10                  15
```

-continued

```
Val Thr Arg Gln Gly Asp Arg Ile Ala Ile Val Ser Gly Leu Arg Thr
            20                  25                  30

Pro Phe Ala Arg Gln Ala Thr Ala Tyr His Gly Val Pro Ala Val Asp
        35                  40                  45

Leu Gly Lys Met Val Val Gly Glu Leu Leu Ala Arg Ser Glu Ile Pro
    50                  55                  60

Pro Asp Val Ile Glu Gln Leu Val Phe Gly Gln Val Val Gln Met Pro
65                  70                  75                  80

Glu Ala Pro Asn Ile Ala Arg Glu Ile Val Leu Gly Thr Gly Met Ser
                85                  90                  95

Val His Thr Asp Ala Tyr Ser Val Ser Arg Ala Cys Ala Thr Ser Phe
            100                 105                 110

Gln Ala Val Ala Asn Val Ala Glu Ser Leu Met Ala Gly Thr Ile Arg
        115                 120                 125

Ala Gly Ile Ala Gly Gly Ala Asp Ser Ser Ser Val Leu Pro Ile Gly
    130                 135                 140

Val Ser Lys Lys Leu Ala Arg Thr Leu Val Asp Ala Asn Lys Ala Arg
145                 150                 155                 160

Thr Ala Gly Gln Arg Leu Lys Leu Phe Ser Arg Leu Arg Leu Arg Asp
                165                 170                 175

Leu Leu Pro Val Pro Pro Ala Val Ala Glu Tyr Ser Thr Gly Leu Arg
            180                 185                 190

Met Gly Asp Thr Ala Glu Gln Met Ala Lys Thr His Gly Ile Thr Arg
        195                 200                 205

Glu Gln Gln Asp Ala Leu Ala His Arg Ser His Gln Leu Ala Ala Gln
    210                 215                 220

Ala Trp Ala Glu Gly Lys Leu Arg Glu Glu Val Met Thr Ala Tyr Thr
225                 230                 235                 240

Pro Pro Tyr Arg Glu Pro Leu Ser Glu Asp Asn Asn Ile Arg Lys Asn
                245                 250                 255

Ser Ser Leu Ala Asp Tyr Thr Lys Leu Arg Pro Ala Phe Asp Arg Lys
            260                 265                 270

His Gly Thr Val Thr Ala Ala Asn Ser Thr Pro Leu Thr Asp Gly Ala
        275                 280                 285

Ala Ala Val Ile Leu Met Thr Glu Ser Arg Ala Arg Glu Leu Gly Leu
    290                 295                 300

Thr Pro Leu Gly Tyr Leu Arg Ser Tyr Ala Phe Thr Ala Val Asp Val
305                 310                 315                 320

Trp Gln Asp Met Leu Leu Gly Pro Ala Trp Ser Thr Pro Leu Ala Leu
                325                 330                 335

Glu Arg Ala Gly Leu Thr Met Ala Asp Leu Thr Leu Ile Asp Met His
            340                 345                 350

Glu Ala Phe Ala Ser Gln Thr Leu Ala Asn Leu Lys Leu Leu Ala Ser
        355                 360                 365

Asp Arg Phe Ala Arg Glu Val Leu Gly Arg Ser Gln Ala Thr Gly Glu
    370                 375                 380

Val Asp Glu Ser Lys Phe Asn Val Leu Gly Gly Ser Ile Ala Tyr Gly
385                 390                 395                 400

His Pro Phe Ala Ala Thr Gly Ala Arg Met Ile Thr Gln Thr Leu Asn
                405                 410                 415

Glu Leu Arg Arg Arg Gly Gly Gly Phe Gly Leu Val Thr Ala Cys Ala
            420                 425                 430

Ala Gly Gly Leu Gly Ala Ala Met Val Leu Glu Ala Glu
```

```
        435                 440                 445


<210> SEQ ID NO 24
<211> LENGTH: 456
<212> TYPE: PRT
<213> ORGANISM: Arthrobacter sp.

<400> SEQUENCE: 24

Met Ser Phe Asn Gly Gln Ser Ala Thr Gly Pro Asp Glu Ser Ala Ala
1               5                   10                  15

Ala Pro Ala Ala Thr Pro Gly Ala Gly Leu Leu Arg Lys Ala Val Val
            20                  25                  30

Val Gly Gly Asn Arg Ile Pro Phe Ala Arg Thr Gly Gly Ala Tyr Thr
        35                  40                  45

Lys Ser Ser Asn Gln Asp Met Leu Thr Ala Ala Leu Asp Gly Leu Ile
    50                  55                  60

Ala Arg Phe Gly Leu Ala Asp Glu Arg Ile Gly Glu Val Ala Ala Gly
65                  70                  75                  80

Ala Val Leu Lys His Ser Arg Asp Phe Asn Leu Thr Arg Glu Ala Val
                85                  90                  95

Leu Gly Ser Ala Leu Ser Ala Glu Thr Pro Ala Tyr Asp Leu Gln Gln
            100                 105                 110

Ala Cys Ala Thr Gly Leu Glu Thr Val Leu Gly Leu Ala Asn Lys Ile
        115                 120                 125

Lys Leu Gly Gln Ile Asp Ser Ala Ile Ala Gly Gly Val Asp Ser Ala
    130                 135                 140

Ser Asp Ala Pro Ile Ala Val Ser Glu Gly Leu Arg Glu Val Leu Leu
145                 150                 155                 160

Asp Leu Asn Arg Ala Lys Thr Leu Pro Gln Arg Leu Lys Val Leu Gly
                165                 170                 175

Arg Leu Arg Pro Lys Asp Leu Ala Pro Asp Ala Pro Asn Thr Gly Glu
            180                 185                 190

Pro Arg Thr Gly Leu Ser Met Gly Glu His Gln Ala Leu Thr Thr Ala
        195                 200                 205

Gln Trp Lys Ile Thr Arg Glu Ala Gln Asp Glu Leu Ala Tyr Asn Ser
    210                 215                 220

His Arg Asn Leu Ala Ala Ala Tyr Asp Ala Gly Phe Phe Asp Asp Leu
225                 230                 235                 240

Leu Thr Pro Tyr Arg Gly Leu Asn Arg Asp Ser Asn Leu Arg Ala Asp
                245                 250                 255

Thr Thr Arg Glu Lys Leu Ser Thr Leu Lys Pro Val Phe Gly Lys Asn
            260                 265                 270

Leu Gly Ala Glu Ala Thr Met Thr Ala Gly Asn Ser Thr Pro Leu Thr
        275                 280                 285

Asp Gly Ala Ser Thr Val Leu Leu Ala Ser Glu Glu Trp Ala Asp Ala
    290                 295                 300

His Glu Leu Pro Lys Leu Ala Thr Val Val Asp Gly Glu Ala Ala Ala
305                 310                 315                 320

Val Asp Phe Val His Gly Lys Asp Gly Leu Leu Met Ala Pro Ala Phe
                325                 330                 335

Ala Val Pro Arg Leu Leu Ala Arg Asn Gly Leu Thr Leu Asp Asp Ile
            340                 345                 350

Asp Phe Phe Glu Ile His Glu Ala Phe Ala Gly Thr Val Leu Ser Thr
        355                 360                 365
```

```
Leu Ala Ala Trp Glu Asp Glu Glu Phe Gly Arg Thr Arg Leu Gly Leu
    370                 375                 380

Asp Gly Pro Leu Gly Ser Ile Asp Arg Ala Lys Leu Asn Val Asn Gly
385                 390                 395                 400

Ser Ser Leu Ala Ala Gly His Pro Phe Ala Ala Thr Gly Gly Arg Ile
                405                 410                 415

Val Ala Thr Leu Ala Lys Met Leu His Asp Lys Gly Gln Val Asp Gly
            420                 425                 430

Arg Pro Ala Arg Gly Leu Ile Ser Ile Cys Ala Ala Gly Gly Gln Gly
        435                 440                 445

Val Val Ala Ile Leu Glu Ala Ser
    450                 455


<210> SEQ ID NO 25
<211> LENGTH: 429
<212> TYPE: PRT
<213> ORGANISM: Caulobacter segnis

<400> SEQUENCE: 25

Met Ala Thr Ala Ser Ser Ser Ala Ala Ser Ser Ser Gly Val Trp Leu
1               5                   10                  15

Ala Ala Gly Val Arg Ser Pro Phe Ala Lys Val Asp Gly Ala Leu Ala
            20                  25                  30

Gly His Asp Ala Ile Gly Leu Ser Val Pro Val Val Lys Ala Met Leu
        35                  40                  45

Ala Arg Ala Lys Pro Asp Phe Ala Val Trp Gly Thr Val Ile Pro Asn
    50                  55                  60

Leu Thr Trp Ser Asn Leu Ala Arg Glu Val Leu Leu Asp Ala Gly Gly
65                  70                  75                  80

Asp Pro Thr Ile Pro Ala Phe Ser Thr Val Met Ala Cys Ser Thr Ser
                85                  90                  95

Met Ile Gly Ala Ile Glu Ala Ala Gly Met Val Asp Gly Arg Gly Arg
            100                 105                 110

Asp Leu Ala Leu Val Gly Gly Val Glu Ser Met Ser Arg Val Gln Leu
        115                 120                 125

Gly Leu Ser Val Ala Leu Ser Asp Trp Ile Arg Lys Phe Gln Asn Ala
    130                 135                 140

Lys Thr Gly Gln Gln Arg Leu Ala Ala Leu Gly Ala Leu Asn Leu Lys
145                 150                 155                 160

Asp Val Arg Leu Phe Ile Pro Lys Val Val Asn Arg Val Thr Gly Leu
                165                 170                 175

Ser Met Gly Glu His Thr Glu Ile Thr Ala Lys Glu Trp Asn Leu Ser
            180                 185                 190

Arg Ala Asp Gln Asp Ala Ile Ala Leu Ala Ser His Gln Gly Ala Val
        195                 200                 205

Lys Gly Trp Glu Ser Gly Phe Phe Asp Asp Leu Val Ile Pro Val Gly
    210                 215                 220

Glu Val Lys Arg Asp Gly Ile Pro Arg Lys Asp Thr Ser Leu Glu Lys
225                 230                 235                 240

Leu Ala Lys Leu Gly Pro Ala Phe Asp Lys Thr Ser Gly Lys Gly Thr
                245                 250                 255

Leu Thr Ala Gly Asn Ser Ser Pro Leu Thr Asp Gly Ala Ala Ala Val
            260                 265                 270

Trp Val Gly Ser Ala Ala Gly Met Ala Arg Leu Pro Gly Glu Thr Pro
        275                 280                 285
```

```
Lys Val Arg Leu Val Asp Tyr Glu Val Thr Ser Ile Asp Leu Arg His
    290                 295                 300

Glu Gly Leu Leu Met Ala Pro Ala Tyr Gly Val Pro Arg Met Leu Ala
305                 310                 315                 320

Arg Asn Gly Leu Thr Tyr Ala Asp Val Gly Leu Trp Glu Ile His Glu
                325                 330                 335

Ala Phe Ala Ala Gln Val Leu Ser His Ile Ala Ala Trp Glu Ser Ala
            340                 345                 350

Lys Phe Leu Ser Glu Lys Ala Gly Val Thr Thr Pro Met Gly Ala Phe
        355                 360                 365

Pro Arg Glu Arg Met Asn Pro Asn Gly Gly Ser Leu Ala Leu Gly His
    370                 375                 380

Pro Phe Gly Ala Thr Gly Ala Arg Ile Ile Ser Gln Thr Val Lys Glu
385                 390                 395                 400

Leu Ala Ala Arg Pro Lys Gly Glu Arg Ala Ile Val Ser Ile Cys Ala
                405                 410                 415

Asp Gly Gly Gln Gly Thr Met Met Leu Leu Glu Ser Ala
            420                 425


<210> SEQ ID NO 26
<211> LENGTH: 403
<212> TYPE: PRT
<213> ORGANISM: Dinoroseobacter shibae

<400> SEQUENCE: 26

Met Thr Glu Ala Tyr Ile Tyr Asp Ala Ile Arg Ser Pro Arg Gly Lys
1               5                   10                  15

Gly Arg Lys Asp Gly Ser Leu His Glu Val Thr Ala Val Ser Leu Ser
            20                  25                  30

Ala Gln Thr Leu Asn Ala Ile Lys Asp Arg Asn Gly Leu Thr Gly His
        35                  40                  45

Ala Val Glu Asp Val Ile Trp Gly Asn Val Thr Gln Val Met Glu Gln
    50                  55                  60

Gly Gly Cys Leu Ala Arg Thr Ala Val Leu Ala Ser Asp Leu Asp Glu
65                  70                  75                  80

Ser Ile Pro Gly Leu Ala Ile Asn Arg Phe Cys Ala Ser Gly Leu Glu
                85                  90                  95

Ala Val Asn Leu Ala Ala Asn Gln Val Arg Gly Gly Gly Gly Gln Ala
            100                 105                 110

Tyr Ile Ala Gly Gly Val Glu Met Met Gly Arg Val Pro Met Gly Ser
        115                 120                 125

Asp Gly Ala Ala Ile Ala Ala Asp Pro Ser Val Ala Met Lys Thr Tyr
    130                 135                 140

Phe Val Pro Gln Gly Ile Ser Ala Asp Ile Ile Ala Thr Glu Tyr Gly
145                 150                 155                 160

Ile Ser Arg Asp Asp Ala Asp Ala Leu Ala Val Ala Ser Gln Arg Arg
                165                 170                 175

Ala Lys Ala Ala Trp Asp Glu Asn Arg Phe Asn Gly Ser Val Phe Thr
            180                 185                 190

Val Arg Asp Gln Asn Gly Leu Asn Ile Leu Asp His Asp Glu Tyr Met
        195                 200                 205

Arg Pro Glu Thr Asp Met Gln Ser Leu Gly Ala Leu Lys Pro Ala Phe
    210                 215                 220

Lys Asp Met Gly Glu Gln Met Pro Gly Phe Asp Lys Ile Ala Leu Met
```

```
225                 230                 235                 240

Lys Tyr Pro His Leu Glu Lys Ile Glu His Ile His His Ala Gly Asn
                245                 250                 255

Ser Ser Gly Ile Val Asp Gly Ser Ala Ala Leu Leu Ile Gly Asn Lys
            260                 265                 270

Ala Phe Gly Glu Ala His Gly Leu Lys Pro Arg Ala Val Ile Lys Ala
        275                 280                 285

Thr Ala Lys Ile Gly Thr Asp Pro Thr Ile Met Leu Thr Gly Pro Val
    290                 295                 300

Pro Ala Thr Glu Lys Ile Leu Ala Asp Ser Gly Met Ser Ile Ser Asp
305                 310                 315                 320

Ile Asp Leu Phe Glu Val Asn Glu Ala Phe Ser Ser Val Val Leu Arg
                325                 330                 335

Phe Met Gln Ala Phe Asp Val Asp His Asp Lys Val Asn Val Asn Gly
            340                 345                 350

Gly Ala Ile Ala Met Gly His Pro Leu Gly Ala Thr Gly Ala Met Ile
        355                 360                 365

Leu Gly Thr Leu Leu Asp Glu Leu Glu Arg Thr Gly Lys Gly Thr Gly
    370                 375                 380

Leu Ala Thr Leu Cys Val Ala Ser Gly Met Gly Ala Ala Thr Ile Ile
385                 390                 395                 400

Glu Arg Val


<210> SEQ ID NO 27
<211> LENGTH: 394
<212> TYPE: PRT
<213> ORGANISM: Burkholderia xenovorans

<400> SEQUENCE: 27

Met Thr Arg Asp Thr Arg Asp Val Val Ile Val Asp Ala Val Arg Thr
1               5                   10                  15

Pro Ile Gly Lys Phe Arg Gly Ala Leu Ala Gly Val Arg Ala Asp His
            20                  25                  30

Leu Gly Ala Leu Val Ile Asp Glu Leu Ile Arg Arg Ala Gly Val Lys
        35                  40                  45

Pro Gln Ala Val Asn Asp Val Val Phe Gly Cys Val Thr Gln Ile Gly
    50                  55                  60

Glu Gln Ser Ala Asn Ile Ala Arg Thr Ser Val Leu Gly Ala Gly Trp
65                  70                  75                  80

Pro Glu Thr Ile Pro Gly Leu Thr Ile Asp Arg Lys Cys Gly Ser Gly
                85                  90                  95

Glu Glu Ala Val His Ile Ala Ala Gly Leu Ile Ala Phe Gly Ala Ala
            100                 105                 110

Asp Val Ile Val Ala Gly Gly Ala Glu Ser Met Ser Arg Val Pro Met
        115                 120                 125

Gly Ser Asn Arg Asp Leu His Gly Glu Ala Phe Gly Trp Met Ala Ser
    130                 135                 140

Glu Arg Phe Glu Leu Thr Ser Gln Gly Glu Ala Ala Glu Arg Leu Cys
145                 150                 155                 160

Asp Cys Trp Ala Leu Thr Arg Ala Gln Leu Asp Ala Tyr Ser Val Glu
                165                 170                 175

Ser His Arg Arg Ala Ala Ala Ala Ala Ala Glu Gly Trp Phe Ala Arg
            180                 185                 190

Glu Ile Val Pro Val Pro Val Gly Gln Val Arg Glu Lys Ser Leu Glu
```

```
        195                 200                 205

Gly Glu Ala Ala Leu Phe Ala Ala Asp Glu Thr Ile Arg Pro Gly Thr
    210                 215                 220

Asn Ala Asp Lys Leu Ala Thr Leu Lys Ser Ser Phe Arg Ser Asp Gly
225                 230                 235                 240

Arg Leu Thr Ala Gly Asn Ser Ser Gln Ile Ser Asp Gly Ala Ala Ala
                245                 250                 255

Leu Leu Leu Met Ser Ser Asp Lys Ala Arg Glu Leu Gly Val Lys Ala
            260                 265                 270

Arg Ala Arg Val Arg Ala Val Thr Thr Val Gly Ser Asp Pro Thr Leu
        275                 280                 285

Met Leu Thr Gly Pro Ile Leu Ala Thr Cys Gln Val Leu Glu Lys Ala
    290                 295                 300

Gly Leu Gly Leu Ser Asp Ile Asp Leu Phe Glu Ile Asn Glu Ala Phe
305                 310                 315                 320

Ala Pro Val Pro Leu Val Trp Met Lys Glu Phe Gly Val Pro His Ala
                325                 330                 335

Lys Leu Asn Val Asn Gly Gly Ala Ile Ala Leu Gly His Pro Leu Gly
            340                 345                 350

Ala Ser Gly Ala Arg Ile Met Thr Ser Met Leu His Glu Leu Glu Arg
        355                 360                 365

Arg Gly Ala Arg Tyr Gly Leu Gln Ala Ile Cys Cys Ala Gly Gly Met
    370                 375                 380

Gly Thr Ala Thr Leu Ile Glu Arg Leu Asp
385                 390


<210> SEQ ID NO 28
<211> LENGTH: 382
<212> TYPE: PRT
<213> ORGANISM: Geobacillus kaustophilus

<400> SEQUENCE: 28

Met Arg Glu Ala Val Ile Val Glu Ala Val Arg Thr Pro Val Gly Lys
1               5                   10                  15

Arg Asn Gly Val Phe Arg Asp Val His Pro Val His Leu Ala Ala Val
            20                  25                  30

Val Leu Asp Glu Val Val Arg Arg Ala Gly Met Asp Lys Gly Ala Val
        35                  40                  45

Glu Asp Ile Val Met Gly Cys Val Thr Pro Val Ala Glu Gln Gly Tyr
    50                  55                  60

Asn Ile Gly Arg Leu Ala Ala Leu Glu Ala Gly Phe Pro Ile Glu Val
65                  70                  75                  80

Pro Ala Val Gln Ile Asn Arg Met Cys Gly Ser Gly Gln Gln Ala Ile
                85                  90                  95

His Phe Ala Ala Gln Glu Ile Arg Ser Gly Asp Met Asp Val Thr Ile
            100                 105                 110

Ala Ala Gly Val Glu Ser Met Thr Lys Val Pro Ile Leu Ser Asp Gly
        115                 120                 125

Asn Glu Arg Thr Ile Pro Pro Ser Leu His Glu Lys Tyr Glu Phe Ile
    130                 135                 140

His Gln Gly Val Ser Ala Glu Arg Ile Ala Lys Lys Tyr Gly Leu Thr
145                 150                 155                 160

Arg Glu Glu Leu Asp Ala Tyr Ala Tyr Glu Ser His Gln Arg Ala Leu
                165                 170                 175
```

```
Ala Ala Leu Arg Glu Gly Lys Phe Arg Ala Glu Ile Val Pro Val Lys
            180                 185                 190

Gly Leu Asp Arg Asp Gly Arg Glu Ile Leu Val Thr Asp Asp Glu Gly
        195                 200                 205

Pro Arg Ala Asp Thr Ser Pro Glu Ala Leu Ala Ala Leu Lys Pro Val
    210                 215                 220

Phe Gln Glu Asp Gly Leu Ile Thr Ala Gly Asn Ala Ser Gln Met Ser
225                 230                 235                 240

Asp Gly Ala Ala Ala Val Leu Leu Met Glu Arg Glu Ala Ala Arg Arg
                245                 250                 255

Phe Gly Leu Lys Pro Lys Ala Arg Ile Val Ala Gln Thr Val Val Gly
            260                 265                 270

Ser Asp Pro Thr Tyr Met Leu Asp Gly Val Ile Pro Ala Thr Arg Gln
        275                 280                 285

Val Leu Lys Lys Ala Gly Leu Ser Ile Asp Asp Ile Asp Leu Ile Glu
    290                 295                 300

Ile Asn Glu Ala Phe Ala Pro Val Val Leu Ala Trp Gln Lys Glu Ile
305                 310                 315                 320

Gly Ala Pro Leu Glu Lys Val Asn Val Asn Gly Gly Ala Ile Ala Leu
                325                 330                 335

Gly His Pro Leu Gly Ala Thr Gly Ala Lys Leu Met Thr Ser Leu Val
            340                 345                 350

His Glu Leu Glu Arg Arg Gly Gly Arg Tyr Gly Leu Leu Thr Ile Cys
        355                 360                 365

Ile Gly His Gly Met Ala Thr Ala Thr Ile Ile Glu Arg Glu
    370                 375                 380


<210> SEQ ID NO 29
<211> LENGTH: 378
<212> TYPE: PRT
<213> ORGANISM: Beijerinckia indica

<400> SEQUENCE: 29

Met Thr Lys Val Val Ile Ala Gly Tyr Ile Arg Ser Pro Phe Thr Leu
1               5                   10                  15

Ala Lys Lys Gly Glu Leu Ala Thr Val Arg Pro Asp Asp Leu Ala Ala
            20                  25                  30

Gln Val Val Lys Gly Leu Ile Lys Lys Thr Gly Ile Pro Ala Glu Asp
        35                  40                  45

Ile Glu Asp Leu Leu Leu Gly Cys Ala Phe Pro Glu Gly Glu Gln Gly
    50                  55                  60

Phe Asn Val Ala Arg Leu Val Ser Phe Leu Ala Gly Leu Pro Leu Ser
65                  70                  75                  80

Val Gly Ala Ser Thr Val Asn Arg Phe Cys Gly Ser Ser Met Thr Thr
                85                  90                  95

Val His Met Ala Ala Gly Ala Ile Gln Met Asn Ala Gly Asn Ala Phe
            100                 105                 110

Ile Ala Ala Gly Val Glu Ser Met Ser Arg Val Pro Met Met Gly Phe
        115                 120                 125

Asn Pro Leu Pro Asn Pro Glu Leu Ala Ala Thr Met Pro Gly Ala Tyr
    130                 135                 140

Met Gly Met Gly Asp Thr Ala Glu Asn Val Ala Ala Lys Trp Thr Ile
145                 150                 155                 160

Ser Arg Lys Glu Gln Glu Glu Phe Ala Leu Arg Ser His Gln Arg Ala
                165                 170                 175
```

```
Thr Ala Ala Gln Lys Glu Gly Arg Leu Thr Gly Glu Ile Ile Pro Ile
            180                 185                 190

Thr Gly Arg Lys Gly Thr Ile Thr Thr Asp Gly Cys Ile Arg Pro Asp
        195                 200                 205

Thr Thr Leu Glu Gly Leu Ala Glu Leu Lys Pro Ala Phe Ser Ala Asn
    210                 215                 220

Gly Val Val Thr Ala Gly Thr Ser Ser Pro Leu Thr Asp Gly Ala Ala
225                 230                 235                 240

Ala Val Leu Val Cys Ser Glu Asp Tyr Ala Lys His His His Leu Asp
                245                 250                 255

Val Leu Ala Ser Val Lys Ala Ile Ala Val Ser Gly Cys Ser Pro Glu
            260                 265                 270

Ile Met Gly Ile Gly Pro Val Ala Ala Ser Arg Lys Ala Leu Ala Arg
        275                 280                 285

Ala Gly Leu Glu Ala Gly Gln Ile Asp Ile Val Glu Leu Asn Glu Ala
    290                 295                 300

Phe Ala Ser Gln Ser Ile Ala Cys Met Arg Glu Leu Asn Leu Ser Pro
305                 310                 315                 320

Asp Arg Val Asn Ile Asp Gly Gly Ala Ile Ala Leu Gly His Pro Leu
                325                 330                 335

Gly Ala Thr Gly Ala Arg Ile Val Gly Lys Ala Ala Ser Leu Leu Lys
            340                 345                 350

Arg Glu Lys Gly Lys Tyr Ala Leu Ala Thr Gln Cys Ile Gly Gly Gly
        355                 360                 365

Gln Gly Ile Ala Thr Val Leu Glu Ala Phe
    370                 375


<210> SEQ ID NO 30
<211> LENGTH: 387
<212> TYPE: PRT
<213> ORGANISM: Citrobacter freundii

<400> SEQUENCE: 30

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Asp Pro Thr
        35                  40                  45

Ala Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Ile Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Ile Gly Gly Val Glu His Met Gly His Val Pro Met Ser His
        115                 120                 125

Gly Val Asp Phe His Pro Gly Met Ser Arg Asn Val Ala Lys Ala Ala
    130                 135                 140

Gly Met Met Gly Leu Thr Ala Glu Met Leu Ser Arg Met His Gly Ile
145                 150                 155                 160

Ser Arg Glu Met Gln Asp Ala Phe Ala Ala Arg Ser His Ala Arg Ala
```

```
                165                 170                 175

Trp Ala Ala Thr Gln Ser Gly Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ser Thr Leu Arg Pro
    210                 215                 220

Ala Phe Asp Pro Val Ser Gly Thr Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

Arg Glu Leu Gly Leu Thr Pro Arg Ala Arg Ile Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Thr Ser Asp Ile Gly Leu
    290                 295                 300

Phe Glu Met Asn Glu Ala Phe Ala Ala Gln Ile Leu Pro Cys Ile Lys
305                 310                 315                 320

Asp Leu Gly Leu Met Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
    370                 375                 380

Glu Arg Val
385


<210> SEQ ID NO 31
<211> LENGTH: 398
<212> TYPE: PRT
<213> ORGANISM: Cupriavidus necator

<400> SEQUENCE: 31

Met Lys Gln Leu Gln Asp Ala Tyr Ile Val Ala Ala Thr Arg Ser Pro
1               5                   10                  15

Ile Gly Lys Ala Pro Lys Gly Ala Phe Lys Asn Thr Arg Pro Asp Asp
            20                  25                  30

Leu Leu Ala Thr Ile Leu Lys Ala Ala Val Ala Gln Val Pro Asn Leu
        35                  40                  45

Asp Pro Lys Leu Ile Glu Asp Ala Ile Val Gly Cys Ala Ile Pro Glu
    50                  55                  60

Ala Gln Gln Gly Leu Asn Val Ala Arg Ile Gly Ala Leu Leu Ser Gly
65                  70                  75                  80

Leu Pro Asn Thr Val Gly Gly Ile Thr Val Asn Arg Phe Cys Ala Ser
                85                  90                  95

Gly Val Ser Ala Val Ala Met Ala Ala Asp Arg Ile Arg Val Gly Glu
            100                 105                 110

Ser Asp Val Met Ile Ala Ala Gly Val Glu Ser Met Ser Met Val Pro
        115                 120                 125

Met Met Gly Asn Ser Pro Ser Met Ser Pro Glu Ile Phe Thr Arg Asp
    130                 135                 140
```

```
Glu Asn Val Gly Ile Ala Tyr Gly Met Gly Leu Thr Ala Glu Lys Val
145                 150                 155                 160

Ala Gln Gln Trp Gln Val Ser Arg Glu Asp Gln Asp Ala Phe Ser Leu
                165                 170                 175

Ala Ser His Gln Lys Ala Ile Ala Ala Gln Gln Ala Gly Glu Phe Lys
            180                 185                 190

Asp Glu Ile Thr Pro Ile Glu Ile Val Glu Arg Phe Pro Asp Leu Ala
        195                 200                 205

Ser Gly Gln Val Asn Val Lys Thr Arg Thr Ile Ser Leu Asp Glu Gly
    210                 215                 220

Pro Arg Pro Glu Thr Ser Leu Glu Gly Leu Gly Lys Leu Arg Pro Val
225                 230                 235                 240

Phe Ala Asn Lys Gly Ser Val Thr Ala Gly Asn Ser Ser Gln Thr Ser
                245                 250                 255

Asp Gly Ala Gly Ala Leu Ile Leu Val Ser Glu Lys Ile Leu Lys Gln
            260                 265                 270

Phe Asn Leu Val Pro Leu Ala Arg Phe Val Ser Phe Ala Val Arg Gly
        275                 280                 285

Val Pro Pro Glu Ile Met Gly Ile Gly Pro Lys Glu Ala Ile Pro Ala
    290                 295                 300

Ala Leu Lys Ala Ala Gly Leu Thr Gln Asp Gln Leu Asp Trp Ile Glu
305                 310                 315                 320

Leu Asn Glu Ala Phe Ala Ala Gln Ser Leu Ala Val Met Arg Asp Leu
                325                 330                 335

Gln Leu Asp Pro Ala Lys Val Asn Arg Met Gly Gly Ala Ile Ala Leu
            340                 345                 350

Gly His Pro Leu Gly Ala Thr Gly Ala Ile Arg Ser Ala Thr Val Val
        355                 360                 365

His Ala Leu Arg Arg His Asn Leu Lys Tyr Gly Met Val Thr Met Cys
    370                 375                 380

Val Gly Thr Gly Met Gly Ala Ala Gly Ile Phe Glu Arg Val
385                 390                 395
```

<210> SEQ ID NO 32
<211> LENGTH: 415
<212> TYPE: PRT
<213> ORGANISM: Gordonia bronchialis

<400> SEQUENCE: 32

```
Met Ala Pro Cys Ser Val Lys Ala Met Pro Glu Ala Val Ile Val Ala
1               5                   10                  15

His Ala Arg Ser Pro Ile Gly Arg Ala Gly Lys Gly Ser Leu Lys Asp
            20                  25                  30

Val Arg Pro Asp Glu Leu Ser Arg Gln Met Val Ala Ala Ala Leu Ala
        35                  40                  45

Lys Val Pro Glu Leu Ala Pro Ser Asp Ile Glu Asp Ile His Trp Gly
    50                  55                  60

Ile Gly Gln Pro Gly Gly Gln Gly Gly Tyr Asn Ile Ala Arg Val Ile
65                  70                  75                  80

Ala Val Glu Leu Gly Tyr Asp His Ile Pro Gly Val Thr Val Asn Arg
                85                  90                  95

Tyr Cys Ser Ser Ser Leu Gln Thr Thr Arg Met Ala Leu His Ala Ile
            100                 105                 110

Lys Ala Gly Glu Ala Asp Val Leu Ile Ser Gly Gly Val Glu Ser Val
        115                 120                 125
```

-continued

```
Ser Ser Phe Gly Ile Ser Gly Gly Ala Asp Gly Ala Pro Asp Ser Lys
    130                 135                 140

Asn Pro Val Phe Asp Asp Ala Gln Ala Arg Thr Ala Lys Ala Ala Glu
145                 150                 155                 160

Gly Gly Ala Pro Ala Trp Thr Asp Pro Arg Glu Gln Gly Leu Ile Pro
                165                 170                 175

Asp Val Tyr Ile Ala Met Gly Gln Thr Ala Glu Asn Val Ala Ser Phe
            180                 185                 190

Thr Gly Ile Ser Arg Glu Asp Gln Asp Arg Trp Ser Val Leu Ser Gln
        195                 200                 205

Asn Arg Ala Glu Glu Ala Ile Asn Ala Gly Phe Phe Glu Arg Glu Ile
    210                 215                 220

Asp Pro Val Thr Leu Pro Asp Gly Ser Thr Val Asn Thr Asp Asp Gly
225                 230                 235                 240

Pro Arg Ala Gly Thr Thr Tyr Glu Lys Val Ser Gln Leu Lys Pro Val
                245                 250                 255

Phe Arg Pro Asp Gly Thr Val Thr Ala Gly Asn Ala Cys Pro Leu Asn
            260                 265                 270

Asp Gly Ala Ala Ala Leu Val Ile Met Ser Asp Ser Lys Ala Lys Gln
        275                 280                 285

Leu Gly Leu Thr Pro Leu Ala Arg Val Val Ala Thr Ala Ala Thr Gly
    290                 295                 300

Leu Ser Pro Glu Ile Met Gly Leu Gly Pro Ile Glu Ala Ile Arg Lys
305                 310                 315                 320

Val Leu Arg Ile Ser Gly Met Ser Leu Ser Asp Ile Asp Leu Val Glu
                325                 330                 335

Ile Asn Glu Ala Phe Ala Val Gln Val Leu Gly Ser Ala Asn Glu Leu
            340                 345                 350

Gly Ile Asp His Asp Lys Leu Asn Val Ser Gly Gly Ala Ile Ala Leu
        355                 360                 365

Gly His Pro Phe Gly Met Thr Gly Ala Arg Ile Thr Thr Thr Leu Leu
    370                 375                 380

Asn Asn Leu Gln Thr Arg Asp Lys Thr Phe Gly Ile Glu Ser Met Cys
385                 390                 395                 400

Val Gly Gly Gly Gln Gly Met Ala Met Val Leu Glu Arg Leu Ser
                405                 410                 415


<210> SEQ ID NO 33
<211> LENGTH: 393
<212> TYPE: PRT
<213> ORGANISM: Burkholderia sp.

<400> SEQUENCE: 33

Met Arg Glu Ala Val Ile Val Ser Thr Ala Arg Thr Pro Leu Thr Lys
1               5                   10                  15

Ala His Arg Gly Glu Phe Asn Ile Thr Pro Gly Pro Thr Leu Ala Ser
            20                  25                  30

Phe Ala Val Arg Ala Ala Val Glu Arg Ser Gly Val Asp Pro Asp Ile
        35                  40                  45

Ile Glu Asp Ala Ile Leu Gly Cys Gly Tyr Pro Glu Gly Thr Thr Gly
    50                  55                  60

Arg Asn Val Ala Arg Gln Ser Val Ile Arg Ala Gly Leu Pro Leu Ser
65                  70                  75                  80

Ile Ala Gly Thr Thr Val Asn Arg Phe Cys Ala Ser Gly Leu Gln Ala
```

-continued

```
                85                  90                  95

Ile Ala Met Ala Ala Gly Arg Ile Val Val Asp Gly Ala Pro Ala Met
            100                 105                 110

Ile Ala Gly Gly Val Glu Ser Ile Ser Asn Ile Gln Thr Arg Glu Asp
        115                 120                 125

Gly Val Ser Gly Leu Asp Pro Trp Ile Val Glu His Lys Pro Ser Leu
    130                 135                 140

Tyr Thr Ala Met Ile Asp Thr Ala Asp Ile Val Ala Arg Arg Tyr Gly
145                 150                 155                 160

Ile Ser Arg Glu Ala Gln Asp Gln Phe Ser Val Glu Ser Gln Arg Arg
            165                 170                 175

Thr Ala Glu Ala Gln Gln Ala Gly Arg Tyr Ala Asp Glu Ile Ile Pro
            180                 185                 190

Val Thr Thr Thr Met Ala Ile Thr Asp Lys Glu Thr Arg Ala Val Ser
        195                 200                 205

Tyr Arg Glu Val Thr Val Ser Ala Asp Asn Cys Asn Arg Pro Gly Thr
    210                 215                 220

Thr Tyr Glu Ala Leu Ala Lys Leu Ala Pro Val Lys Gly Pro Asp Gln
225                 230                 235                 240

Phe Ile Thr Ala Gly Asn Ala Ser Gln Asn Ala Asp Gly Ala Ser Ala
            245                 250                 255

Cys Val Leu Met Glu Ala Lys Ala Ala Glu Arg Ala Asn Phe Ala Pro
            260                 265                 270

Leu Gly Ala Phe Arg Gly Leu Ala Leu Ala Gly Cys Glu Pro Asp Glu
        275                 280                 285

Met Gly Ile Gly Pro Val Leu Ala Val Pro Lys Leu Leu Ala Arg His
    290                 295                 300

Gly Leu Thr Val Asp Asp Ile Gly Leu Trp Glu Leu Asn Glu Ala Phe
305                 310                 315                 320

Ala Ser Gln Ala Val Tyr Cys Gln Lys Arg Leu Glu Ile Pro Ser Glu
                325                 330                 335

Arg Leu Asn Val Asn Gly Gly Ala Ile Ser Ile Gly His Pro Phe Gly
            340                 345                 350

Met Thr Gly Ser Arg Leu Val Gly His Val Leu Ile Glu Gly Arg Arg
        355                 360                 365

Arg Gly Val Lys Tyr Ala Val Val Thr Met Cys Met Ala Gly Gly Met
    370                 375                 380

Gly Ala Ala Gly Leu Phe Glu Ile Tyr
385                 390


<210> SEQ ID NO 34
<211> LENGTH: 403
<212> TYPE: PRT
<213> ORGANISM: Glutamicibacter arilaitensis

<400> SEQUENCE: 34

Met Gln Gln Ala Tyr Leu Tyr Asp Ala Ile Arg Thr Pro Phe Gly Lys
1               5                   10                  15

Ile Gly Gly Ala Leu Ser Ser His Arg Pro Asp Asp Leu Ala Ala His
            20                  25                  30

Val Val Arg Glu Leu Val Ala Arg Ser Pro Lys Leu Asp Val Ala Asp
        35                  40                  45

Ile Asp Glu Ser Ile Phe Gly Asn Ala Asn Gly Ala Gly Glu Glu Asn
    50                  55                  60
```

Arg Asn Val Ala Arg Met Ala Thr Leu Leu Ala Gly Leu Pro Thr Ser
65 70 75 80

Leu Pro Gly Thr Thr Met Asn Arg Leu Cys Gly Ser Ser Leu Asp Ala
85 90 95

Ser Ile Ala Ala Ser Arg Gln Ile Ala Thr Gly Asp Ala Asp Leu Val
100 105 110

Leu Val Gly Gly Val Glu Ser Met Ser Arg Ala Pro Trp Val Leu Pro
115 120 125

Lys Thr Glu Arg Pro Phe Pro Met Ser Asn Leu Glu Leu Ala Asn Thr
130 135 140

Thr Leu Gly Trp Arg Leu Val Asn Pro Ala Met Pro Gly Glu Trp Thr
145 150 155 160

Val Ser Leu Gly Glu Ala Thr Glu Gln Leu Arg Glu Lys His Gly Ile
165 170 175

Ser Arg Glu Asp Gln Asp Glu Phe Ser Ala Ala Ser His Gln Arg Ala
180 185 190

Ala Ala Ala Trp Gln Ala Gly Lys Tyr Asp Asn Leu Val Val Pro Val
195 200 205

Pro Pro Ala Asn Lys Arg Gly Thr Glu Val Thr Arg Asp Glu Thr Ile
210 215 220

Arg Ala Asp Ser Thr Ala Gln Thr Leu Ser Lys Leu Arg Thr Val Phe
225 230 235 240

Arg Thr Gly Glu Asn Ala Thr Val Thr Ala Gly Asn Ala Ser Pro Met
245 250 255

Ser Asp Gly Ala Ser Ala Ala Phe Ile Gly Ser Glu Arg Gly Gly Glu
260 265 270

Leu Leu Gly Ala Ala Pro Ile Ala Arg Ile Ala Ser Asn Gly Ala Ala
275 280 285

Ala Leu Asp Pro Gln Phe Phe Gly Phe Ala Pro Val Glu Ala Ala Asn
290 295 300

Lys Ala Leu Ala Lys Ala Gly Leu Lys Trp Ser Asp Ile Ala Ala Val
305 310 315 320

Glu Leu Asn Glu Ala Phe Ala Ala Gln Ser Leu Ala Cys Ile Arg Ala
325 330 335

Trp Asp Ile Asp Pro Ala Ile Val Asn Ala Trp Gly Gly Ala Ile Ser
340 345 350

Ile Gly His Pro Leu Gly Ala Ser Gly Leu Arg Ile Leu Gly Thr Val
355 360 365

Ala Arg Arg Leu Ala Glu Ser Gly Glu Arg Tyr Gly Leu Ala Ala Ile
370 375 380

Cys Ile Gly Val Gly Gln Gly Leu Ala Val Val Val Glu Asn Ile Asn
385 390 395 400

Ala Thr Lys

<210> SEQ ID NO 35
<211> LENGTH: 401
<212> TYPE: PRT
<213> ORGANISM: Escherichia coli

<400> SEQUENCE: 35

Met Arg Glu Ala Phe Ile Cys Asp Gly Ile Arg Thr Pro Ile Gly Arg
1 5 10 15

Tyr Gly Gly Ala Leu Ser Ser Val Arg Ala Asp Asp Leu Ala Ala Ile
20 25 30

```
Pro Leu Arg Glu Leu Leu Val Arg Asn Pro Arg Leu Asp Ala Glu Cys
        35                  40                  45

Ile Asp Asp Val Ile Leu Gly Cys Ala Asn Gln Ala Gly Glu Asp Asn
    50                  55                  60

Arg Asn Val Ala Arg Met Ala Thr Leu Leu Ala Gly Leu Pro Gln Ser
65                  70                  75                  80

Val Ser Gly Thr Thr Ile Asn Arg Leu Cys Gly Ser Gly Leu Asp Ala
                85                  90                  95

Leu Gly Phe Ala Ala Arg Ala Ile Lys Ala Gly Asp Gly Asp Leu Leu
            100                 105                 110

Ile Ala Gly Gly Val Glu Ser Met Ser Arg Ala Pro Phe Val Met Gly
        115                 120                 125

Lys Ala Ala Ser Ala Phe Ser Arg Gln Ala Glu Met Phe Asp Thr Thr
    130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Glu Ile Val Pro Val
        195                 200                 205

Val Leu Lys Asn Lys Lys Gly Val Val Thr Glu Ile Gln His Asp Glu
    210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
        275                 280                 285

Gly Val Glu Pro Arg Leu Met Gly Leu Gly Pro Val Pro Ala Thr Arg
    290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350

Ile Ala Leu Gly His Pro Leu Gly Met Ser Gly Ala Arg Leu Ala Leu
        355                 360                 365

Ala Ala Ser His Glu Leu His Arg Arg Asn Gly Arg Tyr Ala Leu Cys
    370                 375                 380

Thr Met Cys Ile Gly Val Gly Gln Gly Ile Ala Met Ile Leu Glu Arg
385                 390                 395                 400

Val


<210> SEQ ID NO 36
<211> LENGTH: 394
<212> TYPE: PRT
<213> ORGANISM: Cupriavidus necator

<400> SEQUENCE: 36
```

-continued

```
Met Thr Arg Glu Val Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
    130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
    290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390
```

<210> SEQ ID NO 37
<211> LENGTH: 427
<212> TYPE: PRT

<213> ORGANISM: Clostridium viride

<400> SEQUENCE: 37

```
Met Ala Gln Phe Val Thr Ala Gln Glu Ala Val Lys His Ile Pro Asn
1               5                   10                  15

Gly Ser Arg Val Val Leu Ala His Ser Thr Gly Glu Pro Arg Thr Leu
            20                  25                  30

Val Lys Ala Met Val Glu Asn Tyr Glu Gln Tyr Lys Asp Val Glu Val
        35                  40                  45

Cys His Met Leu Gly Leu Gly Pro Tyr Glu Tyr Thr Asn Pro Glu Met
    50                  55                  60

Lys Gly His Leu Trp His Asn Ser Leu Phe Met Gly Pro Gly Gly Arg
65                  70                  75                  80

Lys Ala Phe Asn Glu Asn Arg Leu Asp Phe Thr Pro Gly Tyr Phe Cys
                85                  90                  95

Asp Ser Ile Lys Phe Phe Arg Glu Gly Tyr Leu Pro Val Asp Val Leu
            100                 105                 110

Met Met Thr Val Ser Pro Pro Asp Lys His Gly Tyr Val Thr Cys Gly
        115                 120                 125

Ile Thr Cys Asp Phe Thr Met Pro Ala Phe Glu Cys Ala Lys Met Val
    130                 135                 140

Ile Val Gln Val Asn Lys Asn Met Pro Arg Thr Phe Gly Gln Thr Ala
145                 150                 155                 160

Ile His Leu Asp Asp Ile Asp Phe Ala Val Glu Ala Asp Asp Pro Leu
                165                 170                 175

Tyr Gly Ser Val Pro Gly Glu Leu Thr Asp Ile Asp Arg Lys Ile Gly
            180                 185                 190

Glu His Cys Ala Ser Leu Ile Asn Asp Gly Ala Cys Leu Gln Leu Gly
        195                 200                 205

Ile Gly Gly Ile Pro Asn Ala Val Leu Thr Tyr Leu Thr Glu Lys Asn
    210                 215                 220

Asp Met Gly Ile His Ser Glu Met Leu Ser Asp Gly Ile Leu Gln Leu
225                 230                 235                 240

Ile Lys Ala Gly Asn Ile Asn Asn Ser Lys Lys Gln Ile His Val Gly
                245                 250                 255

Lys Ser Ala Val Thr Phe Leu Asn Gly Ser Gln Glu Leu Tyr Asp Tyr
            260                 265                 270

Val Asp Asp Asn Pro Ser Val Glu Phe Tyr Pro Val Asp Tyr Ile Asn
        275                 280                 285

Asp Pro Tyr Val Ile Gly Lys Asn Asp Asn Met Val Ser Val Asn Ser
    290                 295                 300

Ala Leu Ser Val Asp Leu Met Gly Gln Ile Val Ala Asp Asn Leu Ser
305                 310                 315                 320

Ala Thr Arg Gln Ile Ser Gly Ala Gly Gly Phe Val Asp Phe Val Arg
                325                 330                 335

Gly Ala Thr Ile Ser Lys Gly Gly Ile Ser Ile Val Ala Met Pro Ser
            340                 345                 350

Thr Ala Ala Gly Gly Lys Ala Ser Arg Ile Glu Met Met Phe Asp Ala
        355                 360                 365

Gly Arg Pro Ile Thr Leu Thr Arg Phe Glu Ser Phe Tyr Val Val Thr
    370                 375                 380

Glu Tyr Gly Ile Ala Lys Met Arg Gly Asn Ser Leu Arg Thr Arg Ala
385                 390                 395                 400
```

```
Arg Gln Leu Ile Glu Ile Ala His Pro Asp Phe Arg Asp Glu Met Lys
                405                 410                 415

Glu Phe Tyr Glu Lys Arg Phe Gly Glu Lys Tyr
            420                 425
```

<210> SEQ ID NO 38
<211> LENGTH: 1179
<212> TYPE: DNA
<213> ORGANISM: Pseudomonas putida

<400> SEQUENCE: 38

```
atgaacgatg tggtcattgt ggctgcaacg cgcactgcaa ttggcagctt tcagggagcg     60
ttggctacgg tgccagccgt agatctggga gctgccgtca tcaaacagct cctgaaacag    120
accggcttag acccagcaca ggtagatgag gtaatcctgg ggcaagtgct cactgctggt    180
gccggccaga atccggcacg ccaagcggca atcaaagctg gactgccgtt ttcggttccg    240
gcattaaccc tgaacaaagt gtgtggctct ggtctgaaag cactgcatct ggcagcacaa    300
gcgattcgct gtggtgatgc ggaggtagtt atcgcaggtg gccaggagaa catgtccttg    360
gccccttatg tgatgcctag cgcgcgtacc gggcaacgca tgggccatgg ccagctcatt    420
gatagcatga ttaccgacgg tttatgggat gcgttcaatg actaccacat gggcattacg    480
gccgagaacc tggtggacaa gtacggcctg tctcgcgaac agcaggatgc ttttgcggct    540
gaatcgcagc gcaaagcggt cgcggctatc gaagcaggcc ggtttgacgc ggagatcacg    600
cccattgtgt tgccgcagaa gaaaggggaa ccgaaagtgt tcgcacgtga tgaacaaccg    660
cgtccggata ccacagccga atcgcttgcc aaattacgtc ctgcgttcaa gaaagatggc    720
agtgtaacag ccgggaacgc gtcaagcctg aatgatggcg ctgccgccgt tctgctgatg    780
agcgccgcta aagcggaagc gctggggtta cccgttttgg cgaaaatcgc cgcttatgcg    840
tcagccggtg tcgatccggc gattatgggt atcggtccag tgtccgccac tcagcgttgc    900
ttggacaaag ccggttggca gctggcggaa cttgacctga ttgaagcgaa cgaagccttt    960
gcggcgcaag cactggccgt tggcaatgca cttgcgtggg atgcggcacg cgtgaacgtt   1020
aatggcggtg cgattgccct tggacatccg attggggcta gtggttgccg tgtcctggtt   1080
accctcctgc acgaaatgat caaacgggac gtcaagaaag gcctggcgac cctgtgcatt   1140
ggtggtggtc aaggcgttgc gctggccatt gaacgctaa                          1179
```

<210> SEQ ID NO 39
<211> LENGTH: 1182
<212> TYPE: DNA
<213> ORGANISM: Sphingomonas wittichii

<400> SEQUENCE: 39

```
atggaggaca tttacattgt tggcgctgcc cgtacggcaa ttgcggactt tggaggcgcc     60
ttaaaggacg ttccaccagc tgatcttggc gtcattgtgg cacgtgctgc tctggaacgc    120
gctgggctcg aaccgggtga tgttcagaac gtagtaatgg gccaggtgat gcctaccgaa    180
ccgcgtgatg cctacttagc tcgcatggtg ggtgtgactg ctggtgtccc gatcgaaacc    240
ccagccctca cactgaatcg cctgtgtgga agcggagttg aggcaatcgt taccggcgca    300
aaagccatgg ttctgggaga atcggatatt gtccttgcgg gtggcgcgga agtcatgagc    360
cgtgttcctc acgtggtaaa aggtgcgcgt tggggtacca aaatggggaa tgtcgagatg    420
accgatggtc tgatcgaggc gttgtccgat ccgttcgaca aagtgcacat gggcattacc    480
gcggaaaacg tcgccgaacg gtaccagatc actcgcgaag cacaggatgc tcttgctctg    540
```

cagggtcatc aacgtgcggc acgcgcgatc gccgagggtc gcttcaaagc ccagattgtc 600
cctgtggaag tgaaaacgcg caaaggcgtt gtggcgttcg ataccgacga gcacgttcgc 660
ggggatgtgt ctgcggaaga actggcgaaa ctgcgtccgg tctttaagaa ggatggcacc 720
gtaacagccg ccaatgcgtc aggcatcaac gatggcgcag caatggtggt cttggcaacg 780
aagaaagccg tcgacgcgaa agggttgaaa cccttagccc gcatcttgtc gtggggtcat 840
gcaggggtag aaccgctgta tatgggcatt ggccccgtaa aagctgttcc gattgcgctg 900
gaacgcgcag gcttaactct ggcggatatc gacgtgattg aggccaatga agcctttgcc 960
gcgcaagcat gcgcagttgc gcaggaactc gggtttgacc cggataaagt gaacccgaac 1020
ggcagtggcg ttgcgctggg ccatccggta ggtgcgacag gtgcgatcct gaccgtgaaa 1080
acggtgtatg agctggaacg gattggaggt cgctatggtc tgatcacgat gtgcattggc 1140
ggcggtcaag ggattgccat ggtggtggaa cgttgtgcgt aa 1182

<210> SEQ ID NO 40
<211> LENGTH: 1197
<212> TYPE: DNA
<213> ORGANISM: Pseudomonas reinekei

<400> SEQUENCE: 40
atgaagaacg cgttgattgt ctctcctctg cgtactccga tcgggaagtt tggcggtgca 60
ctggctccgc ttaccgcgga acatctcgcc agtttcatga tctcgcaagt gatggcgcgt 120
accggcgtgc caggccattc gctggatgag gtgattgtgg cccagtctta tgcgagctcc 180
gaagccccgt gcattggtcg ctatgcggcg ttgagtgccg gcttaccggt ggaagtaccc 240
ggatataccc tggatcgccg ctgtggttca gggctgcagg ctgtcattga tgccagcatg 300
atggtcaaaa ccggtaatgc cgaagccgtt ctggtggtag gggttgaaag catgtcgaat 360
atcgagtact actcaaccga tatgcgctgg ggtgctcgcg ccggtagtgt ccggtttcat 420
gatcggttgg agcgtggtcg cgagcgcagt caaccgagcg aacgctttgg ccacatttcg 480
gggatgccag aaacggcgga caatctggcc ctcgactatg gcatctcacg ggaagaggcc 540
gatagcttca gcgttcgtag ccaccagaat gcagctgcgg cgtggcgtga gggtcgtttt 600
gcggatgaag tggtggcagt ggacgtacct ggtaaacgtg gcgctgtgac acgcgtcacg 660
attgatgagg gtattcgcga agatgcctct ctggagtcca tgaaagcttt acgcttgatc 720
cgtccggaag gcgtttgcac tgcgggcaac agttcgcagc agaacgatgc ggcggcaggc 780
tgtctggttg tatccccgga atacgcagct cgccatggcc tgactccgat ggctcgtctg 840
gtcgactggg cggcagcagg ctgtgaacca tcccgcatgg ggattggccc cgttcctgcg 900
acccagaaac tgctgatgcg tacagggtta tctctggcag aactggacct catcgagctt 960
aacgaagcgt ttgcagccca agcgctcgcc gtactgaaaa cgtggggtct ggatgacctg 1020
tcccgcgtta acgtcaacgg atcaggcatt agcttaggcc atccgatcgg tgcaacgggt 1080
gttcgcatca tgaccaccct tctgcacgaa atgcgtcgtc gtgaagcccg ctatggcctg 1140
gaaacgatgt gcattggagg tggccaggga ttagcggcac ttttcgaacg cgtgtaa 1197

<210> SEQ ID NO 41
<211> LENGTH: 1203
<212> TYPE: DNA
<213> ORGANISM: Pseudomonas putida

<400> SEQUENCE: 41

```
atgcgcgatg tctttatctg cgacgccatc cgtacgccga ttggtcggtt tggcggtgca     60
ctggcgggtg ttcgcgcaga tgatctggcg gccgttccgt tgaaagccct tatcgaaccg    120
aatccagccg tacagtggga tcaggttgac gaggtgttct tcggttgtgc gaaccaagcg    180
ggagaggaca atcgcaacgt cgcgcgcatg gccctgctct tagctgggct gccagagagc    240
attccgggag tcacgctgaa tcgtctgtgc gctagtggca tggatgcgat cggtactgcg    300
tttcgtgcta ttgcctctgg cgaaatggaa ctggcgattg caggtggggt cgaatcgatg    360
tcgcgtgcac cctttgtgat gggcaaagcg gaatccggtt atagccgcaa catgaagctt    420
gaggatacca ctattggttg gcgcttcatc aacccgctga tgaaatccca gtatggagta    480
gactccatgc ccgaaactgc ggacaacgtt gccgatgact accaggttag ccgtgcggat    540
caagatgcgt tcgcactgcg ctcacaacag aaagccgcag ctgcacaagc agcggggttc    600
tttgccgaag aaatcgtgcc ggtccgcatt gctcacaaga aaggcgaaac cattgtggaa    660
cgcgacgaac atctgcggcc ggaaaccacg ttagaggcgt tgaccaagct caaaccggtg    720
aatggcccgg ataaaaccgt tacggctggg aatgcaagcg gcgtgaacga tggtgctgca    780
gccttgatcc tggcgtctgc tgaggccgtg aagaaacacg gtctgacacc acgtgcgcgt    840
gtacttggca tggccagtgg cggtgtggct cctcgcgtca tgggaattgg cccggttcct    900
gcggtgcgca aactgacaga acgcttaggc gtggcagtga gcgactttga tgtgattgaa    960
ctgaacgaag cgtttgcgag tcaggggttg gcagtactgc gcgaactggg tgttgcggat   1020
gatgccccac aagtcaaccc taatggcggt gcaattgccc tgggtcatcc gctcggcatg   1080
tcaggggccc gtctggtttt aaccgcgctg catcagctgg agaaatcggg cggccgtaaa   1140
ggcttagcca ccatgtgtgt gggcgtaggt cagggactcg cgcttgctat cgaacgtgtc   1200
taa                                                                  1203
```

<210> SEQ ID NO 42
<211> LENGTH: 1209
<212> TYPE: DNA
<213> ORGANISM: Burkholderia xenovorans

<400> SEQUENCE: 42

```
atgagcgaaa cgcacatgag cggcaccaaa gccgatccca tcgtgattgt cggagtggct     60
cgcaccccta tggcagcctt tcagggcgac tttgcgacct tgtcggcacc gcagttaggg    120
tcagtggcca ttcaagccgc tgttcagcgt gccggactga aaccggaaca gatcgatgaa    180
gtcgtaatgg ggtgtgtact gccagctggt ctgggtcagg ctcctgcacg gcaagctgcg    240
cttggcgcgg gattaccgct ggccactggc tcaacgacgg tcaacaaaat gtgcggctct    300
ggcatgcgtg cagcgatgtt tgcccacgac atgctcgctg ccggctcagt tgacgtaatt    360
gtagcgggcg gtatggaatc catgacaaat gcgccgtatc tgcttcccaa ggcgcgtgcg    420
ggaatgcgca tggggcatgg gcaggtgatt gaccacatgt tctatgatgg tctggaagat    480
gcatacgaga aaggtcgcct tatgggcagc tttgccgagg aatgtgcagc gagtttcgac    540
ttcacccgtg aagcgcaaga tgcttttgcg gtggaatcgc tggcccgtgc gaaacgtgca    600
aatgaagatg gctcgtttgc ctgggaaatt gccccagtta aagtcgaatc tcgcaaaggt    660
gaagtgacga tcgatcggga tgagcagccg tttaaagcga acatcgagaa aatcccgacc    720
ttaaagccgg cgttcagcaa aacggggact gttacggcgg ccaacagcag ttccatttcc    780
gatggtgcag ctgcgctggt tatgatgcgc gaaagcactg ccaaacgcct cggcgttcag    840
ccgattgcgc gcgttgtcgg ccattctacc ctggcacaag aaccggcgaa atttaccacc    900
```

gccccagttg gtgctatccg caagctgttc gagaagaatg gctggcgtgc ggatgaagtc 960
gacctgttcg aagtgaacga agcgtttgcg gtggtgacaa tggcggcaat gaaagaacac 1020
catctgcctc atgagaaagt gaacgtcaat ggtggtgcct gcgcattagg ccatccgatt 1080
ggcgcaagtg gagcacgcat cttggtaacc ttgattggtg ccctgaagaa acgcggtggt 1140
aaacgtggtg tggctactct gtgcattggc ggtggcgagg caacagcgat ggggatcgag 1200
ctcgtgtaa 1209

<210> SEQ ID NO 43
<211> LENGTH: 1203
<212> TYPE: DNA
<213> ORGANISM: Burkholderia xenovorans

<400> SEQUENCE: 43
atgacggaag cgttcctgtg tgatgcgatc cgcacgccga ttggccggta tgcgggcgcg 60
cttagctccg tacgcgcaga tgatctgggt gcggtaccgt tgaaagccct tatggagcgt 120
aacaaagagg ttgactggaa tgccatcgac gacgttatct acgggtgcgc aaaccaagct 180
ggagaggata accgcaacgt tgcccggatg tcgctcctct tagctggcct gccgcaaggt 240
gttcctggaa cgacagtgaa tcgcttgtgt ggcagtggca tggacgcggt tggcattgca 300
gcacgtgcca tcaagtcagg ggaagcagct ctgatggttg caggcggggt ggaaagcatg 360
tcacgtgcgc cgtttgtgac gggaaaagcc accagcgcct tttcccggca ggcagaaatc 420
tacgatacca ccattggttg gcgctttgtc aacccgctga tgaagaaact ctatggcgtc 480
gatagcatgc cggaaaccgg tgagaatgtt gccaccgact acaacattag ccgcgcagat 540
caagacgctt tcgccttacg ctctcagcag aaagcggcac gtgcgcagcg tgatggcact 600
ctggcacagg aaatcgtggg tgttaccatt gcccagaaga aaggcgatcc agtcaccgtg 660
tcgcaggacg aacatccgcg cgaaaccagt cttgacgccc tggctaaact gaaaggtgtg 720
gtgcgtcccg atgggaccgt aactgctggc aacgctagtg gggtcaacga tggggcagcg 780
gcgttgctgc tggcgaatga ggaaacagcc cgtcgtttcg gtttgactcc ccgtgcacgc 840
gtgcttggta ttgccaccgc aggtgtagct cctcgcgtga tgggcattgg accagcccct 900
gcgacgcaga aactgttagc gcgtctgaat atgtccctgg atcagttcga tgtcatcgaa 960
ctgaacgaag cgtttgcgtc gcaaggcatt gcggtcctgc gcgcgttagg agtcgctgat 1020
gacgataccc gtgtgaatcc gaatggcggt gccattgccc tcggtcatcc actgggtatg 1080
tctggtgcgc gcctggtgac tacggcgatg tatcaactgc accgcacaca aggccgcttt 1140
gctctgtgca cgatgtgcat cggcgtgggt cagggcattg cgattgccat tgaacgcgta 1200
taa 1203

<210> SEQ ID NO 44
<211> LENGTH: 1221
<212> TYPE: DNA
<213> ORGANISM: Rhodococcus jostii

<400> SEQUENCE: 44
atggccgaag tgttcctcgt ggatggtgcg cgtaccccac aaggtcgcta tggaggtgcc 60
ctggcgggtg ttcgccctga cgatctggca ggcttggtgg ttgcggaagc cgcgcgtcgc 120
gcaggaattc cgggagatgc ggtggacgaa gtgatccttg ggcagcgaa tcaagcaggc 180 gaggataacc gcgatgtggc tcgtatggct gtactcctgg cgggcctgcc cgatagcgtc 240
ccaggctata ccgtcaatcg cctgtgtgcg tcgggcctta ctgctgtggc gagtgccgcg 300
cacaccattc gcagcggcga agctgacatc gtcattgcgg gaggggtgga atcaatgacg 360
cgtgctcctt gggtaatggc caaaccgggt accccatggg cacgtccggg tgaagttgcg 420
gacacgagct tgggctggcg tttcacgaat ccccgcttta ccgccgctga tcgcgatgta 480
ccggccggtg ctgggcctga tgtccgcaaa gtaaccctgt cgatgggcga aactgcggag 540
gaagttgccg ccctggaagg cgtaacccgt gcggaatccg acgcatttgc tctccgttct 600
caggaacgtg cgatcgcagc ggttgatgcc ggtcggtttg aacgggagat tgttccggtg 660
ccggttcgcg atggcgaact ggcagcggac gagacaccgc gtcgtggtac gacactggag 720
aaattaggga gtctgaaacc cgtgtttcgt acgggcggta ttgtcactgc agggtccagc 780
agttctctgt ctgatggcgc ggcagcctta gttgtcgcca gcgaagcagc ggtggaaaag 840
tacggcctga ccgtccgcgg ccgcattgtc acgtcggcct cagcgggcat tgcaccgaac 900
gtgatgggtc ttggtccggt gccagcgact cgcaaagcgc tggcacgggc gaactggtcc 960
atcagcgatc tgggtgctgc ggagttgaac gaagcgttcg cagcacagag tctgggcgtt 1020
atccgccagt taaagctgga cgagtcgatc gtaaatgctg acggtggggc cattgctctc 1080
ggacatccgt tgggctgctc aggtgcccgc atcttactga ccctgttagg gcgcatggaa 1140
cgcgaaggcg cccgtcgcgg tcttgccaca ctgtgcgtgg gtgttggcca gggcgtggcc 1200
atgctgattg aggccccgta a 1221

<210> SEQ ID NO 45
<211> LENGTH: 1344
<212> TYPE: DNA
<213> ORGANISM: Bdellovibrio bacteriovorus

<400> SEQUENCE: 45
atgaagtcac cacgcgacgt tgtgctcgtc gaaggtgttc ggacaccgtt cgcaaaagcg 60
ggtaccaaac tgaaaaaagt ccacccagct gaactgggca aagtggcgct taaacaggtc 120
attgcgcaaa cgaacctgga tgtcaacctt gtggatgaag tgatcatcgg gaatactgga 180
aacccaccag attcggtgaa catctctcgt gttgttgccc tgaatgccgg tattccgctc 240
aaaacctcag cgtacacggt acaccgcaat tgcgcatctg cccttgaaag cattagtaac 300
ggctatgaga aaatcaaatc cggcacgatg gatgttattc tggcgggtgg taccgagaat 360
atgtcacaaa tgccgacttt accgccgaag aaattccagg aaatctatga gaaactgttt 420
gctgcaaaag gcccgaaaca agctctgccc ctgctgtgga gtctgttcaa agcggatgtg 480
aagcagatca aagccctgtt aagtgggaat atgcgtgacg agtacttccc ggtgatttcg 540
gtgatgatgg gcttaaccga tccctttgtg ggcattaaca tgggccagac tgccgaaatc 600
ttggcgaaag aatggggcct gtctcgcgaa acccaggata agttcgccct gcgttcccat 660
cagctggcga gcaaagccat gaaagagggt cgtatgcggg aagaaattgc accggtgtat 720
ctcgccccgg aatacaagga agttattagc gaggatatcg gtcctcgtga tacccagacg 780
atggaagcgc tggccaaact gaaaccgttc tttgacaaag cgacaggctc tattaccgca 840
ggcaacagct gtcccattac cgatggagcg gccatggttc tgatgatgtc gcgcgagaaa 900
gcagaagcgc tgggctataa gcctttggca accattcgct cctatgggtt tgcgggcttg 960
gaaccggaac gcatgggttt aggtcctgta tactccacac ctgtagctct caaacgcgca 1020
ggattaagca tgaaagacat tgggttggtc gaattgaatg aagcgtttgc tgctcaagtc 1080
ttatcgtgcc agaaagcgtt tgatagcgac aagtttggcc aggaaaagct tggtctgagt 1140

-continued agcaaaatcg gcgaaatccg cgacgacatt ctgaacgtga atggcggtgc tattgcactg 1200
ggtcatccgg taggtgccac cggtacgcgc atcgttctga cgctggcgaa agagatgaaa 1260
cgtcgtaaca cccagtttgg gttggccact ctgtgtattg gcggaggcca aggaggtagc 1320
atgattctcg aaaatgaggg gtaa 1344

<210> SEQ ID NO 46
<211> LENGTH: 1338
<212> TYPE: DNA
<213> ORGANISM: Cronobacter turicensis

<400> SEQUENCE: 46
atgttttcgc ttctgcaggg gaacgtcatg tctcaagctc tgccgcttgt cacgcgtcag 60
ggcgatcgca ttgcgatcgt ttccggcttg cgcaccccat ttgcccgcca agctaccgcg 120
tatcacgggg ttcctgccgt ggatctgggc aaaatggtag ttggggagct gctggcccgt 180
tcggaaattc caccggatgt cattgagcag ctggtattcg gtcaggtagt acagatgcca 240
gaagcgccga acattgcacg ggagattgtg ctgggtacgg gtatgtccgt tcacacagat 300
gcgtatagcg tcagccgcgc ctgtgcgact agcttccagg cagtggccaa tgtggcggaa 360
agtctgatgg ctggcacgat tcgtgcagga atcgcaggcg gagccgatag ctcaagtgtg 420
ctgccgattg gtgtcagcaa gaaactggct cgtaccctgg tggacgcgaa taaagcccgt 480
acagccggcc agcgcctgaa actgttctct cgcttacgcc tgcgtgatct gttgccggtt 540
cctccggcgg ttgctgagta ctcaacgggt ttacgcatgg gagatacggc cgaacagatg 600
gcgaaaacgc atgggatcac gcgtgaacag caagatgcac ttgcgcatcg ttctcaccaa 660
ctcgcagccc aagcgtgggc agagggcaaa ctccgcgaag aagttatgac cgcttacacc 720
ccaccgtatc gtgaaccgct gagtgaggac aataacatcc ggaagaattc gagcttggcg 780
gactacacca aactgcgtcc ggcatttgac cggaaacatg gcactgtgac agctgcaaac 840
tccacccctc ttacggatgg cgccgcggca gtgatcctga tgacagaatc acgcgcccgc 900
gaactggggt tgaccccgtt gggttatctg cgctcgtacg ctttcaccgc tgtcgatgtc 960
tggcaggaca tgttgttagg tcccgcctgg agtactcccc tcgcgctgga acgcgcgggt 1020
ttaaccatgg ccgatctgac gctgatcgac atgcatgaag cgtttgcctc tcagaccctt 1080
gcgaacctca aactgctcgc gtcagatcgc tttgcacgcg aagtgttagg tcgttcccaa 1140
gctaccggcg aagtagacga gagcaagttc aatgtgttgg gtggcagcat tgcgtatggc 1200
catccgtttg cggcgactgg tgcgcgcatg attacccaga ctctgaacga actgcgtcgt 1260
cgcggtggag gctttggctt agttaccgca tgcgcagcgg gcggtttagg ggcagccatg 1320
gtgctggaag ccgaataa 1338

<210> SEQ ID NO 47
<211> LENGTH: 1371
<212> TYPE: DNA
<213> ORGANISM: Arthrobacter sp.

<400> SEQUENCE: 47
atgtccttta acgggcaatc cgcaaccggt ccggatgaaa gtgcagcggc gcctgctgcc 60
acacctggtg cgggtctgtt gcgcaaagcg gtagttgtgg gcggaaaccg catcccattt 120
gcccgtacgg gtggtgctta tacgaagagc agcaatcagg acatgctgac agcggcgctg 180
gacggcctga ttgctcgctt tggcctggcg gatgaacgca ttggggaagt ggcggctggt 240

```
gcggttctga agcattcacg cgacttcaac ttaacgcggg aagccgtgtt aggcagtgcc    300
ctctctgccg aaaccccggc atacgatctg cagcaggcat gtgcgacagg actggaaacg    360
gtactcggtc tggccaacaa aatcaaatta ggccagattg attccgccat tgccggtgga    420
gttgattctg cgtctgacgc cccgattgcg gttagcgagg gtctgcgcga agtcctgctg    480
gacctgaatc gcgcgaaaac cctgccgcaa cgcctcaaag tgctggggcg cttacgtccc    540
aaagatctgg ccccagatgc gccgaatacg ggagaacccc gtaccggact gtccatgggc    600
gaacatcagg ccctgacaac tgcacagtgg aagattaccc gcgaagcaca ggacgagttg    660
gcatacaaca gccatcgcaa cctcgcggct gcgtatgacg caggcttctt tgacgacctc    720
ttgacgccgt atcgtggtct taaccgtgac tcgaacttac gcgcggatac cacgcgtgag    780
aaattgtcaa cgctgaaacc ggtctttggc aagaatctgg gcgctgaagc gactatgacc    840
gccggcaact cgaccccgct taccgatggc gccagtaccg tgcttctggc gagcgaggaa    900
tgggctgatg cgcacgaatt accgaaactg gccactgtgg tggatggcga agcagcagcg    960
gtcgattttg tccatggcaa agacggtctg ttaatggcgc cagcgttcgc ggtacctcgg   1020
ctgttggcac gcaatggcct tactctcgac gatatcgatt tcttcgagat tcatgaggcc   1080
tttgctggca ccgtgttgag taccettgca gcttgggaag atgaagagtt cggtcgtacc   1140
cgtctgggcc ttgatggtcc actggggtcg attgatcgtg caaaactgaa tgtgaatggg   1200
tcgtcattgg cagctgggca cccgtttgcg gcgactggcg gccgtatcgt agccaccctg   1260
gccaaaatgc tgcacgataa agggcaagtt gatggtcggc cggctcgcgg tctgatcagc   1320
atctgcgcag ccggcggtca aggcgtcgtt gccattctgg aagctagcta a             1371
```

```
<210> SEQ ID NO 48
<211> LENGTH: 1290
<212> TYPE: DNA
<213> ORGANISM: Caulobacter segnis

<400> SEQUENCE: 48

atggccacag cgagttcctc ggcggcatcc tcttccggtg tctggttagc tgcgggtgtt     60
cgcagcccat ttgccaaagt agatggtgcg ttagccggtc atgacgccat tgggttatcg    120
gtgcccgtgg tcaaagcgat gttagcacgt gccaaaccgg actttgcggt ttggggtact    180
gtgatcccga acctcacgtg gagtaacctg gcccgtgagg tcctgttgga tgccggtggt    240
gatccgacga ttccggcgtt ttccacggtt atggcttgca gcaccagcat gattggcgcg    300
attgaagcag ccggcatggt ggatggccgt ggtcgcgatc tggcgctggt aggcggcgtg    360
gaaagcatgt cacgtgtgca gttgggcctg agtgttgcac tgagcgattg gattcgcaag    420
ttccagaacg cgaaaaccgg ccaacagcgg ctcgcggctc tgggagccct taacctgaaa    480
gatgtacgct tattcatccc gaaggtcgtt aaccgtgtta cgggactgtc aatgggagaa    540
cataccgaga ttaccgcgaa agagtggaat ttgtctcgtg cagaccaaga tgccattgct    600
ctggcttcgc atcagggtgc cgtgaaaggc tgggaaagcg gattctttga cgacctggtc    660
attccagtgg gcgaagtgaa acgcgatgga atcccgcgca aagacacatc tctggagaag    720
ctcgcaaaac tgggcccagc ctttgacaaa accagtggca aaggcaccct gaccgcgggg    780
aattcctcac cccttaccga tggtgcggct gcggtttggg taggttctgc agctggcatg    840
gcgcgtttac cgggtgagac accgaaggtt cgtctggtcg actacgaagt caccagcatc    900
gatctgcgtc atgaaggcct gttgatggcg ccggcttatg ggtaccgcg catgctcgcc     960
cgcaatgggc tgacttatgc cgatgttggg ctgtgggaaa tccacgaagc tttcgcagca   1020
```

caggtgttga gccacattgc ggcatgggaa tcggccaagt tcctgagcga gaaagccggc 1080
gtgactacgc ctatgggtgc atttcctcgc gaacgcatga acccgaatgg cggctctctg 1140
gctcttggtc acccatttgg tgcaactggc gcgcgcatca tttcgcagac cgtgaaagaa 1200
ctggcagcgc gccctaaagg ggaacgggcg atcgtgagta tctgtgcgga tggtgggcaa 1260
ggcacgatga tgcttctgga atcagcctaa 1290

<210> SEQ ID NO 49
<211> LENGTH: 1212
<212> TYPE: DNA
<213> ORGANISM: Dinoroseobacter shibae

<400> SEQUENCE: 49
atgacggaag cctacatcta tgacgcgatt cgctcaccac gtggtaaagg gcgcaaagat 60
ggctccctgc atgaagtcac tgcggtcagc ctgagtgccc aaaccctgaa tgcgattaaa 120
gaccgcaatg gcctgaccgg gcatgcggtt gaagatgtga tttggggtaa cgtcacccag 180
gtaatggaac agggtggatg tctggcacgt acggcggtac ttgcgtctga tctggatgag 240
agcattcctg gcttagcgat caaccgcttt tgcgccagcg gtttagaagc cgtcaatttg 300
gcggccaatc aagtgcgtgg aggcggtgga caggcataca ttgctggcgg cgttgagatg 360
atgggtcgcg ttcccatggg tagcgatggc gccgcaatcg cagccgaccc gtctgtggcg 420
atgaaaacct actttgtgcc gcaaggtatt tccgccgata tcatcgcaac ggaatatggc 480
attagccgcg atgatgcgga tgccctggct gtagcgtcgc aacgtcgggc taaagctgcg 540
tgggatgaga accgcttcaa tgggtccgtg tttaccgttc gcgatcagaa cggtctgaac 600
attctggacc acgacgagta tatgcgtcct gaaactgaca tgcagagcct gggtgcactg 660
aaaccggctt tcaaagatat gggtgaacag atgcccggtt tcgacaagat tgcgctcatg 720
aagtatccgc atttagagaa aatcgaacac attcatcacg ccggtaactc gtcaggcatt 780
gttgatggga gtgcagcgct ccttatcggc aataaagcct tcggcgaagc tcatggcctt 840
aaaccacgtg cagtgatcaa agccacagcc aagatcggaa ccgatccgac gattatgctg 900
actggcccgg ttccagcgac cgaaaagatt ttggcagatt ctggcatgag tatctcagac 960
attgatctgt tcgaagtgaa cgaggccttt tcgtcggtcg tgttgcggtt tatgcaggcg 1020
tttgatgtcg accacgacaa agtgaacgtg aatggcggtg cgattgcaat ggggcatccg 1080
ttgggtgcaa caggcgcgat gattctgggc accctgctcg atgagctgga acgtacgggc 1140
aaagggaccg ggttagctac actgtgcgtt gctagtggaa tgggcgcggc tacgatcatc 1200
gaacgcgtat aa 1212

<210> SEQ ID NO 50
<211> LENGTH: 1185
<212> TYPE: DNA
<213> ORGANISM: Burkholderia xenovorans

<400> SEQUENCE: 50
atgactcgcg atacgcgcga cgtggtgatc gtagatgcgg ttcgcacacc aattggcaaa 60
ttccgtggtg ccttggctgg tgtacgtgcc gatcatctgg gtgcactcgt cattgacgaa 120
ctgatccgcc gtgccggtgt caaaccgcag gcggtgaacg atgtggtctt tgggtgcgtt 180
acccagatcg gtgagcagtc agcgaacatt gcccgcacct ctgtgttagg ggcgggatgg 240
ccggaaacca tcccaggcct gaccattgac cgcaagtgtg gtagtgggga agaagcagtg 300

```
cacattgccg ccggcctgat cgcgtttggc gcagcggatg tgatcgttgc cggtggcgct    360

gaatctatgt cgcgtgtccc gatgggtagc aatcgggatc tgcatggcga agcattcggg    420

tggatggctt cagagcgctt cgagctgacc tcgcaaggcg aggccgccga acgtctgtgc    480

gattgttggg cgctgacacg tgcgcaactt gacgcgtact cggtagagtc tcatcgccgc    540

gctgcagcgg ctgcggctga aggctggttt gcgcgcgaga ttgtgcccgt tccagttggt    600

caggtgcgcg aaaagtccct cgaaggcgaa gccgcgttat ttgccgctga tgaaacgatt    660

cgccctggca ccaatgcgga caaactggcg accttgaaat cctcgtttcg cagtgatggt    720

cgcctgacag ccgggaatag ctcacagatt agcgatggtg cggcagcact tctgctgatg    780

agcagtgaca aagcacgtga actcggagtc aaagctcgtg cccgggttcg tgcggttacc    840

acggtgggta gtgatccgac cctcatgctt acgggaccga ttcttgcgac ttgtcaggta    900

ctggagaaag cgggcttagg tttgagcgat atcgacctgt tcgagatcaa cgaagcgttt    960

gcgcctgtac cgctggtctg gatgaaggaa ttcggtgttc cccacgcaaa actgaacgtg   1020

aatggcgggg ccattgcact gggccatccg ttaggcgcat ccggcgcacg tatcatgacg   1080

agcatgttgc acgaactgga acgccgggga gcacgttatg gcctgcaagc catttgctgc   1140

gctggaggta tgggcactgc cacgctgatt gaacgcttag attaa                   1185
```

<210> SEQ ID NO 51
<211> LENGTH: 1149
<212> TYPE: DNA
<213> ORGANISM: Geobacillus kaustophilus

<400> SEQUENCE: 51

```
atgcgtgaag ctgtgattgt agaagccgta cgcacacctg tcgggaaacg gaatggcgta     60

ttccgcgatg tgcatcccgt acatctggca gcggtcgtgt tggatgaagt cgtccgtcgc    120

gcagggatgg ataaaggtgc ggttgaggac atcgtgatgg ggtgtgtgac ccctgtggca    180

gagcaaggtt acaacattgg ccgtttagca gctctggagg ccggcttccc gattgaggtg    240

ccagcggttc agattaaccg catgtgcggc agtggacagc aggccatcca ttttgccgcc    300

caagaaatcc gcagtggcga tatggatgtc acgattgcgg ccggtgtgga atcgatgacc    360

aaagtcccca ttctcagcga tgggaatgag cgcaccattc cgccaagcct ccacgaaaag    420

tacgagttca tccaccaagg tgtatctgcg gaacgcattg cgaagaaata cggactgaca    480

cgcgaagagt tggacgcgta tgcgtatgaa agccaccagc gtgcccttgc tgcactgcgt    540

gaaggcaaat ttcgggcgga aatcgttccg gtaaaaggcc ttgatcgtga tggccgcgaa    600

atcctggtga ccgacgatga aggtccgcgt gctgatacta gcccggaagc cttagcagcg    660

ctgaaaccgg tgtttcagga agatggcctg attaccgcgg gtaatgcttc ccagatgtct    720

gatggcgcag ccgccgttct ccttatggaa cgtgaagcgg cacgtcgctt tggcctgaaa    780

cctaaagctc gcattgtcgc gcaaaccgtt gtgggatcag acccgaccta tatgctggat    840

ggtgttattc cggcaactcg tcaggtcctg aagaaggccg ggctgtcgat cgacgacatt    900

gacctgatcg aaatcaacga ggcgtttgcg ccggttgttc tggcttggca gaaagaaatt    960

ggcgccccgc tggagaaagt gaacgtgaat ggtggtgcga ttgccttagg ccatccactg   1020

ggtgcaactg gcgcgaaact gatgacgtcc ttggttcacg agttagaacg gcgcggtgga   1080

cgctatggcc tgttgacgat ctgcattggg catggtatgg cgacggctac gatcattgaa   1140

cgcgaataa                                                           1149
```

-continued

```
<210> SEQ ID NO 52
<211> LENGTH: 1137
<212> TYPE: DNA
<213> ORGANISM: Beijerinckia indica

<400> SEQUENCE: 52

atgaccaaag tggtcattgc aggctacatt cgctcaccgt ttaccctggc gaagaaaggg      60

gaactggcca cggtgcgtcc tgacgatttg gcagctcaag tcgtgaaagg cctgatcaag     120

aaaaccggca ttccggccga ggacatcgaa gatctgcttc tggggtgtgc gttcccagaa     180

ggtgaacagg gcttcaacgt agctcgcctg gtttcgtttc tggcgggtct gccgctgtcg     240

gtgggcgcaa gcaccgtgaa tcgcttttgt ggctcttcga tgactaccgt tcacatggca     300

gcaggagcca ttcagatgaa cgcaggaaac gcctttatcg cggctggtgt cgaaagcatg     360

agccgcgtac cgatgatggg cttcaatcct ctgccgaatc ccgaattggc cgcgacaatg     420

cctggcgcct atatgggcat gggtgatacg gctgagaatg tggctgccaa atggaccatt     480

tcccggaaag aacaggaaga attcgccctg cgtagccatc aacgtgcgac tgccgcgcag     540

aaggaaggac gtttgaccgg tgaaattatc ccgattaccg gccggaaagg gacgatcacg     600

acggatggct gcattcgtcc cgataccaca cttgagggtc tggcagaact caaaccggcg     660

ttctcagcta atggagtcgt aaccgcgggt acttcctctc cgctgacgga tggcgccgct     720

gccgttctcg tgtgcagtga ggactatgcg aaacatcacc acttagacgt tttagcgagc     780

gtgaaagcta tcgcggtaag cggttgctct ccggagatta tggggattgg tccagttgcg     840

gcctcacgca aggccttagc gcgtgcaggc ctggaagcgg gtcagatcga tattgtcgaa     900

ttgaacgaag cttttgccag tcagtccatt gcgtgtatgc gcgaactgaa cctgagtccg     960

gaccgcgtta acatcgatgg tggcgcgatt gcactgggcc atccactcgg ggcgacaggg    1020

gcgcgcatcg tgggaaaagc agcatcgctg ctcaaacgcg agaaaggcaa atacgcctta    1080

gcgactcagt gcattggtgg tggccaaggt atcgccaccg ttcttgaggc attttaa       1137


<210> SEQ ID NO 53
<211> LENGTH: 1164
<212> TYPE: DNA
<213> ORGANISM: Citrobacter freundii

<400> SEQUENCE: 53

atggaacagg tcgtgatcgt cgatgccatt cgcacgccaa tgggccgttc aaaaggtgga      60

gcctttcgca atgtgcgcgc cgaagatctg tctgcacatc tgatgcgctc tctgctggcc     120

cgtaaccccg cattagatcc gacagcgctg gacgacatct attggggctg tgtgcagcag     180

acactggaac aagggttcaa cattgcgcgt aatgctgctc tgctggcgga aatccctcac     240

agtgtgccag cagtaacggt taatcgcttg tgtggctcca gcatgcaagc tctccatgat     300

gctgcacgca tgatcatgac cggcgatgcg caagcgtgcc tcattggtgg tgtagaacac     360

atgggccatg tccccatgtc acacggggta gactttcacc cgggtatgag ccgcaatgtg     420

gccaaagcag ccggtatgat gggcttaact gcggagatgc tgtcccgcat gcacggcatt     480

agtcgtgaaa tgcaggatgc ctttgcagcg cgcagtcatg cgcgtgcttg ggcggccact     540

caatctgggg ccttcaagaa cgagattatt ccgactggcg gccatgatgc ggatggggta     600

ctcaaacagt tcaactacga tgaggtgatt cggccggaaa ccaccgttga agccttgtcg     660

accttacgcc cggcctttga tcctgtttct ggtaccgtta ccgcgggcac gtcgtccgcg     720

ttgagcgacg gtgcggcagc catgcttgtg atgtcagaaa gccgtgctcg tgaacttggc     780
```

-continued

```
ttaacaccgc gtgcgcgcat tcgtagcatg gcagtggttg gatgtgatcc gagcattatg    840

gggtatggac cagtcccggc ttcgaaactc gccttgaaga aagcgggcct gagcacgtcc    900

gacattgggc tgtttgaaat gaacgaagct tttgcagcgc agattctgcc gtgcatcaaa    960

gacctgggtc tgatggagca gatcgacgag aaaatcaacc tgaatggcgg tgcaatcgcc   1020

cttggccatc ctctgggttg cagtggtgcg cgcatttcga ccacgctgtt aaacctgatg   1080

gaacgcaaag atgtccagtt cggtcttgcg accatgtgca ttggactggg tcaaggcatc   1140

gcaaccgtgt tcgagcgggt ttaa                                          1164
```

<210> SEQ ID NO 54
<211> LENGTH: 1197
<212> TYPE: DNA
<213> ORGANISM: Cupriavidus necator

<400> SEQUENCE: 54

```
atgaaacagt tacaggatgc gtacattgtt gcggccactc gcagtccgat tggaaaagca     60

cccaagggag ccttcaagaa tacgcgcccg gacgatctgt tagcgacgat ccttaaagcc    120

gctgtggccc aggtgccgaa tctcgatccg aaactgatcg aagatgcgat cgtcggttgc    180

gcaatccctg aggctcagca aggcctgaat gtagcccgca ttggtgcgct gctgagtgga    240

ctgccaaaca cggttggcgg cattaccgtt aatcggtttt gcgcatctgg ggtcagcgct    300

gttgcgatgg cagccgatcg cattcgcgtc ggtgaatccg acgtcatgat tgctgccggt    360

gtggagtcaa tgagcatggt gcccatgatg ggtaactctc cgagcatgag tccggaaatc    420

tttacccgtg acgaaaacgt tggcattgcc tatgggatgg gtctgacagc cgagaaagtg    480

gctcagcagt ggcaagtaag ccgcgaagat caggatgcgt tttcgctggc atcccaccag    540

aaagcaattg ccgcgcaaca ggcaggcgaa ttcaaggatg agatcacccc gattgagatt    600

gtggagcgtt tccctgacct ggcaagtggg caagtgaacg taaagacccg cacgattagc    660

ctggatgaag gcccacgtcc ggaaacctct cttgaaggct tgggtaaact ccgtccggtc    720

tttgccaaca aaggctcagt aaccgcaggc aatagctcgc agacttcgga cggtgcaggc    780

gcgctgattt tggtgtcgga gaaaatcctg aaacagttca acctggtacc gttggcgcgg    840

tttgtgtcat ttgccgtccg tggtgttccg ccggaaatca tgggtattgg tcccaaagaa    900

gcgatccctg cagctctgaa agccgcgggc ctgacccaag accaactgga ttggatcgaa    960

ctcaacgaag cctttgcggc gcaatccctc gctgtgatgc gtgaccttca gttagatcca   1020

gcaaaagtga atcgcatggg tggcgcgatt gcgctgggcc atccattggg agctaccggc   1080

gcgatccgta gcgcgacagt cgttcatgcc ttacgtcgcc acaacctgaa atatgggatg   1140

gttacgatgt gtgtggggac tgggatgggt gctgcgggca ttttcgaacg cgtttaa      1197
```

<210> SEQ ID NO 55
<211> LENGTH: 1248
<212> TYPE: DNA
<213> ORGANISM: Gordonia bronchialis

<400> SEQUENCE: 55

```
atggcccctt gctcagtgaa agcgatgcca gaagcagtga tcgtagctca tgcacgtagt     60

cccattggtc gtgctggtaa aggctcgtta aaggatgtcc gtcctgacga actgagccgc    120

cagatggtag ccgctgctct cgcgaaagtg ccggaactgg caccctcgga catcgaggat    180

attcactggg gtattggcca gccaggcggc caaggtgggt acaatattgc gcgtgtcatt    240

gccgtggaat tgggctatga tcacatcccg ggtgtgaccg tgaatcgtta ttgctcgtcg    300
```

-continued

```
agcctgcaga ccacacgcat ggcactgcat gcgattaaag caggagaagc ggatgttctc    360
attagtggag gggttgagag tgttagcagc tttggcattt ccggtggggc agatggcgcc    420
ccggatagta agaacccagt attcgatgac gcgcaagcac ggaccgcgaa agctgccgaa    480
ggtggagcac cggcttggac tgatccacgt gagcaaggct tgattccgga tgtttacatc    540
gcaatgggcc aaacggccga aaacgtagcc tcttttaccg gcatctctcg cgaagatcag    600
gatcggtggt ctgtcctgag ccagaatcgc gccgaagagg ccattaacgc gggcttcttc    660
gaacgcgaga tcgacccggt tacgcttccg gatggtagca cggttaacac cgatgatggc    720
cctcgtgcgg gcactaccta tgagaaagtc tcacagctga aaccggtgtt tcgccctgat    780
ggcaccgtga ctgcgggcaa tgcgtgtccg ctcaatgacg gtgctgccgc actggtgatt    840
atgtccgaca gcaaagcgaa gcaactgggt ttaacgccct tagcgcgtgt ggtggcgaca    900
gcggccactg gactgtcacc ggaaatcatg ggtctgggtc cgattgaagc catccgcaaa    960
gttctgcgca tctctgggat gtccctgagc gacattgacc tggtcgaaat caacgaagcc   1020
tttgcagtcc aggtactggg gagtgcgaac gagttgggga ttgaccacga caaactgaac   1080
gtgtcaggtg gcgctattgc gttgggtcat ccgtttggca tgaccggggc ccgcattacc   1140
acgacgcttc tgaacaatct gcagacacgc gataaaacct tcggaatcga atccatgtgt   1200
gttggcggtg gccagggtat ggcgatggtc cttgaacgct tatcgtaa                1248
```

<210> SEQ ID NO 56
<211> LENGTH: 1182
<212> TYPE: DNA
<213> ORGANISM: Burkholderia sp.

<400> SEQUENCE: 56

```
atgcgtgagg ctgtgattgt ctccaccgca cgtacgccct tgaccaaagc gcatcgtggc     60
gagttcaaca tcacaccagg cccaaccctc gcctcgtttg ctgttcgcgc agcagtagaa    120
cggagtggtg tcgaccctga tatcattgag gatgcgatcc tgggttgcgg ctatccggaa    180
ggcaccactg gccgcaatgt tgcacgccaa agcgttattc gtgccggtct gccactgtcc    240
attgcaggca caacggtcaa tcggttttgt gcctcaggcc ttcaggcaat tgcgatggca    300
gctgggcgca ttgtggtcga tggagcgccg gcaatgattg cgggcggtgt tgagagcatt    360
tcgaacatcc agacccgcga agatggagtg tctggcctgg acccgtggat tgtcgagcac    420
aaaccctcac tgtacactgc gatgatcgat acagcggata ttgttgctcg ccgttatggg    480
attagtcgcg aagctcagga tcagtttagc gtggagagcc aacgtcgcac tgccgaggcg    540
caacaagcgg gacgttatgc agacgagatt atcccggtta ccacgaccat ggccattacg    600
gacaaggaaa cccgtgcggt aagctatcgc gaagtgacgg tgtctgccga caattgcaac    660
cgtccgggga cgacctacga agcattagcg aaacttgcgc cggtaaaagg tcctgatcag    720
ttcattaccg cagggaatgc gtcccagaac gcggatggtg cctcggcgtg cgtactgatg    780
gaagcgaaag ccgccgaacg ggccaacttt gcgccactgg gcgcgtttcg cggcttagct    840
ttggctgggt gtgaaccgga tgaaatgggg attggtccgg ttcttgctgt cccgaaactc    900
ctggcacgcc atggcttaac ggtggacgat atcggtttgt gggaactcaa cgaagccttt    960
gccagtcagg ccgtatactg ccagaaacgc ctggaaatcc cttctgaacg cctgaacgtg   1020
aatggtggtg ccatttcaat cggtcatccg ttcggcatga ctggcagccg tctggtgggc   1080
cacgttctga tcgaaggacg ccgccgtggc gtcaagtacg cggtggtgac catgtgtatg   1140
```

gccggtggca tgggtgcggc tggtctgttc gaaatctatt aa 1182

<210> SEQ ID NO 57
<211> LENGTH: 1212
<212> TYPE: DNA
<213> ORGANISM: Arthrobacter arilaitensis

<400> SEQUENCE: 57
atgcagcagg catacctgta tgacgcgatt cgcaccccgt tcggtaagat cggtggtgcc 60
ctgagcagtc accgtcccga tgatctggcc gcacatgtcg tacgcgaact ggttgcacgc 120
agccccaaac tggacgtagc cgatatcgac gaaagcatct ttggcaatgc caacggtgct 180
ggcgaagaaa accgcaatgt agcgcgtatg gctacgttac tcgcgggatt gccgacttcg 240
ctcccgggaa cgaccatgaa ccgcctttgc ggttctagct tggatgcgag tattgccgcc 300
tcacgccaga ttgccacagg cgatgcggac cttgttctgg tgggtggcgt ggaaagcatg 360
tcccgtgcgc catgggtcct gcctaaaacc gaacgtccat ttccgatgtc gaacctggaa 420
ttagcgaata cgacgcttgg atggcgtctg gtgaatccgg caatgccagg ggaatggact 480
gtgtcgttag gcgaagcgac cgaacaactg cgcgaaaagc acggtatctc gcgcgaggat 540
caggacgagt tcagtgctgc gtcacatcag cgtgcagcag cagcctggca agcgggcaaa 600
tacgacaacc tcgtggttcc tgtcccgccg gcaaacaaac gcggcacgga agtgacacgc 660
gatgaaacga ttcgcgccga tagcactgcg caaaccctgt ccaaattacg taccgtcttt 720
cgcaccggcg aaaacgcgac tgtcaccgct gggaatgcct ctccaatgag tgatggtgcg 780
agcgctgctt tcattgggtc agaacgtggc ggtgaactgt taggcgccgc gcctattgct 840
cgcatcgcgt ctaatggcgc cgctgcgctt gatccgcagt tctttgggtt tgccccggtt 900
gaggcagcga acaaagcact ggcgaaagca ggactgaagt ggtccgacat tgctgcggtg 960
gagctgaacg aggcctttgc agcccagtct ctcgcgtgta tccgggcgtg ggatattgat 1020
ccggcgattg tgaatgcatg ggcggtgca atctccattg gccatccgtt gggtgctagc 1080
gggctgcgta ttctgggcac agttgcgcgt cgcctggcgg aatcagggga gcggtatggt 1140
ctggccgcca tctgcattgg cgttggtcaa ggcttggctg ttgtagtgga gaacatcaat 1200
gccaccaaat aa 1212

<210> SEQ ID NO 58
<211> LENGTH: 1206
<212> TYPE: DNA
<213> ORGANISM: Escherichia coli

<400> SEQUENCE: 58
atgcgtgaag cctttatttg tgacggaatt cgtacgccaa ttggtcgcta cggcggggca 60
ttatcaagtg ttcgggctga tgatctggct gctatccctt tgcgggaact gctggtgcga 120
aacccgcgtc tcgatgcgga gtgtatcgat gatgtgatcc tcggctgtgc taatcaggcg 180
ggagaagata accgtaacgt agcccggatg gcgactttac tggcggggct gccgcagagt 240
gtttccggca caaccattaa ccgcttgtgt ggttccgggc tggacgcact ggggtttgcc 300
gcacgggcga ttaaagcggg cgatggcgat ttgctgatcg ccggtggcgt ggagtcaatg 360
tcacgggcac cgtttgttat gggcaaggca gccagtgcat tttctcgtca ggctgagatg 420
ttcgatacca ctattggctg gcgatttgtg aacccgctca tggctcagca atttggaact 480
gacagcatgc cggaaacggc agagaatgta gctgaactgt taaaaatctc acgagaagat 540
caagatagtt ttgcgctacg cagtcagcaa cgtacggcaa aagcgcaatc ctcaggcatt 600

-continued ctggctgagg agattgttcc ggttgtgttg aaaaacaaga aaggtgttgt aacagaaata 660
caacatgatg agcatctgcg cccggaaacg acgctggaac agttacgtgg gttaaaagca 720
ccatttcgtg ccaatggggt gattaccgca ggcaatgctt ccggggtgaa tgacggagcc 780
gctgcgttga ttattgccag tgaacagatg gcagcagcgc aaggactgac accgcgggcg 840
cgtatcgtag ccatggcaac cgccggggtg gaaccgcgcc tgatggggct tggtccggtg 900
cctgcaactc gccgggtgct ggaacgcgca gggctgagta ttcacgatat ggacgtgatt 960
gaactgaacg aagcgttcgc ggcccaggcg ttgggtgtac tacgcgaatt ggggctgcct 1020
gatgatgccc cacatgttaa ccccaacgga ggcgctatcg ccttaggcca tccgttggga 1080
atgagtggtg cccgcctggc actggctgcc agccatgagc tgcatcggcg taacggtcgt 1140
tacgcattgt gcaccatgtg catcggtgtc ggtcagggca tcgccatgat tctggagcgt 1200
gtttga 1206

<210> SEQ ID NO 59
<211> LENGTH: 1185
<212> TYPE: DNA
<213> ORGANISM: Cupriavidus necator

<400> SEQUENCE: 59
atgacgcgtg aagtggtagt ggtaagcggt gtccgtaccg cgatcgggac ctttggcggc 60
agcctgaagg atgtggcacc ggcggagctg ggcgcactgg tggtgcgcga ggcgctggcg 120
cgcgcgcagg tgtcgggcga cgatgtcggc cacgtggtat tcggcaacgt gatccagacc 180
gagccgcgcg acatgtatct gggccgcgtc gcggccgtca acggcggggt gacgatcaac 240
gcccccgcgc tgaccgtgaa ccgcctgtgc ggctcgggcc tgcaggccat tgtcagcgcc 300
gcgcagacca tcctgctggg cgataccgac gtcgccatcg gcggcggcgc ggaaagcatg 360
agccgcgcac cgtacctggc gccggcagcg cgctggggcg cacgcatggg cgacgccggc 420
ctggtcgaca tgatgctggg tgcgctgcac gatcccttcc atcgcatcca catgggcgtg 480
accgccgaga atgtcgccaa ggaatacgac atctcgcgcg cgcagcagga cgaggccgcg 540
ctggaatcgc accgccgcgc ttcggcagcg atcaaggccg gctacttcaa ggaccagatc 600
gtcccggtgg tgagcaaggg ccgcaagggc gacgtgacct tcgacaccga cgagcacgtg 660
cgccatgacg ccaccatcga cgacatgacc aagctcaggc cggtcttcgt caaggaaaac 720
ggcacggtca cggccggcaa tgcctcgggc ctgaacgacg ccgccgccgc ggtggtgatg 780
atggagcgcg ccgaagccga gcgccgcggc ctgaagccgc tggcccgcct ggtgtcgtac 840
ggccatgccg gcgtggaccc gaaggccatg ggcatcggcc cggtgccggc gacgaagatc 900
gcgctggagc gcgccggcct gcaggtgtcg gacctggacg tgatcgaagc caacgaagcc 960
tttgccgcac aggcgtgcgc cgtgaccaag gcgctcggtc tggacccggc caaggttaac 1020
ccgaacggct cgggcatctc gctgggccac ccgatcggcg ccaccggtgc cctgatcacg 1080
gtgaaggcgc tgcatgagct gaaccgcgtg cagggccgct acgcgctggt gacgatgtgc 1140
atcggcggcg ggcagggcat tgccgccatc ttcgagcgta tctga 1185

<210> SEQ ID NO 60
<211> LENGTH: 1284
<212> TYPE: DNA
<213> ORGANISM: Clostridium viride

<400> SEQUENCE: 60

-continued

```
atggcgcagt ttgtcactgc tcaggaagcc gttaaacaca tcccgaatgg cagccgtgtg     60
gtgcttgcgc attctacagg agaaccgcgt actctggtga aggcaatggt tgaaaactac    120
gagcagtata aagacgtcga ggtttgccac atgctgggcc tgggacctta cgaatacacc    180
aatccggaga tgaaagggca tctgtggcac aactcgctct ttatgggccc aggtggacgg    240
aaagccttta acgaaaatcg ccttgacttt acgccagggt acttctgcga tagcatcaaa    300
ttctttcgtg agggctatct gcccgttgat gtgctgatga tgaccgtatc gcctccagat    360
aaacatgggt atgtgacgtg tgggattacg tgcgatttca ctatgccagc atttgaatgc    420
gccaaaaatgg tcatcgtcca ggtgaacaag aatatgccgc gcacgttcgg tcaaaccgca   480
atccacctgg acgacatcga tttcgcggta gaagcagatg atccgctgta tggcagtgta    540
ccgggtgaat tgacagacat tgatcgcaaa attggtgaac attgtgcctc gttaatcaac    600
gatggcgctt gtctgcaatt agggattggc ggcattccga atgccgtctt gacctatctc    660
accgaaaaaa acgatatggg cattcattcc gagatgctct ctgatggcat tctgcagctg    720
attaaagccg gcaacatcaa caatagcaag aaacagattc acgtgggtaa atcagcggtt    780
accttcttga acggtagtca ggaactgtac gattatgtgg acgataatcc gagcgtagaa    840
ttttatccgg tggattacat caacgacccc tacgttattg gcaagaacga caatatggtg    900
tccgttaatt cagcgttatc ggtggatctg atggggcaaa ttgttgcaga taacctgagt    960
gcgacgcgcc agatctctgg tgctggtggt ttcgtagact ttgtccgtgg agccaccatc   1020
tcaaaaggcg gcatcagcat tgtggctatg cctagcactg cggctggtgg taaagcgagt   1080
cggattgaaa tgatgtttga tgccggtcgc ccgattaccc tgacacgctt tgagagcttc   1140
tatgttgtca cggaatacgg cattgcgaaa atgcgcggta attccttacg tacccgtgca   1200
cgccaactta tcgaaattgc gcatccggat tttcgtgacg aaatgaaaga gttctatgaa   1260
aagcgctttg gcgagaaata ttaa                                          1284

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 61

His His His His His His His
1               5
```

UNITED STATES PATENT AND TRADEMARK OFFICE
CERTIFICATE OF CORRECTION

PATENT NO.        : 10,920,254 B2
APPLICATION NO.   : 16/683570
DATED             : February 16, 2021
INVENTOR(S)       : Alex Van Eck Conradie et al.

It is certified that error appears in the above-identified patent and that said Letters Patent is hereby corrected as shown below:

On the Title Page

Item [57], "--7-hydroxyheptanoic" should read as -- -7-hydroxyheptanoic --.

In the Claims

Claim 18, Column 174, Line 3, "or, micro-aerobic" should read as -- or micro-aerobic --.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*